US008620592B2

(12) United States Patent
Khan et al.

(10) Patent No.: US 8,620,592 B2
(45) Date of Patent: *Dec. 31, 2013

(54) METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

(75) Inventors: Javed Khan, Derwood, MD (US); Markus Ringner, Lund (SE); Carsten Peterson, Lund (SE); Paul Meltzer, Rockville, MD (US)

(73) Assignee: The United States of America Represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/285,687

(22) Filed: Oct. 31, 2011

(65) Prior Publication Data

US 2012/0046878 A1 Feb. 23, 2012

Related U.S. Application Data

(63) Continuation of application No. 12/858,674, filed on Aug. 18, 2010, now Pat. No. 8,065,092, which is a continuation of application No. 11/928,901, filed on Oct. 30, 2007, now Pat. No. 7,783,431, which is a continuation of application No. 10/133,937, filed on Apr. 25, 2002, now Pat. No. 7,774,143.

(51) Int. Cl.

| | |
|---|---|
| ***G06F 19/00*** | (2011.01) |
| ***G06N 3/00*** | (2006.01) |
| ***G06G 7/00*** | (2006.01) |
| ***G06F 17/10*** | (2006.01) |
| ***G06G 7/58*** | (2006.01) |

(52) U.S. Cl.

USPC ......... 702/19; 702/13; 702/15; 703/2; 703/11

(58) Field of Classification Search

None

See application file for complete search history.

(56) References Cited

U.S. PATENT DOCUMENTS

| | | | |
|---|---|---|---|
| 5,728,527 | A | 3/1998 | Singer et al. |
| 5,800,992 | A | 9/1998 | Fodor et al. |
| 6,238,869 | B1 | 5/2001 | Kris et al. |
| 6,706,867 | B1 | 3/2004 | Lorenz |
| 6,794,137 | B2 | 9/2004 | Blumenberg |
| 7,062,384 | B2 | 6/2006 | Rocke et al. |
| 7,229,774 | B2 | 6/2007 | Chinnaiyan et al. |
| 7,341,552 | B2 | 3/2008 | Zhang et al. |
| 7,370,021 | B2 | 5/2008 | Reeve et al. |
| 7,384,736 | B2 | 6/2008 | Hakonarson |
| 7,402,388 | B2 | 7/2008 | Gillis et al. |
| 7,402,399 | B2 | 7/2008 | Mukherjeei et al. |
| 7,774,143 | B2 | 8/2010 | Khan et al. |
| 7,783,431 | B2 | 8/2010 | Khan et al. |
| 2003/0207278 | A1 | 11/2003 | Khan et al. |
| 2004/0009154 | A1 | 1/2004 | Khan et al. |
| 2008/0181896 | A1 | 7/2008 | Khan et al. |

OTHER PUBLICATIONS

Agilent Technology Webpage, dated Aug. 16, 2007.

Ancoca et al., "On the statistical assessment of classifiers using DNA microarray data", *BMC Bioinformatics*, 7:387 (2006).

Blast Alignment between GenBank Accession No. NM_000612 and SEQ ID No. 72, dated Aug. 16, 2007.

Chen et al., "Diagnosis of the Small Round Blue Cell Tumors Using Multiplex Polymerase Chain Reaction", *Journal of Molecular Diagnostics*, 9(1):80-88 (2007).

Cover page of Nature Medicine, vol. 7, No. 6, Jun. 2001.

ECgene Summary for CCND1 available via URL: <genome.ewha.ac.kr/cgi-bin/ECquery.cgi?organism=human&query=CCND1>, printed May 29, 2008.

ECgene Summary for IGF2 available via URL: <genome.ewha.ac.kr/cgi-bin/ECquery.cgi?organism=human&query=IGF2>, printed May 29, 2008.

Furey et al., *Bioinformatics*, 16(10):906-914 (2000).

GenBank Accession No. N54901, dated Jan. 28, 1997.

GenBank Accession No. NM_000612, dated Oct. 31, 2000.

GenBank Sequence Revision History page printed Aug. 15, 2007.

GeneCard Database Record IGF2 printed Aug. 15, 2007.

GeneCard for IGF2 via URL: <genecards.org/cgi-bin/carddisp.pl?gene=IGF2&snp=93#snp>, printed May 29, 2008.

GeneCard for CCND1 available via URL: <genecards.org/cgi-bin/carddisp.pl?gene=Ccnd1&snp=97#snp>, printed May 29, 2008.

Golub et al., "Molecular Classification of Cancer: Class Discovery and Class Prediction by Gene Expression Monitoring", Science, 286:531-537 (1999).

Gruvberger et al., "Estrogen Receptor Status in Breast Cancer is Associated with Remarkably Distinct Gene Expression Patterns", Cancer Research, 61:5979-5984 (2001).

Herrero et al., *Bioinformatics*, 17(2):126-136 (2001).

(Continued)

*Primary Examiner* — Lori A Clow

(74) *Attorney, Agent, or Firm* — Merchant & Gould PC

(57) ABSTRACT

A method of diagnosing, predicting, or prognosticating about a disease that includes obtaining experimental data, wherein the experimental data is high dimensional data, filtering the data, reducing the dimensionality of the data through use of one or more methods, training a supervised pattern recognition method, ranking individual data points from the data, wherein the ranking is dependent on the outcome of the supervised pattern recognition method, choosing multiple data points from the data, wherein the choice is based on the relative ranking of the individual data points, and using the multiple data points to determine if an unknown set of experimental data indicates a diseased condition, a predilection for a diseased condition, or a prognosis about a diseased condition.

10 Claims, 9 Drawing Sheets

(56) References Cited

OTHER PUBLICATIONS

Image Consortium Record printed Aug. 15, 2007.
Image Id. No. record printed Sep. 21, 2006.
Kim et al., "ECgene: genome annotation for alternative splicing", *Nucleic Acids Research*, 33:D75-D79 (2005).
Khan et al., "Classification and diagnostic prediction of cancers using gene expression profiling and artificial neural networks", Nature Medicine, 7(6):673-679 (2001).
Kwon et al., "DNA Microarray Data Analysis for Cancer Classification Based on Stepwise Discriminant Analysis and Bayesian Decision Theory", Genome Informatics, 12:252-254 (2001).
Li et al., Human Pathology, 2008, 39:1792-1801.
Mateos et al., "Supervised Neural Networks for Clustering Conditions in DNA Array Data after Reducing Noise by Clustering Gene Expression Profiles", *Microarray data analysis II*, Kluwer Academic Publ., pp. 91-103 (2002).
Muller et al., *IEEE Transactions on Neural Networks*, 12(2):181-201 (2001).
NHGRI Protocol, http://www.nhgri.hih.gov/DIR/LGG/SK/HTML/protocol.html, 27 pages (Apr. 25, 2002).
Peterson et al., "JETNET 3.0—A versatile artificial neural network package", Computer Physics Communications, 81:185-220 (1994).
Raychaudhuri et al., Pacific Symposium on Biocomputing (2000) pp. 455-466.
Raychaudhuri et al., *Trends in Biotechnology*, 19(5):189-193 (2001).
Sequence Alignment printed Sep. 11, 2006.
Sperduti et al., "Supervised Neural Networks for the Classification of Structures", IEEE Transaction on Neural Networks, 8(3):714-735 (1997).
Tips for cDNA sequences printed Sep. 21, 2006.
Tusher et al., "Significance analysis of microarrays applied to the ionizing radiation response", PNAS, 98(9):5116-5121 (2001).
U.S. Appl. No. 10/133,937 Office Action dated Jan. 22, 2009.
U.S. Appl. No. 10/159,563 Office Action dated Feb. 12, 2009.
U.S. Appl. No. 10/159,563 Form PTO-892 from Office Action dated Jun. 10, 2008.
Van Gelder et al., "Amplified RNA synthesized from limited quantities of heterogeneous cDNA", Proc. Natl. Acad. Sci. USA, 87(5):1663-1667 (1990).
Wang et al., Human Genetics, 2006, 120:297-300.
Nam,Douglas Kyung, et al., Oligo (dT) primer generates a high frequency of truncated cDNAs through internal poly(A) priming during reverse transcription, PNAS 99(9):6152-6156 (Apr. 2002).
Lawlor, Elizabeth R., et al., Ewing tumor cells activate distinct signaling pathways in monolayer versus anchorage-independent cultures, Nature Genetics 27:88 (2001).
Klein, Ulf., et al., Gene Expression Profiling of B Cell Chronic Lymphocytic Leukemia Reveals a Homogenerous Phenotype Related to memory B Cells, J. Exp. med 194(11) 1625-1638 (Dec. 2001). Retrieved Apr. 20, 2011, from www.jem.rupress.org.
Zhou, Z., et al., *Homo sapiens* secreted frizzled related protein mRNA, complete cds, GenBank Accession No. AF056087.1. Retrieved on Apr. 21, 2011, from http://www.ncbi.nlm.nih.gov/nuccore/AF056087.

METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES

CROSS REFERENCE TO RELATED APPLICATIONS

This application is a continuation of application Ser. No. 12/858,674, filed Aug. 18, 2010, now U.S. Pat. No. 8,065, 092, which is a continuation of application Ser. No. 11/928, 901, filed Oct. 30, 2007, now U.S. Pat. No. 7,783,431, which is a continuation of application Ser. No. 10/133,937, filed Apr. 25, 2002, now U.S. Pat. No. 7,774,143, which applications are incorporated herein by reference in their entirety.

STATEMENT OF GOVERNMENT RIGHTS

The work performed during the development of this invention utilized U.S. Government Funds. The government has certain rights in the invention.

FIELD OF THE INVENTION

The invention relates generally to the use of supervised pattern recognition methods to classify and diagnose disease. More specifically, the invention relates to the use of supervised pattern recognition methods, such as artificial neural networks for the classification, diagnosis, prognosis and prediction of disease using high dimensional data, such as gene expression profiling data.

BACKGROUND OF THE INVENTION

Disease is generally diagnosed based on a myriad of factors, both objective and subjective, including but not limited to symptoms, laboratory test values, demographic factors and environmental factors. Diagnosis relies on a clinician such as a physician or a veterinarian being able to identify and evaluate the relevant factors. Often this task can be difficult, and becomes exceedingly more so as the number of factors to be considered increases.

An example of a disease whose diagnosis is difficult is tumors. Tumors are currently diagnosed on the basis of clinical presentation, routine histology, immunohistochemistry and electron microscopy. However the histological appearance may not reveal the genetic aberrations or underlying biologic processes that contribute to the malignancy. Monitoring global gene expression levels using DNA microarrays would provide an additional tool for elucidating tumor biology as well as the potential for molecular diagnostic classification of cancers. Several studies have demonstrated that gene expression profiling using DNA microarrays is able to classify tumors with a high accuracy, and discover new cancer classes.

A specific type of tumors which could benefit is the small, round blue cell tumors (SRBCTs) of childhood as a model. SRBCTs include, neuroblastoma (NB), rhabdomyosarcoma (RMS), non-Hodgkin lymphoma (NHL) and the Ewing family of tumors (EWS), are so named because of their similar appearance on routine histology. However, accurate diagnosis of SRBCTs is essential because the treatment options, responses to therapy, and prognoses vary widely depending on the diagnosis. As their name implies, these cancers are difficult to distinguish by light microscopy, and currently no single test can precisely distinguish these cancers.

In clinical practice, several techniques are used for diagnosis, including immunohistochemistry, cytogenetics, interphase fluorescence in situ hybridization and reverse transcription (RT)-PCR. Immunohistochemistry allows the detection of protein expression, but it can only examine one protein at a time. Molecular techniques such as RT-PCR are used increasingly for diagnostic confirmation following the discovery of tumor-specific translocations such as EWS-FLI1; t(11;22)(q24;q12) in EWS, and the PAX3-FKHR; t(2;13)(q35;q14) in alveolar rhabdomyosarcoma (ARMS). However, molecular markers do not always provide a definitive diagnosis, as on occasion there is failure to detect the classical translocations, due to either technical difficulties or the presence of variant translocations.

An example of a diagnostic method replete with such problems is the diagnostic method for Ewing sarcoma. Ewing sarcoma is diagnosed by immunohistochemical evidence of MIC2 expression and lack of expression of the leukocyte common antigen CD45 (excluding lymphoma), muscle-specific actin or myogenin (excluding RMS). However, reliance on detection of MIC2 alone can lead to incorrect diagnosis as MIC2 expression occurs occasionally in other tumor types including RMS and NHL.

One objective factor that can, in certain circumstances, be entirely predictive of a diseased state is the genetic makeup of the individual. Genetic makeup of an individual can also be considered in terms f the level of expression of the genes of that individual through gene expression data.

DNA microarray technology is a recently developed high throughput technology for monitoring gene expression at the transcription level. Its use is akin to performing tens of thousands of northern blots simultaneously, and has the potential for parallel integration of the expression levels of an entire genome. A DNA microarray consists of DNA probes immobilized on a solid support such as a glass microscope slide. The DNA probes can be double stranded cDNA or short (25 mers) or long (50-70 mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 mers) sets are commercially available for human, mouse and other organisms at the Operon company website.

Another technique for fabricating oligonucleotides microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink jet onto glass surfaces.

One method of utilizing gene expression data from microarrays is given by Tusher et al., PNAS 98(9) p. 5116-21, April, 2001. The method of Tusher et al. is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

DNA microarrays would be an invaluable tool for disease diagnosis. Gene-expression profiling using DNA microarrays permits a simultaneous analysis of multiple markers, and can be used for example to categorize cancers into subgroups. The only limitation associated with the use of DNA microarrays is the vast amount of data generated thereby. A method that would allow for the easy and automated use of DNA microarray data in disease diagnosis is therefore desirable. Despite the many statistical techniques to analyze gene-expression data, none so far has been rigorously tested for their ability to accurately distinguish diseases belonging to several diagnostic categories. Such methods have also not been used to extract the genes or features that are the most important for the classification performance. Such genes would also generally be those that are of use to biologists and physicians as offering avenues to research in investigating cures.

Therefore, there remains a need for a method of using gene expression data to diagnose, predict, or prognosticate about a disease condition.

However, these other methods have not been used to extract the genes or features that are most important for the classification performance and which also will be of interest to cancer biologists.

SUMMARY OF THE INVENTION

In accordance with the invention, there is provided a method of diagnosing, predicting, and/or prognosticating about a disease including obtaining experimental data, wherein the experimental data includes high dimensional data, filtering noise from the data, reducing the dimensionality of the data by using one or more methods of analysis, training a supervised pattern recognition and/or classification method, ranking individual data from the overall data based on the relevance of the individual data to the diagnosis, prediction, prognosis or classification, choosing multiple individual data members, wherein the choice is based on the relative ranking of the individual data, and using the chosen data to determine if an unknown set of experimental data indicates a particular diseased condition, prognosis, prediction, or classification.

The invention offers a method of diagnostic classification of cancers from their gene-expression signatures and also identifies the genes that contributed to this classification. One embodiment of the method diagnoses SRBCTs of childhood, which occasionally present diagnostic difficulties.

The invention also offers a method of diagnosing, predicting, and/or prognosticating about SRBCTs including obtaining gene expression data, filtering noise from the gene expression data, reducing the dimensionality of the data by using principal component analysis (PCA), training an ANN, ranking the individual genes from the gene expression data, choosing multiple genes from the gene expression data, wherein the choice is based on the relative ranking of the individual genes and using the chosen genes to determine if an unknown set of gene expression data indicates a particular diseased condition, prognosis, and/or a prediction.

Methods of the invention can be utilized in a number of different applications. For example, diagnostic chips can be fabricated based on the identification of the diagnostic genes. Such chips would be very useful in clinical settings, as it would allow clinicians to diagnose cancers from a relatively small set of genes instead of purchasing entire gene sets.

Methods of the invention can also be used to define which patients with the same types of cancers are likely to respond to treatment. This would allow a physician to intensify treatment for those with a more negative prognosis based on their gene expression profiles as detected utilizing a method of the invention.

Methods of the invention can also be used for identifying pharmaceutical targets. Pharmaceutical companies can utilize methods of the invention to determine which genes to target in efforts to target specific diseases.

Methods of the invention can also be utilized as a research tool for analyzing all types of gene expression data including cDNA and oligonucleotide microarray data.

Methods of the invention can also be utilized to identify and rank, by importance, the genes that contribute to a diagnosis. A minimal set of genes that can correctly classify and identify diagnostic categories can also be determined using methods of the invention.

Methods of the invention identify the most significant genes, by calculating the sensitivity of the classification to a change in the expression level of each gene. A list of genes, ranked by their significance to the classification, is produced thereby. In an embodiment of the invention utilized for classifying SRBCTs the most important 96 genes reduced the misclassifications to zero. This allows for cost effective fabrication of SRBCT subarrays for diagnostic use. When a method of the invention used the 96 genes on 25 unknown samples, all 20 samples of SRBCTs and 5 non-SRBCTs were correctly classified.

One embodiment of the invention calibrates ANN models on the expression profiles of 63 SRBCTs of 4 diagnostic categories. Preferred embodiments of the invention utilize linear (that is no hidden layers) ANN models because of the high performance achieved. Methods of the invention may utilize other linear methods as well, and methods of the invention can easily accommodate nonlinear features of expression data if required. Hidden layers will be utilized for non linear data. Preferably, both tumor samples and cell line samples are used in order to compensate for heterogeneity within unknown samples (which contain both malignant and stromal cells) based on possible artifacts due to growth of cell lines in tissue culture.

Data from such samples is complementary, because tumor tissue, though complex, provides a gene-expression pattern representative of tumor growth in vivo, while cell lines contain a uniform malignant population without stromal contamination. Despite using only neuroblastoma (NB) cell lines for calibrating the ANN models, all four NB tumors among the test samples were correctly diagnosed with high confidence. This not only demonstrates the high similarity of NB cell lines to the tumors of origin, but also validates the use of cell lines for ANN calibration. One embodiment of a method of the invention accurately classified all 63 training SRBCTs and showed no evidence of over-training, thereby demonstrating the robustness of this method.

DETAILED DESCRIPTION OF THE PREFERRED EMBODIMENTS

The invention is a method of classifying, diagnosing, prognosticating about, and predicting disease conditions or other biological states using supervised pattern recognition methods to analyze high dimensional data.

Figure 1:
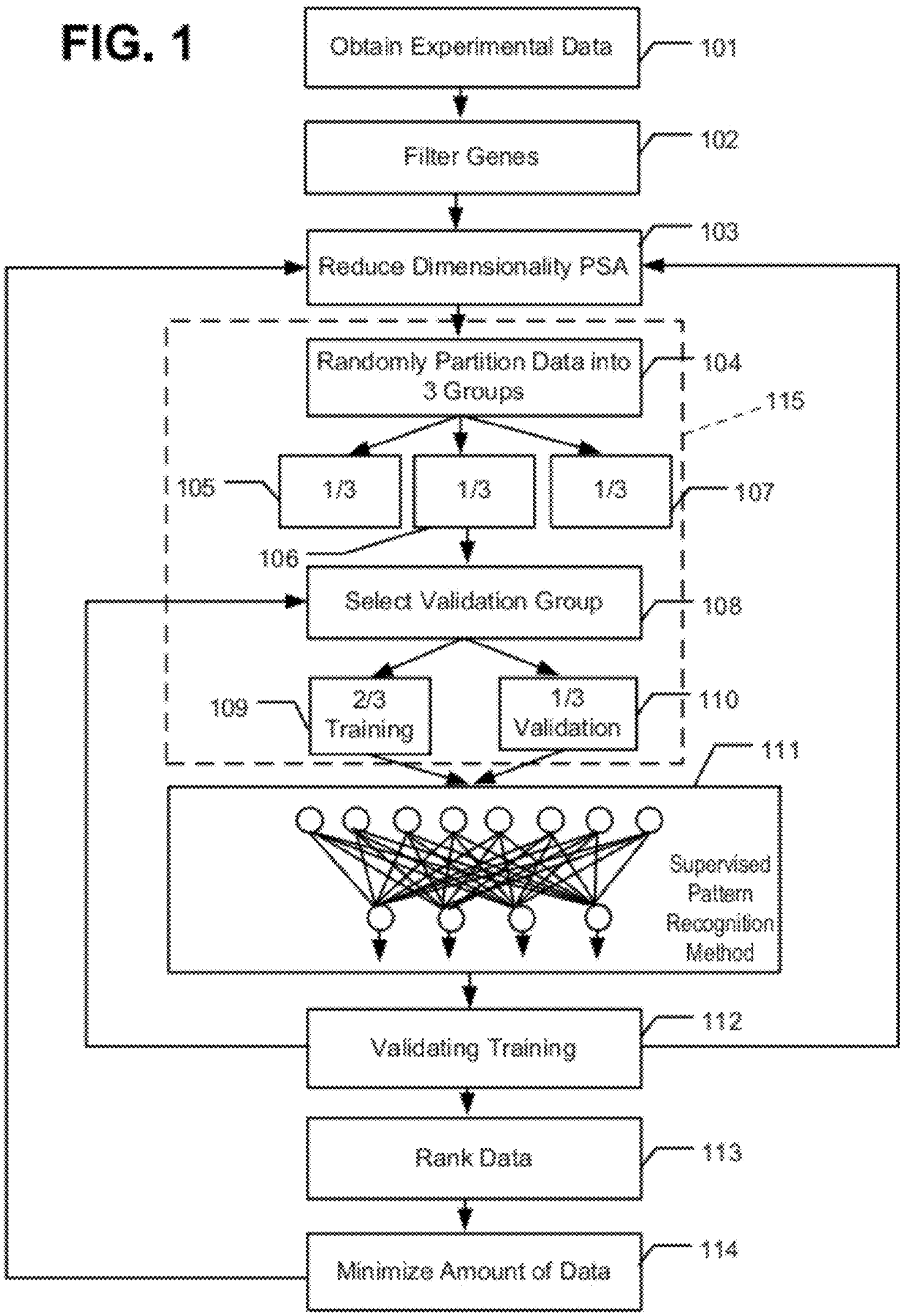
FIG. 1 illustrates a process flow for a method to classify and diagnose diseases using artificial neural networks according to one embodiment of the invention.

One embodiment of the invention is illustrated in FIG. 1. This process flow describes an embodiment of the method that includes obtaining experimental data 101, filtering the data 102, reducing the dimensionality of the data 103, setting up a validation method 115, training a supervised pattern recognition method 111, validating the outcome of the supervised pattern recognition method 112, and once the supervised pattern recognition method is validated, ranking the data based on the outcome of the supervised pattern recognition method 113. Further detail and more specific embodiments of methods of the invention are described below.

Any diagnostic categories can be diagnosed using the technology described here. It includes distinguishing patients with multiple sclerosis, rheumatoid arthritis, and other inflammatory or autoimmune diseases. It may also diagnose other systemic diseases based on gene expression profiles of white cells, including infections with particular organisms, cancer, or myocardial infarctions.

Obtaining Experimental Data

The first step in methods of the invention is to obtain experimental data. Experimental data utilized in methods of the invention is high dimensional data. High dimensional data is data that has at least hundreds of individual pieces of information associated with one sample. An example of high dimensional data useful in methods of the invention is gene expression data. Gene expression data is high dimensional data because each sample or person has a large number of gene expression levels. Generally speaking, gene expression data generally has thousands of gene expression levels for each sample. Other examples of high dimensional data useful in the invention include but are not limited to protein arrays and protein chips, cell array based expression analysis, analysis of patterns of single nucleotide polymorphisms in disease conditions, and comparative genomic hybridization on methaphase, BAC genomic, cDNA and oligonucleotide arrays.

Preferably, the gene expression data is obtained through use of DNA microarray technology. DNA microarrays are preferred as a source of data because they generally offer a more complete picture of the interactions of a large number of genes with a limited number, or even one experiment. An example of a general description of how gene expression data can be obtained by using cDNA microarray technology is given below.

DNA microarrays, although a relatively new technology, have already been saddled with a number of different names, biochip, DNA chip, gene chip, genome chip, cDNA microarray, and gene array. The use of any of these terms herein refers generally to DNA microarrays. The underlying principle of DNA microarrays is base pairing or hybridization i.e., A-T and G-C for DNA, and A-U and G-C for RNA.

DNA microarrays provide a medium for matching known and unknown DNA samples based on the base pairings given above. DNA microarrays can either be fabricated by high-speed robotics or can be fabricated in a laboratory setting. They are generally patterned on glass, but can also be fabricated on nylon substrates. Microarrays generally have sample spot sizes of less than 200 μm diameter, and generally contain thousands of DNA spots on one microarray.

One method of fabricating cDNA microarrays begins by first producing gene-specific DNA by polymerase chain reaction (PCR) amplification of purified template plasmid DNAs from cloned expressed sequence tags (ESTs). The PCR product is then purified, resuspended and printed onto a substrate. cDNA microarrays are also commercially available from a number of sources, including but not limited to Affymetric, Inc. (Santa Clara, Calif.), Agilent Technologies (Palo Alto, Calif.), and Research Genetics (Huntsville, Ala.).

One general procedure for a cDNA microarray experiment begins by preparing DNA samples and arraying them (either with an arraying robot, or by hand), to form a DNA microarray. Next, the RNA samples are extracted from the cells of interest, purified, reverse transcribed into cDNA and differentially fluorescently labeled to create probes. Then, the fluorescently labeled cDNA probes are hybridized to the cDNA microarray. If a probe contains a cDNA whose sequence is complementary to the DNA on a given spot, the cDNA probe will hybridize to that spot. After the cDNA probes are hybridized to the array, and any loose probe has been washed away, the microarray is imaged to determine how much of each probe is hybridized to each spot. This indicates how much of each gene from the microarray is expressed in the two samples.

The experimental high dimensional data, preferably obtained from gene expression experiments, preferably performed using cDNA microarrays, is then further analyzed by a method of the invention.

Filtering the Data

The next step in a method of the invention is filtering the data 102 to remove individual pieces of data that are deemed undesirable. This filtering step functions to eliminate weak and/or problematic data from further use in the method. Accomplishment of the step of filtering depends greatly on the type of high dimensional data utilized. Any method known to those of ordinary skill in the art can be used to eliminate data determined to be undesirable.

One basis for carrying out this filtering, if a DNA microarray is being utilized for obtaining the high dimensional data, is the intensity of the fluorescence from the individual microarray spots. This basis of omitting data is based on failure or error in the imaging of the specific spots. A preferred method of performing initial data filtering on cDNA microarray data to remove those spots where imaging was a problem is to utilize the intensity of the various spots and utilize only those spots that have an intensity over a certain threshold value. Other methods of filtering DNA microarray data include but are not limited to eliminating spots in which the number of pixels represented is less than a threshold defined by the user, eliminating spots in which the standard deviation of the signal on the spots is too large, as defined by the user, eliminating spots in which the background intensity of a single spot is too high, or any combination thereof. In addition quality values based on intensity, can be assigned to each spot, standard deviation of intensity, background and/or size of each spot, then a spot could be eliminated if its quality value falls below a threshold as defined by the user.

Reducing the Dimensionality of the Data

The next step in methods of the invention is reducing the dimensionality of the data 103. The number of samples needed to calibrate a classifier with good predictive ability, depends critically on the number of features used in the design of the classifier. In the case of high-dimensional data, such as microarray data, where the number of samples is much smaller than the number of individual pieces of data there exists a large risk of over-fitting. There are two different solutions to this problem. First, the calibration process can be carefully monitored using a cross-validation scheme to avoid over-fitting (see below). Second, the dimension of the data can be reduced, either by using a dimensional reduction algorithm or by selecting a smaller set of data for input to the supervised pattern recognition method. Dimensionality reduction allows the number of parameters representing each sample to be reduced. This allows for the design of a classifier that has less risk of over-fitting, thereby increasing its predictive ability.

Examples of methods of reducing the dimensionality of the data include but are not limited to principal component analysis (PCA), weighted gene analysis, t-test, rank based Wilcoxon or Mann-Whitney tests, signal-to-noise statistic, Fisher's discriminant analysis, or ANOVA tests.

In a preferred embodiment of the invention, PCA is used to reduce the dimensionality of the data.

In the case of PCA on gene expression data, reduction of the dimensionality is achieved by rotating gene expression space, such that the variance of the expression is dominated by as few linear combinations of genes as possible Even though the formal dimension of the problem is given by the number of individual data points, the effective dimension is just one less than the number of samples. Hence the eigenvalue problem underlying PCA can be solved without diagonalizing 2308×2308 matrices by using singular value decomposition. Thus each sample is represented by 88 numbers, which are the results of projections of the data using the PCA eigenvectors.

A potential risk when using PCA on relatively few samples is that components might be singled out due to strong noise in the data. It could be argued that the outputs (labels) should be included in the dimensional reduction, using e.g. the Partial Least Squares (PLS) algorithm, in order to promote components with strong relevance for the output. However, based on explorations with similar data sets, this is not optimal; bias is introduced and implicitly "over-trains" from the outset by including the outputs in the procedure.

Setting Up a Validation Method for the Supervised Pattern Recognition Method

Once the data has been filtered 102 and its dimensionality reduced 103, a validation method is set up for monitoring and validating the training of the supervised pattern recognition method 115. Any method commonly used by those of skill in the art for validating the training of a supervised pattern recognition method can be used.

In one embodiment, the first step in setting us a validation method is to randomly divide the data into three groups of data, 105, 106, and 107. Then, one of those groups is chosen as a validation group 108. The first two of the groups 105 and 106 are combined into a training group 109, which is used to train the supervised pattern recognition method 111 and the third group 107 is used to validate the performance of the supervised pattern recognition method 111, once trained, and is called a validation group 110.

In this specific preferred embodiment, the 3-fold cross validation procedure (steps 104 through 110) is performed on all of the samples. A data group having 63 samples is given as an example. The 63 known (labeled) samples are randomly shuffled 104 and split into 3 equally sized groups (105, 106, and 107). The supervised pattern recognition method 111 is then calibrated as discussed below using the training group 109. The third group, a validation group 110, is reserved for testing predictions. Comparisons with the known answers refer to the results from the validation group 110 (i.e. when using a model, the samples used for training the model are never used in predictions). This procedure is repeated 3 times, each time with a different group used for validation. The random shuffling 104 is done about 100 to 10000 times. For each shuffling, one supervised pattern recognition method 111 model is generated. Thus, in total each sample belongs to a validation group 110, 1250 times and 3750 supervised pattern recognition methods 111 have been calibrated.

Training the Supervised Pattern Recognition Method

The supervised pattern recognition method 111 is then trained. The specific method of training the supervised pattern recognition method 111 is dependent on the specific form that the supervised pattern recognition method 111 takes. The choice of the supervised pattern recognition method 111 and the training thereof is well within one of skill in the art, having read this specification.

One example of a supervised pattern recognition method is an artificial neural network (ANN). ANNs are computer-based algorithms that are modeled on the structure and behavior of neurons in the human brain and can be trained to recognize and categorize complex patterns. Pattern recognition is achieved by adjusting parameters of the ANN by a process of error minimization through learning from experience. They can be calibrated using any type of input data, such as gene-expression levels generated by cDNA microarrays, and the output can be grouped into any given number of categories. ANNs have been recently applied to clinical problems such as diagnosing myocardial infarcts and arrhythmias from electrocardiograms and interpreting radiographs and magnetic resonance images. However, ANNs have not been used to decipher gene-expression signatures of SRBCTs or for diagnostic classification.

In embodiments where an artificial neural network (ANN) is employed as the supervised pattern recognition method 111, calibration is preferably performed using JETNET (C. Peterson, T. Roegnvaldsson and L. Loennblad, "JETNET 3.0—A versatile artificial neural network package," *Computer Physics Communications* 81, 185-220 (1994)). Preferably, the software is used with a learning rate $\eta=0.7$, momentum coefficient $p=0.3$ and the learning rate is decreased with a factor 0.99 after each iteration. Initial weight values are chosen randomly from [−r, r] where $r=0.1/\max_i F_i$ and the "fanin" $F_i$ is the number of nodes connecting to node i. The calibration is performed using a training set and it is monitored both for the training set and a validation set, which is not subject to calibration (see below). The weight values are updated after every 10 samples and the calibration is terminated after 100 passes (epochs) through the entire training set. In one embodiment of a method of the invention, the resulting parameters for the completed training of a supervised pattern recognition method 111 defines a "model".

In preferred embodiments, due to the limited amount of calibration data and the fact that four output nodes are needed (Ewing's sarcoma (EWS), Burkitt's lymphoma (BL), neuroblastoma (NB) and rhabdomyo sarcoma (RMS)), linear perceptrons (LP) with 10 input nodes representing the PCA components described above are utilized. In other words, the supervised pattern recognition method 111 generally contains 44 parameters including four threshold units. Since 10 components could be used without risking "over-training" the optimization of the number of components to a smaller number is generally not necessary.

The possibility of using all the PCA components as inputs followed by a subsequent pruning of weights to avoid "overfitting" is also one alternative. This resulted in the dominant 4-8 PCA components (depending on the composition of the training set 107) being the surviving inputs. Generally, the less dominant PCA components contain variance not related to separating the four cancers, but rather to, for example, experimental conditions (noise) or variance related to subgroupings within a cancer type.

Verifying the Outcome of the Supervised Pattern Recognition Method

Once the supervised pattern recognition method 111 is trained, the next step is to determine whether the validation of the supervised pattern recognition method 111 is successful 112. This step determines whether the supervised pattern recognition method 111 adequately predicted the results for the validation data set 110 using any number of performance measurements and error measurements.

Any method known to those of ordinary skill in the art can be utilized to evaluate the performance of the training of the supervised pattern recognition method 111. Generally speaking, the performance is evaluated by comparison with some predetermined level of correct predictions that the user has determined is acceptable.

If the performance of the supervised pattern recognition method 111 is sufficiently poor, and a measure of error is greater than an allowable threshold, the processing may return to module 103 where the dimensionality of the data is reduced in a different manner and the entire training and validation process is repeated.

Ranking the Data

Once module 112 determines that the network 111 has been adequately trained, the processing proceeds to rank the output of the supervised pattern recognition method 113.

The outcome of the supervised pattern recognition method 111 can be looked at either independently or in a compiled form. Each supervised pattern recognition method 111 gives a number between 0 (not this disease type) and 1 (this disease type) as an output for each disease type. If the predictions are viewed independently, the maximal output is forced to 1 while the other outputs are forced to 0. Then it is determined how many of the predictions are correct. If the predictions are viewed in a compiled form, all of the predicted outputs are considered in their numerical form, after which all of the numbers are averaged and the resulting average is forced to 0 or 1.

In one embodiment of the method, the predictions, as compiled, are used to classify samples. For validation samples the compilation is based on 1250 models, while for additional unknown samples all 3750 models are used in the compilation.

In one embodiment, each sample is classified as belonging to the disease type corresponding to the largest average in the compilation. In addition, it is desirable to be able to reject the second largest vote as well as test samples that do not belong to any of the disease types. In order to reject those samples that do not belong, a distance $d_c$ from a sample to the ideal vote for each disease type is defined as:

$$d_c = \frac{1}{2}\sum_{i=1}^{4}(o_i - \delta_{i,c})^2 \quad (1)$$

where c is a disease type, $o_i$ is the average from the compilation for disease type i, and $\delta_{i,c}$ is unity if i corresponds to disease type c and zero otherwise. The distance is normalized such that the distance between two ideal samples belonging to different disease categories is unity. Based on the validation group, an empirical probability distribution of its distances is generated for each disease type.

The empirical probability distributions are preferably built using each supervised pattern recognition method 111 independently (not the average from the compilation). Thus, the number of entries in each distribution is given by 1250 multiplied by the number of samples belonging to the disease type. For a given test sample, the possible classifications based on these probability distributions can be rejected. This means that for each disease category a cutoff distance from an ideal sample is defined, within which, based on the validation samples, a sample of this category is expected to be. The distance given by the 95th percentile of the probability distribution is preferably chosen as a cutoff, which means that if a sample is outside of this cutoff distance it cannot be confidently diagnosed. It should be noted that the classification as well as the extraction of important genes (see below) converges using less than 100 supervised pattern recognition method 111 models. 3750 supervised pattern recognition method 111 models are preferred is because sufficient statistics exist for these empirical probability distributions.

For each disease category the sensitivity and specificity of the diagnosis may be calculated (see Table 1 below). Table 1 gives sensitivity, specificity and ROC curve areas for both validation and test samples. Both the sensitivity and the specificity are very high for all categories. It should be noted, that they generally depend on the kind of samples that are used as test samples.

TABLE 1

| Category | Sensitivity | Specificity | ROC curve area |
|---|---|---|---|
| EWS | 93% | 100% | 1.0 |
| BL | 100% | 100% | 1.0 |
| NB | 100% | 100% | 1.0 |
| RMS | 96% | 100% | 1.0 |

For example, in the case of SRBCT classification, using normal muscle samples as tests makes it harder to separate out RMS samples. If only samples from the four categories were used as blind distance cutoffs, it could easily have been designed such that both the sensitivity and the specificity would have been 100% for all diseases. However, it is preferred that the method is tested using a variety of blind tests. If it is desirable to improve rejection of for example normal muscle samples, one could incorporate them as a fifth category in the training process. However, using more samples of all four categories in the training is initially probably the best way to improve the diagnostic separation.

The Receiver Operator Characteristic (ROC) curve area is identical to another more intuitive and easily computed measure of discrimination: the probability that in a randomly chosen pair of samples, one belonging to and one not belonging to the disease category, the one belonging to the category is the one with the closest distance to the ideal for that particular category. Since the ROC curve areas are unity for all disease categories (see Table 1), it is possible to define cutoff distances such that both the sensitivity and the specificity are 100% for all diseases. However, based on the training and validation groups it is difficult to motivate such cutoff distances.

The next step in a method in accordance with the invention is to actually rank the data. This step can in principle be done in two ways; (1) model-independent and (2) model-dependent analysis respectively. Due to the relative small number of samples, the model-dependent analysis is preferred when using ANN models.

The sensitivity (S) of the outputs (o) with respect to any of the 2308 input variables ($x_k$) is defined as:

$$S_k = \frac{1}{N_s}\frac{1}{N_o}\sum_{s=1}^{N_s}\sum_{i=1}^{N_o}\left|\frac{\delta o_i}{\delta x_k}\right| \quad (2)$$

where $N_s$ is the number of samples (63 or 88) and $N_o$ is the number of outputs (4). The procedure for computing $S_k$ involves a committee of 3750 models. In addition we have defined a sensitivity for each output i ($S_i$), which is analogous to Eq. (2) but without the sum over outputs. Furthermore, a sensitivity can be defined for each sample (or subsets of samples) individually, by only using that sample(s) in the sum over samples in Eq. (2). For all these sensitivities the sign of the sensitivity has also been defined. The sign signals whether the largest contribution to the sensitivity stems from positive or negative terms. A positive sign implies that increasing the expression rate of the gene increases the possibility that the sample belongs to this cancer type, while a negative sign means that decreasing the expression rate of the gene increases the same possibility. In other words, the sign does not tell whether a gene is up- or down-regulated but if it is more or less expressed in this cancer type as compared to the others. This means the genes are ranked not only according to their importance for the total classification, but also according to their importance for the different disease categories separately. The genes are preferably given a total rank as well as a separate rank for each disease category. Based on these ranks each gene is classified according to which disease category it is highly expressed in.

In one embodiment, once ranked, a relevant set of data can be selected module 114 by minimizing the amount of data to be used to classify and identify a particular disease. In one embodiment, a pre-determined amount of data having the highest ranking are selected. Of course, other selection methods may be employed without deviating from the spirit and scope of the present invention as recited in the attached claims.

Implementation of Methods of the Invention

Figure 2:
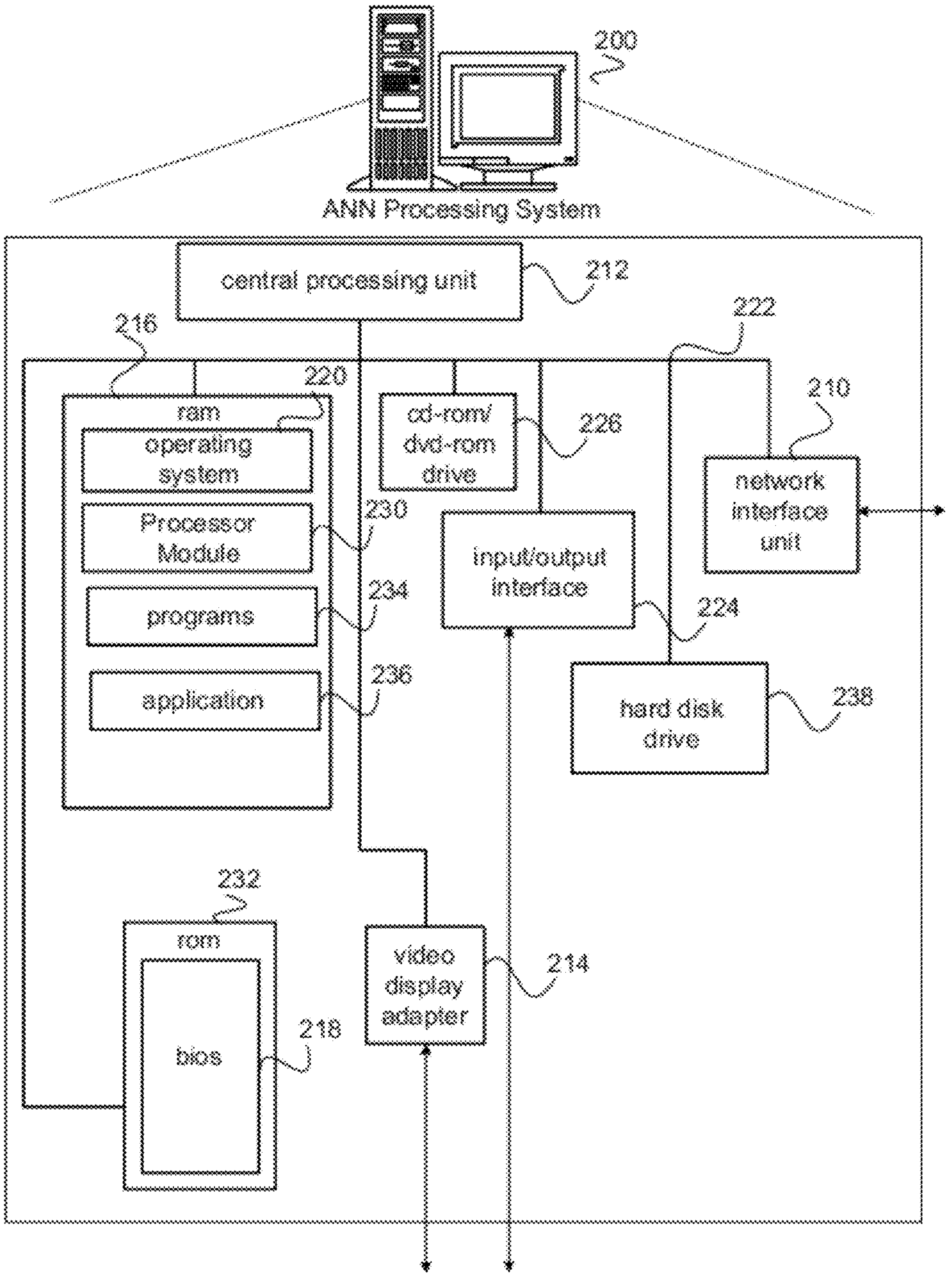
FIG. 2 illustrates a general purpose computing system utilized as part of an artificial neural network according to another embodiment of the invention.

In embodiments of the method in which the supervised pattern recognition method 111 is an artificial neural network, a general purpose computing system as depicted in FIG. 2 can be utilized. An exemplary ANN processing system 200 provides an artificial neural network that also receives experimental data to train the artificial neural network, to verify the output of an artificial neural network, and to identify relevant genes using the neural network.

Those of ordinary skill in the art will appreciate that the ANN processing system 200 may include many more components than those shown in FIG. 2. However, the components shown are sufficient to disclose an illustrative embodiment for practicing the present invention. As shown in FIG. 2, the ANN processing system 200 is connected to a WAN/LAN, or other communications network, via network interface unit 210. Those of ordinary skill in the art will appreciate that network interface unit 210 includes the necessary circuitry for connecting the ANN processing system 200 to a WAN/LAN, and is constructed for use with various communication protocols including the TCP/IP protocol. Typically, network interface unit 210 is a card contained within the ANN processing system 200.

The ANN processing system 200 also includes processing unit 212, video display adapter 214, and a mass memory, all connected via bus 222. The mass memory generally includes RAM 216, ROM 232, and one or more permanent mass storage devices, such as hard disk drive 228, a tape drive, CD-ROM/DVD-ROM drive 226, and/or a floppy disk drive. The mass memory stores operating system 220 for controlling the operation of ANN processing system 200. It will be appreciated that this component may comprise a general purpose server operating system as is known to those of ordinary skill in the art, such as UNIX, LINUX, MAC OS?, or Microsoft WINDOWS NT?. Basic input/output system ("BIOS") 218 is also provided for controlling the low-level operation of ANN processing system 200.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing an ANN processing and network development. More specifically, the mass memory stores applications including ANN processing module 230, programs 234, and other applications 236. ANN processing module 230 includes computer executable instructions which, when executed by ANN processing system 200, performs the logic described above.

The ANN processing system 200 also comprises input/output interface 224 for communicating with external devices, such as a mouse, keyboard, scanner, or other input devices not shown in FIG. 2. Likewise, ANN processing system 200 may further comprise additional mass storage facilities such as CD-ROM/DVD-ROM drive 226 and hard disk drive 228. Hard disk drive 228 is utilized by ANN processing system 200 to store, among other things, application programs, databases, and program data used by ANN processing module 230. For example, customer databases, product databases, image databases, and relational databases may be stored. The operation and implementation of these databases is well known to those skilled in the art.

Figure 3:
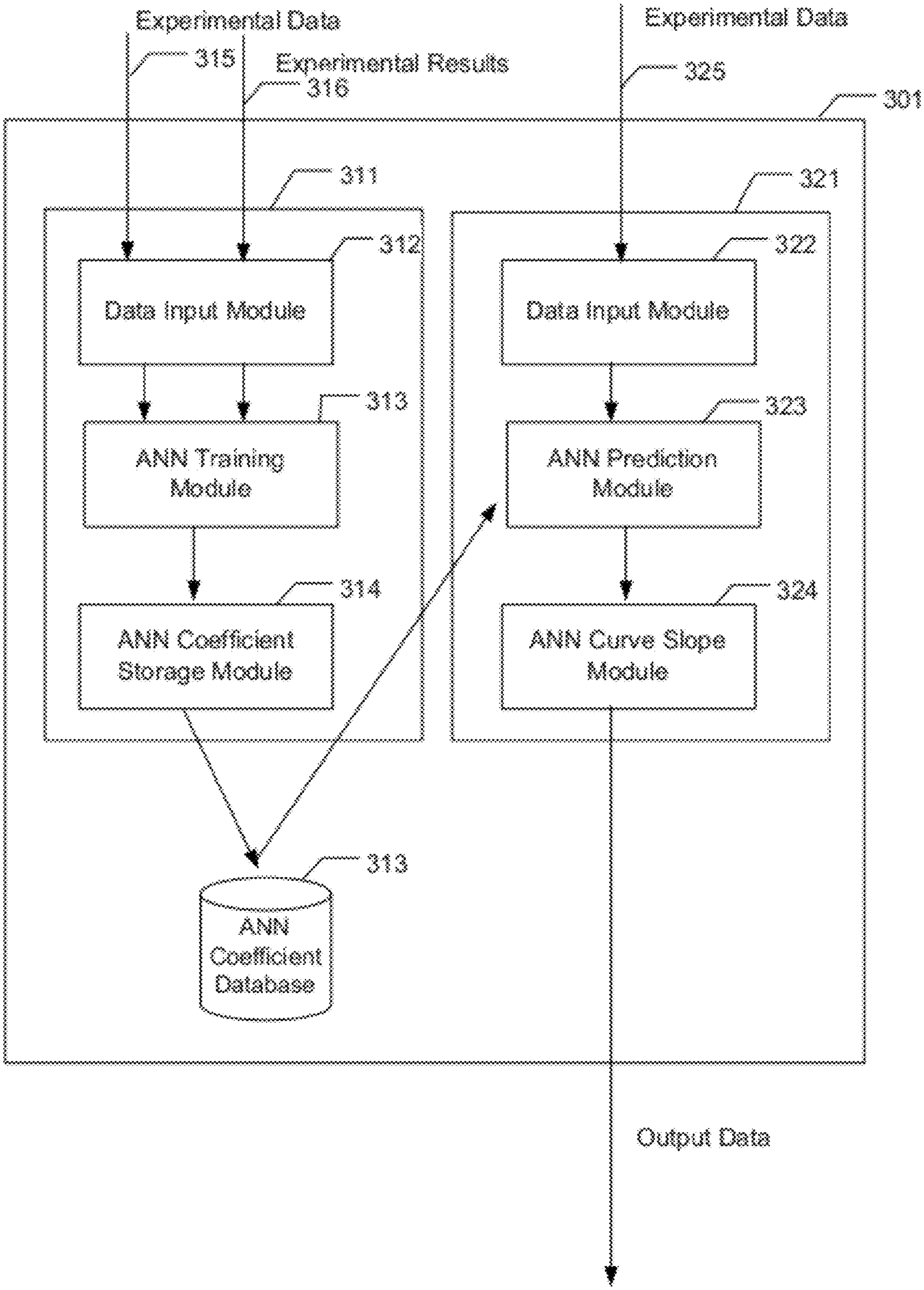
FIG. 3 illustrates a set of processing modules making up an embodiment of an artificial neural network according to the invention.

A set of processing modules making up an embodiment of an artificial neural network according to the invention is illustrated in FIG. 3. The artificial neural network disclosed herein corresponds to a generic neural network of no particular topology for the network of nodes contained therein. The neural network typically utilizes a form of competitive learning for the operation of the nodes within the network. Within competitive learning networks, a large number of data vectors are distributed in a highly dimensional space. These data vectors represent known values for experimental data that typically reflect a probability distribution of the input experimental data. From this probability distribution representation, predictions for unknown values for similar input data may be determined.

In all of these competitive learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the invention as recited within the attached claims. Each of these algorithm architectures represents the same probability distribution relationship; however each of the various algorithm architectures better optimize corresponding processing parameters, which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

Now referring to FIG. 3, an artificial neural network processing system 301 comprises a learning module 311, a prediction module 321, and a database of network node coefficients 313. The learning module 311 is used with a set of experimental data 315 that possesses a corresponding set of experimental results 316 to generate a set of network node coefficients that represent a probability distribution relationship for the experimental data 315-experimental result 316 data set for a particular neural network topology and algorithm architecture. The learning module 311 includes a data learning input module 312 that receives the experimental data 315-experimental result 316 data set generated using the process described above. The learning module 311 also includes an ANN training module 313 that processes the experimental data 315-experimental result 316 data set to generate the coefficients used to specify the probability distribution relationship and an ANN coefficient storage module 314 for storing the coefficients that have been previous generated within the database 313 for later use.

The data processing within the learning module 311 may proceed in a batch processing fashion in which all of the vectors within the experimental data 315-experimental result 316 data set are processed at a single time. In such a process, the experimental data 315-experimental result 316 data set is received by the input module 312, processed by the training module 313, and the generated coefficients are placed within the database 313 by the storage module 314. Alternatively, the experimental data 315-experimental result 316 data set may be processed as a sequence of smaller data sets in which the experimental data 315-experimental result 316 data set data values are generated at different times. In such a process, the training module 313 uses the previously stored coefficients retrieved by the storage module along with a new small data set provided by the input module 312 to generate an updated set of coefficients. These updated coefficients may be once again stored within the database 313 for use at a later time.

Once an artificial neural network 301 has been trained, the prediction module 321 may be used to predict, or classify, a particular test data value 325. The prediction module 321 includes a data prediction input module 322, an ANN prediction module 323, and an ANN curve slope module 324. The data prediction input module 322 receives the input test data generated as described above for use in the prediction module. The ANN prediction module 323 receives and utilizes the network coefficient values for the neural network from the ANN coefficient database 313 to predict the possible result for the probability distribution relationship specified within the neural network. This output value is used by the ANN curve slope module 324 to determine all possible values for a given gene, in the manner discussed above, to determine a curve slope value. This slope value is then output for later use in ranking and classifying the individual genes used to determine the presence, or lack there of, for a disease.

The embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the invention describe the use of an artificial neural network to identify relevant genes associated with diseases and use the identified genes to classify and identify diseases, one skilled in the are will recognize that the use of the processing system discussed above are merely example embodiments of the invention. As long as experimental data is used to self-train a processing system using competitive learning processing, the present invention to would be useable in other data processing systems. It is to be understood that other embodiments may be utilized and operational changes may be made without departing from the scope of the present invention as recited in the attached claims.

WORKING EXAMPLES

The following examples provide a nonlimiting illustration of various embodiments of the invention.

Example 1

Preparation of Microarrays

Preparation of glass cDNA microarrays, probe labeling, hybridization and image acquisition were performed according to the protocol given below, which is a standard NHGRI protocol found at the NIH website.

Gene-specific DNA was produced by PCR amplification of purified template plasmid DNAs from cloned ESTs. The PCR product was purified by ethanol precipitation, thoroughly resuspended in 3×SSC, and printed onto a poly-L-lysine coated slide.

The materials, reagents, and solutions used include: 96 well alkaline lysis miniprep kit (Edge BioSystems, Gaithersburg, Md.); LB Broth (Biofluids, Rockville, Md.); Superbroth (Biofluids, Rockville, Md.); dATP, dCTP, dGTP, dTTP, 100 mM each #27-2035-02, store frozen, −20° C. (Pharmacia, Peapack, N.J.); PCR primer AEK M13F (5'-GTTGTAAAACGACGGCCAGTG-3') (SEQ ID NO: 97) and AEK M13R (5'-CACACAGGAAACAGCTATG-3') (SEQ ID NO: 98) at 1 mM concentration, store frozen, −20° C.; 10×PCR Buffer, #N808-0189, and Ampli-Taq DNA polymerase, # N808-4015 store frozen, −20° C. (Perkin Elmer, Norwalk, Conn.); Carbenicillin (Gibco-BRL, Rockville, Md.); Ethanol (200 Proof USP Ethyl Alcohol); 1M Tris-HCl (pH 8); 0.5M NaEDTA (pH 8); T Low E; Buffer; 20×SSC; Glycerol (enzyme grade); Sodium Acetate (tri-hydrate); Boric Acid; Sodium Hydroxide (1M); Glacial Acetic Acid; Succinic anhydride, #23969-0 and 1-methyl-2-pyrrolidinone, #32863-4 (Aldrich Chemical Co., St. Louis, Mo.); Diethyl Pyrocarbonate (DEPC) treated $H_2O$; Master set of clone-purified, sequence verified human ESTs (e.g. gf211 release, Research Genetics, Huntsville, Ala.); 96 pin inoculating block (#VP 4088, V&P Scientific, Inc, San Diego, Calif.); Airpore Tape Sheets, (#19571, QIAGEN Inc., Valencia, Calif.); Sterile 96-well plate seals, (e.g. #SEAL-THN-STR (Elkay Products, Inc., Shrewsbury, Mass.); 96-well U-Bottom Microtiter Plates, #3799 and 96-well V-Bottom Microtiter Plates, #3894 (Corning Inc., Corning, N.Y.); Thin wall PCR plate and Cylcleseal PCR plate sealer (e.g. #1038-50-0 and #1044-39-4, Robbins Scientific Corp. Sunnyvale, Calif.); household one-gallon sealable storage bags (e.g. Glad Lock); heat sealable storage bags and heat sealer; 0.2 mm Sterile Filtration unit; Diamond scribe for writing on slides; Pyrex baking dish (~24×34×5 cm); UV transparent plastic wrap (e.g. Glad Cling Wrap); 30 slide rack (stainless steel) #113 and 30 slide glass tank, #122 (Shandon Lipshaw, Pittsburgh, Pa.); 1 L glass tank; 1 L glass beaker; 1 L graduated; cylinder; Stir bar; Slide Box (plastic with no paper or cork liners), (e.g. #60-6306-02, PGC Scientific, Gaithersburg, Md.); PCR heat cycler (e.g. DNA Engine Tetrad, MJ Research, Waltham, Mass.); Centrifuge with a horizontal ("swinging bucket") rotor with a depth capacity of 6.2 cm for spinning microtiter plates and filtration plates (e.g. Sorvall Super T 21, Sorvall Inc., Newtown, Conn.); 37° C. Shaker incubator with holders for deep-well plates; 37° C. Waterbath; 65° C. Incubator; Vortex mixer; Immunowash microtiter plate washer, #1575 (BioRad, Hercules, Calif.); pH Meter; Platform Shaker; UV Stratalinker 2400, (Stratagene La Jolla, Calif.); Stirrer/Hotplate; Robotic slide printer; −80° C. Freezer; −20° C. Freezer; 45% (w/v) Sterile Glycerol; 450 grams enzyme grade glycerol per liter 9 Autoclave and store at room temperature); T low E Buffer; 1M Tris-HCl (pH 8.0) 10 mL; 0.5 M EDTA (pH 8.0) 0.2 mL; DEPC treated $H_2O$ 990 mL (Autoclave and store at room temperature); Carbenicillin stock solution (1 gram of carbenicillin in 10 mls of sterile water, Sterile filter with a 0.2 micron filter, Store frozen at −20° C.); LB with 100 μg/ml carbenicillin (Add 1 ml of carbenicillin stock solution to 1 liter of LB, Make fresh); 3M Sodium Acetate pH=6.0 (408.24 grams sodium acetate (tri-hydrate) per liter, 3M acetic acid (172.4 ml per liter), Titrate the pH of the 3M sodium acetate solution to pH 6.0 with the 3M acetic acid solution, Filter sterilize using a 0.2 micron filter, Store at room temperature); Ethanol/acetate mix (Ethanol (100%) 950 ml, Sodium acetate pH=6.0, 50 ml); 1000 ml 3×SSC; DEPC $H_2O$ 42.5 ml; 20×SSC 7.5 ml; 50 ml 70% Ethanol; Ethanol (100%) 350 ml; DEPC $H_2O$ 150 ml; 500 ml.

The first step was to grow the EST clones. The cDNA clones were obtained from Research Genetics (Huntsville, Ala.) and were their standard microarray set, which consisted of 3789 sequence-verified known genes and 2778 sequence-verified ESTs.

The sealed master plates were incubated over night at 37° C. Most suppliers provide low density bacterial cultures. Replicating directly from these dilute stocks frequently results in non-growth in the secondary culture. If making the template from a plate that had previously been cultured to high density before freezing, this initial growth step should not be used, as it will reduce the viability of the cultures.

A set of standard 96 well round (U) bottom plates were then prepared by labeling all plates and placing 100 μl of LB broth containing 100 ?g/ml carbenicillin in each well. These plates were used as working copies. To preserve the master set of plates, it was useful to make replicate copies of the master plate to serve as working copies when the master plate was first replicated. The EST clones were then checked to insure that they were in a vector conferring ampicillin resistance, as is common with human IMAGE clones.

The master plates were spun briefly (about two minutes) at 1000 rpm in a horizontal microtiter plate rotor to remove condensation and droplets from the seals before opening. Bacterial culture fluid on the sealers can easily be transferred from one well to others, cross-contaminating the stocks.

Then a container was partially filled with 100% alcohol. The 96 pin-replicating tool was dipped in the alcohol, removed and then the pins were flamed.

The inoculation block was allowed to cool briefly, then the replicating tool was dipped in the master plate and then into the daughter plate. This was repeated as necessary for each plate inoculated. It is useful to color the plate corner near the A-1 well of all master and daughter plates with a marker pen before beginning the replication process in order to reduce mistakes in the relative orientation of the plates. The suggested plates have a notch at this corner as well.

The inoculated LB plates, with the lids on, were placed into a one gallon sealable bag containing a moistened paper towel and grow overnight at 37° C. Many 37° C. incubators tend to dry out microtiter plate cultures. Placing the plates in a highly humidified bag avoids this problem.

Next, deep well plates were filled with 1 ml of Superbroth (100 μg/ml carbenicillin) per well. These plates served as the source of culture for template preparation. Using the replicating tool, the deep well plates were then inoculated directly from the freshly grown LB plates. Next, the openings of the deep well plates were covered with Qiagen Airpore Tape Sheets and the plastic lids were placed over the sheet. The plates were then placed in a 37° C. shaker incubator at 200 RPM for twenty-four hours. 50 μl of 45% (w/v) sterile glycerol was added to each well of any working plates that are to be frozen (−80° C.) and subsequently used as culture sources.

After the EXT clones were grown, the plasmid templates have to be isolated. First, the lysis buffer (Edge Biosystems Kit) was warmed to 37° C. to dissolve the SDS. Then the RNAse solution was added to the resuspension buffer (Edge Biosystems Kit), 1 ml/100 ml, and stored at 4° C. The receiving plates were prepared from the Edge Biosystems Kit by adding 350 μl of ethyl alcohol to each well of the receiving plates. The filter plate was then placed on top and secured with tape. The bacterial cultures in the deep well plates were centrifuged at 1500×g for seven minutes in a centrifuge equipped with a horizontal rotor for 96-well plates. They were then briefly inverted and excess media was tapped out on a clean paper towel. The pellets will loosen and may be lost when pouring off excess media if this step is delayed.

The pellet was then resuspended in 100 μl of Resuspension Buffer, and Vortexed until the entire pellet was re-suspended. This step is critical. Poor resuspension of the cells results in clumps of cells that do not lyse in subsequent steps. This reduces the yield and decreases the purity of the product. 100 μl of Lysis Buffer was then added and the solution was mixed gently by rocking the plates from side to side, to avoid shearing the bacterial chromosomal DNA. 100 μl of Precipitation buffer was added to each well and briefly mixed. Then, 100 μl of Neutralization buffer was added to each well and Vortexed.

The contents of the deep wells were then transferred to the waiting filter plates/receiving plate stacks using the wide bore pipette tips provided in the kits. The stacked plates were then centrifuged at 1500×g for twelve minutes in a centrifuge equipped with a horizontal rotor for 96-well plates. The stacked plates were then removed from the centrifuge. The filter plates were removed and discarded. The alcohol and filtrate were decanted from the receiver plate and the excess alcohol was touched off on clean paper towels. 500 μl of 70% ethanol was added to each well and immediately decanted and excess alcohol was touched off with a clean paper towel. Then, the plates were placed in a clean drawer without their lids, covered with a clean paper towel and allowed to dry overnight.

The next day, the DNA was resuspended in 200 μl of T Low E Buffer. The top was sealed with plate sealer and rehydrated at 4° C. for at least two days before using. They were stored at −20° C. in the interim.

After the plasmid templates have been isolated, the EST inserts were amplified. For each 96 well plate to be amplified, a PCR reaction mixture was prepared containing the following ingredients: 1000 μl of 10×PCR Buffer, 20 ?L of dATP (100 mM), 20 ?L of dGTP (100 mM), 20 ?L of dCTP (100 mM), 20 ?L of dTTP (100 mM), 5 ?L of AEK M13F primer (1 mM), 5 μL of AEK M13R primer (1 mM), 100 μL of AmpliTaq polymerase (5 U/μl), and 8800 mL of $H_2O$. The 96-well PCR plates were then labeled and 100 μl of the PCR reaction mixture from above was aliquoted to each well. The plates were then gently tapped to insure that no air bubbles were trapped at the bottom of the wells. 1 μl of purified EST plasmid template from above was then added to each well. The donor and recipient plates were then marked at the corner, near the A1 well to facilitate correct orientation during transfer of the template. It was important to make sure that the pipette tips were all submerged in the PCR reaction mix when delivering the template. Missing the liquid was easier when multi-channel pipettes were used.

The following thermal cycle series was then performed: 1 initial cycle of heating to 96° C. and holding for 30 sec, 25 cycles of denaturing at 94° C. for 30 sec, reannealing at 55° C. for 30 sec, and extending at 72° C. for 150 sec, one final cycle of holding at 72° C. for 5 minutes, then cooling to ambient temperature. After the above cycle, the plates were held at 4° C. while quality controls were performed.

The quality control was done by agarose gel electrophoresis of the ESTs. If this was the first time the template for these ESTs was being amplified, 2 μl of each PCR product was analyzed on a 2% agarose gel. If amplified products from this template had been previously tested, then one row of wells from each plate amplified was analyzed. Gel imaging allowed a rough quantitation of product while giving an excellent characterization of the product. Band size, as well as the number of bands observed in the PCR products, contributed to an understanding of the final results of the hybridization. The use of gel well formats suitable for loading from 96 well plates and programmable pipetters made this form of analysis feasible on a large scale.

The materials, reagents and solutions for the quality control check included: Electrophoresis apparatus with capacity for four 50 well combs, (e.g. #D3, Owl Scientific, Woburn, Mass.); 50× Tris-Acetate Electrophoresis BufferM; Agarose; Dye Solution (Xylene Cyanol/Bromophenol Blue) (e.g. #351-081-030, Quality Biological Inc., Gaithersburg Md.); Glycerol (enzyme grade); Ethidium Bromide solution (10 mg/ml); 100 base-pair ladder size standard; Programmable, 12-channel pipetter (e.g. #2019, Matrix Technologies, Lowell, Mass.); Disposable microtiter mixing trays (e.g. Falcon #353911, Becton Dickinson, Franklin Lake, N.J.); Electrophoresis power supply; 1×TAE Buffer; 50×TAE Buffer 40 ml; Ethidium Bromide (10 mg/ml) 0.1 ml and Water 960 ml; 1000 ml; Loading Buffer; Glycerol (enzyme grade) 4.0 ml, DEPC Water 0.9 ml, and Dye Solution* 0.1 ml for a total of 5.0 ml (*This solution is 0.25% (w/v) Xylene Cyanol and 0.25% (w/v) Bromophenol Blue); 100 bp Size Standards; DNA ladder (1 mg/ml) 50 μl, 1 M Tris-HCl (pH 8.0) 5 μl, 0.5 M EDTA (pH 8.0) 5 μl, and Loading Buffer 440 μl for a total of 500 μl The electrophoresis was carried out with a 2% agarose gel (1×TAE) with four combs (50 tooth) that was submerged in an electrophoresis apparatus with sufficient 1× TAE buffer to just cover the surface of the gel. A reservoir of Loading Buffer was prepared, using 12 wells of a microtiter plate. Then a pipetter was programmed to sequentially carry out the following steps: fill with 2 μl, fill with 1 μl, fill with 2 μl, mix a volume of 5 μl five times, expel 5 μl. Twelve (12) disposable tips were then placed on the pipetter. 2 μl of PCR product from wells A1-A12 of the PCR plate were loaded, followed by 1 μl of air, then 2 μl of Loading Buffer from the reservoir. The tips were then placed in clean wells of a disposable mixing tray and the pipette was allowed to mix the sample and loading dye. The pipette tip was then placed in a 50 well row so that the tip containing the PCR product from well A1 is in the second well of the row, and the other tips are in every other succeeding well.

The process was repeated (changing tips each time), to load PCR plate row B starting in the 3rd well, interleaved with the A row, the C row starting at well 26, and the D row at well 27, interleaved with the C row. Then 5 μl of 100 bp Size Standards were placed in wells 1 and 50. This process was repeated, to load samples from rows E, F, G, and H in the second, 50 well row of gel wells, to load samples from two 96 well PCR plates per gel, or single row samples from 16 PCR plates. To reduce diffusion and mixing, a voltage was applied to the gel for a minute between loading each well strip. This caused the DNA to enter the gel, and reduced band spreading and sample loss.

A voltage was then applied to the gel and it was run until the bromophenol blue (faster band) had nearly migrated to the next set of wells. For a gel that is 14 cm in the running dimension, and 3 cm between each row of wells, 200 volts were applied for 15 minutes. Digital photos of the gel were taken and the images stored for future reference. The gels should show bands of fairly uniform brightness distributed in size between 600 to 2000 base-pairs. Further computer analysis of such images can be carried out with image analysis packages to provide a list of the number and size of bands. Ideally this information can be made available during analysis of the data from hybridizations involving these PCR products.

After the quality control checks are run on the plates, the next step involves purifying the PCR products. 96 well V-bottom plates were filled with 200 μl per well of ethanol/acetate mix. The ethanol acetate solution used for precipitation is less acidic (pH 6) than is typically used. In this instance, more acidic solutions produce precipitates which are harder to resuspend without improving yield.

100 μl per well of PCR product was transferred into V-bottom plates and mixed by pipetting a volume of 75 μl per well four times. The plates were then placed in a −80° C. freezer for one hour or stored overnight at −20° C. The plates were stored at −20° C. if they were to be left for more than one hour, because aggressive precipitation produces precipitates which are hard to resuspend. The plates were then thawed to reduce brittleness and melt any ice, which may have formed in the wells.

The plates were loaded into a centrifuge with a horizontal microtiter plate rotor and spun at 2600×g for 40 minutes at 4° C. Next, the supernatant from each well was aspirated using the Immunowash plate washer. Settings for the depth of aspiration by the plate washer needed to be adjusted to suit the microtiter plates used. It is advisable to leave approximately 10-20 ml in the bottom of the well to avoid disturbing the pellet.

200 μl of 70% ethanol was delivered to each well in the plate using the Immunowash plate washer, and the plates were centrifuged at 2600×g for 40 minutes. The supernatant was aspirated from each well using the Immunowash plate washer, and the plates were dried overnight in a closed drawer. They should not be dried in a speed-vac because desiccated PCR products are hard to resuspend.

After the PCR products were purified, they were then resuspended by adding 40 μl of 3×SSC per well. The plates were then sealed with a foil sealer, taking care to achieve a tight seal over each well. The plates were then placed in heat sealable bags with paper towels moistened with 3×SSC and the bag was sealed with a heat sealer. The high external humidity within the sealed bag helped to keep the volumes in the individual wells from varying. The bags were then placed in a 65° C. incubator for 2 hours. The heat in the incubator was then turned off, and the plates were allowed to cool gradually in the incubator to avoid condensation on the sealers. The plates were stored at −20° C.

The yield of the PCR suspension was then checked by fluorometric determination of DNA concentration. 1 μl of resuspended PCR product from one row of wells from each plate on a 2% agarose gel was analyzed as previously described. Adequate precipitation and resuspension produced very intense bands, with no material failing to leave the loading well, and no smear of material from the band towards the loading well.

While it would be ideal to be able to exactingly quantify each EST PCR product and spot each DNA species at equivalent concentrations, it is impractical for most labs to do so when thousands of ESTs must be prepared. Fortunately, it is possible to use a strategy where excess DNA is spotted, so that the exact quantities used do not produce much variation in the observed results. When using this strategy, it is necessary to track the average productivity of the PCR reactions. Fluorometry provides a simple way to obtain an approximate concentration of the double-stranded PCR product in the PCR reaction mix.

Next, the double stranded DNA was quantified. The materials, reagents, and solutions necessary include: reference double-stranded DNA (0.5 mg/ml) (e.g. #15612-013 Gibco/BRL, Bethesda, Md.), 96 well plates for fluorescent detection (e.g. #7105, Dynex, Chantilly, Va.), Fluorometer (e.g. #LS50B, Perkin Elmer, Norwalk, Conn.), FluoReporter Blue dsDNA Quantitation Kit (#F-2962, Molecular Probes, Eugene, Oreg.), TE, 12 channel multi-pipetters, Computer equipped with Microsoft Excel software, Ds-DNA Standards: 50 μg/ml, 100 μg/ml, 250 μg/ml, 500 μg/ml, μl TE 90, 80, 50, 0 μl ds-DNA (0.5 mg/ml) 10, 20, 50, 100, (It is good practice to check both the integrity (agarose gel) and the concentration (absorbance) of the standard before use); Fluor Buffer (Hoechst 33258 solution (contains the dye at an unspecified concentration in a 1:4 mixture of DMSO:$H_2O$) (from kit) 25 μl, TNE Buffer (TNE Buffer is 10 mM Tris-HCl (pH 7.4), 2 M NaCl, 1 mM EDTA) (from kit) 10 ml.

The double stranded DNA was quantified as follows. 96 well plates were labeled for fluorescence assay. 200 μl of Fluor Buffer was added to each well. 1 μl of PCR product from each well in a row of a PCR plate was added to a row of the fluorometry plate. Samples were added to rows A through G of the fluorometry plate. In the final row of the fluorometry plate 1 μl of each of the series of ds-DNA standards 0 μg/ml (TE only), 50, 100, 250 and 500 μg/ml ds-DNA were added. This series was repeated twice in the final row.

The fluorometer was set for excitation at 346 nm and emission at 460 nm, and adjusted as necessary to read the plate. If the fluorometer used did not support automated analysis, the data table was exported to Excel. The response for the standards was tested to see that it was linear and reproducible from the range of 0 to 500 μg/ml of ds-DNA.

Next, the concentration of ds-DNA in the PCR reactions was calculated using the following equation, after subtracting the average 0 μg/ml value from all other sample and control values:

[ds-DNA(μg/ml)]=((PCR sample value)/(average 100 μg/ml value))*100

Constantly tracking the yields of the PCRs makes it possible to rapidly detect many ways in which PCR can fail or perform poorly. This assay can also be applied after precipitation and resuspension of the PCR products to monitor overall recovery of product. 1 μl of amplified products from one row of wells from each amplified plate by fluorometry was analyzed.

Slides were then coated with poly-L-lysine to have a surface that is both hydrophobic and positively charged. The hydrophobic character of the surface minimizes spreading of the printed spots, and the charge appears to help position the DNA on the surface in a way that makes cross-linking more efficient.

Materials, reagents, and solutions for coating the slides includes: Gold Seal Microscope Slides (#3011, Becton Dickinson, Franklin Lake, N.J.), Ethanol (100%), Poly-L-lysine (#P8920, Sigma, St. Louis, Mo.), 50 Slide Stainless Steel Rack, #900401, and 50 Slide Glass Tank, #900401, (Wheaton Science Products, Millville, N.J.), Sodium Hydroxide, Stir Plate, Stir Bar, Platform Shaker, 30 Slide Rack, #196, plastic, and 30 slide Box, #195, plastic, (Shandon Lipshaw, Pittsburgh, Pa.), Sodium Chloride, Potassium Chloride, Sodium Phosphate Dibasic Heptahydrate, Potassium Phosphate Monobasic, Autoclave, 0.2 mm Filter: Nalgene, Centrifuge: Sorvall Super 20, Slide Box (plastic with no paper or cork liners), (e.g. #60-6306-02, PGC Scientific, Gaithersburg, Md.), 1 L Glass Beaker; 1 L Graduated Cylinder, 1M Sodium Borate (pH 8.0) (Dissolve 61.83 g of Boric acid in 900 ml of DEPC $H_2O$. Adjust the pH to 8.0 with 1N NaOH. Bring volume up to one liter. Sterilize with a 0.2 micron filter and store at room temperature), Cleaning Solution ($H_2O$ 400 ml, Ethanol 600 ml, NaOH 100 g—Dissolve NaOH in $H_2O$. Add ethanol and stir until the solution clears. If the solution does not clear, add $H_2O$ until it does), and Poly-L-lysine Solution (poly-L-lysine (0.1% w/v) 35 ml PBS 35 ml $H_2O$ 280 ml 350 ml)

First, the slides are placed into 50 slide racks and the racks are placed in glass tanks with 500 ml of cleaning solution. Gold Seal Slides are highly recommended, as they have been found to have consistently low levels of autofluorescence. It was important to wear powder free gloves when handling the slides to avoid contamination.

The tanks are placed on platform shakers for two hours at 60 rpm. After being shook, the cleaning solution was poured out, and the slides were then washed in $H_2O$ for three minutes. This wash was repeated four times. The slides were then transferred to 30 slide plastic racks and placed into small plastic boxes for coating. The slides were then submerged in 200 ml poly-L-lysine solution per box. The slide boxes were then placed on platform shaker for one hour at 60 rpm. The slides were rinsed three times with $H_2O$, and submerged in $H_2O$ for one minute, and then centrifuged for two minutes at 400×g and the slide boxes used for coating were dried.

The slides were then placed back into the slide box used for coating and allowed to stand overnight before transferring to a new slide box for storage. This allowed the coating to dry before it was handled. The slides were allowed to age for two weeks on the bench, in a new slide box, before they were printing on. The coating dried slowly, becoming more hydrophobic with time.

Slide boxes used for long term storage should be plastic and free of cork lining. The glue used to affix the cork will leach out over time and give slides stored in these types of boxes a greasy film that has a high degree of autofluorescence. All glassware and racks used for slide cleaning and coating should be cleaned with highly purified $H_2O$ only, and detergent should not be used.

Once the slides were coated, they were printed. The variety of printers and pens for transferring PCR products from titer plates to slides precludes highly detailed descriptions of the process. The following steps provide a general description of the processing.

The print pens were pre-cleaned according to the manufacturer's specification. The printer slide deck was then loaded with poly-L-lysine coated slides from above. The plates containing the purified EST PCR products were thawed and centrifuged briefly, (about two minutes) at 1000 rpm in a horizontal microtiter plate rotor to remove condensation and droplets from the seals before being opening. 5 to 10 μl of the purified EST PCR products were transferred to a plate that served as the source of solution for the printer. Printing with quill-type pens usually requires that the volume of fluid in the print source was sufficiently low, so that when the pen was lowered to the bottom of the well, it was submerged in the solution to a depth of less than a millimeter. This keeps the pen from carrying a large amount of fluid on the outside of the pen shaft and producing variable, large spots on the first few slides printed.

A repetitive test print was run on the first slide. In this operation, the pens were loaded with the DNA solution, and then the pens serially deposited this solution on the first slide in the spotting pattern specified for the print. This test was run to check the size and shape of the specified spotting pattern, as well as its placement on the slide. It also served to verify that the pens were loading and spotting, and that a single loading produced as many spots as were required to deliver material to every slide in the printer. If one or more of the pens was not performing at the desired level, it was re-cleaned or substituted with another pen and tested again. If all pens were performing, the full print was carried out.

At the end of the print, the slides were removed from the printer, labeled with the print identifier and the slide number by writing on the edge of the slide with a diamond scribe and placed in a dust free slide box to age for one week. It was useful to etch a line, which outlined the printed area of the slide, onto the first slide. This served as a guide to locate the area after the slides have been processed, and the salt spots were then washed off.

The slides were placed, printed side face up, in a casserole dish and covered with cling wrap. The slides were then exposed to a 450 mJ dose of ultraviolet irradiation in the Stratalinker. Slides should have been and were aged at ambient temperature in a closed slide box for one week prior to blocking The slides were then transferred to a 30 slide stainless steel rack and the rack was placed into a small glass tank. 6.0 g succinic anhydride was dissolved in 325 ml 1-methyl-2-pyrrolidinone in a glass beaker by stirring with a stir bar. Nitrile gloves were worn and the work was carried out in a chemical fume hood while handling 1-methyl-2-pyrrolidinone (a teratogen).

25 ml 1M sodium borate buffer (pH 8.0) was added to the beaker. The solution was allowed to mix for a few seconds, then rapidly poured into a glass tank with slides. Succinic anhydride hydrolyzed quite rapidly once the aqueous buffer solution was added. To obtain quantitative passivation of the poly-L-lysine coating, it was critical that the reactive solution be brought in contact with the slides as quickly as possible. The glass tank was placed on a platform shaker in a fume hood for 20 minutes. Small particulates resulting from precipitation of reaction products may be visible in the fluid.

While the slides were incubating on the shaker a boiling $H_2O$ bath was prepared to denature the DNA on the slides. After the slides were incubated for 20 minutes, they were transferred into the boiling $H_2O$ bath. The heating element was immediately turned off after the slides were submerged in the bath. The slides were allowed to stand in the $H_2O$ bath for 2 minutes. The slides were then transferred into a glass tank filled with 100% ethanol and incubated for 4 minutes. The slides were removed and centrifuged at 400 rpm for 3 minutes in a horizontal microtiter plate rotor to dry the slides. The slides were then transferred to a clean, dust free slide box and allowed to stand overnight before being used for collection of gene expression data.

Example 2

Cell Culture and Tumor Samples

The source and other information for the cell lines and tumor samples used herein are described in TABLE 2 below for both the training set and the test samples.

TABLE 2

Supplement Table: Known Molecular Characteristics of Samples.

| Sample Label | Histological Diagnosis | Molecular Markers | Source Label | Source |
|---|---|---|---|---|
| EWS-C1 | EWS-C | EWS-FLI1, 10-6 | A4573 | NCI |
| EWS-C2 | EWS-C | EWS-FLI1, type I | TC71 | NCI |
| EWS-C3 | EWS-C | EWS-FLI1, type I | TC106 | NCI |
| EWS-C4 | EWS-C | EWS-FLI1, type I | 5838 | NCI |
| EWS-C6 | EWS-C | EWS-FLI1, type I | A673 | NCI |
| EWS-C7 | EWS-C | EWS-FLI1, type I | ES-CL1 | MSKCC |
| EWS-C8 | EWS-C | EWS-FLI1, type I | TC32 | NCI |
| EWS-C9 | EWS-C | EWS-FLI1, type II | SK-ES-1 | ATCC |
| EWS-C10 | EWS-C | EWS-FLI1, type II | SK-N-MC | ATCC |
| EWS-C11 | EWS-C | EWS-FLI1, type II | RDES | ATCC |
| EWS-T1 | EWS-T | EWS-FLI1, type I | ES20 | MSKCC |

TABLE 2-continued

Supplement Table: Known Molecular Characteristics of Samples.

| Sample Label | Histological Diagnosis | Molecular Markers | Source Label | Source |
|---|---|---|---|---|
| EWS-T2 | EWS-T | EWS-FLI1, type II | ES13 | MSKCC |
| EWS-T3 | EWS-T | EWS-FLI1, type I | ES16 | MSKCC |
| EWS-T4 | EWS-T | EWS-FLI1, type I | ES17 | MSKCC |
| EWS-T6 | EWS-T | EWS-FLI1, 7-8 | ES22 | MSKCC |
| EWS-T7 | EWS-T | EWS-ERG, 7-9 | ES25 | MSKCC |
| EWS-T9 | EWS-T | EWS-FLI1, type I | 9602P006 | CHTN |
| EWS-T11 | EWS-T | EWS-FLI1, type I | 9703P152 | CHTN |
| EWS-T12 | EWS-T | EWS-FLI1, type I | 9704P218 | CHTN |
| EWS-T13 | EWS-T | EWS-FLI1, type I | ES23 | MSKCC |
| EWS-T14 | EWS-T | EWS-FLI1, type I | 9605P074 | CHTN |
| EWS-T15 | EWS-T | EWS-FLI1, type I | 9609P027 | CHTN |
| EWS-T19 | EWS-T | EWS-FLI1, type I | SARC75 | CHTN |
| RMS-C2 | ERMS-C | — | RD | ATCC |
| RMS-C3 | ARMS-C | ND | RH4 | NCI |
| RMS-C4 | ARMS-C | PAX3-FKHR | RH3 | NCI |
| RMS-C5 | ARMS-C | PAX3-FKHR | RH5 | NCI |
| RMS-C6 | ARMS-C | PAX3-FKHR | RH28 | NCI |
| RMS-C7 | ARMS-C | ND | RH30 | NCI |
| RMS-C8 | ERMS-C | — | CTR | ATCC |
| RMS-C9 | ARMS-C | PAX3-FKHR | RH4 | NCI |
| RMS-C10 | ARMS-C | PAX3-FKHR | RMS13 | NCI |
| RMS-C11 | ERMS-C | — | TE671 | ATCC |
| RMS.T1 | ARMS-T | PAX3-FKHR | RMS3 | MSKCC |
| RMS.T2 | ARMS-T | PAX3-FKHR | RMS6 | MSKCC |
| RMS.T3 | ERMS-T | — | RMS2 | MSKCC |
| RMS.T4 | ERMS-T | no PAX-FKHR | RMS5 | MSKCC |
| RMS.T5 | ARMS-T | PAX3-FKHR | RMS10 | MSKCC |
| RMS.T6 | RMS-T | ND | RT1 | CHTN |
| RMS.T7 | ERMS-T | — | RT4 | CHTN |
| RMS.T8 | RMS-T | ND | RT5 | CHTN |
| RMS.T10 | RMS-T | ND | RT2 | CHTN |
| RMS.T11 | ERMS-T | — | RHAB2 | CHTN |
| NB-C1 | NB-C | MYCN amp | KCNR | NCI |
| NB-C2 | NB-C | — | GICAN | NCI |
| NB-C3 | NB-C | — | SK-N-AS | ATCC |
| NB-C4 | NB-C | MYCN amp | LAN5 | NCI |
| NB-C5 | NB-C | MYCN amp | SK-N-BE2 | ATCC |
| NB-C6 | NB-C | MYCN amp | SK-N-DZ | ATCC |
| NB-C7 | NB-C | — | GICAN | NCI |
| NB-C8 | NB-C | — | NGP | NCI |
| NB-C9 | NB-C | — | SH-SY5Y | ATCC |
| NB-C10 | NB-C | MYCN amp | SK-N-FI | ATCC |
| NB-C11 | NB-C | Single copy MYCN | SK-N-SH | ATCC |
| NB-C12 | NB-C, | MYCN amp | CHP-134B | NCI |
| BL-C1 | BL-C | — (RAI) | RAMOS | ATCC |
| BL-C2 | BL-C | — | ST486 | ATCC |
| BL-C3 | BL-C | — | CA46 | ATCC |
| BL-C4 | BL-C | — | ST486 | ATCC |
| BL-C5 | BL-C | — | RAJI | ATCC |
| BL-C6 | BL-C | — | MC116 | ATCC |
| BL-C7 | BL-C | — | DAUDI | ATCC |
| BL-C8 | BL-C | — | SULTAN | ATCC |
| Test1 | NB-C | MYCN amp | IMR32 | ATCC |
| Test2 | EWS-C | ND | CHOP1 | NCI |
| Test3 | Osteosarcoma-C | — | OsA-CI | ATCC |
| Test4 | ARMS-T | — | ARMD1 | CHTN |
| Test5 | Sarcoma | — | A204 | ATCC |
| Test6 | EWS-T | EWS-FLI1, type I | 9608P053 | CHTN |
| Test7 | BL-C | — | EB1 | ATCC |
| Test8 | NB-C | — | SMSSAN | NCI |
| Test9 | Sk. Muscle | — | SkM1 | CHTN |
| Test10 | ERMS-T | — | ERDM1 | CHTN |
| Test11 | Prostate Ca.-C | — | PC3 | ATCC |
| Test12 | EWS-T | — | SARC67 | CHTN |
| Test13 | Sk. Muscle | — | SkM2 | CHTN |
| Test14 | NB-T | Single copy MYCN | NB3 | DZNSG |
| Test15 | BL-C | — | EB2 | ATCC |
| Test16 | NB-T | Single copy MYCN | NB1 | DZNSG |
| Test17 | ARMS-T | — | ARMD2 | CHTN |
| Test18 | BL-C | — | GA10 | ATCC |
| Test19 | EWS-T | ND | ET3 | CHTN |
| Test20 | EWS-T | EWS-FLI1, type I | 9903P1339 | CHTN |
| Test21 | EWS-T | EWS-FLI1, type II | ES23 | MSKCC |
| Test22 | ERMS-T | — | ERMD2 | CHTN |
| Test23 | NB-T | Single copy MYCN | NB2 | DZNSG |
| Test24 | ERMS-T | no PAX-FKHR | RMS4 | MSKCC |
| Test25 | NB-T | Single copy MYCN | NB4 | DZNSG |

Supplement Table: Known molecular characteristics of samples. Table labels and abbreviations are described in Table 1 in the manuscript. EWS and ARMS samples with noted translocations were verified by RT-PCR.

ND; not determined.

Amp.: amplification.

All the original histological diagnoses were made at tertiary hospitals, which have reference diagnostic laboratories with extensive experience in the diagnosis of pediatric cancers. Approximately 20% of all samples in each category were randomly selected, blinded and set aside for testing. To augment this test set, we added 4 neuroblastoma tumors and 5 non-SRBCT samples (also blinded to the authors performing the analysis). The EWSs had a spectrum of the expected translocations, and the RMSs were a mixture of both ARMS containing the PAX3-FKHR translocation and embryonal rhabdomyosarcoma (ERMS). The NBs contained both MYCN amplified and single copy samples. The NHLs were cell lines derived from BL. TABLE 2 gives details of these samples as well.

This protocol details the methods used to extract RNA from cells, purify the RNA by a combination of phase extraction and chromatography, and prepare a labeled cDNA copy of the message fraction of the purified RNA. The protocol also describes the process of making fluorescent cDNA representations of the message pools within the isolated total RNA pools. This is accomplished by using the pure total RNA as a substrate for reverse transcription in the presence of nucleotides derivatized with either a Cy3 or a Cy5 fluorescent tag.

The materials, reagents, and solutions needed include: Trizol Reagent (#15596-018, Life Technologies, Rockville, Md.); RNeasy Maxi Kit (#75162, Qiagen, Valencia, Calif.); Chloroform; Ethanol (200 Proof USP Ethyl Alcohol); DPBS (Dulbecco's phosphate buffered saline); 3M sodium acetate (pH 5.2); dATP, dCTP, dGTP, dTTP, 100 mM each, store frozen, −20° C. (#27-2035-02, Pharmacia, Peapack, N.J.); pd(T)12-18 resuspend at 1 mg/ml, and store frozen −20° C. (#27-7858, Amersham Pharmacia Biotech); Anchored oligo primer (anchored; 5'-TTT TTT TTT TTT TTT TTT TTV N-3') (SEQ ID NO: 99); resuspend at 2 mg/ml, store frozen −20° C. (e.g. #3597-006, Genosys); CyTM3-dUTP, 1 mM, and CyTM5-dUTP, 1 mM, store −20° C., light sensitive; RNasinâ Rnase inhibitor, store −20° C. (#N211A, Promega); SUPERSCRIPT™ II Rnase H' Reverse Transcriptase Kit, store −20° C., (#18064-014, Life Technologies, Rockville, Md.); C0t-1 DNA, 1 mg/ml, store frozen −20° C. (#15279-011, Life Technologies, Rockville, Md.); 0.5M EDTA (pH 8.0); 1 N NaOH; 1M TRIS-HCL; (pH7.5); TE pH 7.4; DEPC water 50× Tris Acetate Buffer; 15 ml round bottom; polypropylene centrifuge tubes; 50 ml conical polypropylene centrifuge tubes; 1.5 ml; Eppendorf tubes; 0.2 ml thin wall PCR tube; MicroCon 100 (Amicon Cat No. 42412); High speed centrifuge for 15 ml tubes; Clinical centrifuge with horizontal rotor for 50 ml conical tubes; Tissue homogenizer (e.g. Polytron PT1200 with Polytron-Aggregate-Dispergier-und-Mischtechnik 147a Ch6014 #027-30-520-0, Brinkmann Instruments Inc., Westbury, N.Y.); RPE Buffer (Add 4 volumes of ethanol per volume of RPE concentrate supplied in Quiagen Kit0; RW1 Buffer (Supplied in Qiagen Kit) 75% EtOH (Ethanol (100%) 375 ml, and DEPC H2O 125 ml for a total of 500 ml); 10× low T dNTP Mix (25 μL dGTP (100 mM), 25 μL dATP (100 mM), 25 μL dCTP (100 mM), 10 μL dTTP (100 mM), and 415 μL DEPC $H_2O$ for a total of 500 μL); 5× First Strand Buffer (Provided with Superscript II); TAE Buffer (50× Tris Acetate Electrophoresis Buffer 20 ml, and DEPC $H_2O$ 980 mL for a total of 1000 ml).

If the cells that were used were harvested from tissue culture, the cell pellet was washed twice in DPBS. If the cells that were used were from tissue culture, 1 ml of Trizol was added per $2\times10^7$ cells and mixed by shaking If tissue was being used, 100 mg of frozen tissue was added directly to 4 ml of Trizol, and dissociate by homogenization with a rotating blade tissue homogenizer.

Whatever the source, 2/10 volume of chloroform was added to the cells and shook for 15 seconds, and then allowed to stand for 3 minutes, followed by centrifugation at 12,000×g for 15 minutes at 4° C. The supernatant was taken off and added to a polypropylene tube, while recording the volume of the supernatant.

Then 0.53 volumes of ethanol were slowly added to the supernatant while vortexing, this produced a final ethanol concentration of 35%. The ethanol was added drop by drop and allowed to mix completely with the supernatant before more ethanol is added. If a high local concentration of ethanol is produced, the RNA in that vicinity will precipitate.

The supernatant from an extraction of $2\times10^7$ to $1\times10^8$ cells was added to an RNeasy maxi column, which is seated in a 50 ml centrifuge tube. The tube was then centrifuged at 2880×g in a clinical centrifuge with a horizontal rotor at room temperature for 5 minutes. The flow-through was then poured back onto the top of the column and centrifuged again. This step is necessary because a significant amount of RNA is not captured by the column matrix in the first pass of the RNA containing solution through the column.

The flow-through was discarded and 15 ml of RW1 buffer was added to the column, followed by centrifugation at 2880×g for 5 minutes. The flow-through was discarded again and then 10 ml of RPE buffer was added, followed again by centrifugation at 2880×g for 5 minutes. Once again, the flow through was discarded and another 10 ml of RPE buffer was added, and the column was centrifuged at 2880×g for 10 minutes.

Next, the column was placed in a fresh 50 ml tube and add 1 ml of DEPC treated water from the kit was added to the column, and the column was allowed to stand for 1 minute. The column was then centrifuged at 2880×g for 5 minutes, and another 1 ml of water was added to the column. The column was allowed to stand for 1 minute, followed by centrifugation at 2880×g for 10 minutes.

Then, 400 μl portions of the column eluate was aliquoted to 1.5 ml Eppendorf tubes, to which 1/10 volume of 3M sodium acetate (pH 5.2) was added, along with 1 ml of ethanol. The tubes were then allowed to stand for 15 minutes, after which they were centrifuged at 12000×g at 4 C for 15 minutes. The pellet was then washed two times in 75% EtOH and stored at −80° C.

The RNA was resuspended at approximately 1 mg/ml in DEPC $H_2O$. It was then concentrated to greater than 7 mg/ml by centrifugation on a MicroCon 100 filter unit, centrifuged at 500×g, checking as necessary to determine the rate of concentration. This step removes many residual, small to medium sized, molecules that inhibit the reverse transcription reaction in the presence of fluorescently derivatized nucleotides. The concentration of RNA in the concentrated sample was then determined by spectrophotometry, and the sample was stored at −80° C.

If an anchored oligo dT primer was used, the primer was annealed to the RNA in the following 17 μl reaction (a 0.2 ml thin wall PCR tube was used so that incubations could be carried out in a PCR cycler):

| Component | addition for Cy5 labeling | addition for Cy3 labeling |
|---|---|---|
| Total RNA (>7 mg/ml) | 150-200 μg | 50-80 μg |
| Anchored primer (2 μg/μl) | 1 μl | 1 μl |
| DEPC H2O | to 17 μl | to 17 μl |

If an oligo dT(12-18) primer was used, the primer was annealed to the RNA in the following 17 μl reaction:

| Component | addition for Cy5 labeling | addition for Cy3 labeling |
|---|---|---|
| Total RNA (>7 mg/ml) | 150-200 μg | 50-80 μg |
| dT(12-18) primer (1 μg/μl) | 1 μl | 1 μl |
| DEPC H2O | to 17 μl | to 17 μl |

The incorporation rate for Cy5-dUTP is less than that of Cy3-dUTP, so more RNA is labeled to achieve more equivalent signal from each species.

It was then heated to 65° C. for 10 minutes and cooled on ice for 2 minutes. Then, 23 μl (8 μl of 5× first strand buffer, 4 μl of 10× low T dNTPs mix, 4 μl of Cy5 or Cy3 dUTP (1 mM), 4 μl of 0.1 M DTT, 1 μl of Rnasin (30 u/?l), and 2 ?l of Superscript II (200 u/?l)) of reaction mixture containing either Cy5-dUTP or Cy3-dUTP nucleotides was added, mixed well by pipetting and a brief centrifuge spin was used to concentrate it in the bottom of the tube. Superscript polymerase is very sensitive to denaturation at air/liquid interfaces, so we were careful to suppress foaming in all handling of this reaction.

It was then incubated at 42° C. for 30 min., after which 2 μl Superscript II was added, making sure the enzyme was well mixed in the reaction volume and incubated at 42° C. for 30-60 min. Then, 5 μl of 0.5M EDTA was added, making sure the reaction was stopped with EDTA before adding NaOH (the next step), since nucleic acids precipitate in alkaline magnesium solutions.

Then, 10 μl 1N NaOH was added and it was incubated at 65? C for 60 minutes to hydrolyze residual RNA, after which it was cooled to room temperature. The purity of the sodium hydroxide solution used in this step is crucial. Slight contamination or long storage in a glass vessel can produce a solution that will degrade the Cy5 dye molecule, turning the solution yellow. Some researchers achieve better results by reducing the time of hydrolysis to 30 minutes.

It was then neutralized by adding 25 μl of 1M Tris-HCl (pH 7.5). Then, the labeled cDNA was desalted by adding the neutralized reaction, 400 μl of TE pH 7.5 and 20 μg of human C0t-1 DNA to a MicroCon 100 cartridge. It was then pipetted to mix, and spun for 10 minutes at 500×g. 200 μl TE pH 7.5 was added, and the solution was then concentrated to about 20-30 μl (approximately 8-10 min at 500×g). Alternatively, a smaller pore MicroCon 30 was used to speed the concentration step. In this case, the first wash was centrifuged for approximately 4.5 minutes at 16,000×g and the second (200 μl wash) for about 2.5 minutes at 16,000×g.

It was then recovered by inverting the concentrator over a clean collection tube and spinning for 3 min at 500×g. In some cases, the cy5 labeled cDNA formed a gelatinous blue precipitate that was recovered in the concentrated volume. The presence of this material signaled the presence of contaminants. The more extreme the contamination, the greater the fraction of cDNA which will be captured in this gel. Even if heat solubilized, this material tends to produce uniform, nonspecific binding to the DNA targets. When concentrating by centrifugal filtration, the times required to achieve the desired final volume were variable. Overly long spins can remove nearly all the water from the solution being filtered. When fluor-tagged nucleic acids are concentrated onto the filter in this fashion, they are very hard to remove, so it is necessary to approach the desired volume by conservative approximations of the required spin times. If control of volumes proves difficult, the final concentration can be achieved by evaporating liquid in the speed-vac. Vacuum evaporation, if not to dryness, does not degrade the performance of the labeled cDNA.

Next, a 2-3 μl aliquot of the Cy5 labeled cDNA was taken for analysis, leaving 18-28 μl for hybridization. This probe was run on a 2% agarose gel (6 cm wide×8.5 cm long, 2 mm wide teeth) in Tris Acetate Electrophoresis Buffer (TAE). For maximal sensitivity when running samples on a gel for fluor analysis, a loading buffer with minimal dye was used and no ethidium bromide was added to the gel or running buffer.

The gel was then scanned on a Molecular Dynamics Storm fluorescence scanner (setting: red fluorescence, 200 micron resolution, 1000 volts on PMT). Successful labeling produces a dense smear of probe from 400 bp to >1000 bp, with little pile-up of low molecular weight transcripts. Weak labeling and significant levels of low molecular weight material indicates a poor labeling. A fraction of the observed low molecular weight material is unincorporated fluor nucleotide.

Next, the fluorescent cDNA had to be hybridized to the microarray. The volume of hybridization solution required was first determined. The rule of thumb is to use 0.033 μl for each mm 2 of slide surface area covered by the cover slip used to cover the array. An array covered by a 24 mm by 50 mm cover slip required 40 μl of hybridization solution. The volume of the hybridization solution is critical. When too little solution is used, it is difficult to seat the cover slip without introducing air bubbles over some portion of the arrayed ESTs, and the cover slip will not sit at a uniform distance from the slide. If the cover slip is bowed toward the slide in the center, there will be less labeled cDNA in that area and hybridization will be non-uniform. When too much volume is applied, the cover slip will move easily during handling, leading to misplacement relative to the arrayed ESTs, and non-hybridization in some areas of the array.

For a 40 μl hybridization, the Cy3 and Cy5 labeled cDNAs were pooled into a single 0.2 ml thin wall PCR tube and the volume was adjusted to 30 μl by either adding DEPC $H_2O$, or removing water in a SpeedVac. If a vacuum device was used to remove water, high heat or heat lamps were not used to accelerate evaporation because the fluorescent dyes could be degraded.

For a 40 μl hybridization the following components were combined:

| | High Sample Blocking | High Array Blocking |
|---|---|---|
| Cy5 + Cy3 probe | 30 μl | 28 μl |
| Poly d(A) (8 mg/ml) | 1 μl | 2 μl |
| Yeast tRNA (4 mg/ml) | 1 μl | 2 μl |
| Human C0t-1 DNA (10 mg/ml) | 1 μl | 0 μl |
| 20x SSC | 6 μl | 6 μl |
| 50x Denhardt's blocking solution | 1 μl (optional) | 2 μl |
| Total volume | 40 ul | 40 ul |

Arrays and samples can vary somewhat, making it necessary to vary the composition of the hybridization cocktail. In cases where there is residual hybridization to control repeat DNA samples on the array, more C0t-1 DNA was used, as in the High Sample Blocking formulation. When there is diffuse background or a general haze on all of the array elements, more of the non-specific blocker components was used, as in the High Array Blocking formulation.

The components were mixed well by pipetting, heated at 98° C. for 2 minutes in a PCR cycler, cooled quickly to 25° C. and 0.6 ul of 10% SDS was added. It was then centrifuged for 5 min at 14,000×g. The fluor labeled cDNAs have a tendency to form small, very fluorescent, aggregates which result in bright, punctate background on the array slide. Hard centrifugation will pellet these aggregates, allowing you to avoid introducing them to the array.

The labeled cDNA was applied to a 24 mm×50 mm glass cover slip and then touched with the inverted microarray. Applying the hybridization mix to the array and cover slipping it is an operation which requires some dexterity to get the positioning of the cover slip and the exclusion of air bubbles just right. It was helpful to practice this operation with buffer and plain slides before attempting actual samples. The hybridization solution was added to the cover slip first, since some aggregates of fluor remain in the solution and will bind to the first surface they touch.

The slide was then placed in a microarray hybridization chamber, 5 μl of 3×SSC was added to the reservoir, if the chamber provided one, or at the scribed end of the slide and the chamber was sealed. The chamber was submerged in a 65° C. water bath and the slide was allowed to hybridize for 16-20 hours. There are a wide variety of commercial hybridization chambers. It was worthwhile to prepare a mock hybridization with a blank slide, load it in the chamber and incubate it to test for leaks, or drying of the hybridization fluid, either of which cause severe fluorescent noise on the array.

Next, the unbound fluorescent cDNA was washed off. The hybridization chamber was removed from the water bath, cooled and carefully dried off. The chamber was unsealed and the slide was removed. As there may be negative pressure in the chamber after cooling, it is necessary to remove water from around the seals so that it was not pulled into the chamber and onto the slide when the seals are loosened.

The slide was placed, with the cover slip still affixed, into a Coplin jar filled with 0.5×SSC/0.01% SDS wash buffer. The cover slip was allowed to fall from the slide and then removed from the jar with a forceps. The slide was allowed to wash for 2-5 minutes. The slide was transferred to a fresh Coplin jar filled with 0.06×SSC, and allowed to wash for 2-5 minutes. The sequence of washes may need to be adjusted to allow for more aggressive noise removal, depending on the source of the sample RNA. Useful variations are to add a first wash which is 0.5×SSC/0.1% SDS or to repeat the normal first wash twice.

The slide was then transferred to a slide rack and centrifuged at low rpm (700-1000) for 3 minutes in a clinical centrifuge equipped with a horizontal rotor for microtiter plates. If the slide is simply air dried, it frequently acquires a fluorescent haze. Centrifuging off the liquids results in a lower fluorescent background. As the rate of drying can be quite rapid, it is suggested that the slide be placed in the centrifuge immediately upon removal from the Coplin jar.

Image analysis was performed using DeArray software (Chen, Y., Dougherty, E. R. and Bittner, M. L. Ratio-based decisions and the quantitative analysis of cDNA microarray images, *Biomedical Optics* 2, 364-374 (1997).

Example 3

Data Analysis

To calibrate ANN models to recognize cancers in each of the four SRBCT categories, gene-expression data from cDNA microarrays as obtained via Examples 1 and 2 above were used. The 63 training samples included both tumor biopsy material (13 EWS and 10 RMS) and cell lines (10 EWS, 10 RMS, 12 NB and 8 Burkitt lymphomas (BL; a subset of NHL). For two samples, ST486 (BL-C2 and C4) and GICAN (NB-C2 and C7), we performed two independent microarray experiments to test the reproducibility of the experiments and these were subsequently treated as separate samples.

Genes were filtered based on the intensity of the fluorescence gathered from the cDNA microarray. This type of filtering was designed to remove spots for which image analysis failed. Genes were filtered by requiring that a gene have a red intensity greater than 20 across all experiments. The number of genes that passed this filter was 2308. Each slide was normalized across all experiments. Therefore the expression level was based on a relative (or normalized) red intensity (RRI) for each gene, RRI=mean intensity of that spot/mean intensity of filtered genes. The natural logarithm (ln) of RRI was used as a measure of the expression levels.

Principal component analysis (PCA) further reduced the dimensionality. To allow for a supervised regression model with no over-training (when we have low number of parameters as compared to the number of samples), the dimensionality of the samples was reduced by PCA using centralized ln (RRI) values as input. Thus each sample was represented by 88 numbers, which are the results of projection of the gene expressions using PCA eigenvectors. We used the 10 dominant PCA components for subsequent analysis. These 10 dominant components contained 63% of the variance in the data matrix. The remaining PCA components contained variance unrelated to separating the four cancers.

Figure 5:
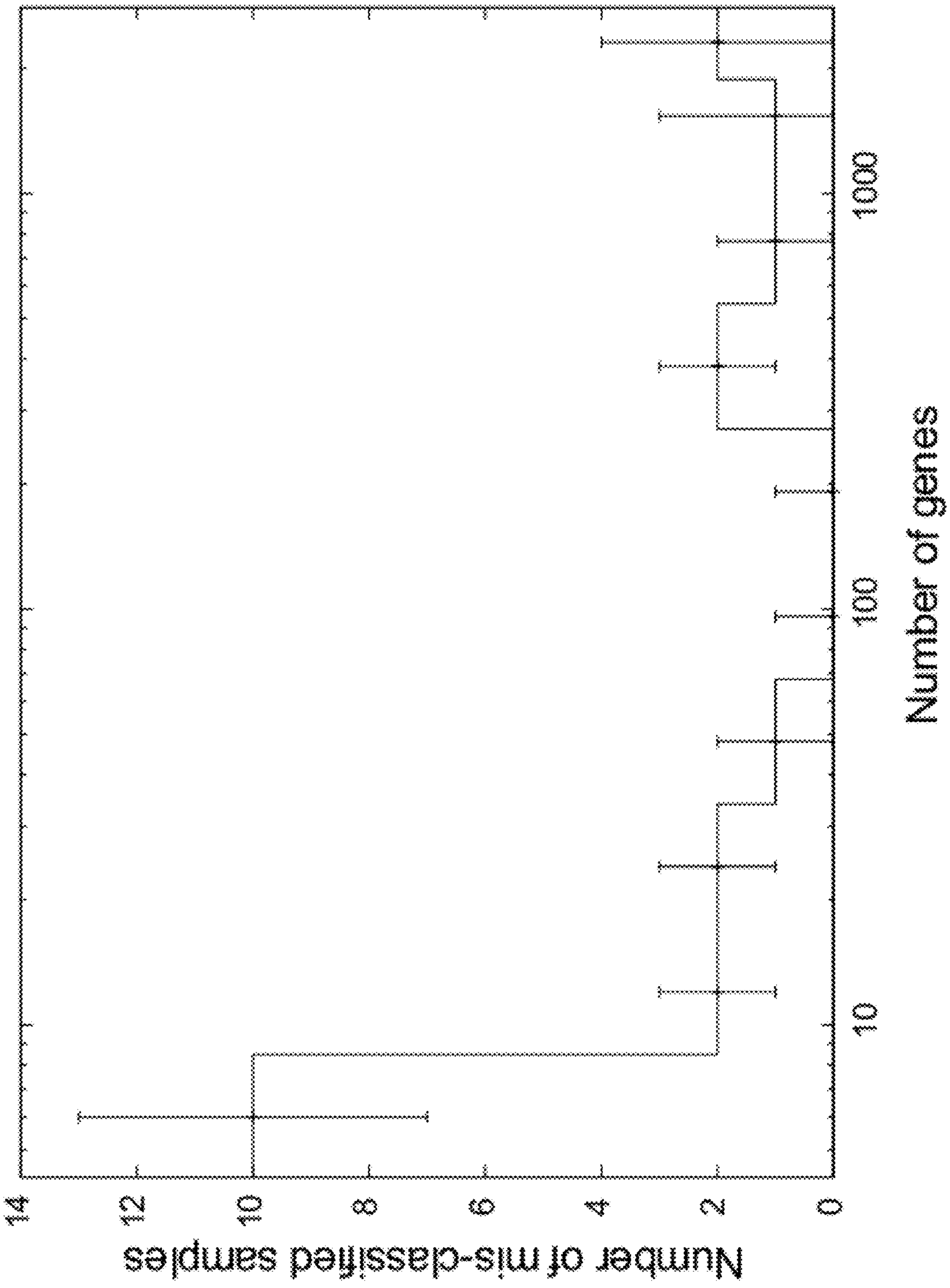
FIG. 5 represents a plot of the average number of misclassified samples for all 3750 models plotted against an increasing number of used genes.

We classified the training samples in the 4 categories using a 3-fold cross validation procedure: the 63 training (labeled) samples were randomly shuffled and split into 3 equally sized groups. Each linear ANN model was then calibrated with the 10 PCA input variables (normalized to centralized z-scores) using 2 of the groups, with the third group reserved for testing predictions (validation). This procedure was repeated 3 times, each time with a different group used for validation. The random shuffling was redone 1250 times and for each shuffling we analyzed 3 ANN models. Thus, in total, each sample belonged to a validation set 1250 times, and 3750 ANN models were calibrated. The three-fold cross-validation procedure produced at total of 3750 ANN models, and the training and validation was successful, see FIG. 5.

Figure 4:
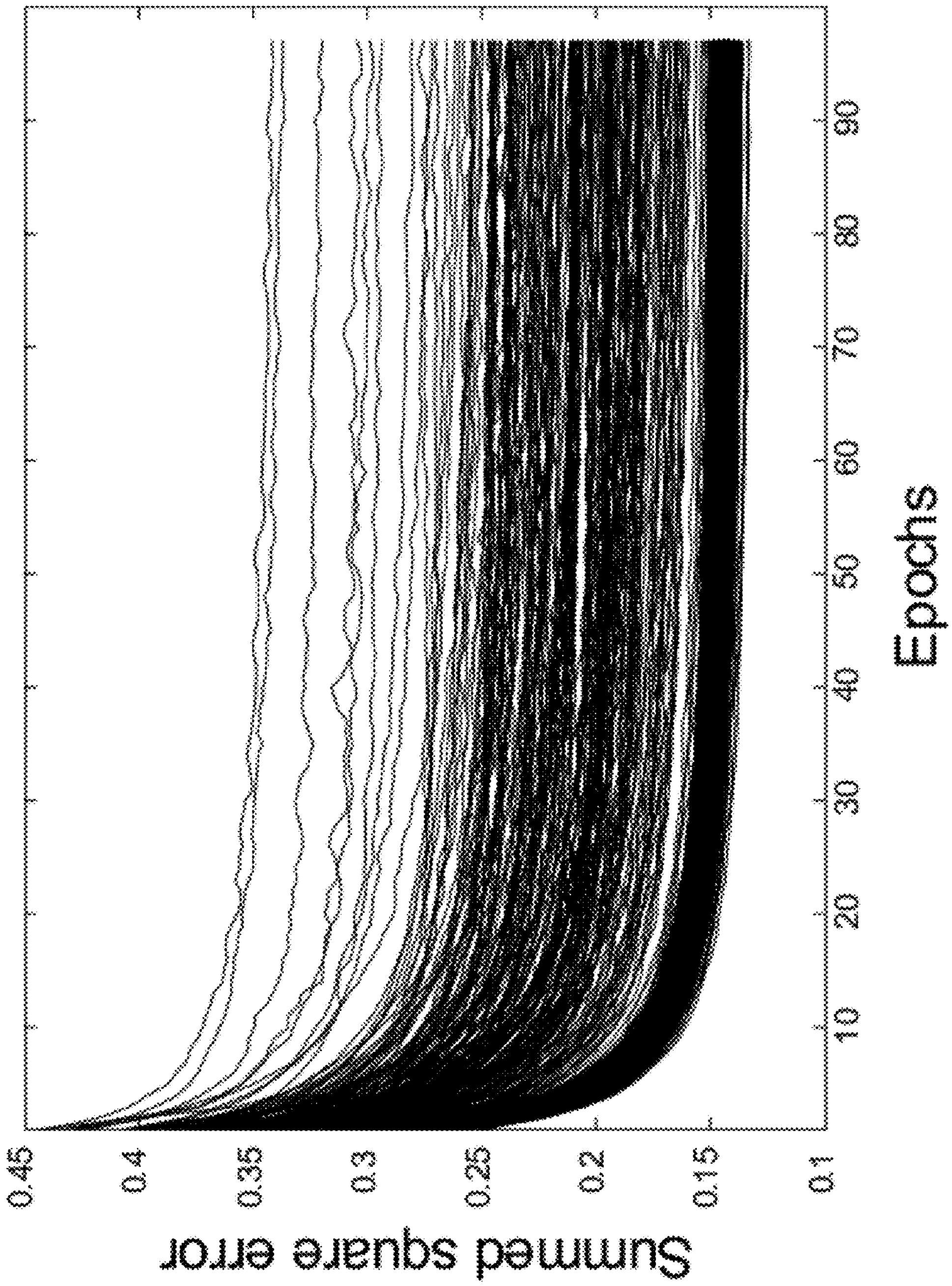
FIG. 4 represents a plot of the average classification error per sample (using a summed square error function) plotted during the training iterations (epochs) for both the training and validation samples.

In addition, there was no sign of 'over-training' of the models, as would be shown by a rise in the summed square error for the validation set with increasing training iterations or 'epochs', see FIG. 4.

For each diagnostic category (EWS, RMS, NB or BL), each ANN model gave an output between 0 (not this category) and 1 (this category). The 1250 outputs for each validation sample were used as a committee as follows. We calculated the average of all the predicted outputs (a committee vote) and then a sample was classified as a particular cancer if it received the highest committee vote for that cancer. In clinical settings, it is important to be able to reject a diagnostic classification including samples not belonging to any of the four diagnoses. Therefore, to be able to reject classification we did as follows. A squared Euclidean distance was computed for each cancer type, between the committee vote for a sample and the 'ideal' output for that cancer type; normalized such that it is unity between cancer types as described above. Using the 1250 ANN models for each validation sample we constructed for each cancer type an empirical probability distribution for the distances. Using these distributions, samples are only diagnosed as a specific cancer if they lie within the 95th percentile. All 3750 models were used to classify the additional 25 test samples.

Using these ANN models, all of the 63 training samples were correctly assigned/classified to their respective categories, having received the highest committee vote (average output) for that category.

Diagnostic results for the 63 training samples can be seen in TABLE 3 below.

TABLE 3

Training sample characteristics

| Sample Label | Source Label | Histological Diagnsosis | ANN Committee Vote EWS | RMS | NB | BL | Source |
|---|---|---|---|---|---|---|---|
| EWS-C1 | A4573 | EWS-C | 0.91 | 0.02 | 0.27 | 0.04 | NCI |
| EWS-C2 | TC71 | EWS-C | 0.85 | 0.03 | 0.16 | 0.08 | NCI |
| EWS-C3 | TC106 | EWS-C | 0.89 | 0.04 | 0.10 | 0.08 | NCI |
| EWS-C4 | 5838 | EWS-C | 0.87 | 0.09 | 0.08 | 0.04 | NCI |
| EWS-C6 | A673 | EWS-C | 0.93 | 0.11 | 0.03 | 0.05 | NCI |
| EWS-C7 | ES-CL1 | EWS-C | 0.94 | 0.06 | 0.08 | 0.04 | MSKCC |
| EWS-C8 | TC32 | EWS-C | 0.98 | 0.05 | 0.04 | 0.04 | NCI |
| EWS-C9 | SK-ES-1 | EWS-C | 0.94 | 0.10 | 0.03 | 0.05 | ATCC |
| EWS-C10 | SK-N-MC | EWS-C | 0.81 | 0.22 | 0.03 | 0.06 | ATCC |
| EWS-C11 | RDES | EWS-C | 0.93 | 0.05 | 0.03 | 0.07 | ATCC |
| EWS-T1 | ES20 | EWS-T | 0.99 | 0.04 | 0.03 | 0.06 | MSKCC |
| EWS-T2 | ES13 | EWS-T | 0.95 | 0.08 | 0.06 | 0.04 | MSKCC |
| EWS-T3 | ES16 | EWS-T | 0.97 | 0.10 | 0.05 | 0.03 | MSKCC |
| EWS-T4 | ES17 | EWS-T | 0.93 | 0.14 | 0.11 | 0.02 | MSKCC |
| EWS-T6 | ES22 | EWS-T | 0.97 | 0.12 | 0.04 | 0.04 | MSKCC |
| EWS-T7 | ES25 | EWS-T | 0.99 | 0.04 | 0.03 | 0.04 | MSKCC |
| EWS-T9 | 9602P006 | EWS-T | 0.95 | 0.13 | 0.03 | 0.03 | CHTN |
| EWS-T11 | 9703P152 | EWS-T | 0.99 | 0.03 | 0.06 | 0.03 | CHTN |
| EWS-T12 | 9704P218 | EWS-T | 1.00 | 0.02 | 0.03 | 0.03 | CHTN |
| EWS-T13 | ES23 | EWS-T | 0.67 | 0.28 | 0.16 | 0.04 | MSKCC |
| EWS-T14 | 9605P074 | EWS-T | 0.99 | 0.02 | 0.04 | 0.05 | CHTN |
| EWS-T15 | 9609P027 | EWS-T | 0.99 | 0.03 | 0.06 | 0.03 | CHTN |
| EWS-T19 | SARC75 | EWS-T | 0.93 | 0.06 | 0.09 | 0.04 | CHTN |
| RMS-C2 | RD | ERMS-C | 0.06 | 0.81 | 0.11 | 0.03 | ATCC |
| RMS-C3 | RH4 | ARMS-C | 0.04 | 0.84 | 0.05 | 0.03 | NCI |
| RMS-C4 | RH3 | ARMS-C | 0.00 | 0.88 | 0.11 | 0.05 | NCI |
| RMS-C5 | RH5 | ARMS-C | 0.01 | 0.91 | 0.09 | 0.04 | NCI |
| RMS-C6 | RH28 | ARMS-C | 0.00 | 0.87 | 0.07 | 0.07 | NCI |
| RMS-C7 | RH30 | ARMS-C | 0.01 | 0.88 | 0.09 | 0.03 | NCI |
| RMS-C8 | CTR | ERMS-C | 0.03 | 0.86 | 0.07 | 0.03 | ATCC |
| RMS-C9 | RH4 | ARMS-C | 0.05 | 0.86 | 0.03 | 0.05 | NCI |
| RMS-C10 | RMS13 | ARMS-C | 0.01 | 0.90 | 0.14 | 0.03 | NCI |
| RMS-C11 | TE671 | ERMS-C | 0.07 | 0.77 | 0.08 | 0.03 | ATCC |
| RMS-T1 | RMS3 | ARMS-T | 0.02 | 0.93 | 0.03 | 0.06 | MSKCC |
| RMS-T2 | RMS6 | ARMS-T | 0.06 | 0.86 | 0.03 | 0.04 | MSKCC |
| RMS-T3 | RMS2 | ERMS-T | 0.08 | 0.80 | 0.07 | 0.02 | MSKCC |
| RMS-T4 | RMS5 | ERMS-T | 0.07 | 0.93 | 0.03 | 0.03 | MSKCC |
| RMS-T5 | RMS10 | ARMS-T | 0.05 | 0.84 | 0.08 | 0.03 | MSKCC |
| RMS-T6 | RT1 | RMS-T | 0.04 | 0.93 | 0.05 | 0.03 | CHTN |
| RMS-T7 | RT4 | ERMS-T | 0.10 | 0.75 | 0.05 | 0.05 | CHTN |
| RMS-T8 | RT5 | RMS-T | 0.06 | 0.90 | 0.05 | 0.02 | CHTN |
| RMS-T10 | RT2 | RMS-T | 0.02 | 0.92 | 0.06 | 0.03 | CHTN |
| RMS-T11 | RHAB2 | ERMS-T | 0.03 | 0.76 | 0.06 | 0.03 | CHTN |
| NB-C1 | KCNR | NB-C | 0.00 | 0.08 | 0.93 | 0.03 | NCI |
| NB-C2 | GICAN | NB-C | 0.03 | 0.10 | 0.70 | 0.08 | NCI |
| NB-C3 | SK-N-AS | NB-C | 0.01 | 0.26 | 0.64 | 0.04 | ATCC |
| NB-C4 | LAN5 | NB-C | 0.02 | 0.03 | 0.85 | 0.06 | NCI |
| NB-C5 | SK-N-BE2 | NB-C | 0.02 | 0.02 | 0.92 | 0.06 | ATCC |
| NB-C6 | SK-N-DZ | NB-C | 0.02 | 0.02 | 0.89 | 0.09 | ATCC |
| NB-C7 | GICAN | NB-C | 0.07 | 0.05 | 0.80 | 0.08 | NCI |
| NB-C8 | NGP | NB-C | 0.00 | 0.06 | 0.96 | 0.04 | NCI |
| NB-C9 | SH-SY5Y | NB-C | 0.06 | 0.04 | 0.85 | 0.04 | ATCC |
| NB-C10 | SK-N-FI | NB-C | 0.00 | 0.12 | 0.91 | 0.03 | ATCC |
| NB-C11 | SK-N-SH | NB-C | 0.06 | 0.01 | 0.95 | 0.05 | ATCC |
| NB-C12 | CHP-134B | NB-C | 0.02 | 0.24 | 0.41 | 0.06 | NCI |
| BL-C1 | RAMOS(RA1) | BL-C | 0.03 | 0.06 | 0.08 | 0.90 | ATCC |
| BL-C2 | ST486 | BL-C | 0.04 | 0.12 | 0.04 | 0.82 | ATCC |
| BL-C3 | CA46 | BL-C | 0.07 | 0.09 | 0.02 | 0.89 | ATCC |
| BL-C4 | ST486 | BL-C | 0.04 | 0.06 | 0.08 | 0.80 | ATCC |
| BL-C5 | RAJI | BL-C | 0.10 | 0.04 | 0.04 | 0.87 | ATCC |
| BL-C6 | MC116 | BL-C | 0.10 | 0.02 | 0.09 | 0.87 | ATCC |
| BL-C7 | DAUDI | BL-C | 0.09 | 0.04 | 0.02 | 0.93 | ATCC |
| BL-C8 | SULTAN | BL-C | 0.20 | 0.03 | 0.03 | 0.89 | ATCC |

Source label refers to the original name of the sample as labeled by the source. Histological diagnosis is defined as cancer type suffixed with -T for a tumor sample and -C for a cell line. Highlighted in gray is the ANN classification of the samples. NCI: National Cancer Institute, National Institutes of Health, ATCC: American Type Culture Collection, MSKCC: Memorial Sloan-Kettering Cancer Center, CHTN: Cooperative Human Tissue Network.

Example 4

Optimization of Genes Utilized for Classification

The contribution of each gene to the classification by the ANN models was determined by measuring the sensitivity of the classification to a change in the expression level of each gene, using the 3750 previously calibrated models.

The sensitivity to the different genes was determined by the absolute value of the partial derivative of the output with respect to the gene expressions, averaged over samples and ANN models. A large sensitivity implied that changing the expression influences the output significantly.

Figure 6:
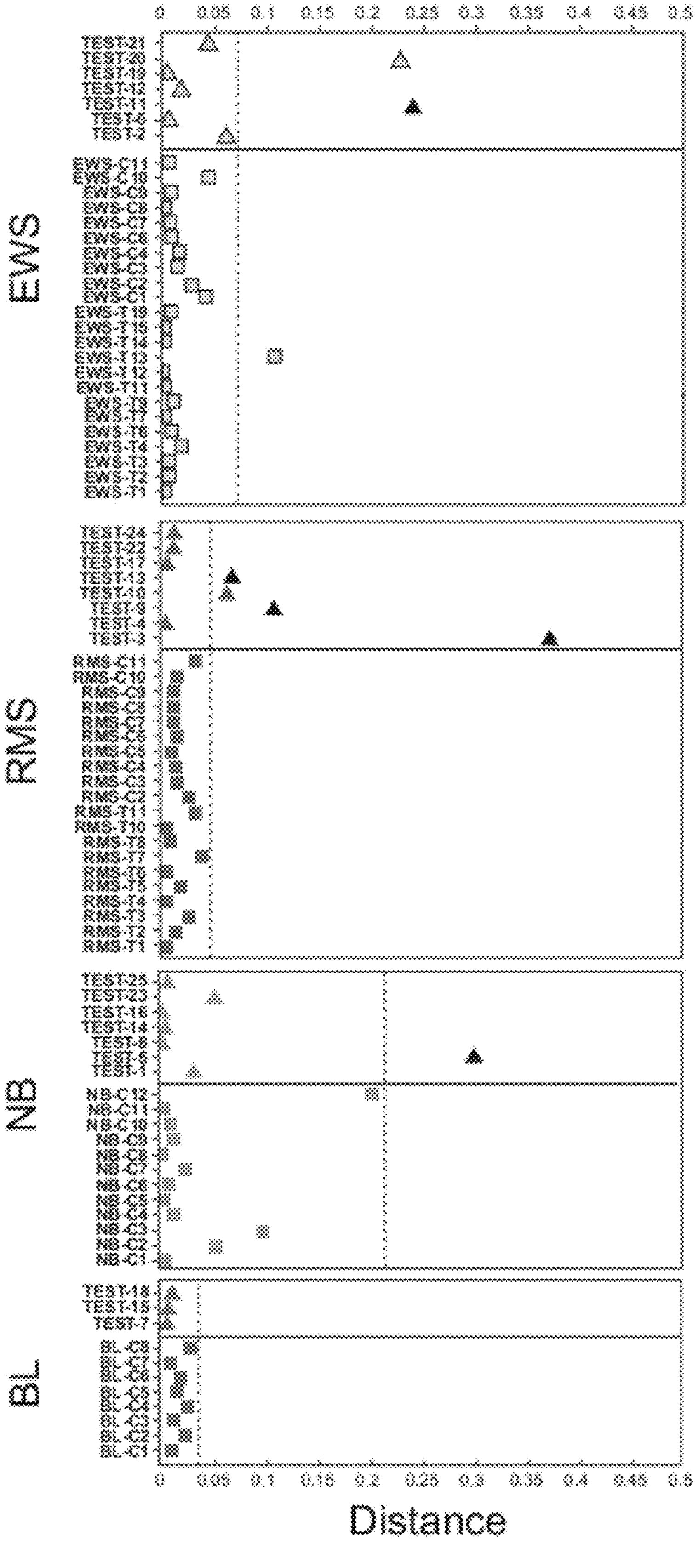
FIG. 6 represents a plot of the distance from the samples committee vote to the ideal vote for that diagnostic category.
Figure 7:
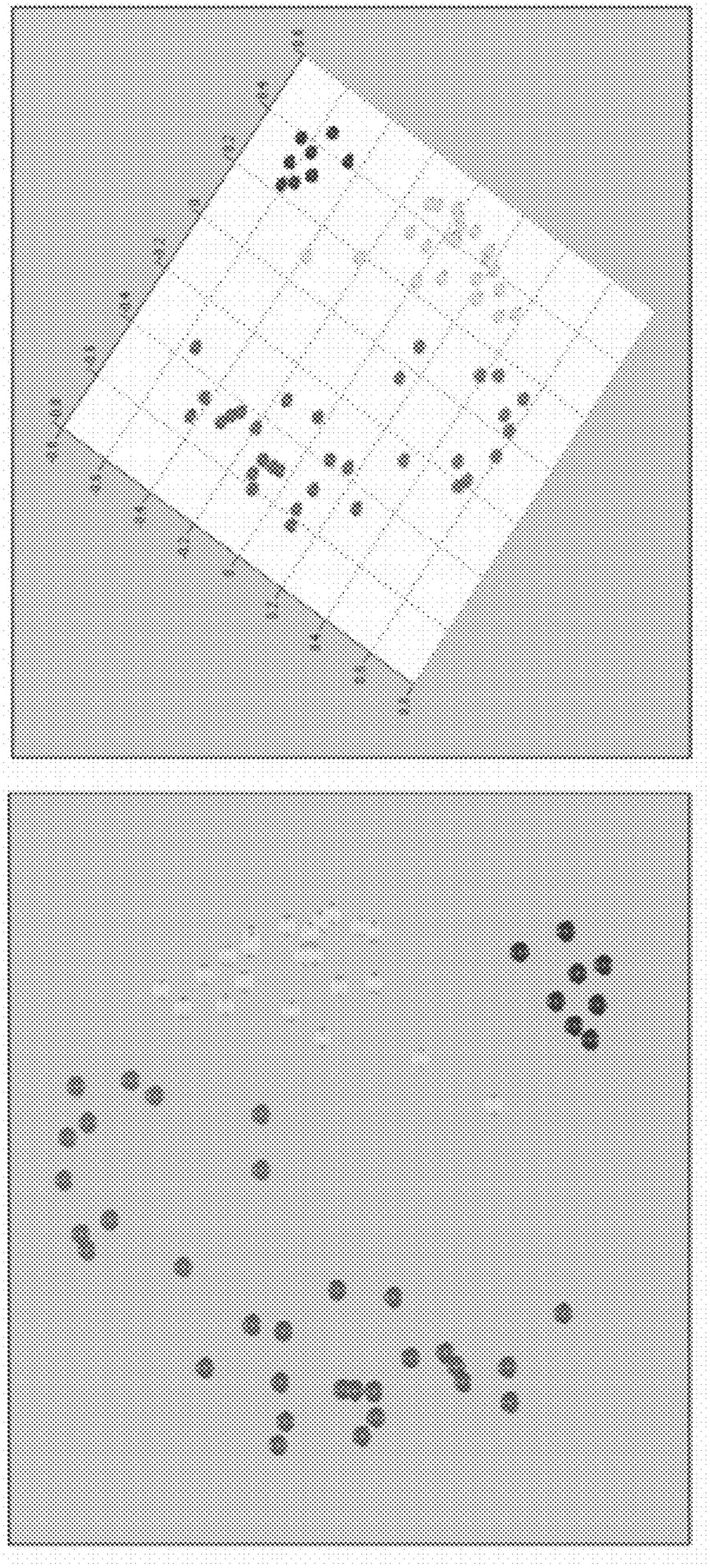
FIG. 7 represents two projections of the MDS plot of the training samples.
Figure 8:
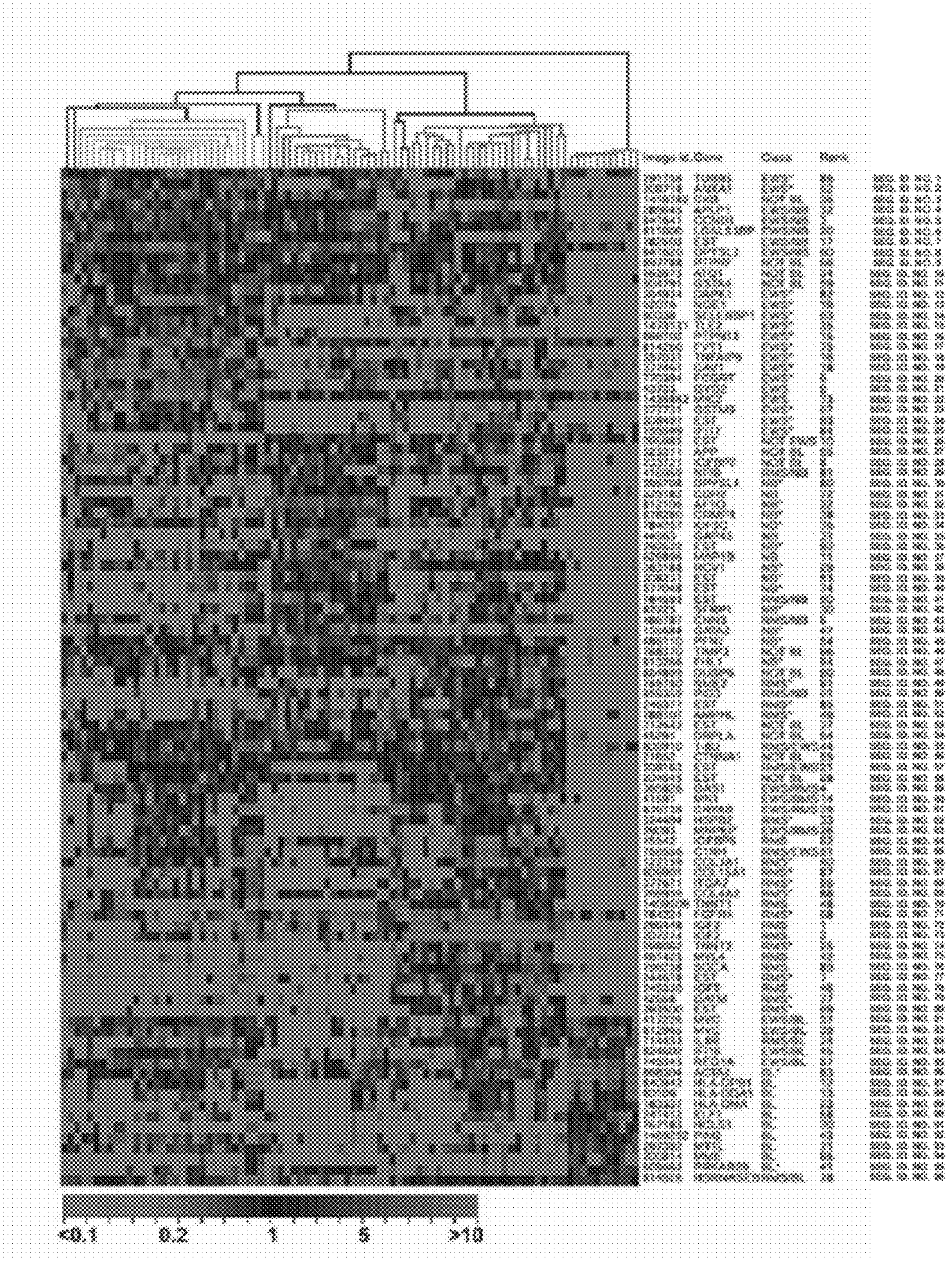
FIG. 8 represents a hierarchical clustering of the samples and genes, where each row represents one of the 96 cDNA clones, and each column represents a separate sample.

In this way the genes were ranked according to their significant for the classification. We then determined the classification error rate using increasing numbers of these ranked genes. The classification error rate minimized to 0% at 96 genes, see FIG. 5. The 10 dominant PCA components for these 96 genes contained 79% of the variance in the data matrix. Using only these 96 genes, we recalibrated the ANN models and again correctly classified all 63 samples, see FIG. 6. Moreover, multidimensional scaling (MDS) analysis using these 96 genes clearly separated the four cancer types, see FIG. 7. The top 96 discriminators represented 93 unique genes, see FIG. 8, as IGF2 was represented by three independent clones and MYC by two.

Of the 96 genes, 13 were anonymous expressed sequence tags (ESTs); 16 genes were specifically expressed in EWS, 20 in RMS, 15 in NB and 10 in BL. Twelve genes were good discriminators on the basis of lack of expression in BL and variable expression in the other three types. One gene (EST; Clone ID 295985) discriminated EWS from other cancer types by its lack of expression in this cancer. The remainder of the genes was expressed in two of the four cancer types. To our knowledge, of the 61 genes that were specifically expressed in cancer type, 41 have not been previously reported as associated with these diseases.

Example 5

Diagnostic Classification and Hierarchical Clustering

The diagnostic classification capabilities of these ANN models were then tested on a set of 25 blinded test samples. Samples were classified to a diagnostic category if they received the highest vote for that category. As this classifier had only four possible outputs, all samples were classified to one of the four categories. We therefore established a diagnostic classification method based on a statistical cutoff to enable us to reject a diagnosis of a sample classified to a given category. If a sample falls outside the 95th percentile of the probability distribution of distances between samples and their ideal output (for example for EWS it is EWS=1, RMS=NB=BL=0), its diagnosis is rejected.

TABLE 4

| Sample | ANN committee vote | | | | ANN | ANN | Histological | Source | |
|---|---|---|---|---|---|---|---|---|---|
| label | EWS | RMS | NB | BL | classification | diagnosis | diagnosis | label | Source |
| Test 1 | 0.01 | 0.07 | 0.76 | 0.06 | NB | NB | NB-C | IMR32 | ATCC |
| Test 2 | 0.67 | 0.06 | 0.08 | 0.09 | EWS | EWS | EWS-C | CHOP1 | NCI |
| Test 3 | 0.11 | 0.17 | 0.16 | 0.11 | RMS | — | Osteosarcoma-C | OsA-Cl | ATCC |
| Test 4 | 0.00 | 0.95 | 0.06 | 0.03 | RMS | RMS | ARMS-T | ARMD1 | CHTN |
| Test 5 | 0.11 | 0.11 | 0.25 | 0.10 | NB | — | Sarcoma- C | A204 | ATCC |
| Test 6 | 0.98 | 0.04 | 0.10 | 0.03 | EWS | EWS | EWS-T | 9608P053 | CHTN |
| Test 7 | 0.05 | 0.02 | 0.05 | 0.93 | BL | BL | BL-C | EB1 | ATCC |
| Test 8 | 0.00 | 0.05 | 0.94 | 0.04 | NB | NB | NB-C | SMSSAN | NCI |
| Test 9 | 0.22 | 0.60 | 0.03 | 0.06 | RMS | — | Sk. Muscle | SkM1 | CHTN |
| Test 10 | 0.10 | 0.68 | 0.11 | 0.04 | RMS | — | ERMS-T | ERDM1 | CHTN |
| Test 11 | 0.39 | 0.04 | 0.28 | 0.15 | EWS | — | Prostate Ca.-C | PC3 | ATCC |
| Test 12 | 0.89 | 0.05 | 0.14 | 0.03 | EWS | EWS | EWS-T | SARC67 | CHTN |
| Test 13 | 0.20 | 0.7 | 0.03 | 0.05 | RMS | — | Sk. Muscle | SkM2 | CHTN |
| Test 14 | 0.03 | 0.02 | 0.90 | 0.07 | NB | NB | NB-T | NB3 | DZNSG |
| Test 15 | 0.06 | 0.03 | 0.05 | 0.91 | BL | BL | BL-C | EB2 | ATCC |
| Test 16 | 0.03 | 0.02 | 0.93 | 0.05 | NB | NB | NB-T | NB1 | DZNSG |
| Test 17 | 0.01 | 0.90 | 0.05 | 0.03 | RMS | RMS | ARMS-T | ARMD2 | CHTN |
| Test 18 | 0.06 | 0.04 | 0.04 | 0.88 | BL | BL | BL-C | GA10 | ATCC |
| Test 19 | 0.99 | 0.02 | 0.04 | 0.05 | EWS | EWS | EWS-T | ET3 | CHTN |
| Test 20 | 0.40 | 0.30 | 0.10 | 0.06 | EWS | — | EWS-T | 9903P1339 | CHTN |
| Test 21 | 0.81 | 0.19 | 0.12 | 0.04 | EWS | EWS | EWS-T | ES23 | MSKCC |
| Test 22 | 0.01 | 0.88 | 0.09 | 0.04 | RMS | RMS | ERMS-T | ERMD2 | CHTN |
| Test 23 | 0.07 | 0.08 | 0.70 | 0.06 | NB | NB | NB-T | NB2 | DZNSG |
| Test 24 | 0.05 | 0.87 | 0.06 | 0.03 | RMS | RMS | ERMS-T | RMS4 | MSKCC |
| Test 25 | 0.05 | 0.02 | 0.89 | 0.06 | NB | NB | NB-T | NB4 | DZNSG |

Source label refers to the original name of the sample as designated by the source. Histological diagnosis is defined as cancer type suffixed with –T for a tumor sample and –C for a cell line. Normal skeletal muscle (Sk. Muscle) is also included in the test set. The ANN classification as determined by the committee vote is bolded, NCI: National Cancer Institute, National Institutes of Health, ATCC: American Type Culture Collection, MSKCC: Memorial Sloan-Kettering Cancer Center, CHTN; Cooperative Human Tissue Network, DZNSG: German Cancer Research Center, Heidelberg.

The test samples contained both tumors (5 EWS, 5 RMS and 4 NB) and cell lines (1 EWS, 2 NB and 3 BL). The ability of these models to reject a diagnosis on 5 non-SRBCTs was also tested (consisting of 2 normal muscle tissues (Tests 9 and 13) and 3 cell lines including an undifferentiated sarcoma (Test 5), osteosarcoma (Test 3) and a prostate carcinoma (Test 11)). Using the 3750 ANN models calibrated with the 96 genes, we correctly classified 100% of the 20 SRBCT tests (FIG. 6 and TABLE 4) as well as all 63 training samples, see TABLE 2. Three of these samples, Test 10, Test 20 and EWS-T13 were correctly assigned to their categories (RMS, EWS and EWS respectively), having received the highest vote for their respective categories. However, their distance from a perfect vote was greater than the expected 95th percentile distance (FIG. 6); therefore, we could not confidently diagnose them by this criterion. All of the five non-SRBCT samples were excluded from any of the four diagnostic categories, since they fell outside the 95th percentiles. Using these criteria for all 88 samples, the sensitivity of the ANN models for diagnostic classification was 93% for EWS, 96% for RMS and 100% for both NB and BL. The specificity was 100% for all four diagnostic categories.

Figure 9:
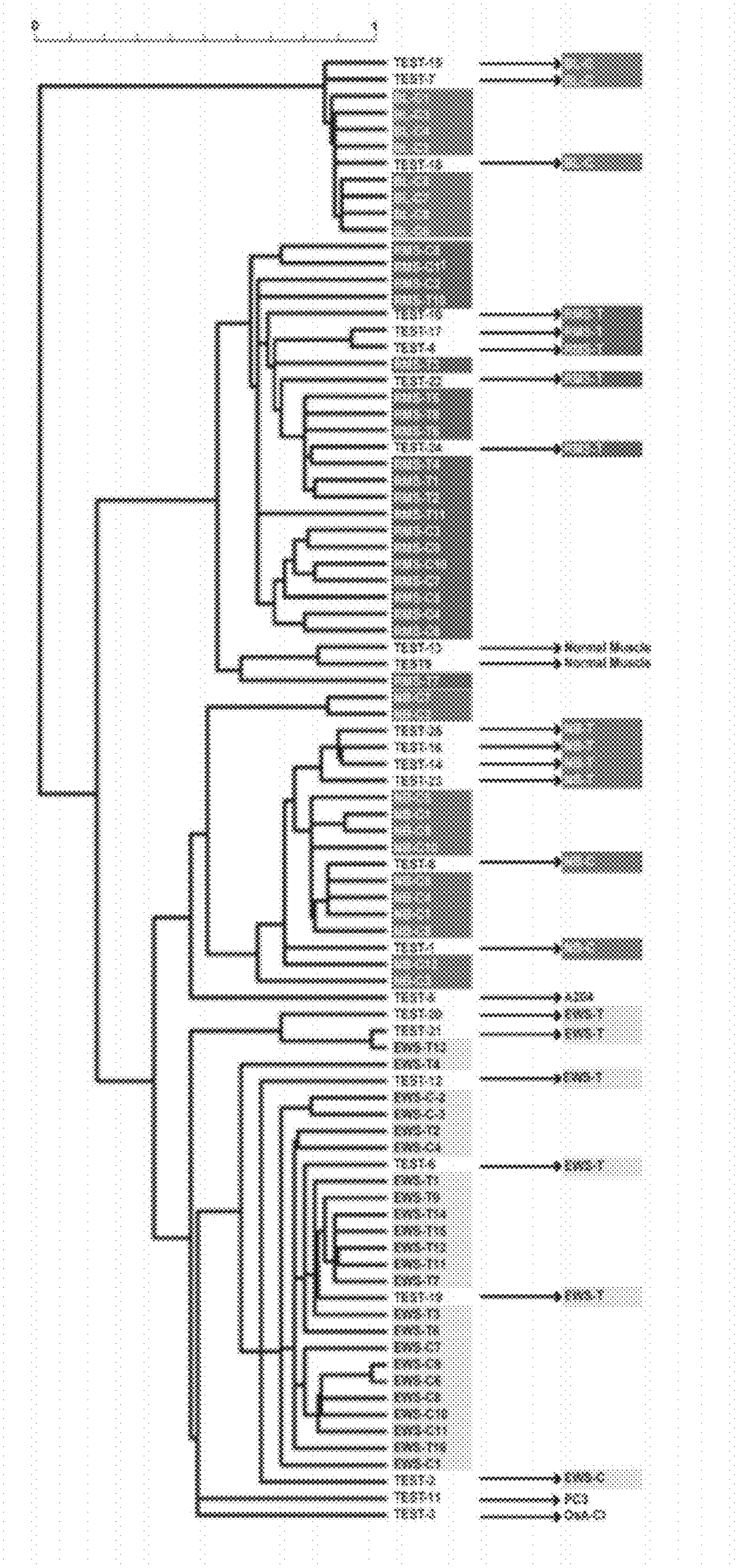
FIG. 9 represents a hierarchical clustering dendrogram of the samples in FIG. 8.

Also, hierarchical clustering using the 96 genes, identified from the ANN models, correctly clustered all 20 of the test samples (FIG. 9). Moreover, the two pairs of samples that were derived from two cell lines, BL-C2 and C4 (ST486) and NB-C2 and C7 (GICAN), were adjacent to one another in the same cluster.

Example 6

Expression of FGFR4 on SRBCT Tissue Array

To confirm the effectiveness of the ANN models to identify genes that show preferential high expression in specific cancer types at the protein level, we performed immunohistochemistry on SRBCT tissue arrays for the expression of fibroblast growth factor receptor 4 (FGFR4). This tyrosine kinase receptor is expressed during myogenesis but not in adult muscle, and is of interest because of its potential role in tumor growth and in prevention of terminal differentiation in muscle. Moderate to strong cytoplasmic immunostaining for FGFR4 was seen in all 26 RMSs tested (17 alveolar, 9 embryonal). We also observed generally weaker staining in EWS and NHL in agreement with the microarray results, except for one of anaplastic large cell lymphoma that was strongly positive (data not shown).

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and a computer data product containing a computer program for classifying and diagnosing disease using artificial neural networks.

The above specification, examples and data provide a complete description of the manufacture and use of the composition of the invention. Since many embodiments of the invention can be made without departing from the spirit and scope of the invention, the invention resides in the claims hereinafter appended.

The claimed invention is:

1. A method of determining whether a subject has a cancer selected from the group consisting of neuroblastoma, rhabdomyosarcoma, non-Hodgkin's lymphoma, and Ewing's tumor comprising:

(a) processing a biological sample from a subject whose cancer is unknown to obtain high dimensional experimental data selected from the group consisting of gene expression levels, protein expression levels, single nucleotide polymorphisms, or comparative genomic analysis;

(b) detecting the presence of a first set of multiple data points in the high dimensional experimental data, wherein the first set of multiple data points is predictive for distinguishing the presence of neuroblastoma, rhabdomyosarcoma, non-Hodgkin's lymphoma, and Ewing's tumor from one another, as determined by training a supervised pattern recognition method using data obtained from a biological sample known to be either a neuroblastoma, rhabdomyosarcoma, non-Hodgkin's lymphoma, or Ewing's tumor to obtain a probability distribution relationship between the data obtained from each of the biological samples and the type of cancer; ranking individual data points from said first set of high dimensional data by determining the sensitivity of the data point to the classification of each type of cancer, wherein said ranking is dependent on an outcome of said supervised pattern recognition method; and choosing a first set of multiple data points from said high dimensional data as predictive for the type of cancer, wherein said choice is based on said relative ranking of said individual data points; and (c) determining whether the sample from the subject whose cancer is unknown can be classified as one of neuroblastoma, rhabdomyosarcoma, non-Hodgkin's lymphoma, or Ewing's tumor by detecting the presence of said first set of multiple data points in data obtained from the biological sample.

2. The method of claim 1, wherein processing the biological sample comprises isolating nucleic acids or proteins from the biological sample and detecting the nucleic acids or proteins from the sample to determine gene expression levels, protein expression levels, single nucleotide polymorphisms, or comparative genomic analysis of each sample.

3. The method of claim 1, wherein said high dimensional data is gene expression data.

4. The method of claim 3, wherein said gene expression data is obtained by using a cDNA or an oligonucleotide microarray.

5. The method of claim 1, wherein said first set of multiple data points comprise at least 96 individual data points.

6. The method of claim 1, wherein the first set of multiple data points is determined by the method comprising:

(a) processing a first biological sample known to be of neuroblastoma, a second biological sample known to be of rhabdomyosarcoma, a third biological sample known to be of non Hodgkin's lymphoma, and a fourth biological sample known to be of Ewing tumor to obtain a first set of high dimensional experimental data;

(b) filtering said first set of data by removing data that does not meet a predetermined threshold;

(c) reducing the dimensionality of said first set of data.

7. A computer implemented method comprising:

providing a computing device comprising a central processing unit having instructions for implementing steps of a method comprising:

(a) receiving high dimensional experimental data from a biological sample from a subject whose type of cancer is unknown and providing the high dimensional data to a receiver module;

(b) detecting the presence of a first set of multiple data points in the high dimensional experimental data, wherein the first set of multiple data points is predictive for distinguishing a cancer selected from the group consisting of neuroblastoma, rhabdomyosarcoma, non-Hodgkin's lymphoma, and Ewing's tumor as determined by training a supervised pattern recognition method using data obtained from a biological sample known to be either a neuroblastoma, rhabdomyosarcoma, non-Hodgkin's lymphoma, or Ewing's tumor to obtain a probability distribution relationship between the data obtained from each of the biological samples and the type of cancer; ranking individual data points from said first set of high dimensional data by determining the sensitivity of the data point to the classification of each type of cancer, wherein said ranking is dependent on an outcome of said supervised pattern recognition method; and choosing a first set of multiple data points from said high dimensional data as predictive for the type of cancer, wherein said choice is based on said relative ranking of said individual data points using a diagnostic module; and (c) determining whether the biological sample from the subject whose cancer is unknown can be classified as one of neuroblastoma, rhabdomyosarcoma, non-Hodgkin's lymphoma, or Ewing's tumor the by identifying the presence of said first set of multiple data points in data obtained from the biological sample.

8. The method of claim 7, further comprising obtaining high dimensional experimental data from the biological sample by a method comprises isolating nucleic acids or proteins from each biological sample and detecting the nucleic acids or proteins from each sample to determine gene expression levels, protein expression levels, single nucleotide polymorphisms, or comparative genomic analysis of each sample.

9. The method of claim 7, wherein the first set of multiple data points is determined by a method comprising:

(a) receiving high dimensional experimental data from a first biological sample known to be of neuroblastoma, a second biological sample known to be of rhabdomyosarcoma, a third biological sample known to be of non-Hodgkin's lymphoma, and a fourth biological sample known to be of Ewing tumor by a receiver module of the computer;

(b) filtering the experimental data by removing data that does not meet a predetermined threshold by a filter module;

(c) reducing the dimensionality of the experimental data using one or more methods;

(d) dividing the experimental data into a training data set and a validation data set;

(e) generating a first probability distribution relationship between the experimental data and the type of cancer using the training data and a training module;

(f) validating the performance of the first probability distribution relationship using the validation data set;

(g) choosing a first set of multiple data points from said high dimensional data as predictive for the type of cancer, wherein said choice is based on said relative ranking of said individual data points using a ranking module.

10. A non-transitory computer readable storage medium comprising:

a receiver module for receiving data representing experimental gene expression data obtained from a biological sample from a subject whose type of cancer is unknown; and a diagnostic module containing instructions to distinguish between the presence of one of a cancer selected from the group neuroblastoma, rhabdomyosarcoma, non-Hodgkin's lymphoma, and Ewing's tumor by detecting the presence of a first set of multiple data points in gene expression data obtained from a biological sample from the subject, wherein the first set of multiple data points is predictive for the type of cancer selected from the group consisting of neuroblastoma, rhabdomyosarcoma, non-Hodgkin's lymphoma, and Ewing's tumor as determined by a trained supervised pattern recognition method.

* * * * *

SEQUENCE LISTING

```
<160> NUMBER OF SEQ ID NOS: 99

<210> SEQ ID NO 1
<211> LENGTH: 2318
<212> TYPE: DNA
<213> ORGANISM: Homo sapiens

<400> SEQUENCE: 1

cgcagggacc gtgctccgcc gtctccgccg catcttccac cctcgccgcc gccgcagctc     60

cccgcgctcg tgccaccgcc gccgcgtcca ccctcagcgc caccgccatg cgggagatcg    120

tgcacctgca ggccggccag tgcggcaacc agatcggggc caagttttgg gaggttatca    180

gtgacgaaca tggcatcgac cccacaggca cataccatgg ggacagtgac ctgcaactgg    240

agaggatcaa cgtgtactac aacgaggcca caggaggaaa ttatgtcccc agagcggtgc    300

tggtggacct ggaacccggc accatggact ctgtccgttc tggcccccttc ggtcagatct    360

ttcggccgga caacttcgtg tttggccaat ccggagccgg caacaactgg gcaaaggggc    420

actacacgga gggcgcagag ctggtggacg ctgtcctgga cgtagtccgg aaggaggccg    480

agagctgcga ctgccttcag ggcttccagc tgacccactc gctgggggt ggcacggggt    540

ccggaatggg cacgctgctc atcagtaaga tccgcgagga gttcccagac cgcatcatga    600

acaccttcag cgtggtgccc tcgcccaaag tgtcagacac ggtggtggag ccctacaacg    660

ccacgctgtc tgtgcaccag ctggtggaga atacggatga gacctactgc atcgacaacg    720

aggcactcta cgacatctgt ttccgcaccc tcaagctgac cacccccacc tacggggacc    780

tcaaccacct ggtgtcggcc accatgagcg gggtcaccac ctgcctgcgc ttcccgggcc    840

agctgaacgc cgacctgcgc aagctggccg tcaacatggt tccctttcct cgcctgcact    900

tcttcatgcc cggcttcgca cccctgacca gccggggcag ccagcagtac cgggccctga    960

cggtgcccga gctcacccag cagatgttcg atgccaagaa catgatggcg gcgtgcgacc   1020

cgcgccacgg ccgctacctg accgtggccg ccgtgttccg gggccgcatg tccatgaagg   1080

aggtggacga gcagatgctg agcgtgcaga gcaagaacag cagctacttc gtggagtgga   1140
```

-continued tccccaacaa cgtgaagacg gccgtgtgcg acatcccgcc ccgcggcctg aagatggccg 1200
cgaccttcat cggcaacagc acggccatcc aggagctgtt caagcgcatc tccgagcagt 1260
tcacggccat gttccggcgc aaggccttct tgcactggta cacgggcgag ggcatggacg 1320
agatggagtt caccgaggcc gagagcaaca tgaatgacct ggtatctgag taccagcagt 1380
accaggacgc cacggccgag gagggcgagt tcgaggagga ggcggaggag gaggtggcct 1440
aggctgctcc catcgcttcc cacctgtccc ctcgaggctt ctgacctttg atccgctagg 1500
ccccccatct ctgaacccta gagccccgct ttccctccaa ggctgactcc ccgctgaccc 1560
taacaatacc tttggagctc gctttacctc tggctacttc atctccgacc ctggctcccc 1620
tttgagccct aatttatctt taaccccctt gagctcttcc aaccttgaca ttcccaggag 1680
gagccccgct tcaccccttc tgactctgga aaccgcacct ttaactttgc agaccttcct 1740
tcacccctga cttctgcttc acctttgacc tctgccccc atgaatccca ttttacctct 1800
agacctataa gttctggttt atgtttgacc cctccctctg agctgcactt caccgctgac 1860
cttgcctcac ctttaacccc ccacctgagc cccagctcct acctctgacc ccaacttctc 1920
tttgatctct gaatcccctc tgactccaac ttctctttca ccctctatga gtcccatttt 1980
acttctacac ctgcaagtcc tggtttatat tggacccctc cctccgagct gcagttcacc 2040
tttgaccttg cctcaccttt caccccccac cccccacagc gtcagctcct acctctgacc 2100
ccagcttctc tctgattccc acaggcccca tgcatcctcc ctgcctcact cccctcagcc 2160
cctgccgacc ttagcttatc tgggagagaa acaaggcctg gtgcctgtga ggaagagagg 2220
tcacccctac cctccctccc cgcttccctg cctcaccctc aataaataaa ttaattgttg 2280
tcatggaaaa aaaaaaaaaa aaaaaaaaaa aaaaaaaa 2318

<210> SEQ ID NO 2
<211> LENGTH: 1399
<212> TYPE: DNA
<213> ORGANISM: Homo sapiens

<400> SEQUENCE: 2
agtgtgaaat cttcagagaa gaatttctct ttagttcttt gcaagaaggt agagataaag 60
acactttttc aaaaatggca atggtatcag aattcctcaa gcaggcctgg tttattgaaa 120
atgaagagca ggaatatgtt caaactgtga agtcatccaa aggtggtccc ggatcagcgg 180
tgagccccta tcctaccttc aatccatcct cggatgtcgc tgccttgcat aaggccataa 240
tggttaaagg tgtggatgaa gcaaccatca ttgacattct aactaagcga aacaatgcac 300
agcgtcaaca gatcaaagca gcatatctcc aggaaacagg aaagcccctg gatgaaacac 360
ttaagaaagc ccttacaggt caccttgagg aggttgtttt agctctgcta aaaactccag 420
cgcaatttga tgctgatgaa cttcgtgctg ccatgaaggg ccttggaact gatgaagata 480
ctctaattga gattttggca tcaagaacta acaaagaaat cagagacatt aacagggtct 540
acagagagga actgaagaga gatctggcca aagacataac ctcagacaca tctggagatt 600
ttcggaacgc tttgcttttct cttgctaagg gtgaccgatc tgaggacttt ggtgtgaatg 660
aagacttggc tgattcagat gccagggcct tgtatgaagc aggagaaagg agaaagggga 720
cagacgtaaa cgtgttcaat accatcctta ccaccagaag ctatccacaa cttcgcagag 780
tgtttcagaa atacaccaag tacagtaagc atgacatgaa caaagttctg gacctggagt 840
tgaaaggtga cattgagaaa tgcctcacag ctatcgtgaa gtgcgccaca agcaaaccag 900
ctttctttgc agagaagctt catcaagcca tgaaaggtgt tggaactcgc cataaggcat 960

-continued tgatcaggat tatggtttcc cgttctgaaa ttgacatgaa tgatatcaaa gcattctatc 1020
agaagatgta tggtatctcc ctttgccaag ccatcctgga tgaaaccaaa ggagattatg 1080
agaaaatcct ggtggctctt tgtggaggaa actaaacatt cccttgatgg tctcaagcta 1140
tgatcagaag actttaatta tatattttca tcctataagc ttaaatagga aagtttcttc 1200
aacaggatta cagtgtagct acctacatgc tgaaaaatat agcctttaaa tcatttttat 1260
attataactc tgtataatag agataagtcc atttttttaaa aatgttttcc ccaaaccata 1320
aaaccctata caagttgttc tagtaacaat acatgagaaa gatgtctatg tagctgaaaa 1380
taaaatgacg tcacaagac 1399

<210> SEQ ID NO 3
<211> LENGTH: 1432
<212> TYPE: DNA
<213> ORGANISM: Homo sapiens

<400> SEQUENCE: 3
gctgttcggc ctgcgtcgct ccgggagctg ccgacggacg gagcgccccc gcccccgccc 60
ggccgcccgc ccgccgccgc catgcccttc tccaacagcc acaacgcact gaagctgcgc 120
ttcccggccg aggacgagtt ccccgacctg agcgcccaca acaaccacat ggccaaggtg 180
ctgacccccg agctgtacgc ggagctgcgc gccaagagca cgccgagcgg cttcacgctg 240
gacgacgtca tccagacagg cgtggacaac ccgggccacc cgtacatcat gaccgtgggc 300
tgcgtggcgg gcgacgagga gtcctacgaa gtgttcaagg atctcttcga ccccatcatc 360
gaggaccggc acggcggcta caagcccagc gatgagcaca agaccgacct caaccccgac 420
aacctgcagg gcggcgacga cctggacccc aactacgtgc tgagctcgcg ggtgcgcacg 480
ggccgcagca tccgtggctt ctgcctcccc ccgcactgca gccgcgggga gcgccgcgcc 540
atcgagaagc tcgcggtgga agccctgtcc agcctggacg gcgacctggc gggccgatac 600
tacgcgctca agagcatgac ggaggcggag cagcagcagc tcatcgacga ccacttcctc 660
ttcgacaagc ccgtgtcgcc cctgctgctg gcctcgggca tggcccgcga ctggcccgac 720
gcccgcggta tctggcacaa tgacaataag accttcctgg tgtgggtcaa cgaggaggac 780
cacctgcggg tcatctccat gcagaagggg ggcaacatga aggaggtgtt cacccgcttc 840
tgcaccggcc tcacccagat tgaaactctc ttcaagtcta aggactatga gttcatgtgg 900
aaccctcacc tgggctacat cctcacctgc ccatccaacc tgggcaccgg gctgcgggca 960
ggtgtgcata tcaagctgcc caacctgggc aagcatgaga agttctcgga ggtgcttaag 1020
cggctgcgac ttcagaagcg aggcacaggc ggtgtggaca cggctgcggt gggcggggtc 1080
ttcgacgtct ccaacgctga ccgcctgggc ttctcagagg tggagctggt gcagatggtg 1140
gtggacggag tgaagctgct catcgagatg gagcagcggc tggagcaggg ccaggccatc 1200
gacgacctca tgcctgccca gaaatgaagc ccggcccaca cccgacacca gccctgctgc 1260
ttcctaactt attgcctggg cagtgcccac catgcacccc tgatgttcgc cgtctggcga 1320
gcccttagcc ttgctgtaga gacttccgtc acccttggta gagtttattt ttttgatggc 1380
taagatactg ctgatgctga aataaactag ggttttggcc tgcctgcgtc tg 1432

<210> SEQ ID NO 4
<211> LENGTH: 2384
<212> TYPE: DNA
<213> ORGANISM: Homo sapiens

<400> SEQUENCE: 4

-continued

```
gagctcctgt caccgctggg gccgggccgg gcgggagtgc aggggacgtg agggcgcaag     60
ggccgggaca tggggcccgc cagccccgct gctcgcggtc taagtcgccg cccgggccag    120
ccgccgctgc cgctgctgct gccactattg ctgctgcttc tgcgcgcgca gcccgccatc    180
gggagcctgg ccggtgggag ccccggcgcg gccgaggccc cggggtcggc ccaggtggct    240
ggactatgcg ggcgcctaac ccttcaccgg gacctgcgca ccggccgctg ggaaccagac    300
ccacagcgct ctcgacgctg tctccgggac ccgcagcgcg tgctggagta ctgcagacag    360
atgtacccgg agctgcagat tgcacgtgtg gagcaggcta cgcaggccat ccccatggag    420
cgctggtgcg gggggttcccg gagcggcagc tgcgcccacc cccaccacca ggttgtgccc    480
ttccgctgcc tgcctggtga atttgtgagt gaggccctgc tggtgcctga aggctgccgg    540
ttcttgcacc aggagcgcat ggaccaatgt gagagttcaa cccggaggca tcaggaggca    600
caggaggcct gcagctccca gggcctcatc ctgcacggct cgggcatgct cttaccctgt    660
ggctcggatc ggttccgtgg tgtggagtat gtgtgctgtc cccctccagg gacccccgac    720
ccatctggga cagcagttgg tgacccctcc acccggtcct ggcccccggg gagcagagta    780
gagggggctg aggacgagga agaggaggaa tccttcccac agccagtaga tgattacttc    840
gtggagcctc cgcaggctga agaggaagag gaaacggtcc cacccccaag ctcccataca    900
cttgcagtgg tcggcaaagt cactcccacc ccgaggccca cagacggtgt ggatatttac    960
tttggcatgc ctggggaaat cagtgagcac gaggggttcc tgagggccaa gatggacctg   1020
gaggagcgta ggatgcgcca gattaatgag gtgatgcgtg aatgggccat ggcagacaac   1080
cagtccaaga acctgcctaa agccgacaga caggccctga atgagcactt ccagtccatt   1140
ctgcagactc tggaggagca ggtgtctggt gagcgacagc gcctggtgga aacccacgcc   1200
acccgcgtca tcgcccttat caacgaccag cgccgggctg ccttggaggg cttcctggca   1260
gccctgcagg cagatccgcc tcaggcggag cgtgtcctgt tggccctgcg gcgctacctg   1320
cgtgcggagc agaaggaaca gaggcacacg ctgcgccact accagcatgt ggccgccgtg   1380
gatcccgaga aggcacagca gatgcgcttc caggtgcata cccaccttca agtgattgag   1440
gagagggtga atcagagcct gggcctgctt gaccagaacc cccacctggc tcaggagctg   1500
cggccccaaa tccaggaact cctccactct gaacacctgg gtcccagtga attggaagcc   1560
cctgcccctg ggggcagcag cgaggacaag ggtgggctgc agcctccaga ttccaaggat   1620
gacaccccca tgacccttcc aaaagggtcc acagaacaag atgctgcatc ccctgagaaa   1680
gagaagatga acccgctgga acagtatgag cgaaaggtga atgcgtctgt tccaaggggt   1740
ttccctttcc actcatcgga gattcagagg gatgagctgg caccagctgg gacaggggtg   1800
tcccgtgagg ctgtgtcggg tctgctgatc atgggagcgg gcggaggctc cctcatcgtc   1860
ctctccatgc tgctcctgcg caggaagaag ccctacgggg ctatcagcca tggcgtggtg   1920
gaggtggacc ccatgctgac cctggaggag cagcagctcc gcgaactgca gcggcacggc   1980
tatgagaacc ccacttaccg cttcctggag gaacgaccct gacccggccc ccttcacccc   2040
ttcagccgag cccagacctc ccctcttcct ggagccccag aaccccaact cccagcctag   2100
ggcagcaggg agtcttgaag tgatcatttc acacccttttt gtgagacggc tggaaattct   2160
tatttcccct ttccaattcc aaaattccat ccctaagaat tcccagatag tcccagcagc   2220
ctccccacgt ggcacctcct caccttaatt tattttttaa gtttatttat ggctctttaa   2280
ggtgaccgcc accttggtcc tagtgtctat tccctggaat tcaccctctc atgtttccct   2340
actaacatcc caataaagtc ctcttcccta aaaaaaaaaa aaaa                    2384
```

<210> SEQ ID NO 5
<211> LENGTH: 1325
<212> TYPE: DNA
<213> ORGANISM: Homo sapiens

<400> SEQUENCE: 5
gcagtagcag cgagcagcag agtccgcacg ctccggcgag gggcagaaga gcgcgaggga 60
gcgcggggca gcagaagcga gagccgagcg cggacccagc caggacccac agccctcccc 120
agctgcccag gaagagcccc agccatggaa caccagctcc tgtgctgcga agtggaaacc 180
atccgccgcg cgtaccccga tgccaacctc ctcaacgacc gggtgctgcg ggccatgctg 240
aaggcggagg agacctgcgc gccctcggtg tcctacttca aatgtgtgca gaaggaggtc 300
ctgccgtcca tgcggaagat cgtcgccacc tggatgctgg aggtctgcga ggaacagaag 360
tgcgaggagg aggtcttccc gctggccatg aactacctgg accgcttcct gtcgctggag 420
cccgtgaaaa agagccgcct gcagctgctg ggggccactt gcatgttcgt ggcctctaag 480
atgaaggaga ccatccccct gacggccgag aagctgtgca tctacaccga cggctccatc 540
cggcccgagg agctgctgca aatggagctg ctcctggtga acaagctcaa gtggaacctg 600
gccgcaatga ccccgcacga tttcattgaa cacttcctct ccaaaatgcc agaggcggag 660
gagaacaaac agatcatccg caaacacgcg cagaccttcg ttgcctcttg tgccacagat 720
gtgaagttca tttccaatcc gccctccatg gtggcagcgg ggagcgtggt ggccgcagtg 780
caaggcctga acctgaggag ccccaacaac ttcctgtcct actaccgcct cacacgcttc 840
ctctccagag tgatcaagtg tgacccagac tgcctccggg cctgccagga gcagatcgaa 900
gccctgctgg agtcaagcct gcgccaggcc cagcagaaca tggaccccaa ggccgccgag 960
gaggaggaag aggaggagga ggaggtggac ctggcttgca cacccaccga cgtgcgggac 1020
gtggacatct gaggggccca ggcaggcggg cgccaccgcc acccgcagcg agggcggagc 1080
cggccccagg tgctccacat gacagtccct cctctccgga gcattttgat accagaaggg 1140
aaagcttcat tctccttgtt gttggttgtt ttttcctttg ctctttcccc cttccatctc 1200
tgacttaagc aaaagaaaaa gattacccaa aaactgtctt taaaagagag agagagaaaa 1260
aaaaaaaaaa aaaaaaaaaa aaaaaaaaaa aaaaaaaaaa aaaaaaaaaa aaaaaaaaaa 1320
aaaaa 1325

<210> SEQ ID NO 6
<211> LENGTH: 2254
<212> TYPE: DNA
<213> ORGANISM: Homo sapiens

<400> SEQUENCE: 6
aatcgaaagt agactctttt ctgaagcatt tcctgggatc agcctgacca cgctccatac 60
tgggagaggc ttctgggtca aaggaccagt ctgcagaggg atcctgtggc tggaagcgag 120
gaggctccac acggccgttg cagctaccgc agccaggatc tgggcatcca ggcacggcca 180
tgacccctcc gaggctcttc tgggtgtggc tgctggttgc aggaacccaa ggcgtgaacg 240
atggtgacat gcggctggcc gatgggggcg ccaccaacca gggccgcgtg gagatcttct 300
acagaggcca gtggggcact gtgtgtgaca acctgtggga cctgactgat gccagcgtcg 360
tctgccgggc cctgggcttc gagaacgcca cccaggctct gggcagagct gccttcgggc 420
aaggatcagg ccccatcatg ctggacgagg tccagtgcac gggaaccgag gcctcactgg 480
ccgactgcaa gtccctgggc tggctgaaga gcaactgcag gcacgagaga gacgctggtg 540

-continued tggtctgcac caatgaaacc aggagcaccc acaccctgga cctctccagg gagctctcgg 600
aggcccttgg ccagatcttt gacagccagc ggggctgcga cctgtccatc agcgtgaatg 660
tgcagggcga ggacgccctg ggcttctgtg gccacacggt catcctgact gccaacctgg 720
aggcccaggc cctgtggaag gagccgggca gcaatgtcac catgagtgtg gatgctgagt 780
gtgtgcccat ggtcagggac cttctcaggt acttctactc ccgaaggatt gacatcaccc 840
tgtcgtcagt caagtgcttc cacaagctgg cctctgccta tggggccagg cagctgcagg 900
gctactgcgc aagcctcttt gccatcctcc tcccccagga cccctcgttc cagatgcccc 960
tggacctgta tgcctatgca gtggccacag gggacgccct gctggagaag ctctgcctac 1020
agttcctggc ctggaacttc gaggccttga cgcaggccga ggcctggccc agtgtcccca 1080
cagacctgct ccaactgctg ctgcccagga gcgacctggc ggtgcccagc gagctggccc 1140
tactgaaggc cgtggacacc tggagctggg gggagcgtgc ctcccatgag gaggtggagg 1200
gcttggtgga gaagatccgc ttccccatga tgctccctga ggagctcttt gagctgcagt 1260
tcaacctgtc cctgtactgg agccacgagg ccctgttcca gaagaagact ctgcaggccc 1320
tggaattcca cactgtgccc ttccagttgc tggcccggta caaaggcctg aacctcaccg 1380
aggataccta caagccccgg atttacacct cgcccacctg gagtgccttt gtgacagaca 1440
gttcctggag tgcacggaag tcacaactgg tctatcagtc cagacggggg cctttggtca 1500
aatattcttc tgattacttc caagcccccct ctgactacag atactacccc taccagtcct 1560
tccagactcc acaacacccc agcttcctct tccaggacaa gagggtgtcc tggtccctgg 1620
tctacctccc caccatccag agctgctgga actacggctt ctcctgctcc tcggacgagc 1680
tccctgtcct gggcctcacc aagtctggcg gctcagatcg caccattgcc tacgaaaaca 1740
aagccctgat gctctgcgaa gggctcttcg tggcagacgt caccgatttc gagggctgga 1800
aggctgcgat tcccagtgcc ctggacacca acagctcgaa gagcacctcc tccttcccct 1860
gcccggcagg gcacttcaac ggcttccgca cggtcatccg ccccttctac ctgaccaact 1920
cctcaggtgt ggactagacg cgtggccaag ggtggtgaga accggagaac cccaggacgc 1980
cctcactgca ggctcccctc ctcggcttcc ttcctctctg caatgacctt caacaaccgg 2040
ccaccagatg tcgccctact cacctgaggc tcagcttcaa gaaattactg gaaggcttcc 2100
actagggtcc accaggagtt ctcccaccac ctcaccagtt tccaggtggt aagcaccagg 2160
aggccctcga ggttgctctg gatcccccca cagcccctgg tcagtctgcc cttgtcactg 2220
gtctgaggtc attaaaatta cattgaggtt ccta 2254

<210> SEQ ID NO 7
<211> LENGTH: 4213
<212> TYPE: DNA
<213> ORGANISM: Homo sapiens

<400> SEQUENCE: 7
tccactcctg gagcccgcgg accccgagca cgcgcctgac agcccctgct ggcccggcgc 60
gcggcgtcgc caggccagct atggcccccg acccggtggc cgccgagacc gcggctcagg 120
gacctacccc gcgctacttc acctgggacg aggtggccca gcgctcaggg tgcgaggagc 180
ggtggctagt gatcgaccgt aaggtgtaca acatcagcga gttcacccgc cggcatccag 240 gggctcccg ggtcatcagc cactacgccg ggcaggatgc cacggatccc tttgtggcct 300
tccacatcaa caagggcctt gtgaagaagt atatgaactc tctcctgatt ggagaactgt 360
ctccagagca gcccagcttt gagcccacca agaataaaga gctgacagat gagttccggg 420

```
agctgcgggc cacagtggag cggatggggc tcatgaaggc caaccatgtc ttcttcctgc    480
tgtacctgct gcacatcttg ctgctggatg gtgcagcctg gctcaccctt tgggtctttg    540
ggacgtcctt tttgcccttc ctcctctgtg cggtgctgct cagtgcagtt caggcccagg    600
ctggctggct gcagcatgac tttgggcacc tgtcggtctt cagcacctca aagtggaacc    660
atctgctaca tcattttgtg attggccacc tgaagggggc ccccgccagt tggtggaacc    720
acatgcactt ccagcaccat gccaagccca actgcttccg caaagaccca gacatcaaca    780
tgcatccctt cttctttgcc ttggggaaga tcctctctgt ggagcttggg aaacagaaga    840
aaaaatatat gccgtacaac caccagcaca aatacttctt cctaattggg cccccagcct    900
tgctgcctct ctacttccag tggtatattt tctattttgt tatccagcga aagaagtggg    960
tggacttggc ctggatgatt accttctacg tccgcttctt cctcacttat gtgccactat   1020
tggggctgaa agccttcctg ggccttttct tcatagtcag gttcctggaa agcaactggt   1080
ttgtgtgggt gacacagatg aaccatattc ccatgcacat tgatcatgac cggaacatgg   1140
actgggtttc cacccagctc caggccacat gcaatgtcca caagtctgcc ttcaatgact   1200
ggttcagtgg acacctcaac ttccagattg agcaccatct tttcccacg atgcctcgac    1260
acaattacca caaagtggct cccctggtgc agtccttgtg tgccaagcat ggcatagagt   1320
accagtccaa gcccctgctg tcagccttcg ccgacatcat ccactcacta aaggagtcag   1380
ggcagctctg gctagatgcc tatcttcacc aataacaaca gccaccctgc ccagtctgga   1440
agaagaggag gaagactctg gagccaaggc agaggggagc ttgagggaca atgccactat   1500
agtttaatac tcagaggggg ttgggtttgg ggacataaag cctctgactc aaactcctcc   1560
cttttatctt ctagccacag ttctaagacc caaagtgggg ggtggacaca gaagtcccta   1620
ggagggaagg agctgttggg gcaggggtgt aaattatttc ctttttctag tttggcacat   1680
gcaggtagtt ggtgaacaga gagaaccagg agggtaacag aagaggaggg acctactgaa   1740
cccagagtca ggaagagatt taacactaaa attccactca tgccgggcgt ggtggcacgc   1800
gcctgtaatc ccagctaccc aggaggctga ggcaggagaa tcgcttgaac cggggaggtg   1860
gaggttgcag tgagctgaga tcacgccatt gtactccagc ctgggcgaca gagcaagact   1920
ccatttcaaa aaaaaaaaaa aaatccactc atataaaagg tgagctcagc tcactggtcc   1980
atttctcagt ggcttctcca tcctcatttg caaacctcag agggataagg cagttgaacc   2040
tgatgagcaa gaattataac agcaaggaaa cattaatgct tagaattctg agatccagca   2100
caactcagtc tgtgggagct cagctcgctg cccagggata ggtatgacct atgtctgcct   2160
taggctgctg ggagatgcca ttctccagtt tcagaagcag gcagggcaaa ggtcaagact   2220
gtggtattgg ggtcttttgg ctctgaagga tcctggaacc actgattttg gtttattccc   2280
tccagggtct aaagagaaca agaggtgcta gctcttacca aaacagatgg tagagagagt   2340
tgctggctat ttaaaaagct ctttcatctt ttaattcacc tcttcttttc acctctttaa   2400
ccactcctca ggaacagaac acttctagga ctgggggtct tttagctcca taagcaagtg   2460
agcagatggg acaagttagt cttttctccc tagaaacaaa ggggatgccc agtggtttcc   2520
ctttgcttcc caacctaaaa tttcaagttt aataaaatag caattagcag aagtgaccaa   2580
attgggagat aattatcagt catgaggaaa gacacagatt tcggtcataa agaatgtaag   2640
ggctataagt agaaactttc tataacctaa atgatgttat agaattattt ttgagcagga   2700
gcagaaagat taaatatgat cacttcatac ttctaaatca gaaataggaa gattaaaacc   2760
acagaacagt ttgtgatttc tattgctgta gctaggtatc ttactctgtc cactcttgtt   2820
```

-continued caagtatcta actcttctgg aaaccaaata ggctttagaa gagattatcc tatattccta 2880
tcagtataat actaaaatgt aactttttaa tcatctggtt tttaaaagat aaacagttta 2940
gcccatctct ccagagagca aacataggaa tatgactcag gagcctccta gggcttatca 3000
tcagccctca cacccgcttc cccctccaac ccacagcctt tgcttccagg tggcaggatt 3060
actactttgc ctcttcagca gcatctactc taggcatatt gatcatttta gacactggga 3120
gaagagaacc tcaaactagg aggaaaagac agagcctcca cttagttttg ggaggggatg 3180
gcagacagtc aaggagatga gcgtcctaag gcatgttggg atagggtcag atgcaccacc 3240
catggagagg tttgtcaaca caaagacatg gaaggttaga ggtttgtcaa caaaaagaca 3300
tggaaggtta ggtttgtcaa cacaaagaca tggaagatta gaggtttgtc aacacaaaga 3360
cacaggaaga atgggctgca gaagatttag atgttttcca tttgggcaca ttttacttag 3420
ctggagaact aggtttaaaa cagcctgggt aggaaaatta gaagcaagct ggatgcagtg 3480
gctcatgcct gtaatcccaa cacttttggg aggtccaggc aggaggatca cttgggccca 3540
ggaggtcaag cctgcagcga gctgagatca caccactgca ctccagcctg ggtgataga 3600 acaagaccct gtctcaaaaa aaaaaaaaaa caacaaaaac ttagaattga ggagttgtac 3660
ctccattggc ttcctcactc caaaataggt gctgatcctt cctattccta ttctttgcca 3720
ccttttgggt gtggtgtcac cagcctgttt agccaagtag ctttgggcat aggctgccca 3780
atctgagcaa acaccagtga ggctctattg agccaagacc aagtcctcaa agcacctgaa 3840
ccactgtggc cttctcagcc tacagcagtg tggtctctta catggccaca aagggacaca 3900
cagtgacaaa aggctcggaa tgttacaatg gtaaaatgag tgatctcaaa tccactgaca 3960
gatataaaat aggcttagag aggaaaagct gcctctggtc aagtagatca tggcagcatg 4020
aattccaact cactttttta caactccaac ttctatgttt atctttgtta ctttcacttt 4080
tttacaacct ggccagaggc attttttaaa tcaggcccaa tatcagtatt ctttttgtgt 4140
gtgccaattt tgttatcaca tccctatgaa gttgaaaaat aaagttaatt ttgaccaaaa 4200
aaaaaaaaaa aag 4213

<210> SEQ ID NO 8
<211> LENGTH: 4459
<212> TYPE: DNA
<213> ORGANISM: Homo sapiens

<400> SEQUENCE: 8
gtttctctct ctccttctct ctctctctct ctctctcttt tttttccgcc ctagctgggg 60
ctgtgttgga ggagaggaag aaagagagac agaggattgc attcatccgt tacgttcttg 120
aaatttccta atagcaagac cagcgaagcg gttgcaccct tttcaatctt gcaaaggaaa 180
aaaacaaaac aaaacaaaaa aaacccaagt ccccttcccg gcagtttttg ccttaaagct 240
gccctcttga aattaatttt ttcccaggag agagatgtct tatcagggga agaaaaatat 300
tccacgcatc acgagcgatc gtcttctgat caaaggaggt aaaattgtta atgatgacca 360
gtcgttctat gcagacatat acatggaaga tgggttgatc aagcaaatag gagaaaatct 420
gattgtgcca ggaggagtga agaccatcga ggcccactcc cggatggtga tccccggagg 480
aattgacgtc cacactcgtt tccagatgcc tgatcaggga atgacgtctg ctgatgattt 540
cttccaagga accaaggcgg ccctggctgg gggaaccact atgatcattg accacgttgt 600
tcctgagcct gggacaagcc tgctcgctgc ctttgaccag tggagggaat gggccgacag 660
caagtcctgc tgtgactact ctctgcatgt ggacatcagc gagtggcata agggcatcca 720

-continued

```
ggaggagatg gaagcgcttg tgaaggatca cggggtaaat tccttcctcg tgtacatggc    780
tttcaaagat cgcttccagc taacggattg ccagatttat gaagtactga gtgtgatccg    840
ggatattggc gccatagccc aagtccacgc agaaaatggc gacatcattg cagaggagca    900
gcagaggatc ctggatctgg gcatcacggg ccccgaggga catgtgctga gccgacctga    960
ggaggtcgag gccgaagccg tgaatcgtgc catcaccatc gccaaccaga ccaactgccc   1020
gctgtatatc accaaggtga tgagcaaaag ctctgctgag gtcatcgccc aggcacggaa   1080
gaagggaact gtggtgtatg gcgagcccat cactgccagc ttgggaacgg acggctccca   1140
ttactggagc aagaactggg ccaaggctgc tgcctttgtc acctccccac ccttgagccc   1200
tgatccaacc actccagact ttctcaactc cttgctgtcc tgtggagacc tccaggtcac   1260
gggcagtgcc cattgcacgt ttaacactgc ccagaaggct gtaggaaagg acaacttcac   1320
cctgattccg gagggcacca atggcactga ggagcggatg tccgtcatct gggacaaggc   1380
tgtggtcact gggaagatgg atgagaacca gtttgtggct gtgaccagca ccaatgcagc   1440
caaagtcttc aacctttacc cccggaaagg ccgcattgct gtgggatccg atgccgacct   1500
ggtcatctgg gaccccgaca gcgttaaaac catctctgcc aagacacaca acagctctct   1560
cgagtacaac atctttgaag gcatggagtg ccgcggctcc ccactggtgg tcatcagcca   1620
ggggaagatt gtcctggagg acggcaccct gcatgtcacc gaaggctctg gacgctacat   1680
tccccggaag cccttccctg attttgttta caagcgtatc aaggcaagga gcaggctggc   1740
tgagctgaga ggggttcctc gtggcctgta tgacggacct gtgtgtgaag tgtctgtgac   1800
gcccaagaca gtcactccag cctcctcggc caagacgtct cctgccaagc agcaggcccc   1860
acctgtccgg aacctgcacc agtctggatt cagtttgtct ggtgctcaga ttgatgacaa   1920
cattccccgc cgcaccaccc agcgtatcgt ggcgcccccc ggtggccgtg ccaacatcac   1980
cagcctgggc tagagctcct gggctgtgcg tccactgggg actggggatg ggacacctga   2040
ggacattctg agacttcttt cttccttcct tttttttttt ttgttttttt ttttaagagc   2100
ctgtgatagt tactgtggag cagccagttc atggggtccc ccttggggcc ccacaccccg   2160
tctctcacca agagttactg attttgctca tccacttccc tacacatcta tgggtatcac   2220
acccaagact acccaccaag ctcatacagg gaaccacacc caacacttag acatgcgaac   2280
aagcagcccc cagcgagggt ctccttcgcc ttcaacctcc tagtgtctgt tagcatcttc   2340
cttttcatgg ggggagggaa gataaagtga attgcccaga gctgcctttt tcttttcttt   2400
ttaaaaattt taagaagttt tccttgtggg gctggggagg ggccggggtc agggagagtc   2460
tttttttttt tttttttaaa tactaaattg gaacatttaa ttccatatta atacaagggg   2520
tttgaactgg acatcctaat gatgcaatta cgtcatcacc cagctgattc cgggtggttg   2580
gcaaactcat cgtgtctgtc ctgagaggct ccacaatgcc cacccgcatc gccattctgt   2640
agtcttcagg gtcagctgtt gataaagggg caggcttgcg ttattggcct agattttgct   2700
gcagattaaa tcctttgagg attctcttct cttttaccat ttttctgcgt gctctcactc   2760
tctctttctc tctctagctt tttaattcat gaatattttc gtgtctgtct ctctctctct   2820
ctgtgtttcc tccagccctt gtctcggaga cggtgttttc ctcccttgcc ccattatctt   2880
ttcacctccc aggtctacca tttcatggtg gtcgttgggt ccgcctaaag gatttgagcg   2940
tttgccattg caagcatagt gctgtgtcat cctggtccat gtaggactgg tgctaaccac   3000
ctgccatcat gaggatgtgt gctagagtgt gggaccctgg ccaagtgcag gaatgggcca   3060
tgccgtctca cccacagtat cacacgtgga accgcagaca gggcccagaa gctttagagg   3120
```

tatgaggctg cagaaccgga gagattttcc tctgtgcagt gctctctggc taaagtcacg 3180
gtcaaaccta aacaccgagc ctcattaacc caagtgaacc aaccaaagtc accagttcag 3240
aagtgctaag ctaataggag tctgacccga gggcctgctg cttcctggtt aagtatcttt 3300
tgagattcta gaacacatgg gagcttttta ttttcgggga aaaaccgtat tttttcttg 3360 tccaattatt tctaaagaca cactacatag aaagaggccc tataaactca aaaagtcatt 3420
gggaaactta aagtctattc tactttgcaa gaggagaaat gtgttttatg aacgatagat 3480
cacatcagaa ctcctgtggg gaggaaacct tataaattaa acacatggcc cccttagaga 3540
ccacaggtga tgtctgtctc catccttccc tctccttttc tgtcaccttt cccccctagct 3600 ggctcctttg gacctacccc tgtccttgct gacttgtgtt gcattgtatt ccaaacgtgt 3660
ttacaggttc tcttaagcaa tgttgtattt gcaggctttt ctgaatacca aatctgcttt 3720
ttgtaaagcg taaaaacatc acaaagtagg tcattccatc accacccttg tctctctaca 3780
cattttgcct ttggggatct ggttggggtt ttgggttttt tgttgttgtt gtttatttgt 3840
tattttaaag gtaaattgca cttttaaaaa aataattggt tgacttaata tatttgcttt 3900
ttttctcacc tgcacttaga ggaaatttga acaagttgga aaaaaacaat ttttgtttca 3960
attctaagaa acacttgcag ctctagtatt cacttgagtc ttcctgtttt tcctgtaccg 4020
ggtcatggta atttttggtt gttttggttg ttttcttaaa aaacaagtta aaacctgacg 4080
atttctgcag gctgtgtaag catgtttacc tgttggcttg ctttgtgtgt ctgttaaatg 4140
aatgtcatat gtaaatgcta aaataaatcg acagtgtctc agaactgaat aactgcagtg 4200
acttgatgct ctaaaacagt gtaggattta agaatagatg gtttttaatc ctggaaattg 4260
tgattgtgac ccatgagtgg aggaactttc agttctaaag ctgataaagt gtgtagccag 4320
aagagtactt tttttttgt aaccactgtc ttgatggcaa aataattatg gtaaaaaaca 4380
agtctcgtgt ttattattcc ttaagaactc tgtgttatat taccatggaa cgcctaataa 4440
agcaaaatgt ggttgtttc 4459

<210> SEQ ID NO 9
<211> LENGTH: 7718
<212> TYPE: DNA
<213> ORGANISM: Homo sapiens

<400> SEQUENCE: 9
cgggagcggc gggagcggtg gcggcggcag aggcggcggc tccagcttcg gctccggctc 60
gggctcgggc tccggctccg gctccggctc cggctccagc tcgggtggcg gtggcgggag 120
cgggaccagg tggaggcggc ggcggcagag gagtgggagc agcggcccta gcggcttgcg 180
gggggacatg cggaccgacg gcccctggat aggcggaagg agtggaggcc ctggtgcccg 240
gcccttggtg ctgagtatcc agcaagagtg accggggtga agaagcaaag actcggttga 300
ttgtcctggg ctgtggctgg ctgtggagct agagccctgg atggcccctg agccagcccc 360
agggaggacg atggtgcccc ttgtgcctgc actggtgatg cttggtttgg tggcaggcgc 420
ccatggtgac agcaaacctg tcttcattaa agtccctgag gaccagactg ggctgtcagg 480
aggggtagcc tccttcgtgt gccaagctac aggagaaccc aagccgcgca tcacatggat 540
gaagaagggg aagaaagtca gctcccagcg cttcgaggtc attgagtttg atgatggggc 600
agggtcagtg cttcggatcc agccattgcg ggtgcagcga gatgaagcca tctatgagtg 660
tacagctact aacagcctgg gtgagatcaa cactagtgcc aagctctcag tgctcgaaga 720
ggaacagctg ccccctgggt tcccttccat cgacatgggg cctcagctga aggtggtgga 780

-continued

```
gaaggcacgc acagccacca tgctatgtgc cgcaggcgga aatccagacc ctgagatttc    840
ttggttcaag gacttccttc ctgtagaccc tgccacgagc aacggccgca tcaagcagct    900
gcgttcaggt gccttgcaga tagagagcag tgaggaatcc gaccaaggca agtacgagtg    960
tgtggcgacc aactcggcag gcacacgtta ctcagcccct gcgaacctgt atgtgcgagt   1020
gcgccgcgtg gctcctcgtt tctccatccc tcccagcagc caggaggtga tgccaggcgg   1080
cagcgtgaac ctgacatgcg tggcagtggg tgcacccatg ccctacgtga agtggatgat   1140
gggggccgag gagctcacca aggaggatga gatgccagtt ggccgcaacg tcctggagct   1200
cagcaatgtc gtacgctctg ccaactacac ctgtgtggcc atctcctcgc tgggcatgat   1260
cgaggccaca gcccaggtca cagtgaaagc tcttccaaag cctccgattg atcttgtggt   1320
gacagagaca actgccacca gtgtcaccct cacctgggac tctgggaact cggagcctgt   1380
aacctactat ggcatccagt accgcgcagc gggcacggag ggcccctttc aggaggtgga   1440
tggtgtggcc accacccgct acagcattgg cggcctcagc cctttctcgg aatatgcctt   1500
ccgcgtgctg gcggtgaaca gcatcgggcg agggccgccc agcgaggcag tgcgggcacg   1560
cacgggagaa caggcgccct ccagcccacc gcgccgcgtg caggcacgca tgctgagcgc   1620
cagcaccatg ctggtgcagt gggagcctcc cgaggagccc aacggcctgg tgcggggata   1680
ccgcgtctac tatactccgg actcccgccg cccccccgaac gcctggcaca agcacaacac   1740
cgacgcgggg ctcctcacga ccgtgggcag cctgctgcct ggcatcacct acagcctgcg   1800
cgtgcttgcc ttcaccgccg tgggcgatgg ccctcccagc ccaccatcc aggtcaagac   1860
gcagcaggga gtgcctgccc agcccgcgga cttccaggcc gaggtggagt cggacaccag   1920
gatccagctc tcgtggctgc tgccccctca ggagcggatc atcatgtatg aactggtgta   1980
ctgggcggca gaggacgaag accaacagca caaggtcacc ttcgacccaa cctcctccta   2040
cacactagag gacctgaagc ctgacacact ctaccgcttc cagctggctg cacgctcgga   2100
tatgggggtg ggcgtcttca cccccaccat tgaggcccgc acagcccagt ccacccccctc   2160
cgcccctccc cagaaggtga tgtgtgtgag catgggctcc accacggtcc gggtaagttg   2220
ggtcccgccg cctgccgaca gccgcaacgg cgttatcacc cagtactccg tggcccacga   2280
ggcggtggac ggcgaggacc gcgggcggca tgtggtggat ggcatcagcc gtgagcactc   2340
cagctgggac ctggtgggcc tggagaagtg gacggagtac cgggtgtggg tgcgggcaca   2400
cacagacgtg ggccccggcc ccgagagcag cccggtgctg gtgcgcaccg atgaggacgt   2460
gcccagcggg cctccgcgga aggtggaggt ggagccactg aactccactg ctgtgcatgt   2520
ctactggaag ctgcctgtcc ccagcaagca gcatggccag atccgcggct accaggtcac   2580
ctacgtgcgg ctggagaatg gcgagccccg tggactcccc atcatccaag acgtcatgct   2640
agccgaggcc cagtggcggc cagaggagtc cgaggactat gaaaccacta tcagcggcct   2700
gaccccggag accacctact ccgttactgt tgctgcctat accaccaagg gggatggtgc   2760
ccgcagcaag cccaaaattg tcactacaac aggtgcagtc ccaggccggc ccaccatgat   2820
gatcagcacc acggccatga acactgcgct gctccagtgg cacccaccca aggaactgcc   2880
tggcgagctg ctgggctacc ggctgcagta ctgccgggcc gacgaggcgc ggcccaacac   2940
catagatttc ggcaaggatg accagcactt cacagtcacc ggcctgcaca aggggaccac   3000
ctacatcttc cggcttgctg ccaagaaccg ggctggcttg ggtgaggagt tcgagaagga   3060
gatcaggacc cccgaggacc tgcccagcgg cttcccccaa aacctgcatg tgacaggact   3120
gaccacgtct accacagaac tggcctggga cccgccagtg ctggcggaga ggaacgggcg   3180
```

-continued catcatcagc tacaccgtgg tgttccgaga catcaacagc caacaggagc tgcagaacat 3240
cacgacagac acccgcttta cccttactgg cctcaagcca gacaccactt acgacatcaa 3300
ggtccgcgca tggaccagca aaggctctgg cccactcagc cccagcatcc agtcccggac 3360
catgccggtg gagcaagtgt ttgccaagaa cttccgggtg gcggctgcaa tgaagacgtc 3420
tgtgctgctc agctgggagg ttcccgactc ctataagtca gctgtgccct ttaagattct 3480
gtacaatggg cagagtgtgg aggtggacgg gcactcgatg cggaagctga tcgcagacct 3540
gcagcccaac acagagtact cgtttgtgct gatgaaccgt ggcagcagcg caggggggcct 3600 gcagcacctg gtgtccatcc gcacagcccc cgacctcctg cctcacaagc cgctgcctgc 3660
ctctgcctac atagaggacg gccgcttcga tctctccatg ccccatgtgc aagacccctc 3720
gcttgtcagg tggttctaca ttgttgtggt acccattgac cgtgtgggcg ggagcatgct 3780
gacgccaagg tggagcacac ccgaggaact ggagctggac gagcttctag aagccatcga 3840
gcaaggcgga gaggagcagc ggcggcggcg gcggcaggca gaacgtctga agccatatgt 3900
ggctgctcaa ctggatgtgc tcccggagac ctttaccttg gggggacaaga agaactaccg 3960 gggcttctac aaccggcccc tgtctccgga cttgagctac cagtgctttg tgcttgcctc 4020
cttgaaggaa cccatggacc agaagcgcta tgcctccagc ccctactcgg atgagatcgt 4080
ggtccaggtg acaccagccc agcagcagga ggagccggag atgctgtggg tgacgggtcc 4140
cgtgctggca gtcatcctca tcatcctcat tgtcatcgcc atcctcttgt tcaaaaggaa 4200
aaggacccac tctccgtcct ctaaggatga gcagtcgatc ggactgaagg actccttgct 4260
ggcccactcc tctgaccctg tggagatgcg gaggctcaac taccagaccc caggtatgcg 4320
agaccaccca cccatcccca tcaccgacct ggcggacaac atcgagcgcc tcaaagccaa 4380
cgatggcctc aagttctccc aggagtatga gtccatcgac cctggacagc agttcacgtg 4440
ggagaattca aacctggagg tgaacaagcc caagaaccgc tatgcgaatg tcatcgccta 4500
cgaccactct cgagtcatcc ttacctctat cgatggcgtc cccgggagtg actacatcaa 4560
tgccaactac atcgatggct accgcaagca gaatgcctac atcgccacgc agggcccct 4620 gcccgagacc atgggcgatt tctggagaat ggtgtgggaa cagcgcacgg ccactgtggt 4680
catgatgaca cggctggagg agaagtcccg ggtaaaatgt gatcagtact ggccagcccg 4740
tggcaccgag acctgtggcc ttattcaggt gaccctgttg gacacagtgg agctggccac 4800
atacactgtg cgcaccttcg cactccacaa gagtggctcc agtgagaagc gtgagctgcg 4860
tcagtttcag ttcatggcct ggccagacca tggagttcct gagtacccaa ctcccatcct 4920
ggccttccta cgacgggtca aggcctgcaa cccccctagac gcagggccca tggtggtgca 4980
ctgcagcgcg ggcgtgggcc gcaccggctg cttcatcgtg attgatgcca tgttggagcg 5040
gatgaagcac gagaagacgg tggacatcta tggccacgtg acctgcatgc gatcacagag 5100
gaactacatg gtgcagacgg aggaccagta cgtgttcatc catgaggcgc tgctggaggc 5160
tgccacgtgc ggccacacag aggtgcctgc ccgcaacctg tatgcccaca tccagaagct 5220
gggccaagtg cctccagggg agagtgtgac cgccatggag ctcgagttca agttgctggc 5280
cagctccaag gcccacacgt cccgcttcat cagcgccaac ctgccctgca acaagttcaa 5340
gaaccggctg gtgaacatca tgccctacga attgacccgt gtgtgtctgc agcccatccg 5400
tggtgtggag ggctctgact acatcaatgc cagcttcctg gatggttata gacagcagaa 5460
ggcctacata gctacacagg ggcctctggc agagagcacc gaggacttct ggcgcatgct 5520
atgggagcac aattccacca tcatcgtcat gctgaccaag cttcgggaga tgggcaggga 5580
gaaatgccac cagtactggc cagcagagcg ctctgctcgc taccagtact ttgttgttga 5640
cccgatggct gagtacaaca tgccccagta tatcctgcgt gagttcaagg tcacggatgc 5700
ccgggatggg cagtcaagga caatccggca gttccagttc acagactggc cagagcaggg 5760
cgtgcccaag acaggcgagg gattcattga cttcatcggg caggtgcata agaccaagga 5820
gcagtttgga caggatgggc ctatcacggt gcactgcagt gctggcgtgg gccgcaccgg 5880
ggtgttcatc actctgagca tcgtcctgga gcgcatgcgc tatgagggcg tggtcgacat 5940
gtttcagacc gtgaagaccc tgcgtacaca gcgtcctgcc atggtgcaga cagaggacca 6000
gtatcagctg tgctaccgtg cggccctgga gtacctcggc agctttgacc actatgcaac 6060
gtaactaccg ctcccctctc ctccgccacc cccgccgtgg ggctccggag gggacccagc 6120
tcctctgagc cataccgacc atcgtccagc cctcctacgc agatgctgtc actggcagag 6180
cacagcccac ggggatcaca gcgtttcagg aacgttgcca caccaatcag agagcctaga 6240
acatccctgg gcaagtggat ggcccagcag gcaggcactg tggcccttct gtccaccaga 6300
cccacctgga gcccgcttca agctctctgt tgcgctcccg catttctcat gcttcttctc 6360
atggggtggg gttggggcaa agcctccttt ttaatacatt aagtggggta gactgaggga 6420
ttttagcctc ttccctctga tttttccttt cgcgaatccg tatctgcaga atgggccact 6480
gtaggggttg gggtttattt tgttttgttt ttttttttt tttgtatgac ttctgctgaa 6540
ggacagaaca ttgccttcct cgtgcagagc tggggctgcc agcctgagcg gaggctcggc 6600
cgtgggccgg gaggcagtgc tgatccggct gctcctccag cccttcagac gagatcctgt 6660
ttcagctaaa tgcagggaaa ctcaatgttt ttttaagttt tgttttccct ttaaagcctt 6720
tttttaggcc acattgacag tggtgggcgg ggagaagata gggaacactc atccctggtc 6780
gtctatccca gtgtgtgttt aacattcaca gcccagaacc acagatgtgt ctgggagagc 6840
ctggcaaggc attcctcatc accatcgtgt ttgcaaaggt taaaacaaaa acaaaaaacc 6900
acaaaaataa aaaacaaaaa aaacaaaaaa cccaaaaaaa aaaaaaaaaa gagtcagccc 6960
ttggcttctg cttcaaaccc tcaagagggg aagcaactcc gtgtgcctgg ggttcccgag 7020
ggagctgctg gctgacctgg gcccacagag cctggctttg gtccccagca ttgcagtatg 7080
gtgtggtgtt tgtaggctgt ggggtctggc tgtgtggcca aggtgaatag cacaggttag 7140
ggtgtgtgcc acaccccatg cacctcaggg ccaagcgggg gcgtggctgg cctttcaggt 7200
ccaggccagt gggcctggta gcacatgtct gtcctcagag caggggccag atgattttcc 7260
tccctggttt gcagctgttt tcaaagcccc cgataatcgc tcttttccac tccaagatgc 7320
cctcataaac caatgtggca agactactgg acttctatca atggtactct aatcagtcct 7380
tattatccca gcttgctgag gggcagggag agcgcctctt cctctgggca gcgctatcta 7440
gataggtaag tgggggcggg gaagggtgca tagctgtttt agctgaggga cgtggtgccg 7500
acgtccccaa acctagctag gctaagtcaa gatcaacatt ccagggttgg taatgttgga 7560
tgatgaaaca ttcattttta ccttgtggat gctagtgctg tagagttcac tgttgtacac 7620
agtctgtttt ctatttgtta agaaaaacta cagcatcatt gcataattct tgatggtaat 7680
aaatttgaat aatcagattt cttacaaaaa aaaaaaaa 7718

<210> SEQ ID NO 10
<211> LENGTH: 1809
<212> TYPE: DNA
<213> ORGANISM: Homo sapiens

<400> SEQUENCE: 10

-continued

```
cctgctccaa ggtccagaga gctttctggt ctttgcagca ggcctgccgc cttcatgtcc      60
actctcctca tcaatcagcc ccagtatgcg tggctgaaag agctggggct ccgcgaggaa     120
aacgagggcg tgtataatgg aagctgggga ggccggggag aggttattac gacctattgc     180
cccgctaaca acgagccaat agcaagagtc cgacaggcca gtgtggcaga ctatgaagaa     240
actgtaaaga aagcaagaga agcatggaaa atctgggcag atattcctgc tccaaaacga     300
ggagaaatag taagacagat tggcgatgcc ttgcgggaga agatccaagt actaggaagc     360
ttggtgtctt tggagatggg gaaaatctta gtggaaggtg tgggtgaagt tcaggagtat     420
gtggatatct gtgactatgc tgttggttta tcaaggatga ttggaggacc tatcttgcct     480
tctgaaagat ctggccatgc actgattgag cagtggaatc ccgtaggcct ggttggaatc     540
atcacggcat tcaatttccc tgtggcagtg tatggttgga acaacgccat cgccatgatc     600
tgtggaaatg tctgcctctg gaaaggagct ccaaccactt ccctcattag tgtggctgtc     660
acaaagataa tagccaaggt tctggaggac aacaagctgc ctggtgcaat ttgttccttg     720
acttgtggtg gagcagatat tggcacagca atggccaaag atgaacgagt gaacctgctg     780
tccttcactg ggagcactca ggtgggaaaa caggtgggcc tgatggtgca ggagaggttt     840
gggagaagtc tgttggaact tggaggaaac aatgccatta ttgcctttga agatgcagac     900
ctcagcttag ttgttccatc agctctcttc gctgctgtgg gaacagctgg ccagaggtgt     960
accactgcga ggcgactgtt tatacatgaa agcatccatg atgaggttgt aaacagactt    1020
aaaaaggcct atgcacagat ccgagttggg aacccatggg accctaatgt tctctatggg    1080
ccactccaca ccaagcaggc agtgagcatg tttcttggag cagtggaaga agcaaagaaa    1140
gaaggtggca cagtggtcta tgggggcaag gttatggatc gccctggaaa ttatgtagaa    1200
ccgacaattg tgacaggtct tggccacgat gcgtccattg cacacacaga gactttcgct    1260
ccgattctct atgtctttaa attcaagaat gaagaagagg tctttgcatg gaataatgaa    1320
gtaaaacagg gactttcaag tagcatcttt accaaagatc tgggcagaat ctttcgctgg    1380
cttggaccta aaggatcaga ctgtggcatt gtaaatgtca acattccaac aagtggggct    1440
gagattggag gtgcctttgg aggagaaaag cacactggtg gtggcaggga gtctggcagt    1500
gatgcctgga aacagtacat gagaaggtct acttgtacta tcaactacag taaagacctt    1560
cctctggccc aaggaatcaa gtttcagtaa aggtgtttta gatgaacatc ccttaatttg    1620
aggtgttcca gcagctgttt ttggagaaga caaagaagat taaagttttc cctgaataaa    1680
tgcattatta tgactgtgac agtgactaat cccccctatga ccccaaagcc ctgattaaat    1740
caagagattc ctttttttaaa aatcaaaata aaattgttac aacatagcca tagttactaa    1800
aaaaaaaaa                                                            1809
```

<210> SEQ ID NO 11
<211> LENGTH: 1317
<212> TYPE: DNA
<213> ORGANISM: Homo sapiens

<400> SEQUENCE: 11

```
agctcccgcg cgctagagcc gcctgctggt ctcacccagc cgggaccgct gacctggcgc      60
tttgtgcggc tccaggcctc cgagtggact ccagaaagcc tgaaaagcta tcatggcagc     120
aaggcccaag ctccactatc ccaacggaag aggccggatg gagtccgtga gatgggtttt     180
agctgccgcc ggagtcgagt ttgatgaaga atttctggaa acaaaagaac agttgtacaa     240
gttgcaggat ggtaaccacc tgctgttcca acaagtgccc atggttgaaa ttgacgggat     300
```

```
gaagttggta cagacccgaa gcattctcca ctacatagca gacaagcaca atctctttgg    360
caagaacctc aaggagagaa ccctgattga catgtacgtg gaggggacac tggatctgct    420
ggaactgctt atcatgcatc ctttcttaaa accagatgat cagcaaaagg aagtggttaa    480
catggcccag aaggctataa ttagatactt tcctgtgttt gaaaagattt taaggggtca    540
cggacaaagc tttcttgttg gtaatcagct gagccttgca gatgtgattt tactccaaac    600
cattttagct ctagaagaga aaattcctaa tatcctgtct gcatttcctt tcctccagga    660
atacacagtg aaactaagta atatccctac aattaagaga ttccttgaac ctggcagcaa    720
gaagaagcct ccccctgatg aaatttatgt gagaaccgtc tacaacatct ttaggccata    780
aaacaacaca tccatgtgtg agtgacagtg tgttcctaga gatggtattg tctacagtca    840
tgtcttaatg gatcccagct ctgtcatggt gctatctatg tattaagttg ggtcctaagt    900
tgggtctttt gtgtcaacga gatcatctct tctagaaata tcaacctttt ttgtccagta    960
aataattgtt aggggatctt tattggaaaa cttttttgga gaggctggta tttaagttag   1020
atctgattgg gctactcatg tcctgtagcc agttcatcct cataataaga atgggcagga   1080
tctcttgttc tctcctgagt gtctttctac tctcctgagc gtctttctgc tctccttatc   1140
ctgttctctt atccttatcc cctccagtct ctgcctaatt tttagtgttt aataacaacc   1200
gaatgtctag taaatgactc tcctctgagc tgtaataaat aaaatggtag taatgaatgc   1260
aatcagtatt agccaaaata aagaatttat gagtcattaa aaaaaaaaaa aaaaaaa      1317
```

<210> SEQ ID NO 12
<211> LENGTH: 5910
<212> TYPE: DNA
<213> ORGANISM: Homo sapiens

<400> SEQUENCE: 12

```
cggaggacag ccggaccgag ccaacgccgg ggactttgtt ccctccacgg aggggactcg     60
gcaactcgca gcggcagggt ctggggccgg cgcctgggag ggatctgcgc cccccactca    120
ctccctagct gtgttcccgc cgccgccccg gctagtctcc ggcgctggcg cctatggtcg    180
gcctccgaca gcgctccgga gggaccgggg gagctcccag gcgcccggga ctggagactg    240
atgcatgagg ggcctacgga ggcgcaggag cggtggtgat ggtctgggaa gcggagctga    300
agtcccctgg gctttggtga ggcgtgacag tttatcatga ccgtgttcag gcaggaaaac    360
gtggatgatt actacgacac cggcgaggaa cttggcagtg gacagtttgc ggttgtgaag    420
aaatgccgtg agaaaagtac cggcctccag tatgccgcca aattcatcaa gaaaaggagg    480
actaagtcca gccggcgggg tgtgagccgc gaggacatcg agcgggaggt cagcatcctg    540
aaggagatcc agcaccccaa tgtcatcacc ctgcacgagg tctatgagaa caagacggac    600
gtcatcctga tcttggaact cgttgcaggt ggcgagctgt ttgacttctt agctgaaaag    660
gaatctttaa ctgaagagga agcaactgaa tttctcaaac aaattcttaa tggtgtttac    720
tacctgcact cccttcaaat cgcccacttt gatcttaagc ctgagaacat aatgcttttg    780
gatagaaatg tccccaaacc tcggatcaag atcattgact ttgggttggc ccataaaatt    840
gactttggaa atgaatttaa aaacatattt gggactccag agtttgtcgc tcctgagata    900
gtcaactatg aacctcttgg tcttgaggca gatatgtgga gtatcggggt aataacctat    960
atcctcctaa gtggggcctc cccatttctt ggagacacta agcaagaaac gttagcaaat   1020
gtatccgctg tcaactacga atttgaggat gaatacttca gtaataccag tgccctagcc   1080
aaagatttca taagaagact tctggtcaag gatccaaaga agagaatgac aattcaagat   1140
```

-continued

```
agtttgcagc atccctggat caagcctaaa gatacacaac aggcacttag tagaaaagca   1200
tcagcagtaa acatggagaa attcaagaag tttgcagccc ggaaaaaatg gaaacaatcc   1260
gttcgcttga tatcactgtg ccaaagatta tccaggtcat tcctgtccag aagtaacatg   1320
agtgttgcca gaagcgatga tactctggat gaggaagact cctttgtgat gaaagccatc   1380
atccatgcca tcaacgatga caatgtccca ggcctgcagc accttctggg ctcattatcc   1440
aactatgatg ttaaccaacc caacaagcac gggacacctc cattactcat tgctgctggc   1500
tgtgggaata ttcaaatact acagttgctc attaaaagag gctcgagaat cgatgtccag   1560
gataagggcg ggtccaatgc cgtctactgg gctgctcggc atggccacgt cgataccttg   1620
aaatttctca gtgagaacaa atgccctttg gatgtgaaag acaagtctgg agagatggcc   1680
ctccacgtgg cagctcgcta tggccatgct gacgtggctc aagttacttg tgcagcttcg   1740
gctcaaatcc caatatccag gacaaaggaa gaagaaaccc ccctgcactg tgctgcttgg   1800
cacggctatt actctgtggc caaagccctt tgtgaagccg gctgtaacgt gaacatcaag   1860
aaccgagaag gagagacgcc cctcctgaca gcctctgcca ggggctacca cgacatcgtg   1920
gagtgtctgg ccgaacatgg agccgacctt aatgcttgcg acaaggacgg acacattgcc   1980
cttcatctgg ctgtaagacg gtgtcagatg gaggtaatca agactctcct cagccaaggg   2040
tgtttcgtcg attatcaaga caggcacggc aatactcccc tccatgtggc atgtaaagat   2100
ggcaacatgc ctatcgtggt ggccctctgt gaagcaaact gcaatttgga catctccaac   2160
aagtatgggc gaacgcctct gcaccttgcg gccaacaacg gaatcctaga cgtggtccgg   2220
tatctctgtc tgatgggagc cagcgttgag gcgctgacca cggacggaaa gacggcagaa   2280
gatcttgcta gatcggaaca gcacgagcac gtagcaggtc tccttgcaag acttcgaaag   2340
gatacgcacc gaggactctt catccagcag ctccgaccca cacagaacct gcagccaaga   2400
attaagctca agctgtttgg ccactcggga tccgggaaaa ccacccttgt agaatctctc   2460
aagtgtgggc tgctgaggag ctttttcaga aggcgtcggc ccagactgtc ttccaccaac   2520
tccagcaggt tcccaccttc accccctggct tctaagccca cagtctcagt gagcatcaac   2580
aacctgtacc caggctgcga gaacgtgagt gtgaggagcc gcagcatgat gttcgagccg   2640
ggtcttacca aagggatgct ggaggtgttt gtggccccga cccaccaccc gcactgctcg   2700
gccgatgacc agtccaccaa ggccatcgac atccagaacg cttatttgaa tggagttggc   2760
gatttcagcg tgtgggagtt ctctggaaat cctgtgtatt tctgctgtta tgactatttt   2820
gctgcaaatg atcccacgtc aatccatgtt gttgtcttta gtctagaaga gccctatgag   2880
atccagctga acccagtgat ttctggctc agtttcctga agtcccttgt cccagttgaa   2940
gaacccatag ccttcggtgg caagctgaag aacccactcc aagttgtcct ggtggccacc   3000
cacgctgaca tcatgaatgt tcctcgaccg gctggaggcg agtttggata tgacaaagac   3060
acatcgttgc tgaaagagat taggaacagg tttggaaatg atcttcacat ttcaaataag   3120
ctgtttgttc tggatgctgg ggcttctggg tcaaaggaca tgaaggtact tcgaaatcat   3180
ctgcaagaaa tacgaagcca gattgtttcg gtctgtcctc ccatgactca cctgtgtgag   3240
aaaatcatct ccacgctgcc ttcctggagg aagctcaatg gacccaacca gctgatgtcg   3300
ctgcagcagt ttgtgtacga cgtgcaggac cagctgaacc ccctggccag cgaggaggac   3360
ctcaggcgca ttgctcagca gctccacagc acaggcgaga tcaacatcat gcaaagtgaa   3420
acagttcagg acgtgctgct cctggacccc cgctggctct gcacaaacgt cctggggaag   3480
ttgctgtccg tggagacccc acgggcgctg caccactacc ggggccgcta caccgtggag   3540
```

-continued

```
gacatccagc gcctggtgcc cgacagcgac gtggaggagc tgctgcagat cctcgatgcc   3600
atggacatct gcgcccggga cctgagcagc gggaccatgg tggacgtccc agccctgatc   3660
aagacagaca acctgcaccg ctcctgggct gatgaggagg acgaggtgat ggtgtatggt   3720
ggcgtgcgca tcgtgcccgt ggaacacctc accccttcc catgtggcat ctttcacaag   3780
gtccaggtga acctgtgccg gtggatccac cagcaaagca cagagggcga cgcggacatc   3840
cgcctgtggg tgaatggctg caagctggcc aaccgtgggg ccgagctgct ggtgctgctg   3900
gtcaaccacg gccagggcat tgaggtccag gtccgtggcc tggagacgga gaagatcaag   3960
tgctgcctgc tgctggactc ggtgtgcagc accattgaga acgtcatggc caccacgctg   4020
ccagggctcc tgaccgtgaa gcattacctg agcccccagc agctgcggga gcaccatgag   4080
cccgtcatga tctaccagcc acgggacttc ttccgggcac agactctgaa ggaaacctca   4140
ctgaccaaca ccatgggggg gtacaaggaa agcttcagca gcatcatgtg cttcgggtgt   4200
cacgacgtct actcacaggc cagcctcggc atggacatcc atgcatcaga cctgaacctc   4260
ctcactcgga ggaaactgag tcgcctgctg gacccgcccg acccccctggg gaaggactgg   4320
tgccttctcg ccatgaactt aggcctccct gacctcgtgg caaagtacaa caccaataac   4380
ggggctccca aggatttcct ccccagcccc ctccacgccc tgctgcggga atggaccacc   4440
taccctgaga gcacagtggg caccctcatg tccaaactga gggagctggg tcgccgggat   4500
gccgcagacc ttttgctgaa ggcatcctct gtgttcaaaa tcaacctgga tggcaatggc   4560
caggaggcct atgcctcgag ctgcaacagc ggcacctctt acaattccat tagctctgtt   4620
gtatcccggt gagggcagcc tctggcttgg acagggtctg tttggactgc agaaccaagg   4680
gggtgatgta gcccatcctt ccctttggag atgctgaggg tgtttcttcc tgcacccaca   4740
gccaggggga tgccactcct ccctccggct tgacctgttt ctctgccgct acctccctcc   4800
ccgtctcatt ccgttgtctg tggatggtca ttgcagttta agagcagaac agatctttta   4860
ctttggccgc ttgaaaagct agtgtacctc ctctcagtgt tttggactcc atctctcatc   4920
ctccagtacc ttgcttctta ctgataattt tgctggaatt cctaactttt caatgacatt   4980
ttttttaact atcatattga ttgtccttta aaaaagaaaa gtgcatattt atccaaaatg   5040
tgtatttctt atacgctttt ctgtgttata ccatttcctc agcttatctc ttttatattt   5100
gtaggagaaa ctcccatgta tggaatccca ctgtatgatt tataaacaga caatatgtga   5160
gtgccttttg cagaagaggg tgtgtttgaa atcatcggag tcagccagga gctgtcacca   5220
aggaaacgct acctctctgt cccttgctgt atgctgatca tcgccagagg tgcttcaccc   5280
tgagttttgt tttgtattgt tttctgacag tttttctgtt ttgtttggca aggaaagggg   5340
agaagggaat cctcctccag ggtgatttta tgatcagtgt tgttgctcta ggaagacatt   5400
tttccgtttg cttttgttcc aatgtcaatg tgaacgtcca catgaaacct acacactgtc   5460
atgcttcatc attccctctc atctcaggta gaaggttgac acagttgtag ggttacagag   5520
acctatgtaa gaattcagaa gacccctgac tcatcatttg tggcagtccc ttataattgg   5580
tgcatagcag atggtttcca catttagatc ctggtttcat aacttcctgt acttgaagtc   5640
taaaagcaga aaataaagga agcaagtttt cttccatgat tttaaattgt gatcgagttt   5700
taaattgata ggagggaaca tgtcctaatt cttctgtcct gagaagcatg taatgttaat   5760
gttatatcat atgtatatat atatatgcac tatgtatata catatatatt aatactggta   5820
tttttactta atctataaaa tgtcgttaaa aagttgtttg tttttttctt tttttataaa   5880
taaactgttg ctcgttaaaa aaaaaaaaaa                                    5910
```

<210> SEQ ID NO 13
<211> LENGTH: 980
<212> TYPE: DNA
<213> ORGANISM: Homo sapiens

<400> SEQUENCE: 13
gcgcggggga gccattagga ggcgaggaga gaggagggcg cagctcccgc ccagcccagc 60
cctgcccagc cctgcccgga ggcagacgcg ccggaaccgg gacgcgataa atatgcagag 120
cggaggcttc gcgcagcaga gcccgcgcgc cgcccgctcc gggtgctgaa tccaggcgtg 180
gggacacgag ccaggcgccg ccgccggagc cagcggagcc ggggccagag ccggagcgcg 240
tccgcgtcca cgcagccgcc ggccggccag cacccagggc cctgcatgcc aggtcgttgg 300
aggtggcagc gagacatgca cccggcccgg aagctcctca gcctcctctt cctcatcctg 360
atgggcactg aactcactca aaataaaaga gaaaacaaag cagagaagat gggagggcca 420
gagagcgaga ggaagaccac aggagagaag acactgaacg agcttccctt gttttgcctg 480
gaagcccacg ctggctccct ggctctgccc aggatgtgca gtccaaatcc caatccagca 540
gtggggttat gtcgtcccgc ttaccctcag agcccttctc ctggtgctgc ccagacgatc 600
agccagtccc tcctggagag gttctgcatg gcctctagga gagaagtttt cttggcccca 660
ggaaggcctg gtggagggtg gtggttgtgc actgttgctg gacagatgca ttcattcatg 720
tgcacacaca cacacacaca tgcacacaca ggggagcaga tacctgcaga gaagagccaa 780
ccaggtcctg attagtggca agctgcccca caaagggcta tgcctgtgtc ttattgagac 840
accttggcaa agagatggct gattctgggt ggtcctggac atggccgcac ccaagggccc 900
tccaagcctt aatggcaccc tgaagcctcc atgcccaggc caaaagatgc ttttcctccc 960
taaaaaaaaa aaaaaaaaaa 980

<210> SEQ ID NO 14
<211> LENGTH: 1721
<212> TYPE: DNA
<213> ORGANISM: Homo sapiens

<400> SEQUENCE: 14
caccagcaca gcaaacccgc cgggatcaaa gtgtaccagt cggcagcatg gctacgaaat 60
gtgggaattg tggacccggc tactccaccc ctctggaggc catgaaagga cccagggaag 120
agatcgtcta cctgccctgc atttaccgaa acacaggcac tgaggcccca gattatctgg 180
ccactgtgga tgttgacccc aagtctcccc agtattgcca ggtcatccac cggctgccca 240
tgcccaacct gaaggacgag ctgcatcact caggatggaa cacctgcagc agctgcttcg 300
gtgatagcac caagtcgcgc accaagctgg tgctgcccag tctcatctcc tctcgcatct 360
atgtggtgga cgtgggctct gagccccggg ccccaaagct gcacaaggtc attgagccca 420
aggacatcca tgccaagtgc gaactggcct ttctccacac cagccactgc ctggccagcg 480
gggaagtgat gatcagctcc ctgggagacg tcaagggcaa tggcaaaggg ggttttgtgc 540
tgctggatgg ggagacgttc gaggtgaagg ggacatggga gagacctggg ggtgctgcac 600
cgttgggcta tgacttctgg taccagcctc gacacaatgt catgatcagc actgagtggg 660
cagctcccaa tgtcttacga gatggcttca accccgctga tgtggaggct ggactgtacg 720
ggagccactt atatgtatgg gactggcagc gccatgagat tgtgcagacc ctgtctctaa 780
aagatgggct tattcccttg gagatccgct tcctgcacaa cccagacgct gcccaaggct 840
ttgtgggctg cgcactcagc tccaccatcc agcgcttcta caagaacgag ggaggtacat 900

```
ggtcagtgga gaaggtgatc caggtgcccc ccaagaaagt gaagggctgg ctgctgcccg    960

aaatgccagg cctgatcacc gacatcctgc tctccctgga cgaccgcttc ctctacttca   1020

gcaactggct gcatggggac ctgaggcagt atgacatctc tgacccacag agaccccgcc   1080

tcacaggaca gctcttcctc ggaggcagca ttgttaaggg aggccctgtg caagtgctgg   1140

aggacgagga actaaagtcc cagccagagc ccctagtggt caagggaaaa cgggtggctg   1200

gaggccctca gatgatccag ctcagcctgg atgggaagcg cctctacatc accacgtcgc   1260

tgtacagtgc ctgggacaag cagttttacc ctgatctcat cagggaaggc tctgtgatgc   1320

tgcaggttga tgtagacaca gtaaaaggag ggctgaagtt gaaccccaac ttcctggtgg   1380

acttcgggaa ggagcccctt ggcccagccc ttgcccatga gctccgctac cctgggggcg   1440

attgtagctc tgacatctgg atttgaactc caccctcatc acccacactc cctattttgg   1500

gccctcactt ccttggggac ctggcttcat tctgctctct cttggcaccc gacccttggc   1560

agcatgtacc acacagccaa gctgagactg tggcaatgtg ttgagtcata tacatttact   1620

gaccactgtt gcttgttgct cactgtgctg cttttccatg agctcttgga ggcaccaaga   1680

aataaactcg taaccctgtc cttcaaaaaa aaaaaaaaaa a                       1721
```

<210> SEQ ID NO 15
<211> LENGTH: 2588
<212> TYPE: DNA
<213> ORGANISM: Homo sapiens

<400> SEQUENCE: 15

```
ggcacgaggc tctctcctcc ctctttcttc gggcagcctc cccaccaccc cacttcagcc     60

tcccccactc ttgccgcctc catatcatca agctctggtg gcgcctgggg ggcttttcgg    120

atcggcagga tgtacccccca gggaaggcac ccgaccccgc tccagtccgg ccagcccttc    180

aagttctcga tcttggagat ctgcgaccgc atcaaagaag aattccagtt tcttcaggct    240

caataccaca gcctcaagct agaatgtgag aagctggcca gcgagaagac ggaaatgcag    300

cgacattatg tcatgtatta tgagatgtcg tacgggctca acattgaaat gcataagcag    360

gcggagattg tgaagcgtct gagcggtatc tgcgctcaga ttatcccctt cctgacccag    420

gagcatcagc agcaggtgct ccaggccgta gaacgcgcca agcaggtcac cgtgggggag    480

ctgaacagcc tcatcgggca gcagctccag ccgctgtccc accacgcacc ccctgtgccc    540

ctcacccccc gcccagccgg gctggtgggc ggcagtgcta cggggctgct tgctctgtct    600

ggagccctgg ctgcccaggc tcagctggcg gcggctgtca aggaggaccg tgcgggcgtg    660

gaggccgagg ggtccagagt ggagagagcc ccgagcagga gtgcatctcc ctcgcccccct    720

gagagtctcg tggaggagga gcgaccgagt ggccctggtg gtggcgggaa gcagagagca    780

gatgagaagg agccatcagg accttatgaa agcgacgaag acaagagtga ttacaatctg    840

gtggtggacg aggaccaacc ctcagagccc cccagcccgg ctaccacccc ctgcggaaag    900

gtacccatct gcattcctgc ccgtcgggac ctggtggaca gtccagcctc cttggcctct    960

agccttggct caccgctgcc tagagccaag gagctcatcc tgaatgacct tcccgccagc   1020

actcctgcct ccaaatcctg tgactcctcc ccgccccagg acgcttccac cccccgggccc   1080

agctcggcca gtcacctctg ccagcttgct gccaagccag caccttccac ggacagcgtc   1140

gccctgagga gcccccctgac tctgtccagt cccttcacca cgtccttcag cctgggctcc   1200

cacagcactc tcaacggaga cctctccgtg cccagctcct acgtcagcct ccacctgtcc   1260

ccccaggtca gcagctctgt ggtgtacgga cgctcccccg tgatggcatt tgagtctcat   1320
```

```
ccccatctcc gagggtcatc cgtctcttcc tccctaccca gcatccctgg gggaaagccg   1380
gcctactcct tccacgtgtc tgcggacggg cagatgcagc cggttccctt cccctcggat   1440
gcactggtag gcgcgggcat cccgcggcac gcccggcagc tgcacacgct ggcccatggc   1500
gaggtggtct gcgcggtcac catcagcggc tccacacagc atgtgtacac gggcggcaag   1560
ggctgtgtga aggtgtggga cgtgggccag cctggggcca agacgcccgt ggcccagctc   1620
gactgcctga accgagacaa ctacattcgt tcctgcaagt tgctgccgga tggccggagt   1680
ctgatcgtgg gcggtgaggc cagcaccttg tccatttggg acctggcggc gcccaccccc   1740
cgtatcaagg ccgagctgac ttcctcagcc ccagcctgct acgccctggc cgtcagcccc   1800
gacgccaagg tttgcttctc ctgctgcagc gatggcaaca ttgtggtctg ggacctgcag   1860
aatcagacta tggtcaggca gttccagggc cacacggacg gcgccagctg cattgatatt   1920
tccgattacg gcactcggct ctggacaggg ggcctggaca acacggtgcg ctgctgggac   1980
ctgcgggagg gccgccagct gcagcagcat gacttcagct cccagatttt ctccctgggc   2040
cactgcccta accaggactg gctggcggtc ggaatggaga gtagcaacgt ggagatcctg   2100
cacgtccgca agccggagaa ataccagctg cacctccacg agagctgcgt gctgtccctg   2160
aagtttgcct cctgcggacg gtggtttgtg agcaccggga aggacaacct gctcaacgcc   2220
tggaggacgc cgtacggggc cagcattttc cagtccaagg agtcgtcctc agtcctgagt   2280
tgtgacatct ccagaaataa caaatacatc gtgacaggct cgggggacaa gaaggccacc   2340
gtgtatgagg tggtctactg agacatgacc ccccttcctg tacccgaagt ccagactccc   2400
aggggaatca gcagccagga cagacatcct agcagccgcc tcccagccct gcctaggaac   2460
cgtacatccc atctgctctc tggccaacgg cttcacacct tcccctgctg catgtggggg   2520
ccgatgggca ggggacctcg gtggaaataa aatgtatcta tcacatccgc aaaaaaaaaa   2580
aaaaaaaa                                                            2588
```

<210> SEQ ID NO 16
<211> LENGTH: 8133
<212> TYPE: DNA
<213> ORGANISM: Homo sapiens

<400> SEQUENCE: 16

```
cgtccctgca gccctcgccc ggcgctccag tagcaggacc cggtctcggg accagccggt     60
aatatgcacg tgtcactagc tgaggccctg gaggttcggg gtggaccact tcaggaggaa    120
gaaatatggg ctgtattaaa tcaaagtgct gaaagtctcc aagaattatt cagaaaagta    180
agcctagctg atcctgctgc ccttggcttc atcatttctc catggtctct gctgttgctg    240
ccatctggta gtgtgtcatt tacagatgaa aatatttcca atcaggatct tcgagcattc    300
actgcaccag aggttcttca aaatcagtca ctaacttctc tctcagatgt tgaaaagatc    360
cacatttatt ctcttggaat gacactgtat tggggggctg attatgaagt gcctcagagc    420
caacctatta agcttggaga tcatctcaac agcatactgc ttggaatgtg tgaggatgtt    480
atttacgctc gagtttctgt tcggactgtg ctggatgctt gcagtgccca cattaggaat    540
agcaattgtg caccctcatt ttcctacgtg aaacacttgg taaaactggt tctgggaaat    600
ctttctggga cagatcagct ttcctgtaac agtgaacaaa agcctgatcg aagccaggct    660
attcgagatc gattgcgagg aaaaggatta ccaacaggaa gaagctctac ttctgatgta    720
ctagacatac aaaagcctcc actctctcat cagacctttc ttaacaaagg gcttagtaaa    780
tctatgggat ttctgtccat caaagataca caagatgaga attatttcaa ggacatttta    840
```

-continued

```
tcagataatt ctggacgtga agattctgaa aatacattct ccccttacca gttcaaaact    900
agtggcccag aaaaaaaacc catccctggc attgatgtgc tttctaagaa gaagatctgg    960
gcttcatcca tggacttgct ttgtacagct gacagagact tctcttcagg agagactgcc   1020
acatatcgtc gttgtcaccc tgaggcagta acagtgcgga cttcaactac tcctagaaaa   1080
aaggaggcaa gatactcaga tggaagtata gccttggata tctttggccc tcagaaaatg   1140
gatccaatat atcacactcg agaattgccc acctcctcag caatatcaag tgctttggac   1200
cgaatccgag agagacaaaa gaaacttcag gttctgaggg aagccatgaa tgtagaagaa   1260
ccagttcgaa gatacaaaac ttatcatggt gatgtcttta gtacctccag tgaaagtcca   1320
tctattattt cctctgaatc agatttcaga caagtgagaa gaagtgaagc ctcaaagagg   1380
tttgaatcca gcagtggtct cccaggggta gatgaaacct taagtcaagg ccagtcacag   1440
agaccgagca gacaatatga aacacccttt gaaggcaact taattaatca agagatcatg   1500
ctaaaacggc aagaggaaga actgatgcag ctacaagcca aaatggccct tagacagtct   1560
cggttgagcc tatatccagg agacacaatc aaagcgtcca tgcttgacat caccagggat   1620
ccgttaagag aaattgccct agaaacagcc atgactcaaa gaaaactgag gaatttcttt   1680
ggccctgagt ttgtgaaaat gacaattgaa ccatttatat ctttggattt gccacggtct   1740
attcttacta agaaagggaa gaatgaggat aaccgaagga aagtaaacat aatgcttctg   1800
aacgggcaaa gactggaact gacctgtgat accaaaacta tatgtaaaga tgtgtttgat   1860
atggttgtgg cacatattgg cttagtagag catcatttgt ttgctttagc taccctcaaa   1920
gataatgaat atttctttgt tgatcctgac ttaaaattaa ccaaagtggc cccagaggga   1980
tggaaagaag aaccaaagaa aaagaccaaa gccactgtta attttacttt gtttttcaga   2040
attaaatttt ttatggatga tgttagtcta atacaacata ctctgacgtg tcatcagtat   2100
taccttcagc ttcgaaaaga tattttggag gaaaggatgc actgtgatga tgagacttcc   2160
ttattgctgg catccttggc tctccaggct gagtatggag attatcaacc agaggttcat   2220
ggtgtgtctt actttagaat ggagcactat ttgcccgcca gagtgatgga gaaacttgat   2280
ttatcctata tcaaagaaga gttacccaaa ttgcataata cctatgtggg agcttctgaa   2340
aaagagacag agttagaatt tttaaaggtc tgccaaagac tgacagaata tggagttcat   2400
tttcaccgag tgcaccctga gaagaagtca caaacaggaa tattgcttgg agtctgttct   2460
aaaggtgtcc ttgtgtttga agttcacaat ggagtgcgca cattggtcct tcgctttcca   2520
tggagggaaa ccaagaaaat atctttttct aaaaagaaaa tcacattgca aaatacatca   2580
gatggaataa aacatggctt ccagacagac aacagtaaga tatgccagta cctgctgcac   2640
ctctgctctt accagcataa gttccagcta cagatgagag caagacagag caaccaagat   2700
gcccaagata ttgagagagc ttcgtttagg agcctgaatc tccaagcaga gtctgttaga   2760
ggatttaata tgggacgagc aatcagcact ggcagtctgg ccagcagcac cctcaacaaa   2820
cttgctgttc gacctttatc agttcaagct gagattctga agaggctatc ctgctcagag   2880
ctgtcgcttt accagccatt gcaaaacagt tcaaaagaga agaatgacaa agcttcatgg   2940
gaggaaaagc ctagagagat gagtaaatca taccatgatc tcagtcaggc ctctctctat   3000
ccacatcgga aaaatgtcat tgttaacatg gaacccccac cacaaaccgt tgcagagttg   3060
gtgggaaaac cttctcacca gatgtcaaga tctgatgcag aatctttggc aggagtgaca   3120
aaacttaata attcaaagtc tgttgcgagt ttaaatagaa gtcctgaaag gaggaaacat   3180
gaatcagact cctcatccat tgaagaccct gggcaagcat atgttctagg aatgactatg   3240
```

-continued

```
catagttctg gaaactcttc atcccaagta cccttaaaag aaaatgatgt gctacacaaa   3300
agatggagca tagtatcttc accagaaagg gagatcacct tagtgaacct gaaaaaagat   3360
gcaaagtatg gcttgggatt tcaaattatt ggtggggaga agatgggaag actggaccta   3420
ggcatattta tcagttcagt tgcccctgga ggaccagctg acttggatgg atgcttgaag   3480
ccaggagacc gtttgatatc tgtgaatagt gtgagtctgg agggagtcag ccaccatgct   3540
gcaattgaaa ttttgcaaaa tgcacctgaa gatgtgacac ttgttatctc tcagccaaaa   3600
gaaaagatat ccaaagtgcc ttctactcct gtgcatctca ccaatgagat gaaaaactac   3660
atgaagaaat cttcctacat gcaagacagt gctatagatt cttcttccaa ggatcaccac   3720
tggtcacgtg gtaccctgag gcacatctcg gagaactcct ttgggccgtc tgggggcctg   3780
cgggaaggaa gcctgagttc tcaagattcc aggactgaga gtgccagctt gtctcaaagc   3840
caggtcaatg gtttctttgc cagccattta ggtgaccaaa cctggcagga atcacagcat   3900
ggcagccctt ccccatctgt aatatccaaa gccaccgaga aagagacttt cactgatagt   3960
aaccaaagca aaactaaaaa gccaggcatt tctgatgtaa ctgattactc agaccgtgga   4020
gattcagaca tggatgaagc cacttactcc agcagtcagg atcatcaaac accaaaacag   4080
gaatcttcct cttcagtgaa tacatccaac aagatgaatt ttaaaacttt ttcttcatca   4140
cctcctaagc ctggagatat ctttgaggtt gaactggcta aaaatgataa cagcttgggg   4200
ataagtgtca cggtactgtt tgacaaggga ggtgtgaata cgagtgtcag acatggtggc   4260
atttatgtga aagctgttat tccccaggga gcagcagagt ctgatggtag aattcacaaa   4320
ggtgatcgcg tcctagctgt caatggagtt agtctagaag gagccaccca taagcaagct   4380
gtggaaacac tgagaaatac aggacaggtg gttcatctgt tattagaaaa gggacaatct   4440
ccaacatcta aagaacatgt cccggtaacc ccacagtgta ccctttcaga tcagaatgcc   4500
caaggtcaag gcccagaaaa agtgaagaaa acaactcagg tcaaagacta cagctttgtc   4560
actgaagaaa atacatttga ggtaaaatta tttaaaaata gctcaggtct aggattcagt   4620
ttttctcgag aagataatct tataccggag caaattaatg ccagcatagt aagggttaaa   4680
aagctctttc ctggacagcc agcagcagaa agtggaaaaa ttgatgtagg agatgttatc   4740
ttgaaagtga atggagcctc tttgaaagga ctatctcagc aggaagtcat atctgctctc   4800
aggggaactg ctccagaagt attcttgctt ctctgcagac ctccacctgg tgtgctaccg   4860
gaaattgata ctgcgctttt gaccccactt cagtctccag cacaagtact tccaaacagc   4920
agtaaagact cttctcagcc atcatgtgtg gagcaaagca ccagctcaga tgaaaatgaa   4980
atgtcagaca aaagcaaaaa acagtgcaag tccccatcca gaagagacag ttacagtgac   5040
agcagtggga gtggagaaga tgacttagtg acagctccag caaacatatc aaattcgacc   5100
tggagttcag ctttgcatca gactctaagc aacatggtat cacaggcaca gagtcatcat   5160
gaagcaccca agagtcaaga agataccatt tgtaccatgt tttactatcc tcagaaaatt   5220
cccaataaac cagagtttga ggacagtaat ccttcccctc taccaccgga tatggctcct   5280
gggcagagtt atcaacccca atcagaatct gcttcctcta gttcgatgga taagtatcat   5340
atacatcaca tttctgaacc aactagacaa gaaaactgga cacctttgaa aaatgacttg   5400
gaaaatcacc ttgaagactt tgaactggaa gtagaactcc tcattaccct aattaaatca   5460
gaaaaaggaa gcctgggttt tacagtaacc aaaggcaatc agagaattgg ttgttatgtt   5520
catgatgtca tacaggatcc agccaaaagt gatggaaggc taaaacctgg ggaccggctc   5580
ataaaggtta atgatacaga tgttactaat atgactcata cagatgcagt taatctgctc   5640
```

```
cgggctgcat ccaaaacagt cagattagtt attggacgag ttctagaatt acccagaata   5700
ccaatgttgc ctcatttgct accggacata acactaacgt gcaacaaaga ggagttgggt   5760
ttttccttat gtggaggtca tgacagcctt tatcaagtgg tatatattag tgatattaat   5820
ccaaggtccg tcgcagccat tgagggtaat ctccagctat tagatgtcat ccattatgtg   5880
aacggagtca gcacacaagg aatgaccttg gaggaagtta acagagcatt agacatgtca   5940
cttccttcat tggtattgaa agcaacaaga aatgatcttc cagtggtccc cagctcaaag   6000
aggtctgctg tttcagctcc aaagtcaacc aaaggcaatg gttcctacag tgtggggtct   6060
tgcagccagc ctgccctcac tcctaatgat tcattctcca cggttgctgg ggaagaaata   6120
aatgaaatat cgtaccccaa aggaaaatgt tctacttatc agataaaggg atcaccaaac   6180
ttgactctgc ccaaagaatc ttatatacaa gaagatgaca tttatgatga ttcccaagaa   6240
gctgaagtta tccagtctct gctggatgtt gtggatgagg aagcccagaa tcttttaaac   6300
gaaaataatg cagcaggata ctcctgtggt ccaggtacat taaagatgaa tgggaagtta   6360
tcagaagaga gaacagaaga tacagactgc gatggttcac ctttacctga gtattttact   6420
gaggccacca aaatgaatgg ctgtgaagaa tattgtgaag aaaaagtaaa aagtgaaagc   6480
ttaattcaga agccacaaga aaagaagact gatgatgatg aaataacatg ggggaaatgat   6540
gagttgccaa tagagagaac aaaccatgaa gattctgata aagatcattc ctttctgaca   6600
aacgatgagc tcgctgtact ccctgtcgtc aaagtgcttc cctctggtaa atacacgggt   6660
gccaacttaa aatcagtcat tcgagtcctg cggggtttgc tagatcaagg aattccttct   6720
aaggagctgg agaatcttca agaattaaaa cctttggatc agtgtctaat tgggcaaact   6780
aaggaaaaca gaaggaagaa cagatataaa aatatacttc cctatgatgc tacaagagtg   6840
cctcttggag atgaaggtgg ctatatcaat gccagcttca ttaagatacc agttgggaaa   6900
gaagagttcg tttacattgc ctgccaagga ccactgccta caactgttgg agacttctgg   6960
cagatgattt gggagcaaaa atccacagtg atagccatga tgactcaaga agtagaagga   7020
gaaaaaatca aatgccagcg ctattggccc aacatcctag gcaaaacaac aatggtcagc   7080
aacagacttc gactggctct tgtgagaatg cagcagctga agggctttgt ggtgagggca   7140
atgacccttg aagatattca gaccagagag gtgcgccata tttctcatct gaatttcact   7200
gcctggccag accatgatac accttctcaa ccagatgatc tgcttacttt tatctcctac   7260
atgagacaca tccacagatc aggcccaatc attacgcact gcagtgctgg cattggacgt   7320
tcagggaccc tgatttgcat agatgtggtt ctgggattaa tcagtcagga tcttgatttt   7380
gacatctctg atttggtgcg ctgcatgaga ctacaaagac acggaatggt tcagacagag   7440
gatcaatata ttttctgcta tcaagtcatc ctttatgtcc tgacacgtct tcaagcagaa   7500
gaagagcaaa aacagcagcc tcagcttctg aagtgacatg aaaagagcct ctggatgcat   7560
ttccatttct ctccttaacc tccagcagac tcctgctctc tatccaaaat aagatcacag   7620
agcagcaagt tcatacaaca tgcatgttct cctctatctt agaggggtat tcttcttgaa   7680
aataaaaaat attgaaatgc tgtattttta cagctacttt aacctatgat aattatttac   7740
aaaattttaa cactaaccaa acaatgcaga tcttagggat gattaaaggc agcatttgat   7800
gatagcagac attgttacaa ggacatggtg agtctatttt taatgcacca atcttgttta   7860
tagcaaaaat gttttccaat attttaataa agtagttatt ttatagggga tacttgaaac   7920
cagtatttaa gctttaaatg acagtaatat tggcatagaa aaaagtagca aatgtttact   7980
gtatcaattt ctaatgttta ctatatagaa tttcctgtaa tatatttata tacttttttca   8040
```

tgaaaatgga gttatcagtt atctgtttgt tactgcatca tctgtttgta atcattatct 8100
cactttgtaa ataaaaacac accttaaaac atg 8133

<210> SEQ ID NO 17
<211> LENGTH: 2272
<212> TYPE: DNA
<213> ORGANISM: Homo sapiens

<400> SEQUENCE: 17
aggcgcccgc ccgccgcgcg tgattctcgc ctcgccgcag cccagccctg cgcgccttgc 60
ccggcggccc ccgcccggcc gctccgggcc cctggccccg cggagcgatg ctgctgctgg 120
ctgccgcctt cctcgtggcc ttcgtgctgc tgctgtacat ggtgtctccg ctcatcagcc 180
ccaagcccct cgccctgccc ggggcgcatg tggtggttac aggaggttcc agtggcatcg 240
ggaagtgcat tgctatcgag tgctataaac aaggagcttt tataactctg gttgcacgaa 300
atgaggataa gctgctgcag gcaaagaaag aaattgaaat gcactctatt aatgacaaac 360
aggtggtgct ttgcatatca gttgatgtat ctcaagacta taaccaagta gagaatgtca 420
taaaacaagc acaggagaaa ctgggtccag tggacatgct ggtaaattgt gcaggaatgg 480
cagtgtcagg aaaatttgaa gatcttgaag ttagtacctt tgaaaggtta atgagcatca 540
attacctggg cagcgtgtac cccagccggg ccgtgatcac caccatgaag gagcgccggg 600
tgggcaggat cgtgtttgtg tcctcccagg caggacagtt gggattattc ggtttcacag 660
cctactctgc atccaagttt gccataaggg gattggcaga agctttgcag atggaggtga 720
agccatataa tgtctacatc acagttgctt acccaccaga cacagacaca cctggctttg 780
ccgaagaaaa cagaacaaag cctttggaga ctcgacttat ttcagagacc acatctgtgt 840
gcaaaccaga acaggtggcc aaacaaattg ttaaagatgc catacaagga aatttcaaca 900
gttcccttgg ctcagatggg tacatgctct cggccctgac ctgtgggatg gctccagtaa 960
cttctattac tgaggggctc cagcaggtgg tcaccatggg ccttttccgc actattgctt 1020
tgttttacct tggaagtttt gacagcatag ttcgtcgctg catgatgcag agagaaaaat 1080
ctgaaaatgc agacaaaact gcctaatctt cttacccctt ggaagaagac tgtttccaaa 1140
taatttgaac agcttgctgc taaatgggac ccaatttttg gcctatagac acttatgtat 1200
tgttttcgaa tacgtcagat tggaccagtg ctcttcagga atgtggctgc aagcaagggg 1260
ctagaagttc acctcctgac agtattatta atactatgca aatatggaat aggagaccat 1320
ttgattttct aggctttgtg gtagagaggt gaaggtatga gaattaatag cgtgtgaaca 1380
aagtaaagaa caggattcca gaatgatcat taaatttgtt tctatttatt ctttttttgcc 1440 cccctagaga ttaagtccag aaatgtactt tctggcacat aaagaaatct tgaggacttt 1500
gtttaaacct tccataaaaa aacaattttc ggtttctcgg gttctctctc tctgtctctc 1560
tgtctctctg tctctctgtc tctctgtctc tctctctctc tctctttctt tctttgtgta 1620
ttttattcaa gatgagttgg acccattgcc agtgagtctg aatgtcactg acagccctgt 1680
gttgtgctca ggactcactc tgctgctggt ggaaactcat ggcttctctc tctctttgat 1740
cccataaagc tacgaggggg acgggagagg gcagtgcaat gggaagtaaa gagatatttt 1800
ccagtaggaa aagcaatgct ttcttgtctt tagactcaaa tgcttaggga acgtttcatt 1860
tctcattcat ggggaaaggc agcctcctta aatgttttct gaagagcggt aaaatctaga 1920
agcttaagaa tttacagttc cttcaataac catgatgacc tgaagttcac ctatcccatt 1980
ttagcatcta cttgttttttc ccatctcttc ctttccaatt ttgcttatac tgctgtaata 2040

-continued

```
tttttgtaaa aaaaaaaaaa aaggaaaaaa aagaccagct aaaattttcg acttgacttt   2100

ttaacttaac tcatgaatta attaaagcaa atgaaaaaat taaaaagtgt gactttttct   2160

cggagcatat atgtagcttt taggaaaggc tgatgatggt ataaagtttg ctcattaaga   2220

aaaaaagaca aggctgattt tgaagagagt tgcttttgaa ataaaatgat ca           2272


<210> SEQ ID NO 18
<211> LENGTH: 1414
<212> TYPE: DNA
<213> ORGANISM: Homo sapiens

<400> SEQUENCE: 18

gaattcgcac tgctctgaga atttgtgagc agcccctaac aggctgttac ttcactacaa     60

ctgacgatat gatcatctta atttacttat ttctcttgct atgggaagac actcaaggat    120

ggggattcaa ggatggaatt tttcataact ccatatggct tgaacgagca gccggtgtgt    180

accacagaga agcacggtct ggcaaataca agctcaccta cgcagaagct aaggcggtgt    240

gtgaatttga aggcggccat ctcgcaactt acaagcagct agaggcagcc agaaaaattg    300

gatttcatgt ctgtgctgct ggatggatgg ctaagggcag agttggatac cccattgtga    360

agccagggcc caactgatga tttggaaaaa ctggcattat tgattatgga atccgtctca    420

ataggagtga aagatgggat gcctattgct acaacccaca cgcaaaggag tgtggtggcg    480

tctttacaga tccaaagcga atttttaaat ctccaggctt cccaaatgag tacgaagata    540

accaaatctg ctactggcac attagactca agtatggtca gcgtattcac ctgagttttt    600

tagatttga ccttgaagat gacccaggtt gcttggctga ttatgttgaa atatatgaca    660

gttacgatga tgtccatggc tttgtgggaa gatactgtgg agatgagctt ccagatgaca    720

tcatcagtac aggaaatgtc atgaccttga agtttctaag tgatgcttca gtgacagctg    780

gaggtttcca aatcaaatat gttgcaatgg atcctgtatc caaatccagt caaggaaaaa    840

atacaagtac tacttctact ggaaataaaa actttttagc tggaagattt agccacttat    900

aaaaaaaaaa aaggatgatc aaaacacaca gtgtttatgt tggaatcttt tggaactcct    960

ttgatctcac tgttattatt aacatttatt tattattttt ctaaatgtga aagaaataca   1020

taatttaggg aaaattggaa aatataggaa actttaaacg agaaaatgaa acctctcata   1080

atcccactgc atagaaataa caagcgttaa cattttcata tttttttctt tcagtcattt   1140

ttgtatttgt ggtatatgta tatatgtacc tatatgtatt tgcatttgaa attttggaat   1200

cctgctctat gtacagtttt gtattatact ttttaaatct tgaactttat gaacattttc   1260

tgaaatcatt gattattcta caaaaacatg attttaaaca gctgtaaaat attctatgat   1320

atgaatgttt tatgcattat ttaagcctgt ctctattgtt ggaatttcag gtcattttca   1380

taaatattgt tgcaataaat atccttcgga attc                               1414


<210> SEQ ID NO 19
<211> LENGTH: 2704
<212> TYPE: DNA
<213> ORGANISM: Homo sapiens

<400> SEQUENCE: 19

gggagaaacg ttctcactcg ctctctgctc gctgcgggcg ctccccgccc tctgctgcca     60

gaaccttggg gatgtgccta gacccggcgc agcacacgtc cgggccaacc gcgagcagaa    120

caaacctttg gcgggcggcc aggaggctcc ctcccagcca ccgccccct ccagcgcctt    180

tttttccccc catacaatac aagatcttcc ttcctcagtt cccttaaagc acagcccagg    240
```

-continued

```
gaaacctcct cacagttttc atccagccac gggccagcat gtctgggggc aaatacgtag    300
actcggaggg acatctctac accgttccca tccgggaaca gggcaacatc tacaagccca    360
acaacaaggc catggcagac gagctgagcg agaagcaagt gtacgacgcg cacaccaagg    420
agatcgacct ggtcaaccgc gaccctaaac acctcaacga tgacgtggtc aagattgact    480
ttgaagatgt gattgcagaa ccagaaggga cacacagttt tgacggcatt tggaaggcca    540
gcttcaccac cttcactgtg acgaaatact ggttttaccg cttgctgtct gccctctttg    600
gcatcccgat ggcactcatc tggggcattt acttcgccat tctctctttc ctgcacatct    660
gggcagttgt accatgcatt aagagcttcc tgattgagat tcagtgcatc agccgtgtct    720
attccatcta cgtccacacc gtctgtgacc cactctttga agctgttggg aaaatattca    780
gcaatgtccg catcaacttg cagaaagaaa tataaatgac atttcaagga tagaagtata    840
cctgattttt tttcctttta attttcctgg tgccaatttc aagttccaag ttgctaatac    900
agcaacaatt tatgaattga attatcttgg ttgaaaataa aaagatcact ttctcagttt    960
tcataagtat tatgtctctt ctgagctatt tcatctattt ttggcagtct gaatttttaa   1020
aacccattta aatttttttc cttacctttt tatttgcatg tggatcaacc atcgctttat   1080
tggctgagat atgaacatat tgttgaaagg taatttgaga gaaatatgaa gaactgagga   1140
ggaaaaaaaa aaaaaagaaa agaaccaaca acctcaactg cctactccaa aatgttggtc   1200
attttatgtt aagggaagaa ttccagggta tggccatgga gtgtacaagt atgtgggcag   1260
attttcagca aactcttttc ccactgttta aggagttagt ggattactgc cattcacttc   1320
ataatccagt aggatccagt gatccttaca agttagaaaa cataatcttc tgccttctca   1380
tgatccaact aatgccttac tcttcttgaa attttaacct atgatatttt ctgtgcctga   1440
atatttgtta tgtagataac aagacctcag tgccttcctg tttttcacat tttccttttc   1500
aaatagggtc taactcagca actcgcttta ggtcagcagc ctccctgaag accaaaatta   1560
gaatatccat gacctagttt tccatgcgtg tttctgactc tgagctacag agtctggtga   1620
agctcacttc tgggcttcat ctggcaacat ctttatccgt agtgggtatg gttgacacta   1680
gcccaatgaa atgaattaaa gtggaccaat agggctgagc tctctgtggg ctggcagtcc   1740
tggaagccag ctttccctgc ctctcatcaa ctgaatgagg tcagcatgtc tattcagctt   1800
cgtttatttt caagaataat cacgctttcc tgaatccaaa ctaatccatc accggggtgg   1860
tttagtggct caacattgtg ttcccatttc agctgatcag tgggcctcca aggaggggct   1920
gtaaaatgga ggccattgtg tgagcctatc agagttgctg caaacctgac ccctgctcag   1980
taaagcactt gcaaccgtct gttatgctgt gacacatggc ccctccccct gccaggagct   2040
ttggacctaa tccaagcatc cctttgccca gaaagaagat gggggaggag gcagtaataa   2100
aaagattgaa gtattttgct ggaataagtt caaattcttc tgaactcaaa ctgaggaatt   2160
tcacctgtaa acctgagtcg tacagaaagc tgcctggtat atccaaaagc tttttattcc   2220
tcctgctcat attgtgattc tgcctttggg gacttttctt aaaccttcag ttatgatttt   2280
tttttcatac acttattgga actctgcttg atttttgcct cttccagtct tcctgacact   2340
ttaattacca acctgttacc tactttgact ttttgcattt aaaacagaca ctggcatgga   2400
tatagtttta cttttaaact gtgtacataa ctgaaaatgt gctatactgc atacttttta   2460
aatgtaaaga tatttttatc tttatatgaa gaaaatcact taggaaatgg ctttgtgatt   2520
caatctgtaa actgtgtatt ccaagacatg tctgttctac atagatgctt agtccctcat   2580
gcaaatcaat tactggtcca aaagattgct gaaattttat atgcttactg atatatttta   2640
```

caattttta tcatgcatgt cctgtaaagg ttacaagcct gcacaataaa aatgtttaac 2700
ggtt 2704

<210> SEQ ID NO 20
<211> LENGTH: 1440
<212> TYPE: DNA
<213> ORGANISM: Homo sapiens

<400> SEQUENCE: 20
cgggcgcaga agcccctcct cggcgtcctg gtcccggccg tgcccgcggt gtcccgggag 60
gaaggggcgg gccgggggtc gggaggagtc acgtgccccc tcccgcccca ggtcgtcctc 120
tcagcatggg ggtcccgcgg cctcagccct gggcgctggg gctcctgctc tttctccttc 180
ctgggagcct gggcgcagaa agccacctct ccctcctgta ccaccttacc gcggtgtcct 240
cgcctgcccc ggggactcct gccttctggg tgtccggctg gctgggcccg cagcagtacc 300
tgagctacaa tagcctgcgg ggcgaggcgg agccctgtgg agcttgggtc tgggaaaacc 360
aggtgtcctg gtattgggag aaagagacca cagatctgag gatcaaggag aagctctttc 420
tggaagcttt caaagctttg gggggaaaag gtccctacac tctgcagggc ctgctgggct 480
gtgaactggg ccctgacaac acctcggtgc ccaccgccaa gttcgccctg aacggcgagg 540
agttcatgaa tttcgacctc aagcagggca cctggggtgg ggactggccc gaggccctgg 600
ctatcagtca gcggtggcag cagcaggaca aggcggccaa caaggagctc accttcctgc 660
tattctcctg cccgcaccgc ctgcgggagc acctggagag gggccgcgga aacctggagt 720
ggaaggagcc cccctccatg cgcctgaagg cccgacccag cagccctggc ttttccgtgc 780
ttacctgcag cgccttctcc ttctaccctc cggagctgca acttcggttc ctgcggaatg 840
ggctggccgc tggcaccggc cagggtgact tcggccccaa cagtgacgga tccttccacg 900
cctcgtcgtc actaacagtc aaaagtggcg atgagcacca ctactgctgc attgtgcagc 960
acgcggggct ggcgcagccc ctcagggtgg agctggaatc tccagccaag tcctccgtgc 1020
tcgtggtggg aatcgtcatc ggtgtcttgc tactcacggc agcggctgta ggaggagctc 1080
tgttgtggag aaggatgagg agtgggctgc cagccccttg gatctccctt cgtggagacg 1140
acaccggggt cctcctgccc accccagggg aggcccagga tgctgatttg aaggatgtaa 1200
atgtgattcc agccaccgcc tgaccatccg ccattccgac tgctaaaagc gaatgtagtc 1260
aggccccttt catgctgtga gacctcctgg aacactggca tctctgagcc tccagaaggg 1320
gttctgggcc tagttgtcct ccctctggag ccccgtcctg tggtctgcct cagtttcccc 1380
tcctaataca tatggctgtt ttccacctcg ataatataac acgagtttgg gcccgaaaaa 1440

<210> SEQ ID NO 21
<211> LENGTH: 1634
<212> TYPE: DNA
<213> ORGANISM: Homo sapiens

<400> SEQUENCE: 21
ccctaagtga gaggaccaac agttccgaca gcgagcgctc cccagatctg ggccacagca 60
cgcagattcc aagaaaggtg gtgtatgacc agctcaatca gatcctggtg tcagatgcag 120
ccctcccaga aaatgtcatt ctggtgaaca ccactgactg gcagggccag tatgtggctg 180
agctgctcca ggaccagcgg aagcctgtgg tgtgcacctg ctccaccgtg gaggtccagg 240
ccgtgctgtc cgccctgctc acccggatcc agcgctactg caactgcaac tcttccatgc 300
cgaggccagt gaaggtggct gctgtgggag gccagagcta cctgagctcc atcctcaggt 360
tctttgtcaa gtccctggcc aacatgacct ccgactggct tggctacatg cgcttcctca 420
tcatccccct cggttctcac cctgtggcca aatacttggg gtcagtcgac agtaaataca 480
gtagttcctt cctggattct ggttggagag atctgttcag tcgctcggag ccaccagtgt 540
cagagcaact ggacgtggca gggcgggtga tgcagtacgt caacggggca gccacgacac 600
accagcttcc cgtggccgaa gccatgctga cttgccggca taagttccct gatgaagact 660
cctatcagaa gtttattccc ttcattggcg tggtgaaggt gggtctggtt gaagactctc 720
cctccacagc aggcgatggg gacgattctc ctgtggtcag ccttactgtg ccctccacat 780
caccaccctc cagctcgggc ctgagccgag acgccacggc cacccctccc tcctccccat 840
ctatgagcag cgccctggcc atcgtgggga gccctaatag cccatatggg gacgtgattg 900
gcctccaggt ggactactgg ctgggccacc ccggggagcg gaggagggaa ggcgacaaga 960
gggacgccag ctcgaagaac accctcaaga gtgtcttccg ctcagtgcag gtgtcccgcc 1020
tgccccatag tggggaggcc cagctttctg gcaccatggc catgactgtg gtcaccaaag 1080
aaaagaacaa gaaagttccc accatcttcc tgagcaagaa accccgagaa aaggaggtgg 1140
attctaagag ccaggtcatt gaaggcatca gccgcctcat ctgttcttcc ccctccttag 1200
gccccagcct gggcccagac ccatcctccc agccaggttt ccctccagca ggctccttcc 1260
ctccctgtca cctccctctc accaacccgg ggtctgagcc cctcattcct gaccgtccgt 1320
gttctcagga gtggttgagg acacagggcc ccagcccagc cctctgcacc ccccagcccg 1380
gccatctgcg ccccacagcc cctttggagc ttttctcttg tcctctcact ccttcccaga 1440
agtttttgca cagaacttca ttttgaaagt gtttttctca ttctccatac ctcccccaag 1500
ctctcctcca gcccttccca gggctcagcc ctgctgtcct gagcgtctcc tgggccagag 1560
agaggagatg ggggtgggag ggactgagtt gatgttgggt ttttcattca ataaattggt 1620
gatttcttac cgac 1634

<210> SEQ ID NO 22
<211> LENGTH: 1264
<212> TYPE: DNA
<213> ORGANISM: Homo sapiens

<400> SEQUENCE: 22
ggcacgaggg gaggccgggg cggggcgggc gcagccggcg ctgagcttgc agggccgctc 60
ccctcacccg ccccccttcga gtccccgggc ttcgccccac ccggcccgtg ggggagtatc 120
tgtcctgccg ccttcgccca cgccctgcac tccgggaccg tccctgcgcg ctctgggcgc 180
accatggccc gcggggctgc gctggcgctg ctgctcttcg gcctgctggg tgttctggtc 240
gccgccccgg atggtggttt cgatttatcc gatgcccttc ctgacaatga aaacaagaaa 300
cccactgcaa tccccaagaa acccagtgct ggggatgact ttgacttagg agatgctgtt 360
gttgatggag aaaatgacga cccacgacca ccgaacccac ccaaaccgat gccaaatcca 420
aaccccaacc accctagttc ctccggtagc ttttcagatg ctgaccttgc ggatggcgtt 480
tcaggtggag aaggaaaagg aggcagtgat ggtggaggca gccacaggaa agaaggggaa 540
gaggccgacg ccccaggcgt gatccccggg attgtggggg ctgtcgtggt cgccgtggct 600
ggagccatct ctagcttcat tgcttaccag aaaaagaagc tatgcttcaa agaaaatgca 660
gaacaagggg aggtggacat ggagagccac cggaatgcca acgcagagcc agctgttcag 720
cgtactcttt tagagaaata gaagattgtc ggcagaaaca gcccaggcgt tggcagcagg 780
gttagaacag ctgcctgagg ctcctccctg aaggacacct gcctgagagc agagatggag 840
gccttctgtt cacggcggat tctttgtttt aatcttgcga tgtgctttgc ttgttgctgg 900
gcggatgatg tttactaacg atgaatttta catccaaagg gggataggca cttggacccc 960
cattctccaa ggcccggggg ggcggtttcc catgggatgt gaaaggctgg ccattattaa 1020
gtccctgtaa ctcaaatgtc aaccccaccg aggcaccccc ccgtccccca gaatcttggc 1080
tgtttacaaa tcacgtgtcc atcgagcacg tctgaaaccc ctggtagccc cgacttcttt 1140
ttaattaaaa taaggtaagc ccttcaattt gtttcttcaa tatttctttc atttgtaggg 1200
atatttgttt ttcatatcag actaataaaa agaaattaga aaccaaaaaa aaaaaaaaaa 1260
aaaa 1264

<210> SEQ ID NO 23
<211> LENGTH: 1567
<212> TYPE: DNA
<213> ORGANISM: Homo sapiens

<400> SEQUENCE: 23
tcctgggcct ctcaaagtct gagccccgct ccgctgatgc ctgtctgcag aatccgcacc 60
aaccagcacc atgcccatga ctctggggta ctgggacatc cgtgggctgg cccacgccat 120
ccgcttgctc ctggaataca cagactcaag ctatgtggaa aagaagtaca cgctggggga 180
cgctcctgac tatgacagaa gccagtggct gaatgaaaaa ttcaagctgg gcctggactt 240
tcccaatctg ccctacttga ttgatggggc tcacaagatc acccagagca atgccatcct 300
gcgctacatt gcccgcaagc acaacctgtg tggggagaca gaagaggaga agattcgtgt 360
ggacattttg gagaaccagg ttatggataa ccacatggag ctggtcagac tgtgctatga 420
cccagatttt gagaaactga agccaaaata cttggaggaa ctccctgaaa agctaaagct 480
ctactcagag tttctgggga agcggccatg gtttgcagga gacaagatca cctttgtgga 540
tttccttgcc tatgatgtcc ttgacatgaa gcgtatattt gagcccaagt gcttggacgc 600
cttcctaaac ttgaaggact tcatctcccg ctttgagggt ttgaagaaga tctctgccta 660
catgaagtcc agccaattcc tccgaggtct tttgtttgga aagtcagcta catggaacag 720
caaatagggc ccagtgatgc cagaagatgg gagggaggag ccaaccttgc tgcctgcgac 780
cctggaggac agcctgactc cctggacctg ccttcttcct tttccttct ttctactctc 840 ttctcttccc caaggcctca ttggcttcct ttcttctaac atcatccctc cccgcatcga 900
ggctctttaa agcttcagct ccccactgtc ctccatcaaa gtccccctcc taacgtcttc 960
ctttccctgc actaacgcca acctgactgc ttttcctgtc agtgcttttc tcttctttga 1020
gaagccagac tgatctctga gctccctagc actgtcctca aagaccatct gtatgccctg 1080
ctccctttgc tgggtcccta ccccagctcc gtgtgatgcc cagtaaagcc tgaaccatgc 1140
ctgccatgtc ttgtcttatt ccctgaggct cccttgactc aggactgtgc tcgaattgtg 1200
ggtggttttt tgtcttctgt tgtccacagc cagagcttag tggatgggtg tgtgtgtgtg 1260
tgtgttgggg gtggtgatca ggcaggttca taaatttcct tggtcatttc tgccctctag 1320
ccacatccct ctgttcctca ctgtggggat tactacagaa aggtgctctg tgccaagttc 1380
ctcactcatt cgcgctcctg taggccgtct agaactggca tggttcaaag aggggctagg 1440
ctgatgggga agggggctga gcagctccca ggcagactgc cttctttcac cctgtcctga 1500
tagacttccc tgatctagat atccttcgtc atgacacttc tcaataaaac gtatcccacc 1560
gtattgt 1567

<210> SEQ ID NO 24
<211> LENGTH: 900
<212> TYPE: DNA
<213> ORGANISM: Homo sapiens

<400> SEQUENCE: 24
ggcacgagcg tgcgtgctgg cgtgcgttca ctttcagcct ggtgtggggc ttgtaaacat 60
ataacataaa aatggcttcc aaaagagctc tggtcatcct ggctaaagga gcagaggaaa 120
tggagacggt catccctgta gatgtcatga ggcgagctgg gattaaggtc accgttgcag 180
gcctggctgg aaaagaccca gtacagtgta gccgtgatgt ggtcatttgt cctgatgcca 240
gccttgaaga tgcaaaaaaa gagggaccat atgatgtggt ggttctacca ggaggtaatc 300
tgggcgcaca gaatttatct gagtctgctg ctgtgaagga gatactgaag gagcaggaaa 360
accggaaggg cctgatagcc gccatctgtg caggtcctac tgctctgttg gctcatgaaa 420
taggttttgg aagtaaagtt acaacacacc ctcttgctaa agacaaaatg atgaatggag 480
gtcattacac ctactctgag aatcgtgtgg aaaaagacgg cctgattctt acaagccggg 540
ggcctgggac cagcttcgag tttgcgcttg caattgttga agccctgaat ggcaaggagg 600
tggcggctca agtgaaggct ccacttgttc ttaaagacta gagcagcgaa ctgcgacgat 660
cacttagaga aacaggccgt taggaatcca ttctcactgt gttcgctcta aacaaaacag 720
tggtaggtta atgtgttcag aagtcgctgt ccttactact tttgcggaag tatggaagtc 780
acaactacac agagatttct cagcctacaa attgtgtcta tacatttcta agccttgttt 840
gcagaataaa cagggcattt agcaaaaaaa aaaaaaaaaa aaaaaaaaaa aaaaaaaaaa 900

<210> SEQ ID NO 25
<211> LENGTH: 647
<212> TYPE: DNA
<213> ORGANISM: Homo sapiens

<400> SEQUENCE: 25
gctcactgag caccgtccca gcatccggac accacagcgg cccttcgctc cacgcagaaa 60
accacacttc tcataccttc actcaacact tccttcccca aagccagaag atgcacaagg 120
aggaacatga ggtggctgtg ctgggggcac cccccagcac catccttcca aggtccaccg 180
tgattaacat ccacagcgag acctccgtgc ccgaccatgt cgtctggtcc ctgttcaaca 240
ccctcttctt gaactggtgc tgtctgggct tcatagcatt cgcctactcc gtaaagtcta 300
gggacaggaa gatggttggc gacgtgaccg gggcccaggc ctatgcctcc accgccaagt 360
gcctgaacat ctgggccctg attctgggca tcctcatgac cattggattc atcctgttac 420
tggtattcgg ctctgtaaca gtctaccata ttatgttaca gataatacag gaaaaacggg 480
gttactagta gccgcccata gcctgcaacc tttgcactcc actgtgcaat gctggccctg 540
cacgctgggg ctgttgcccc tgccccttg gtcctgcccc tagatacagc agtttatacc 600
cacacacctg tctacagtgt cattcaataa agtgcacgtg cttgtga 647

<210> SEQ ID NO 26
<211> LENGTH: 2850
<212> TYPE: DNA
<213> ORGANISM: Homo sapiens

<400> SEQUENCE: 26
aaaagaccag gtaattttaa catttgtgga atcacaaatg taaattcata agaagctcta 60
attaaaaaaa aaaagtctga agtatatgag cataacaact taggagtgtg tctacatact 120
taacttttga agttttttgg caactttata tacttttttt aaatttacaa gtctacttaa 180

-continued

```
agacttctta taccccaaat gattaagtta attttagagg tcacctttct cacagcagtg    240
tcacttgaaa tttagtaggg aaggatattg cagtattttt cagtttcctt agcacagcac    300
cacagaaagc agcttattcc ttttgagtgg cagacactcg acggtgcctg cccaactttc    360
ctcctgagtg gcaagcagat gagtctcagt aattcatact gaaccaaaat gccacataca    420
ctaggggcag tcagaaactg gctgagaaat cccccgcctc attcgcccct ctgctcccag    480
gaactagagt ccagttaaag cccctatgcg aaaggccgaa ttccacccca gggtttgtta    540
taacagtggc cagtctgaac cccatttgct cgtgctcaaa acttgattcc cacttgaaag    600
ccttccgggc gcgctgcctc gttgccccgc ccctttggca ggagagaggc agtgggcgag    660
gccgggctgg ggccccgcct cccactcacc tgccggtgcc tgaaattatg tgcggccccg    720
cgggctgctt tccgaggtca gagtgccctg ctgctgtctc agaggcatct gttctgcaaa    780
tcttaggaag aaaaatgtcc ctagtagcaa acgggtgtct tctgtgcata aataagtaca    840
acacaattct ccgaaagttc gggtaaaaag agatgcggta gcagctgccc tgtgtgaagc    900
tgtctacccc gcatctctca ggcgctaagc tcagtttttg tttttgtttt tgttttttta    960
aagaaaagat gtataattgc aggaattttt ttttattttt ttattttcca tcattctata   1020
tatgtgatgg tgaaagatat gcctggaaaa gttttgtttt gaaaagttta ttttctgctt   1080
cgtcttcagt tggcaaaagc tctcaattct ttagcttcca gtttcttttc tctcttttttc   1140
tttgttaggt aattaaaggt atgtaaacaa attatctcat gtagcagggg attttcatgt   1200
tgagaggaat cttccgtgtg agttgtttgg tcacacaaat aaccctttct caattttagg   1260
agtttggatt gtcaaatgta ggtttttctc aaagggggca tataactaca tattgactgc   1320
caagaactat gactgtagca ctaatcagca cacatagagc cacacaatta tttaatttct   1380
aactctctgt ggtccctaga aaaattccgt tgatgtgctt aggttaaagt tctgaagata   1440
cccgttgtac ccttacttga aagtttctaa tcttaagttt tatgaaatgc aataatatgt   1500
atcagctagc aatatttctg tgatcaccaa caactctcag tttgatctta aagtctgaat   1560
aataaaacaa atcccagcag taatacattt cttaaacctc acagtgcatg atatatcttt   1620
tcattctgat cctgtgtttg caaaaatata cacatgtata tcatagttcc tcacttttta   1680
ttcatttgtt ttcctattac ctgtagtaaa tatattagtt agtacatgga atttatagca   1740
tcagctaccc ccaggaacag cacctgacag gcgggggatt ttttttcaag ttgttctaca   1800
tttgcataaa ttatttctat tattattcat gtatgttatt tatttctgaa tcacactagt   1860
cctgtgaaag tacaactgaa ggcagaaagt gttaggattt tgcatctaat gttcattatc   1920
atggtattga tggacctaag aaaataaaaa ttagactaag cccccaaata agctgcatgc   1980
atttgtaaca tgattagtag atttgaatat atagatgtag tattttgggt atctaggtgt   2040
tttatcatta tgtaaaggaa ttaaagtaaa ggactttgta gttgttttta ttaaatatgc   2100
atatagtaga gtgcaaaaat atagcaaaaa taaaaactaa aggtagaaaa gcattttaga   2160
tatgccttaa tttagaaact gtgccaggtg gccctcggaa tagatgccag gcagagacca   2220
gtgcctgggt ggtgcctcct cttgtctgcc ctcatgaaga agcttccctc acgtgatgta   2280
gtgccctcgt aggtgtcatg tggagtagtg ggaacaggca gtactgttga gaggagagca   2340
gtgtgagagt ttttctgtag aagcagaact gtcagcttgt gccttgaggc ttccagaacg   2400
tgtcagatgg agaagtccaa gtttccatgc ttcaggcaac ttagctgtgt acagaagcaa   2460
tccagtgtgg taataaaaag caaggattgc ctgtataatt tattataaaa taaaagggat   2520
tttaacaacc aacaattccc aacacctcaa aagcttgttg catttttttgg tatttgaggt   2580
```

ttttatctga aggttaaagg gcaagtgttt ggtatagaag agcagtatgt gttaagaaaa 2640
gaaaaatatt ggttcgcgta gagtgcaaat tagaactaga aagttttata cgattatcat 2700
tttgagatgt gttaaagtag gttttcactg taaaatgtat tagtgtttct gcattgccat 2760
agggcctggt taaaactttc tcttaggttt caggaagact gtcacataca gtaagctttt 2820
ttccttctga cttataatag aaaatgtttt 2850

<210> SEQ ID NO 27
<211> LENGTH: 3579
<212> TYPE: DNA
<213> ORGANISM: Homo sapiens

<400> SEQUENCE: 27
agtttcctcg gcagcggtag gcgagagcac gcggaggagc gtgcgcgggg gccccgggag 60
acggcggcgg tggcggcgcg ggcagagcaa ggacgcggcg gatcccactc gcacagcagc 120
gcactcggtg ccccgcgcag ggtcgcgatg ctgcccggtt tggcactgct cctgctggcc 180
gcctggacgg ctcgggcgct ggaggtaccc actgatggta atgctggcct gctggctgaa 240
ccccagattg ccatgttctg tggcagactg aacatgcaca tgaatgtcca gaatgggaag 300
tgggattcag atccatcagg gaccaaaacc tgcattgata ccaaggaagg catcctgcag 360
tattgccaag aagtctaccc tgaactgcag atcaccaatg tggtagaagc caaccaacca 420
gtgaccatcc agaactggtg caagcggggc cgcaagcagt gcaagaccca tccccacttt 480
gtgattccct accgctgctt agttggtgag tttgtaagtg atgcccttct cgttcctgac 540
aagtgcaaat tcttacacca ggagaggatg gatgtttgcg aaactcatct tcactggcac 600
accgtcgcca aagagacatg cagtgagaag agtaccaact tgcatgacta cggcatgttg 660
ctgccctgcg gaattgacaa gttccgaggg gtagagtttg tgtgttgccc actggctgaa 720
gaaagtgaca atgtggattc tgctgatgcg gaggaggatg actcggatgt ctggtggggc 780
ggagcagaca cagactatgc agatgggagt gaagacaaag tagtagaagt agcagaggag 840
gaagaagtgg ctgaggtgga agaagaagaa gccgatgatg acgaggacga tgaggatggt 900
gatgaggtag aggaagaggc tgaggaaccc tacgaagaag ccacagagag aaccaccagc 960
attgccacca ccaccaccac caccacagag tctgtggaag aggtggttcg agaggtgtgc 1020
tctgaacaag ccgagacggg gccgtgccga gcaatgatct cccgctggta ctttgatgtg 1080
actgaaggga agtgtgcccc attcttttac ggcggatgtg gcggcaaccg gaacaacttt 1140
gacacagaag agtactgcat ggccgtgtgt ggcagcgcca tgtcccaaag tttactcaag 1200
actacccagg aacctcttgc ccgagatcct gttaaacttc ctacaacagc agccagtacc 1260
cctgatgccg ttgacaagta tctcgagaca cctggggatg agaatgaaca tgcccatttc 1320
cagaaagcca aagagaggct tgaggccaag caccgagaga gaatgtccca ggtcatgaga 1380
gaatgggaag aggcagaacg tcaagcaaag aacttgccta aagctgataa gaaggcagtt 1440
atccagcatt tccaggagaa agtggaatct ttggaacagg aagcagccaa cgagagacag 1500
cagctggtgg agacacacat ggccagagtg gaagccatgc tcaatgaccg ccgccgcctg 1560
gccctggaga actacatcac cgctctgcag gctgttcctc ctcggcctcg tcacgtgttc 1620
aatatgctaa agaagtatgt ccgcgcagaa cagaaggaca gacagcacac cctaaagcat 1680
ttcgagcatg tgcgcatggt ggatcccaag aaagccgctc agatccggtc ccaggttatg 1740
acacacctcc gtgtgattta tgagcgcatg aatcagtctc tctccctgct ctacaacgtg 1800
cctgcagtgg ccgaggagat tcaggatgaa gttgatgagc tgcttcagaa agagcaaaac 1860

```
tattcagatg acgtcttggc caacatgatt agtgaaccaa ggatcagtta cggaaacgat   1920
gctctcatgc catctttgac cgaaacgaaa accaccgtgg agctccttcc cgtgaatgga   1980
gagttcagcc tggacgatct ccagccgtgg cattcttttg gggctgactc tgtgccagcc   2040
aacacagaaa acgaagttga gcctgttgat gcccgccctg ctgccgaccg aggactgacc   2100
actcgaccag gttctgggtt gacaaatatc aagacggagg agatctctga agtgaagatg   2160
gatgcagaat tccgacatga ctcaggatat gaagttcatc atcaaaaatt ggtgttcttt   2220
gcagaagatg tgggttcaaa caaaggtgca atcattggac tcatggtggg cggtgttgtc   2280
atagcgacag tgatcgtcat caccttggtg atgctgaaga agaaacagta cacatccatt   2340
catcatggtg tggtggaggt tgacgccgct gtcaccccag aggagcgcca cctgtccaag   2400
atgcagcaga acggctacga aaatccaacc tacaagttct ttgagcagat gcagaactag   2460
acccccgcca cagcagcctc tgaagttgga cagcaaaacc attgcttcac tacccatcgg   2520
tgtccattta tagaataatg tgggaagaaa caaacccgtt ttatgattta ctcattatcg   2580
ccttttgaca gctgtgctgt aacacaagta gatgcctgaa cttgaattaa tccacacatc   2640
agtaatgtat tctatctctc tttacatttt ggtctctata ctacattatt aatgggtttt   2700
gtgtactgta aagaatttag ctgtatcaaa ctagtgcatg aatagattct ctcctgatta   2760
tttatcacat agccccttag ccagttgtat attattcttg tggtttgtga cccaattaag   2820
tcctacttta catatgcttt aagaatcgat gggggatgct tcatgtgaac gtgggagttc   2880
agctgcttct cttgcctaag tattcctttc ctgatcacta tgcattttaa agttaaacat   2940
ttttaagtat ttcagatgct ttagagagat ttttttttcca tgactgcatt ttactgtaca   3000
gattgctgct tctgctatat ttgtgatata ggaattaaga ggatacacac gtttgtttct   3060
tcgtgcctgt tttatgtgca cacattaggc attgagactt caagcttttc ttttttttgtc   3120
cacgtatctt tgggtctttg ataaagaaaa gaatccctgt tcattgtaag cacttttacg   3180
gggcgggtgg ggaggggtgc tctgctggtc ttcaattacc aagaattctc caaaacaatt   3240
ttctgcagga tgattgtaca gaatcattgc ttatgacatg atcgctttct acactgtatt   3300
acataaataa attaaataaa ataaccccgg gcaagacttt tctttgaagg atgactacag   3360
acattaaata atcgaagtaa ttttgggtgg ggagaagagg cagattcaat tttctttaac   3420
cagtctgaag tttcatttat gatacaaaag aagatgaaaa tggaagtggc aatataaggg   3480
gatgaggaag gcatgcctgg acaaaccctt cttttaagat gtgtcttcaa tttgtataaa   3540
atggtgtttt catgtaaata aatacattct tggaggagc                          3579
```

<210> SEQ ID NO 28
<211> LENGTH: 1433
<212> TYPE: DNA
<213> ORGANISM: Homo sapiens

<400> SEQUENCE: 28

```
attcggggcg agggaggagg aagaagcgga ggaggcggct cccgctcgca gggccgtgca     60
cctgcccgcc cgcccgctcg ctcgctcgcc cgccgcgccg cgctgccgac cgccagcatg    120
ctgccgagag tgggctgccc cgcgctgccg ctgccgccgc cgccgctgct gccgctgctg    180
ccgctgctgc tgctgctact gggcgcgagt ggcggcggcg gcggggcgcg cgcggaggtg    240
ctgttccgct gcccgccctg cacacccgag cgcctggccg cctgcgggcc cccgccggtt    300
gcgccgcccg ccgcggtggc cgcagtggcc ggaggcgccc gcatgccatg cgcggagctc    360
gtccgggagc cgggctgcgg ctgctgctcg gtgtgcgccc ggctggaggg cgaggcgtgc    420
```

```
ggcgtctaca ccccgcgctg cggccagggg ctgcgctgct atccccaccc gggctccgag    480

ctgcccctgc aggcgctggt catgggcgag ggcacttgtg agaagcgccg ggacgccgag    540

tatggcgcca gcccggagca ggttgcagac aatggcgatg accactcaga aggaggcctg    600

gtggagaacc acgtggacag caccatgaac atgttgggcg ggggaggcag tgctggccgg    660

aagcccctca agtcgggtat gaaggagctg gccgtgttcc gggagaaggt cactgagcag    720

caccggcaga tgggcaaggg tggcaagcat caccttggcc tggaggagcc caagaagctg    780

cgaccacccc ctgccaggac tccctgccaa caggaactgg accaggtcct ggagcggatc    840

tccaccatgc gccttccgga tgagcggggc cctctggagc acctctactc cctgcacatc    900

cccaactgtg acaagcatgg cctgtacaac ctcaaacagt gcaagatgtc tctgaacggg    960

cagcgtgggg agtgctggtg tgtgaacccc aacaccggga agctgatcca gggagccccc   1020

accatccggg gggaccccga gtgtcatctc ttctacaatg agcagcagga ggcttgcggg   1080

gtgcacaccc agcggatgca gtagaccgca gccagccggt gcctggcgcc cctgcccccc   1140

gcccctctcc aaacaccggc agaaaacgga gagtgcttgg gtggtgggtg ctggaggatt   1200

ttccagttct gacacacgta tttatatttg gaaagagacc agcaccgagc tcggcacctc   1260

cccggcctct ctcttcccag ctgcagatgc cacacctgct ccttcttgct ttccccgggg   1320

gaggaagggg gttgtggtcg gggagctggg gtacaggttt ggggaggggg aagagaaatt   1380

tttatttttg aacccctgtg tcccttttgc ataagattaa aggaaggaaa agt          1433
```

<210> SEQ ID NO 29
<211> LENGTH: 2370
<212> TYPE: DNA
<213> ORGANISM: Homo sapiens

<400> SEQUENCE: 29

```
cctggaactc tagcacgccg agtgaacttg aatctttggc tatttaagga ggactgggtt     60

tgttgtgaag ttgcggtgat ccagcgcaga gccccgtcct gattgatcgc atcgcggggc    120

tcagatgact gtaaaatgaa tagatgaaat tcttgcttct cgaagatttt cttgggcatc    180

tcccggaaag tgcgttttaa ggcgaagtca tgatgtattc tcccatctgt ctcactcagg    240

atgaatttca cccattcatg gaagcacttc ttccacatgt ccgtgcaatt gcctatactt    300

ggttcaacct gcaggctcga aaacgcaagt actttaaaaa gcatgagaag cgaatgtcaa    360

aggatgaaga aagagcagtc aaagatgagc ttctcagtga aaagcctgaa atcaaacaga    420

agtgggcatc caggctcctt gccaaactgc gcaaagatat tcgccaggag tatcgagagg    480

actttgtgct caccgtgact ggcaagaagc acccgtgctg tgtcttatcc aatcccgacc    540

agaagggtaa gattaggaga atcgactgcc tgcgacaggc agacaaagtc tggcgtctgg    600

atctagtcat ggtgatcctg ttcaaaggca tccccttgga aagtaccgat ggagagcggc    660

tcatgaaatc cccacattgc acaaacccag cactttgtgt ccagccacat catatcacag    720

tatcagttaa ggagcttgat ttgtttttgg catactacgt gcaggagcaa gattctggac    780

aatcaggaag tccaagccac aatgatcctg ccaagaatcc tccaggttac cttgaggata    840

gttttgtaaa atctggagtc ttcaatgtat cagaacttgt aagagtatcc agaacgccca    900

taacccaggg aactggagtc aacttcccaa ttggagaaat cccaagccaa ccatactatc    960

atgacatgaa ctcgggggtc aatcttcaga ggtctctgtc ttctccacca agcagcaaaa   1020

gacccaaaac tatatccata gaygaaaata tggaaccaag tcctacagga gacttttacc   1080

cctctccaag ttcaccagct gctggaagtc gaacatggca cgaaagagat caagatatgt   1140
```

```
cttctccgac tactatgaag aagcctgaaa agccattgtt cagctctgca tctccacagg   1200
attcttcccc aagactgagc actttccccc agcaccacca tcccggaata cctggagttg   1260
cacacagtgt catctcaact cgaactccac ctccaccttc accgttgcca tttccaacac   1320
aagctatcct tcctccagcc ccatcgagct acttttctca tccaacaatc agatatcctc   1380
cccacctgaa tcctcaggat actctgaaga actatgtacc ttcttatgac ccatccagtc   1440
cacaaaccag ccagtcctgg tacctgggct agcttggttc ctttccaagt gtcaaatagg   1500
acacccatct taccggccaa tgtccaaaat tacggtttga acataattgg agaacctttc   1560
cttcaagcag aaacaagcaa ctgagggaaa aagaaacaca acaatagttt aagaaatttt   1620
ttttttaaat aaaaaaaagg aaaagaggaa gactggacaa aacaacacaa aggcagaaag   1680
gaaagaaact gaagaaagaa gataatagac cagcaattgc agcacttaca atcactaatt   1740
cccttaaggt taaactgtaa tgacataaaa agggtcgatg atatttcact gatggtagat   1800
cgcagcccct gcaacgtagc ctttgttaca tgaagtccgc tgggaaatag atgttctgtc   1860
tctatgacaa tatattttaa ctgactttct agatgcctta atatttgcat gataagctag   1920
ttttattggt ttagtattct tgttgtttac gcatggaatc actattcctg gttatctcac   1980
caacgaaggc taggaggcgg cgtcagagat gctgggtgac agagccatga gccagccatt   2040
ttataagcac tctgatttct aaaagttaaa aaaaatatat gaaatctctg tagcctttag   2100
ttatcagtac agatttatta aatttcggcc cttaacccag ccttttccag tgtgtaaccc   2160
agtttgaaat cttaaaaaaa gaaaaaatga aaaaaaaagg aaaaaaagaa aaaaggaaaa   2220
aaacagtttg aacacaaagg ctctatggaa gaaatgcctc tatgtaggtg aagtgttctc   2280
tctgcatgca acagtaaaaa ttaatataat attttcccca caaaagaaac acttaacaga   2340
gggcaagtgc aatttattaa atttatattc                                   2370
```

<210> SEQ ID NO 30
<211> LENGTH: 2699
<212> TYPE: DNA
<213> ORGANISM: Homo sapiens

<400> SEQUENCE: 30

```
gcccagcggg ggcgggactg gaacggagcc gtgcggcccc gcgcgctcgc agtctgtctc     60
ccgccgtccc cacgcacgcg tcccggctca cgcgtccgcc cgcccgcccc cgcttgtgcc    120
gcccctacca gagaccccca ggagcaggat gtccttccag ggcaagaaaa gcatcccccg    180
gatcacgagt gaccgccttc tgatcagagg tgggaggatc gtgaatgacg accagtcctt    240
ttacgctgat gtgcacgtgg aagatggctt gataaaacaa atcggagaaa acctcatcgt    300
ccctgggggc atcaagacca ttgacgccca cggcctgatg gtccttcctg gtggcgttga    360
cgtccacaca aggctgcaga tgcctgtcct gggcatgaca ccggctgacg acttctgtca    420
gggcaccaag gcagcgctag caggaggaac caccatgatc ttggaccacg tcttccccga    480
cacgggtgtg agcctgctgg cggcctacga gcggtggcgg gagcgggcgg acagcgcggc    540
ctgctgcgac tactccctgc acgtggacat cacccgatgg catgagagca tcaaggagga    600
gctggaggcc ctggtcaagg agaagggtgt gaactccttc ctggtcttca tggcatacaa    660
ggaccggtgc cagtgcagcg acagccagat gtacgagatc ttcagcatca tccgggacct    720
gggggccttg gcccaggtgc acgctgagaa cggggacatc gtggaggagg agcagaagcg    780
gttgctggag ctcggcatca ctggccccga gggccacgtg ctcagccacc ccgaggaggt    840
ggaggctgag gcggtgtacc gagctgtcac catcgccaag caggcaaact gcccgctgta    900
```

cgtcaccaag gtgatgagca agggggcggc cgacgccatc gctcaggcca agcgcagagg 960
ggtggtcgtg tttggggagc ccatcaccgc cagcctgggc accgacggtt cacactactg 1020
gagcaagaac tgggccaagg ccgcagcctt cgtcacatca ccccctgtca acccagaccc 1080
caccacggca gaccacctca cctgcttgct gtccagcggg gacctccagg tgacaggcag 1140
cgcccactgc accttcacca ctgcccagaa ggctgtgggc aaggacaact tcgcgctgat 1200
ccccgagggc accaacggca ttgaggagcg catgtcgatg gtctgggaga aatgtgtggc 1260
ctctgggaag atggacgaga atgagttcgt cgcggtgacc agtacaaatg ctgccaaaat 1320
cttcaatttt tacccaagga aggggcgagt ggctgtgggc tctgacgctg acctggtcat 1380
atggaacccc aaggccacca agatcatctc tgccaagacc cacaatctga acgtggagta 1440
caacatcttc gagggagtgg agtgccgggg agcgcctgcc gtggtcataa gtcagggccg 1500
agtggcgctg gaggacggga agatgtttgt caccccgggg gcgggccgct tcgtccctcg 1560
gaaaacattc ccggactttg tctacaagag gatcaaagct cgcaacaggc tggcggagat 1620
ccacggtgtg ccccgtgggc tgtatgacgg gcccgtccac gaggtgatgg tgcctgccaa 1680
gccagggagt ggcgctccgg cccgcgcgtc ctgcccaggc aagatctccg tgcctcctgt 1740
gcgcaaccta catcagtcgg ggttcagcct atctgggtct caggctgatg accacatcgc 1800
ccgacgcaca gcacagaaga tcatggcacc acctggcggc cgctccaaca tcacctctct 1860
ctcctagacg cccaggaccg gccctgtgag ccgtgctggc cccacccgag gccgcggggg 1920
ccccagggca ctcgcccccc tccttagcat ttcttttgt agaagtttct cgaaggtgct 1980
tggcggtctt gccttccccc tccccacagg ctctccttgt ggggtcccag gtcctgctgc 2040
caagagcccc tcaagagaag ggctgaacct ggggagatgt cactgccagg gtgaggtgga 2100
gccacatggc agggacaatg ccggcagcct gagcccaggc accccagtgc ccgctgggcc 2160
cagcctgggg acagggaacc tgccgggctc acagtgtggg agcagctgga caccaggctt 2220
cttggtgaac cggcgagggg ccgagtcccg cctggtgggc atttgctgcc gcctccccac 2280
caccagtcac tgcctcgcag agccctacac tcccgcagcc gctcctcaga ggcctgtgcc 2340
catcgcaggc ctgggaggaa agtgggcgca gagccctcct gctcacacag ctgctgagac 2400
ttcagggacc catcagaact tggtgcagca cagccccgcc cgtggagggt cccttttacg 2460
caccccaagg cccacaccta agcttccatg tagccctcat ccagggaagt tttgcgatcc 2520
tttaggaaga cactgtcctc ttattacaga ttgtgtattt ccgtaggctt cttagtagca 2580
gctttgtaca ctgaggacac tgtagccagg aacctgtgca tgccacccac cgcctggaca 2640
ggcagtcatc ctgcctctga tgtgaatcag gcccattaaa gacgtctggg tttgaagcc 2699

<210> SEQ ID NO 31
<211> LENGTH: 4122
<212> TYPE: DNA
<213> ORGANISM: Homo sapiens

<400> SEQUENCE: 31
tttgtcatca gctcgctctc cattggcggg gagcggagag cagcgaagaa gggggtgggg 60
aggggagggg aagggaaggg ggtggaaact gcctggagcc gtttctccgc gccgctgttg 120
gtgctgccgc tgcctcctcc tcctccgccg ccgccgccgc cgccgccgcc tcctccggct 180
cttcgctcgg cccctctccg cctccatgtg ccggatagcg ggagcgctgc ggaccctgct 240
gccgctgctg gcggccctgc ttcaggcgtc tgtagaggct tctggtgaaa tcgcattatg 300
caagactgga tttcctgaag atgtttacag tgcagtctta tcgaaggatg tgcatgaagg 360

-continued

```
acagcctctt ctcaatgtga agtttagcaa ctgcaatgga aaaagaaaag tacaatatga    420
gagcagtgag cctgcagatt ttaaggtgga tgaagatggc atggtgtatg ccgtgagaag    480
ctttccactc tcttctgagc atgccaagtt cctgatatat gcccaagaca aagagaccca    540
ggaaaagtgg caagtggcag taaaattgag cctgaagcca accttaactg aggagtcagt    600
gaaggagtca gcagaagttg aagaaatagt gttcccaaga caattcagta agcacagtgg    660
ccacctacaa aggcagaaga gagactgggt catccctcca atcaacttgc cagaaaactc    720
caggggacct tttcctcaag agcttgtcag gatcaggtct gatagagata aaaacctttc    780
actgcggtac agtgtaactg ggccaggagc tgaccagcct ccaactggta tcttcattat    840
caaccccatc tcgggtcagc tgtcggtgac aaagcccctg gatcgcgagc agatagcccg    900
gtttcatttg agggcacatg cagtagatat taatggaaat caagtggaga accccattga    960
cattgtcatc aatgttattg acatgaatga caacagacct gagttcttac accaggtttg   1020
gaatgggaca gttcctgagg gatcaaagcc tggaacatat gtgatgaccg taacagcaat   1080
tgatgctgac gatcccaatg ccctcaatgg gatgttgagg tacagaatcg tgtctcaggc   1140
tccaagcacc ccttcaccca acatgtttac aatcaacaat gagactggtg acatcatcac   1200
agtggcagct ggacttgatc gagaaaaagt gcaacagtat acgttaataa ttcaagctac   1260
agacatggaa ggcaatccca catatggcct ttcaaacaca gccacggccg tcatcacagt   1320
gacagatgtc aatgacaatc ctccagagtt tactgccatg acgttttatg gtgaagttcc   1380
tgagaacagg gtagacatca tagtagctaa tctaactgtg accgataagg atcaacccca   1440
tacaccagcc tggaacgcag tgtacagaat cagtggcgga gatcctactg gacggttcgc   1500
catccagacc gacccaaaca gcaacgacgg gttagtcacc gtggtcaaac caatcgactt   1560
tgaaacaaat aggatgtttg tccttactgt tgctgcagaa aatcaagtgc cattagccaa   1620
gggaattcag cacccgcctc agtcaactgc aaccgtgtct gttacagtta ttgacgtaaa   1680
tgaaaaccct tattttgccc ccaatcctaa gatcattcgc caagaagaag ggcttcatgc   1740
cggtaccatg ttgacaacat tcactgctca ggacccagat cgatatatgc agcaaaatat   1800
tagatacact aaattatctg atcctgccaa ttggctaaaa atagatcctg tgaatggaca   1860
aataactaca attgctgttt tggaccgaga atcaccaaat gtgaaaaaca atatatataa   1920
tgctactttc cttgcttctg acaatggaat tcctcctatg agtggaacag gaacgctgca   1980
gatctattta cttgatatta atgacaatgc ccctcaagtg ttacctcaag aggcagagac   2040
ttgcgaaact ccagacccca attcaattaa tattacagca cttgattatg acattgatcc   2100
aaatgctgga ccatttgctt ttgatcttcc tttatctcca gtgactatta agagaaattg   2160
gaccatcact cggcttaatg gtgattttgc tcagcttaat ttaaagataa aatttcttga   2220
agctggtatc tatgaagttc ccatcataat cacagattcg ggtaatcctc ccaaatcaaa   2280
tatttccatc ctgcgcgtga aggtttgcca gtgtgactcc aacggggact gcacagatgt   2340
ggacaggatt gtgggtgcgg ggcttggcac cggtgccatc attgccatcc tgctctgcat   2400
catcatcctg cttatccttg tgctgatgtt tgtggtatgg atgaaacgcc gggataaaga   2460
acgccaggcc aaacaacttt taattgatcc agaagatgat gtaagagata atattttaaa   2520
atatgatgaa gaaggtggag gagaagaaga ccaggactat gacttgagcc agctgcagca   2580
gcctgacact gtggagcctg atgccatcaa gcctgtggga atccgacgaa tggatgaaag   2640
acccatccac gctgagcccc agtatccggt ccgatctgca gccccacacc ctggagacat   2700
tggggacttc attaatgagg gccttaaagc ggctgacaat gaccccacag ctccaccata   2760
```

```
tgactccctg ttagtgtttg actatgaagg cagtggctcc actgctgggt ccttgagctc   2820

ccttaattcc tcaagtagtg gtggtgagca ggactatgat tacctgaacg actgggggcc   2880

acggttcaag aaacttgctg acatgtatgg tggaggtgat gactgaactt cagggtgaac   2940

ttggtttttg gacaagtaca aacaatttca actgatattc ccaaaaagca ttcagaagct   3000

aggctttaac tttgtagtct actagcacag tgcttgctgg aggctttggc ataggctgca   3060

aaccaatttg ggctcagagg gaatatcagt gatccatact gtttggaaaa acactgagct   3120

cagttacact tgaattttac agtacagaag cactgggatt ttatgtgcct ttttgtacct   3180

ttttcagatt ggaattagtt ttctgtttaa ggctttaatg gtactgattt ctgaaacgat   3240

aagtaaaaga caaaatattt tgtggtggga gcagtaagtt aaaccatgat atgcttcaac   3300

acgcttttgt tacattgcat ttgcttttat taaaatacaa aattaaacaa acaaaaaaac   3360

tcatggagcg attttattat cttgggggat gagaccatga gattggaaaa tgtacattac   3420

ttctagtttt agactttagt ttgttttttt tttttcacta aaatcttaaa acttactcag   3480

ctggttgcaa ataaagggag ttttcatatc accaatttgt agcaaaattg aatttttttca   3540

taaactagaa tgttagacac attttggtct taatccatgt acactttttt atttctgtat   3600

ttttccactt cactgtaaaa atagtatgtg tacataatgt tttattggca tagtctatgg   3660

agaagtgcag aaacttcaga acatgtgtat gtattatttg gactatggat tcaggttttt   3720

tgcatgttta tatctttcgt tatggataaa gtatttacaa aacagtgaca tttgattcaa   3780

ttgttgagct gtagttagaa tactcaattt ttaatttttt taattttttt atttttttatt   3840

ttctttttgg tttggggagg gagaaaagtt cttagcacaa atgttttaca taatttgtac   3900

caaaaaaaaa aaaaaggaaa ggaaagaaag gggtggcctg acactggtgg cactactaag   3960

tgtgtgtttt ttaaaaaaaa aaatggaaaa aaaaaagctt ttaaactgga gagacttctg   4020

acaacagctt tgcctctgta ttgtgtacca gaatataaat gatacacctc tgaccccagc   4080

gttctgaata aaatgctaat tttggaaaaa aaaaaaaaaa aa                     4122
```

<210> SEQ ID NO 32
<211> LENGTH: 1653
<212> TYPE: DNA
<213> ORGANISM: Homo sapiens

<400> SEQUENCE: 32

```
agtcagcacg ggggtgctgg aagagatcgg gaataatagc gcagaccaat gagcctaggg     60

agatgctttc atcgtctctc cttccctcaa gtgttctgga acctatcatt tgaattagcc    120

gagtcaggca ggagggggcg gggaatcctt ccgcccttct taggaggggc tgcattgcag    180

ggggagagtg aactgacaga ctcagtcact gaagagggaa aaggagtgag aagacaaagc    240

cgtcaaagcc ccaacagctt tgtatttctc cagcccggcg cagaccccgg agctcccgag    300

gcactccctc catctttgga acacgccagt aattgattga taacaggaag ctatgaggga    360

ccctgtgagt agccagtaca gttcctttct tttctggagg atgcccatcc cagaactgga    420

tctgtcggag ctggaaggcc tgggtctgtc agatacagcc acctacaagg tcaaagacag    480

cagcgttggc aaaatgatcg ggcaagcaac tgcagcagac caggagaaaa accctgaagg    540

tgatggcctc cttgagtaca gcaccttcaa cttctggaga gctcccattg ccagcatcca    600

ctccttcgaa ctggacttgc tctaaggcca agacttctct ctcccatcac cttgccctca    660

ttgtcttccc tctcaagccc cttcctttcc actcctttcc cattttaatc ttgttctctc    720

cctactgtgt tggtggtgct gatgaatctg ccagagttga gttctatgta tttatttatc    780
```

tatctgtcta ctccatttct ctcaaaagcc ctcaagtcac aaagtaaatg gttcaagcaa 840
tggagtactg ggtcacaggg attcctcctt tcccccccaa atattaactc cagaaactag 900
gcctgactgg ggacacctga gagtagtata gtagtgcaaa atggaagact gatttttgac 960
tctattataa tcagcttcag agattcctta aaccttccta atttcctgct ccagggcagt 1020
aaacacaaat atttcttcaa ggggtgatga aaacctcgga agttttaatt tgaggttatc 1080
tgctacgaaa cagtatttct aaaaggctaa agtgataagt ctcttgcttt tttttgatcc 1140
tgctcttata ttcttttttt tcctcagaga aatcaggagg gtagttagag gtataaaaca 1200
ggaggaaata ttatggaaaa tgaaaatagg gaaaataatt gaatcatttt agaagtagct 1260
aatttctttt ctcaaaagag tgtcccttct tcacacctac tcactttaca actttgctcc 1320
taactgtggg ttgaaaactc tagctaaaga aagttatcaa atcttaacat gcattcctac 1380
tattatgata gtttttaagg tttcaattca atcttctgaa cggcataagt cctattttag 1440
ccttacctcc tgcatttgca atacgtaata ctgatcagtg ggcacagttc ttcagctaca 1500
ttgagaccct gaaatgaaca attatattct gactcgacat cttgtcccca atccttccaa 1560
aaatattgat ggtgatttgt gctaccattt actcgtttat ttaataaaga cattcaatcc 1620
cagaaaaaaa aaaaaaaaaa aaaaaaaaaa aaa 1653

<210> SEQ ID NO 33
<211> LENGTH: 2928
<212> TYPE: DNA
<213> ORGANISM: Homo sapiens

<400> SEQUENCE: 33
ccgatccggg cggtgctggc agccggagcg gcggcgggcg ggccgagcag ccggggcagc 60
cgcgcgtggg catccacggg cgccgagcct ccgtccgtgt ctctatccct cccgggcctt 120
tgtcagcgcg cccgctggga gcggggccga gagcgccggt tccagtcaga cagccccgca 180
ggtcagcggc cgggccgagg gcgccagagg gggccatgtc gtaccagggc aagaagagca 240
tcccgcacat cacgagtgac cgactcctca tcaaaggtgg acggatcatc aacgatgacc 300
aatcccttta tgctgacgtc tacctggagg atggacttat caaacaaata ggagagaact 360
taatcgttcc tggtggagtg aagaccattg aagccaacgg gcggatggtt attcccggag 420
gtattgatgt caacacgtac ctgcagaagc cctcccaggg gatgactgcg gctgatgact 480
tcttccaagg gaccagggcg gcactggtgg gcgggaccac gatgatcatt gaccatgttg 540
ttcctgaacc tgggtccagc ctactgacct ctttcgagaa gtggcacgaa gcagctgaca 600
ccaaatcctg ctgtgattac tccctccacg tggacatcac aagctggtac gatggcgttc 660
gggaggagct ggaggtgctg gtgcaggaca aaggcgtcaa ttccttccaa gtctacatgg 720
cctataagga tgtctaccaa atgtccgaca gccagctcta tgaagccttt accttcctta 780
agggcctggg agctgtgatc ttggtccatg cagaaaatgg agatttgata gctcaggaac 840
aaaagcggat cctggagatg ggcatcacgg gtcccgaggg ccatgccctg agcagacctg 900
aagagctgga ggccgaggcg gtgttccggg ccatcaccat tgcgggccgg atcaactgcc 960
ctgtgtacat caccaaggtc atgagcaaga gtgcagccga catcatcgct ctggccagga 1020
agaaagggcc cctagttttt ggagagccca ttgccgccag cctggggacc gatggcaccc 1080
attactggag caagaactgg gccaaggctg cggcgttcgt gacttcccct cccctgagcc 1140
cggaccctac cacgcccgac tacttgacct ccctactggc ctgtggggac ttgcaggtca 1200
caggcagcgg ccactgtccc tacagcactg cccagaaggc ggtgggcaag gacaacttta 1260
ccctgatccc cgagggtgtc aacgggatag aggagcggat gacggtcgtc tgggacaagg 1320
cggtggctac tggcaaaatg gatgagaacc agtttgtcgc tgtcaccagc accaatgcag 1380
ccaagatctt taacctgtac ccaaggaaag ggcggattgc cgtgggctcg gatgccgacg 1440
tggtcatctg ggaccccgac aagttgaaga ccataacagc caaaagtcac aagtcggcgg 1500
tggagtacaa catcttcgag ggtatggagt gccacggctc ccccactagtg gtcatcagcc 1560 agggcaagat cgtctttgaa gacggaaaca tcaacgtcaa caagggcatg ggccgcttca 1620
ttccgcggaa ggcgttcccg gagcacctgt accagcgcgt caaaatcagg aataaggttt 1680
ttggattgca aggggtttcc aggggcatgt atgacggtcc tgtgtacgag gtaccagcta 1740
cacccaaata tgcaactccc gctccttcag ccaaatcttc gccttctaaa caccagcccc 1800
cacccatcag aaacctccac cagtccaact tcagcttatc aggtgcccag atagatgaca 1860
acaatcccag gcgcaccggc caccgcatcg tggcgccccc tggtggccgc tccaacatca 1920
ccagcctcgg ttgaacgtgg atgcgcggag gagctagcct gaaggattct gggaatcatg 1980
tccatccctt ttcctgtcag tgtttttgaa acccacagtt ttagttggtg ctgatggagg 2040
gagggggaag tcgaaggatg ctctttccct tttctgttta ggaagaagtg gtactagtgt 2100
ggtgtgtttg cttggaaatt ccttgcccca cagttgtgtt catgctgaat ccacctcgga 2160
gcatggtgtt ttcattcccc cttcctagtg aaccacaggt tttagcattg tcttgttctg 2220
tcccttccac ttctaactcc actggctcca tgattctctg agtggtggtt cctttgcacc 2280
ctgtagatgt tctaggatag ttgatgcatg ttactaaatt acgtatgcaa gtctgtgagt 2340
gcgtctgagg ggacatcgcc aaggactgac tgagacacga tgccgagacc tcaagccctg 2400
aggggcagtc ccaaaaccct tacagtgaag atgtttactc attgccccca cctctggtcc 2460
acactagaaa gaagctcgcc ccacctccac ctgtgagatc cgtgaattct cggaatggca 2520
ggggaagcct tgcactaggt tgcagagaag catcctccac atcctgtgtc agaaaccctg 2580
gtctccgtgg cacttgtaac tcaccgtgct gtcttctggt ctgtgtgtgt tcttcaagcc 2640
agctctaggc ttcaggccga gccaggttca cactcagaaa gaggtctccc catccccatt 2700
cggggctgac gatggggggc tgatggctgc ccctgcgtgg cctgagtcct ggtccctctg 2760
aggcagttga cggggcagtc agatttttaa agttttgtac aaagttttcc tttgtaatca 2820
ctcccatttt tacttaacaa ccaacttgtt gtggctctta tttctgaatt caaagcttgt 2880
gaaaaaataa agaaaatgaa ctgcccactg aaaaaaaaaa aaaaaaaa 2928

<210> SEQ ID NO 34
<211> LENGTH: 4913
<212> TYPE: DNA
<213> ORGANISM: Homo sapiens

<400> SEQUENCE: 34
cctcccagcg tccccaccct aggaggctgc atgcggattg aagacgtgcg cctgggggct 60
gggccggccc cgctgatccc gacctagcga gcaggatagc aggaccgccc aggctgcgga 120
ggggctcggg ggcaggaagg tcagagcagc aagatggcca gtaagaccaa ggccagcgag 180
gccctcaagg tggtggcccg gtgccgcccc ctcagcagga aggaggaggc tgctggtcac 240
gagcagatcc tgaccatgga cgtgaaactg ggccaggtga ccctgcggaa cccccgcgcc 300
gccccggggg agctgcccaa gaccttcacc tttgacgccg tgtatgatgc cagctccaag 360
caggccgacc tgtatgacga aaccgtgagg cccctgatag actccgtgct ccagggtttc 420
aatggcacgg tgtttgccta tggccagacg ggcactggca agacctatac catgcagggg 480

-continued

```
acctgggtgg agcccgagct gcgcggggtc atcccgaatg cctttgagca catcttcacc    540
cacatctccc gctcccagaa ccaacagtac ctggtccggg cctcctattt ggagatctac    600
caggaagaga ttcgagacct gctctccaag gagccgggca agaggctaga gctgaaagag    660
aaccccgaga ctggcgtcta catcaaggac ctctcctcct tcgtcaccaa gaatgtcaag    720
gagattgagc atgtgatgaa cctggggaac cagacccggg ctgtgggcag cacccacatg    780
aatgaggtca gctcccgctc ccatgccatc ttcatcatca ctgtggagtg cagcgaacgt    840
ggctctgatg gccaggacca catccgagtg ggcaagctca acctcgtgga cctggctggc    900
agcgagaggc agaacaaggc aggccccaac acagcgggag gggcagccac accatcctcg    960
ggtggcggtg gtggcggtgg aggcagtggt ggtggtgctg gtggagagag gcctaaggaa   1020
gcctccaaaa tcaacctctc attatctgcc ctgggcaacg tgattgctgc cctggcgggc   1080
aacaggagca cccacattcc ctaccgggac tccaagctga cccggctgct ccaggactcc   1140
ctggggggga atgcgaagac catcatggta gccacactgg ggccagcttc tcacagctac   1200
gatgagagcc tctccacctt gcgctttgcc aaccgagcca agaacatcaa gaacaagccc   1260
cgggtgaacg aggaccccaa ggacacactg ctgcgggaat tccaagagga gattgcccgc   1320
ctgaaggccc agctggagaa gagggggatg ctggggaagc ggccccggag gaagagcagc   1380
cgcaggaaga aggccgtgtc cgccccgcct gggtaccctg agggcccagt gattgaggct   1440
tgggtggcag aagaggagga tgacaacaac aacaaccacc gcccgcccca gcccatcctg   1500
gagtcagcct tggagaagaa catggagaat tacctgcagg aacagaagga gcggctggag   1560
gaggagaagg cagccatcca ggatgaccgc agcctggtga gcgaggagaa gcagaagctg   1620
ctggaggaga aggagaagat gctggaggac ctgcggcggg aacagcaggc cacagagctg   1680
cttgcggcca agtacaaggc catggagagc aagctcctca tcgggggcag gaacatcatg   1740
gatcacacca acgaacagca gaagatgttg gaactgaaga ggcaggagat tgccgagcag   1800
aaacgtcgtg agcgggagat gcagcaggag atgatgctcc gggacgagga gactatggag   1860
ctccggggca cctacacatc cctgcagcag gaggtggagg tcaaaaccaa gaaactcaag   1920
aagctctacg ccaagctgca ggcggtgaag gcggagatcc aggaccagca tgatgagtat   1980
atccgcgtgc ggcaggacct ggaggaggcg cagaacgagc agacccgcga actcaagctc   2040
aagtacctaa tcatcgagaa cttcatcccg ccggaggaga agaacaagat catgaaccgg   2100
cttttcctgg actgtgagga ggagcagtgg aagttccagc cactggtgcc agccggcgtc   2160
agtagcagcc agatgaagaa gcggccaaca tctgcagtgg gctacaagag gcctatcagc   2220
cagtatgctc gggttgccat ggcaatgggg tcccacccca ggtacagggc tgaaaacata   2280
atgtttctgg agttggatgt gtcccctcca gctgtctttg agatggaatt ctctcacgac   2340
caagaacaag accctcgtgc gctacacatg gagaggctca tgcgattgga cagctttctg   2400
gaaagacctt ccacgtctaa agtccgaaag tccagatcct ggtgccagag tcctcagcgg   2460
cctccacctt ccaccacaca tgcctccctg gcctctgctt ctctgcgccc tgcaacagtg   2520
gcggaccatg agtgacaacc atcacgtcag gctgcccatc caatagactc ctgggatggg   2580
gcagccaacc ctggctcatc tcatctgccg cttggtgcgt gtgcgtgtgc gtgcatgtgc   2640
gtgtgcgtgt gtgcaggggt gagaatctgg cagatggtgc ctctgcctgc tcttcttcgc   2700
ctcctttatt taattcatgt tatttattcg cggacgtctg ttcgtgttgg ggagatgccc   2760
tcgcctgagc cgtctgggcc taccgtggtc actgcgtacg ctctttttct tctgacttga   2820
gagctccccc agtcagatct caggcttgtc cccctgtcag ctgcctccag aagggaaggt   2880
```

agccagtgcc tgagaagaca gtcccttttc tacccaccgc actccataac ctccatcttc 2940
tcccacactg atggcgagca gcccctgagc actttctggg actgggagac tgcttggtgt 3000
tccctgagga caagagacat cctgacagtg ttgggcatct gctccccgtg gacacagccc 3060
cactctccac tttctgagcc tcagacaacc tcattcagcc tcttgggctc cttttcaagg 3120
acattaataa cctcaccaac atagctcatg cccttcagct ttgacaagaa ctcacggctt 3180
cccaaactct gctttctgcc caccttggat gggaactgtg gaccaagcaa ttaccatcgc 3240
cttggaacct gcaggaaatg gaacagcaat tgagacaact tgaacagtca tcaacggaag 3300
tccctccact ggattccttt gtttctgtcc cctccgagga gtcattttgg tcgacaggct 3360
ctcaaggcaa ctccccattt tcaagaggct gctcctgcct gcttcgatca tttctccctg 3420
cagctgccta gaccccgttc acagtgggag gagtcaatgt cattctaccc ctcgctaaac 3480
gaagatatta acatctattg ctttttccct tcatctgtca caggaaacag aagcccaggc 3540
acaatctttt ccagctttgc ctgttacccc tgtttctgaa ttgcatcttt aaggtattat 3600
tttgttgaca atagatcctt tattcactag ttacgcaaat tggttcctag ggggatactc 3660
cttaccttcc tttgtgatgg cccaaaatgt ctctaggtat ctcaagtgat aagtaaattt 3720
ctacaaaaaa aaaatggtta atgttcattg actggctttt taagtgtata ttttggagga 3780
cgggtgaaga ggtcataacg aaagcaagcg agtgaattag gatttcaaag tgccctaata 3840
gtgtgagtct ccagttccta gaatatgaag agtgctgtcg ttggggtgaa accatgagac 3900
tgacagatct gcctgaaatg gggggtgtgg gaggtggtgg cgggggttat tctctttcct 3960
tcaggaaatg aacccttctt acatcattca agttctgctc tgaggatcaa gcttgggtct 4020
gatttaactc agcgacactg tcatttctgc ttcattactg gactagaggg ttgagccacc 4080
cacttgccat ttgctcctgt ccttccagga aatcacaatt ttcatcagag cccaagagat 4140
tatttgagac tcaggattca gatcagaggt tcgactgtgg ctgggacagg agttgtgtgt 4200
agaaattcac caggtggcct gagcgcaggg ggacctccag gctgcgttga gcagcctctc 4260
ccactgacct ctttctcgtt tgtggacaaa gcagcacgta tcacctcatt catcacttgg 4320
acacatcgcc tttgcattgt cttgtcacac ctccctcaca gtcttatagc acaatatacc 4380
caaatcagcc cccccagtcc gaggctgggc ccaaggtatg gtcggaggag gagctcctgc 4440
ctgcggtttt gtgtatgtgt gtatgtgtgt gcgtgtttgt gtgcgtgttt acctccacag 4500
gggacactct acactcagtg taagatctgc tgggaacagg gccaccagga gtgcgtggat 4560
ctcagtctct ctgtctctct ttctctcctt ttaattttgg tgtatcaaat atttgattga 4620
caaagtaagg gccttgatta ggaccaaatt ctcgtgtgtt gctatggtct ttatttagga 4680
caacaattaa caatgcagtg gcccattctt gtcactctac acatatgact atacgggaca 4740
tatgtaatat ataaatatat atataaaaca ttcccctctg tccccttggc ttcggatgga 4800
ggaatttctg ttgagctgaa atgcacctgc agctgggtgc tgccagcagc ttgcaggccc 4860
cagccctgtt ccaatcaatg cagttgacaa taaaggaatg agtatcgtca cgg 4913

<210> SEQ ID NO 35
<211> LENGTH: 1231
<212> TYPE: DNA
<213> ORGANISM: Homo sapiens

<400> SEQUENCE: 35
gaattccaga aaagaggtgg agaggggggg aataagaaag agagagaagg aaaggagaga 60
aggcaggaag aaggcaaggg acgagacaac catgctgtgc tgtatgagaa gaaccaaaca 120
ggttgaaaaa aatgatgacg accaaaagat tgaacaagat ggtatcaaac cagaagataa 180
agctcataag gccgcaacca aaattcaggc tagcttccgt ggacacataa caaggaaaaa 240
gctcaaagga gagaagaagg atgatgtcca agctgctgag gctgaagcta ataagaagga 300
tgaagcccct gttgccgatg gggtggagaa gaagggagaa ggcaccacta ctgccgaagc 360
agccccagcc actggctcca agcctgatga gcccggcaaa gcaggagaaa ctccttccga 420
ggagaagaag ggggagggtg atgctgccac agagcaggca gccccccagg ctcctgcatc 480
ctcagaggag aaggccggct cagctgagac agaaagtgcc actaaagctt ccactgataa 540
ctcgccgtcc tccaaggctg aagatgcccc agccaaggag gagcctaaac aagccgatgt 600
gcctgctgct gtcactgctg ctgctgccac cacccctgcc gcagaggatg ctgctgccaa 660
ggcaacagcc cagcctccaa cggagactgg ggagagcagc caagctgaag agaacataga 720
agctgtagat gaaaccaaac ctaaggaaag tgcccggcag gacgagggta aagaagagga 780
acctgaggct gaccaagaac atgcctgaac tctaagaaat ggctttccac atccccaccc 840
tcccctctcc tgagcctgtc tctccctacc ctcttctcag ctccactctg aagtcccttc 900
ctgtcctgct cacgtctgtg agtctgtcct ttcccaccca ctagccctct ttctctctgt 960
gtggcaaaca tttaaaaaaa aaaaaaaaaa gcaggaaaga tcccaagtca aacagtgtgg 1020
cttaaacatt ttttgtttct tggtgttgtt atggcaagtt tttggtaatg atgattcaat 1080
cattttggga aattcttgca ctgtatccaa gttatttgat ctggtgcgtg tggccctgtg 1140
ggagtccact ttcctctctc tctctctctc tgttccaagt gtgtgtgcaa tgttccgttc 1200
atctgaggag tccaaaatat tgagtgaatt c 1231

<210> SEQ ID NO 36
<211> LENGTH: 1587
<212> TYPE: DNA
<213> ORGANISM: Homo sapiens

<400> SEQUENCE: 36
ccacgcgtcc gcgttcttgc tacaattgta ccatctggta attcctgaaa atgtcaattt 60
ttttgtgtta atatttttgg tttcaaacaa taacaaatgt ctctagaaag aaattttaag 120
aaagcttaat taatagtaaa aatgcctttc ctgaaataat cttggaaaat tttttaaatg 180
tcaaaatgat gagtcatgct aatacattga gggtttgttt ttttgtttgt ttgtttgttt 240
ttgagacaga gtttcgctct tgttgcccag gctggagtgc aatggcccga tctcagctca 300
ccgcaacctc cacctcccgg attccagcga ttctcctgcc tcagcctaca ttaagggttt 360
tgtcagacaa ttgtcacacg aagaatagtg tcacttatct gctcttgaca cacagaactg 420
gcctggcata tagctttcca gattttactc aaacttggta ctccagtttg aaaatttaaa 480
ttttgactgc tgattagctg gaaagcctag ttttaatgga aagaaagttt gcttttaaaa 540
ctgaaagtag tttcttttg ctaacaaatc taacttcata cataattggc catattagta 600
aaacacctca tgatagcagt gtatatatag tcttgtttgt agttggaagt catcttttag 660
gagttattct caaatatata taatagctac ccatgcatca ttattaaaat ccccaaattc 720
aaaaaacctc tgatatatat atataatttt tttttttttt tttttttggc caactgagat 780
tgaaatccaa gtgctggttt ctagttctga acatcaacta aagagttttg gaaatgacag 840
caatttataa caagttcata ttgacttcct ctctatggca ggaagacatt ctgtgctgtt 900
ttgaacagat taaagatttg tgtagtttgt gggaaattga cgtttttgtt taaattccac 960
ccgcgtttgt cttttcctac cacctgtggc caggtgctcg ctggccatca cagttgcgat 1020
tccatgagta gctgctttat gactgctttt tgtactatct ggatgtgccc agagttactt 1080
ctgtacaagc tctgtatctg tgtccgttga gaacattatt ttaacaagaa gaacaccaac 1140
agtagcatga aatataatac tgttttataa ttctaaagct gctgttaatt tatgaagtac 1200
ataataatct aatgtaaact gcagaagtca gagcaagtgc ctacattttg ttatttttgg 1260
cattactaca gagccatgta caatagaaag caatgcaaga cttgtaaact ctcaccactt 1320
cttgtaatat caaatgttcc ccctcaggtt attttgctta tggtacccat gagttgcctc 1380
tctctgtaca tagataaatt gttccaatat tttcctttga tgtttggaac tacagatagt 1440
caagggctgg aaattttagt tttcaatata agcttccagc ttagcaatta cctctagtcc 1500
aagacaatat ttgattccta gttctgtttg gggcaaattt tcatttatct aaataaaatg 1560
caatctaatt aaaaaaaaaa aaaaaaa 1587

<210> SEQ ID NO 37
<211> LENGTH: 9161
<212> TYPE: DNA
<213> ORGANISM: Homo sapiens

<400> SEQUENCE: 37
ctgaaaactg gagagtgtga gagcgggagg agcccccgac cacacaaacc cagcctgggg 60
aggaacctac tagtggctgc accctctttt ttaatagcac caattgtgtt tcccaagatg 120
atgtagagaa tttcagtgct gtgtaccacg tcggaggcag aaattcctct gctgtcccag 180
gagcaggcag ggcagttttt atctggaaaa gctaaaggtc tcctcttttg tttgtgtttt 240
tgtgcctgca caggacaaaa gatccttcat caccgaagtg acgttttaga aacagtggtc 300
ctgatcaacc cttctgatga agcagtcagc accgaggtgc gcttaatgat cactgatgct 360
gcccgacaca agctgctcgt gctgaccggg cagtgctttg aaaataccgg agagctcatt 420
ctccagtccg gctctttctc cttccagaac ttcatagaga ttttcaccga tcaagagatc 480
ggggagttac taagcaccac ccatcctgcc aacaaagcca gcttaaccct gttctgtcct 540
gaagaagggg actggaagaa ctccaatctt gacagacaca atctccaaga cttcatcaat 600
attaaactca attcagcttc tatcttgcca gaaatggaag gactttctga gtttaccgag 660
tatctctcag aatcagtgga agtcccatct ccctttgaca tcttggaacc tcccacatcg 720
ggtggatttc tgaagctctc caagccctgc tgttatattt ttccaggagg gaggggcgat 780
tctgccttgt ttgcagtgaa tggtttcaat atgctcatca atggcggatc agagagaaaa 840
tcctgcttct ggaagctcat ccgacactta gaccgagtgg actccatcct gctcacccac 900
attggggatg acaatttgcc tggaataaac agcatgttac agcggaaaat tgcagagctc 960
gaggaagaac agtcccaggg ctccaccaca aatagtgact ggatgaaaaa cctcatctcc 1020
cctgacttag gagttgtatt tctcaatgta cctgaaaatc tcaaaaatcc agagccaaac 1080
atcaagatga agagaagcat agaagaagcc tgcttcactc tccagtacct aaacaaattg 1140
tccatgaaac cagaacctct gtttagaagt gtaggcaata ctattgatcc tgtcattctt 1200
ttccaaaaaa tgggagtagg taaacttgag atgtatgtgc ttaatccagt caagagcagc 1260
aaggaaatgc agtattttat gcagcagtgg actggtacca acaaagacaa ggctgaattc 1320
attctgccta atggtcaaga agtagatctc ccgatttcct acttaacttc agtctcatct 1380
ttgattgtgt ggcatccagc aaaccctgcg gagaaaatca tccgagtcct gtttcctggg 1440
aacagcaccc agtacaacat cctggaaggg ttggaaaagc tcaaacatct agactttctg 1500
aagcagccac tggccaccca aaaggatctc actggccagg tgcccactcc tgtggtgaaa 1560

-continued

```
caaacaaaac tgaaacagag ggctgatagc cgagaaagtc tgaagccagc cgcaaaacca   1620
cttcctagca aatccgtgcg caaggagtca aaagaagaaa cccctgaggt cacaaaagtg   1680
aatcacgtgg aaaagccacc caaagttgaa agcaaagaaa aggtaatggt gaaaaaagac   1740
aagccagtaa aaacagagac caaaccttca gtgactgaaa aggaggttcc cagcaaagaa   1800
gagccatctc cagtgaaagc cgaggtggct gagaagcaag ccacagatgt caaacccaaa   1860
gctgccaagg agaagacggt gaaaaaggaa acaaaggtaa agcctgaaga caagaaagag   1920
gagaaagaaa agccaaagaa agaagtggct aaaaaggagg acaaaacacc tatcaagaag   1980
gaggaaaaac caaaaaagga agaggtgaaa aaagaagtca aaaaagagat caagaaagaa   2040
gagaaaaaag aacccaagaa agaggttaag aaagaaacac cgccaaagga agtcaagaag   2100
gaagttaaga aggaagagaa gaaggaagtg aaaaaggaag aaaaggaacc caaaaaagaa   2160
attaagaagc tccctaaaga cgcaaagaaa tcatctactc ctctgtctga agcaaaaaaa   2220
ccagctgctt taaaaccaaa agtacccaag aaggaagagt ctgtcaagaa agattctgtt   2280
gctgccggaa agccaaagga gaaggggaaa ataaaagtca ttaagaagga aggcaaggcc   2340
gcagaggctg tcgctgcagc tgtcggcact ggagccacca cagcagctgt catggcggca   2400
gctggaatag cagccattgg ccctgccaaa gaactcgaag ctgagaggtc ccttatgtca   2460
tctcctgagg atctaaccaa ggactttgaa gagttaaagg ctgaagaggt cgatgtaaca   2520
aaggacatca agcctcagct ggagctaatc gaagacgaag agaaactgaa ggaaactgag   2580
ccagtcgaag cctacgtcat ccagaaggag agagaagtca ccaaaggtcc tgccgagtcc   2640
cctgatgagg gaatcactac cactgaaggg gagggcgaat gtgaacagac acctgaggag   2700
ctggagcccg tcgagaagca gggagtagac gacattgaaa aatttgaaga tgaaggagcc   2760
ggttttgaag aatcttcaga gactggagac tatgaagaga aggcagaaac tgaggaggct   2820
gaggagccag aagaggatgg ggaggaacac gtatgtgtga gcgcctccaa gcacagcccc   2880
actgaggatg aggaaagtgc caaggcggag gctgatgcat acatcaggga gaagagggag   2940
tctgtggcca gtggggatga ccgagccgaa gaagacatgg atgaggccat tgagaaagga   3000
gaggctgaac aatctgaaga ggaggctgat gaggaggaca aagctgaaga tgccagagag   3060
gaggaatatg agccggaaaa aatggaagct gaagactatg tgatggctgt ggtcgacaag   3120
gctgcagagg ctggtggtgc cgaggagcag tatggattcc tcaccacacc aaccaagcaa   3180
ctaggagccc agtctcctgg ccgagaacct gcatcttcaa ttcatgatga gactttacct   3240
ggaggctcag agagcgaggc caccgcttct gatgaggaga atcgagaaga ccagcctgag   3300
gaattcactg ccacctctgg ctacactcag tctactattg agatatccag tgagcccacc   3360
cccatggatg agatgtctac ccctcgagac gtgatgagtg atgagaccaa caatgaagag   3420
acggagtccc cttctcagga attcgtaaat atcaccaaat atgaatcttc attgtattct   3480
caggaatact ctaaacctgc tgatgttaca ccgctcaacg gattttctga aggatcaaaa   3540
acagatgcca ctgatggcaa ggattacaat gcttcagcct ctaccatatc accaccctct   3600
tccatggagg aagacaaatt cagcagatct gctttacgtg atgcttactg ctctgaagtg   3660
aaagccagca ccactttgga catcaaagat agcatctcag ctgtttcaag tgaaaaggtc   3720
agcccatcga agagcccgtc cctgagtcca tctccaccat caccccttaga aaagaccccc   3780
ctgggtgaac gtagtgtgaa cttctctctg acgcccaatg agattaaagt ctctgcagag   3840
gcagaagtag ccccggtgtc tcctgaggtg acccaagaag tagttgaaga acattgtgct   3900
agtcctgagg acaagactct ggaagtggtg tcaccatctc agtccgtgac tggcagtgct   3960
```

-continued

```
ggtcacacac cttactatca atctcctact gacgagaaat ccagtcatct ccctacagaa   4020
gtcattgaaa aaccaccagc agttccagtg agttttgaat tcagtgatgc caaagatgag   4080
aatgaaaggg cttcagtaag ccccatggat gagcccgtgc ctgactcaga gtctcctatt   4140
gaaaaagttt tgtctccttt acgcagcccg cccctcattg gatccgagtc tgcttatgaa   4200
agttttctaa gtgctgatga caaggcttct ggcagaggtg ccgaaagtcc ttttgaagaa   4260
aagagtggaa aacaaggctc tccagaccaa gtaagtccag tttctgaaat gacttctact   4320
agtctttacc aagacaaaca ggaagggaaa agcacagact ttgcaccaat aaaagaagac   4380
tttggccaag aaaagaaaac tgatgatgtt gaagccatga gttctcaacc agcactggct   4440
ctggatgaaa ggaaattagg agatgtttct cccacacaaa tagatgtcag tcagtttgga   4500
tcttttaaag aagacactaa gatgtccatt tctgaaggta ctgtctcaga caagtcagct   4560
actcctgttg atgagggcgt agcagaagac acgtactctc atatggaggg tgtggcctca   4620
gtgtccacag cctcagtggc tacgagctca tttccagagc caacaacaga tgatgtgtct   4680
ccatctctgc atgctgaggt tggctcccca cattccacag aagtagatga ctccctttca   4740
gtgtctgttg tgcaaacacc taccacattc caggaaacag aaatgtctcc atctaaagaa   4800
gaatgcccaa gaccgatgtc aatttctcca ccagatttct cccctaaaac tgcaaagtcc   4860
aggacacccg ttcaagatca cagatctgaa cagtcctcaa tgtctattga atttggccaa   4920
gaatctcctg agcaatccct tgctatggac ttcagtcgac agtctccaga tcaccctaca   4980
gtgggtgcag gcgtgcttca catcactgaa aatgggccaa ctgaagtgga ctacagtcct   5040
tctgacatgc aggactccag tttatcacat aagataccac ctatggagga gccgtcctac   5100
acccaagata atgatctttc tgagctcatc tcagtatctc aggtagaggc ctccccgtcc   5160
acctcttctg ctcataccce ttctcagatc gcttctcctc tccaagaaga tactctatcc   5220
gatgttgctc ctcccagaga tatgtcctta tatgcctcac tcacctctga aaaagtgcaa   5280
agtctggaag gagagaagct ctctccaaaa tctgatatct ctccactcac cccacgagag   5340
tcctctcctt tatattcacc tactttttca gattctacct ctgcagtcaa agagaaaaca   5400
gcaacttgcc acagttcctc ttctccacca atagatgcag catccgcaga gccctatggc   5460
ttccgtgcct cagtgttatt cgatacaatg caacaccatc tagccttgaa tagagatttg   5520
tccacacctg gcctggagaa ggacagtgga gggaagacac ctggtgactt tagctatgcc   5580
tatcaaaagc ctgaggaaac aaccaggtcc ccagatgaag aagattatga ctatgagtct   5640
tatgagaaga ccacccggac ctcagatgtg ggtggctatt actatgagaa gatagagaga   5700
accacaaaat ctccaagtga cagtggctac tcctatgaga ccattgggaa aactaccaag   5760
acccctgaag atggtgacta ttcctatgaa attattgaga agaccacacg gacccctgaa   5820
gagggtgggt actcatatga cataagtgaa aagaccacca gcccccccga agtgagtggt   5880
tacagctatg aaaagactga gaggtctaga aggcttctgg atgacatcag caatggctat   5940
gatgactctg aggatggtgg ccacacactt ggggacccca gctactctta tgaaaccact   6000
gagaaaatta ccagtttccc tgagtctgaa ggttattcct atgagacatc tacaaagaca   6060
acacgaaccc ctgatacttc cacatactgt tacgagactg cagagaaaat cactagaacc   6120
cctcaggcat ccacatattc ctacgagact tcagacctat gctacactgc agaaaagaag   6180
tccccctcag aagcccgtca ggatgtcgat ttatgcctcg tgtcctcttg tgaatacaag   6240
caccccaaga cagagctttc accctctttc attaatccca atcctcttga gtggtttgcc   6300
agtgaagaac ccactgaaga atctgaaaag cccctcactc aatcaggggg agccccaccg   6360
```

```
cctccaggag gaaagcaaca gggccgacag tgtgatgaaa cccctcccac ctcagtcagc   6420
gagtcagccc catcccagac cgactctgat gttcccccgg agactgaaga gtgcccctcc   6480
atcacggccg atgccaatat cgactctgaa gacgagtcgg aaaccatccc cacagacaaa   6540
actgtcacgt acaaacacat ggacccacct ccagctcccg tgcaagaccg cagcccttcg   6600
ccacgccacc ctgatgtgtc catggtggac ccagaggcct tggccattga gcagaacctg   6660
ggcaaagctc taaagaaaga tctgaaagag aagaccaaaa ccaaaaagcc aggtacaaag   6720
accaagtcat cttcacctgt caaaaagagt gatgggaagt ctaagccctt ggcagcttca   6780
ccaaaaccag cgggcttgaa agaatcctcg gataaagtgt ccagggtggc ttctcctaag   6840
aagaaagaat ctgtggaaaa ggcagcaaaa cccaccacca ctcctgaggt caaagctgca   6900
cgtggggaag agaaagacaa ggagaccaag aatgctgcca atgcctctgc atccaagtcg   6960
gccaagaccg ccactgcagg accaggaact accaagacga ccaagtcatc tgctgtgccc   7020
ccaggcctcc ctgtgtattt ggacctgtgc tacattccta accacagcaa tagtaagaat   7080
gttgatgtgg aatttttcaa gagagtgcgg tcttcctact acgtggtgag tgggaatgac   7140
cctgctgctg aggagcccag ccgggctgtc ctggacgctt tgttggaagg aaaggctcag   7200
tggggcagca acatgcaggt gacactgatc ccaactcatg actcagaagt gatgagggaa   7260
tggtaccagg agacccatga gaaacagcaa gatctcaaca tcatggtttt agcaagcagc   7320
agcacagtgg ttatgcaaga tgaatccttc cctgcatgca agattgaact gtaaaaacca   7380
aggccagcca caccacagga tctgaacttt gtttccagaa attcttcaat ttgaaatcac   7440
cttttctaaa aagtcaattc atctagttaa gtcgctgaac aattacctgc caaatgctat   7500
actgtgtcat ggtgatgcaa gtcactaaat ttctcagttt ttgctgattg ctaagggaaa   7560
taacagtatt tccacaatag ggttcaaatt cctgcaaaat tacctacccc agttcatctc   7620
tgctgaacat ttggaaacca tgcactagcc aacccaactg acttctgcta ggtagaggca   7680
tttgtcttag agagagagag agcgcgggag agagtgagag agagtgagag cacaaagata   7740
acgcaggaga gagagagaga aagaatgaga aagaaaagga atgcaagaga aggagatgta   7800
atgacagaga gttctggtga gatacccaga gagaaaaaga gagagcaggg tggggtaagg   7860
aggagaaaat aaaccaacaa ttaggtctgc attttctcag gcagtaggca ttctttagtc   7920
tacataggca aagttttcca tttttgtcag tctgagtcat caaaaagagt cttaattttc   7980
taaaacaagt tggctagaag aaagtaaaaa gaacaacact tgttatgagg gcatgtgata   8040
ttttcacatc ttaattaagc tccttcagtt tgaaggctgc acactgacat aatgtagtga   8100
gtgtagactg gccatgcaag tggtttgggc cccattcaga actctcagac tctaaacaca   8160
caagtagatt gatctaaggc atgctcccag catttgtcca cccacttagt ccactctgag   8220
tcgattaacc tgcatgcagc aacacccaag tccaccccaa ttaactgaag caaataccaa   8280
agcagttggg agtacatatg gtagacaatt tgccttagga agtgacttga atgtacaaag   8340
atacttgatg cacttatttt ttaatgtgag acagcaagtt tataaaacat ccatatagga   8400
ttatagatac ttaaaggaac acgtgggtga gcgtgtgtgg gggtactaga agctgatctg   8460
attggtccaa cagtttgatg ctgagtcatg cgtgttgaat ccccacttcag tgcacctgtg   8520
gcctctcagt caaacaagtt gtgcctttca cagcttcttt actactgcaa gttcaagact   8580
gaaatggctt ctatgatcag aactgggaaa acagtgaatc ttatggtgga agaggttctc   8640
agcaagtgta cagtatttac cttcctttgt cttacattgg ctttttaaat tttccattaa   8700
tttcaacata attatgggaa caagtgtaca gaagaatttt ttttttaaga tatgtgagaa   8760
```

-continued

```
cttttcatag atgaactttt taacaaatgt tttcatttac aggaaattgc aaagaaaatt   8820

ctcaagtgat agtctttttt tttaagtgtt tcgtaagaca aaaattgaat aatgtttttt   8880

gaagttctgg caagattgaa gtctgatatt gcagtaatga tatttattaa aaacccataa   8940

ctaccaggaa taatgatacc tcccacccct tgattcccat aacataaaag tgctacttga   9000

gagtgggggga gaatggcatg gtaggctact tttcagggcc ttgacaagta catcacccag   9060

tggtatccta catacttctt tcaagatctt caaccatgag gtaaaagagc caagttcaaa   9120

gaaccctagc acaaatttgc tttgggattt tcttttctgg a                       9161
```

<210> SEQ ID NO 38
<211> LENGTH: 1190
<212> TYPE: DNA
<213> ORGANISM: Homo sapiens

<400> SEQUENCE: 38

```
gccctccaca aagctcctgg gcccctcctc ccttcaagga ttgcgaagaa ctggtcgcaa     60

atcctcctaa gccaccagca tctcggtctt cagctcacac cagccttgag cccagcctgc    120

ggccagggga ccacgcacgt cccacccacc cagcgactcc ccagccgctg cccactcttc    180

ctcactcatg ggaacagca aaagtggggc cctgtccaag gagatcctgg aggagctgca    240

gctgaacacc aagttctcgg aggaggagct gtgctcctgg taccagtcct tcctgaagga    300

ctgtcccacc ggccgcatca cccagcagca gttccagagc atctacgcca agttcttccc    360

cgacaccgac cccaaggcct acgcccagca tgtgttccgc agcttcgatt ccaacctcga    420

cggcaccctg gacttcaagg agtacgtcat cgccctgcac atgaccaccg cgggcaagac    480

caaccagaag ctggagtggg ccttctccct ctacgacgtg gacggtaacg ggaccatcag    540

caagaatgaa gtgctggaga tcgtcatggc tattttcaaa atgatcactc ccgaggacgt    600

gaagctcctt ccagacgatg aaaacacgcc ggaaaagcga gccgagaaga tctggaagta    660

ctttggaaag aatgatgatg ataaacttac agagaaagaa ttcattgagg ggacactggc    720

caataaggaa attctgcgac tgatccagtt tgagcctcaa aaagtgaagg aaaagatgaa    780

gaacgcctga tgccaactgt tcagctgtcc tccctccacc taccactcac atgacacccg    840

tgagcgcctg tgcacacaca cacacatgca cacacacgcg cgcgcacaca cacacacaca    900

catccacccc agggccaaga gaaaggcctg cacacaagcc cacagcacag ctccctgcca    960

aactgaagca tctgtagtga cccactggtt ccttcttcct gggtcttcag cattccctcc   1020

catcatgccc ggtcccaccc ctccctctgt ccaccagccc atgtccctgt gctaatccca   1080

ggattaggcc ataggagtcc taagtgtcac cccgctgtaa gctcctttgt ggagtgctgg   1140

gtaagcagtt tccaataaac gcaagctgag ctggaaaaaa aaaaaaaaaa              1190
```

<210> SEQ ID NO 39
<211> LENGTH: 1880
<212> TYPE: DNA
<213> ORGANISM: Homo sapiens

<400> SEQUENCE: 39

```
aggatgcaag agtcagagtg agggatctgt ccctggatgg ggacaataag ggtcagttc     60

agggggactt ccttgagctc tgaagtttca cctgagaatg ggagattcag aacttggtga    120

cagagtttgt ggagctcact gtgtctttgc tgatccttca gcaaaggaag tgagattgtt    180

tctagctttt ctgtttgggg tgcttctctg tcaactaaaa gtcttcatcc tttaaatatt    240

gcatcatttg tgtatacttc attcattcac ttactcatga cccactcctc gagtgcctgc    300
```

aatgggcaag cgtctgtcct aggagccgtg tgctgggcca cagttaaatc tgagagatca 360
tgtgtggcat ttctcatgga ttgagatgtc tgagtgtcat tgttttgaga gagctagtgg 420
catggtttat aaagctgttt ttcattttct ccatacagga caacagcttt gagcagttca 480
ttattaatta ttgtaacgaa aagctgcaac aaatcttcat tgaacttact cttaaagaag 540
agcaggagga gtatatacgg gaggatatag aatggactca cattgactac ttcaataatg 600
ctatcatttg tgacctaata gaaaataaca caaatggaat cctggccatg ctggatgaag 660
agtgcctcag acctggcaca gtcactgatg agaccttctt agaaaagctg aaccaagtat 720
gtgccaccca ccagcatttt gaaagcagga tgagcaagtg ctctcggttc ctcaatgaca 780
cgtctctgcc tcacagctgc ttcaggatcc agcattatgc tggaaaggtg ctgtaccagg 840
tggaaggatt cgttgacaaa aacaatgacc ttctctatcg agacctgccc caagccatgt 900
ggaaggccag ccatgccctc atcaagtctt tgttccccga agggaatccc gccaagatca 960
acctgaaaag gcctcctaca gcaggctcac agttcaaggc atccgtggcc actctgatga 1020
aaaacctaca gaccaagaac ccaaactata ttaggtattt ttggcacatg aaactttcac 1080
agttcaaatg tgagagcacc ccgaaggaat atcatttttc cctttgcttc aatctgagtg 1140
tagcccaagc agagggtaac taaaatactt acagattaaa taatacctta tctgggattg 1200
gcttaaaaaa tgctccacta tcctttcccc taaaataaga aagtaaaaaa gtaaagtgtg 1260
gtggagaaga tagtagatat ttaatgaagc tcagtggttg agacctaggg gttttcaact 1320
ttctgtatgt ttattattat ttttttaacg gcaagttaaa aaacaaaatg caagtgtttt 1380
ttctggtcag tgttttgcag aaaactcttg ttggcttcat ttgggattct tgttctatta 1440
gcttagagca cagcattgaa gcaagtgctt tagttaactg ctctggcact tcttaggaga 1500
catgcacttt tttcttccct gtgagaggtg taggcctgga gaaagtaatg attcctaaag 1560
caatctgaat tttttccaag gcagtagaaa gaccttctta aaaagggctg ggcgtggtgg 1620
ctcacaccta taatcccaac acttagggag gcggaggcag gtggatcacc tcaggtcagg 1680
aattcgagac tagcctggcc aacatggcaa aaccctgtct ctactaaaaa tataaaaatt 1740
agctgggcgt ggtggcaggg acctataatc ccaactactt gggaggctga ggcaggagaa 1800
tcgcttggag gcagaggttg cagtgagccg aggtcacgcc actgcactcc agcccgggtg 1860
acaatacaag actccatctc 1880

<210> SEQ ID NO 40
<211> LENGTH: 1880
<212> TYPE: DNA
<213> ORGANISM: Homo sapiens

<400> SEQUENCE: 40
aggatgcaag agtcagagtg agggatctgt ccctggatgg ggacaataag gggtcagttc 60
agggggactt ccttgagctc tgaagtttca cctgagaatg ggagattcag aacttggtga 120
cagagtttgt ggagctcact gtgtctttgc tgatccttca gcaaaggaag tgagattgtt 180
tctagctttt ctgtttgggg tgcttctctg tcaactaaaa gtcttcatcc tttaaatatt 240
gcatcatttg tgtatacttc attcattcac ttactcatga cccactcctc gagtgcctgc 300
aatgggcaag cgtctgtcct aggagccgtg tgctgggcca cagttaaatc tgagagatca 360
tgtgtggcat ttctcatgga ttgagatgtc tgagtgtcat tgttttgaga gagctagtgg 420
catggtttat aaagctgttt ttcattttct ccatacagga caacagcttt gagcagttca 480
ttattaatta ttgtaacgaa aagctgcaac aaatcttcat tgaacttact cttaaagaag 540

-continued agcaggagga gtatatacgg gaggatatag aatggactca cattgactac ttcaataatg 600
ctatcatttg tgacctaata gaaaataaca caaatggaat cctggccatg ctggatgaag 660
agtgcctcag acctggcaca gtcactgatg agaccttctt agaaaagctg aaccaagtat 720
gtgccaccca ccagcatttt gaaagcagga tgagcaagtg ctctcggttc ctcaatgaca 780
cgtctctgcc tcacagctgc ttcaggatcc agcattatgc tggaaaggtg ctgtaccagg 840
tggaaggatt cgttgacaaa aacaatgacc ttctctatcg agacctgccc caagccatgt 900
ggaaggccag ccatgccctc atcaagtctt tgttccccga agggaatccc gccaagatca 960
acctgaaaag gcctcctaca gcaggctcac agttcaaggc atccgtggcc actctgatga 1020
aaaacctaca gaccaagaac ccaaactata ttaggtattt ttggcacatg aaactttcac 1080
agttcaaatg tgagagcacc ccgaaggaat atcatttttc cctttgcttc aatctgagtg 1140
tagcccaagc agagggtaac taaaatactt acagattaaa taatacctta tctgggattg 1200
gcttaaaaaa tgctccacta tcctttcccc taaaataaga aagtaaaaaa gtaaagtgtg 1260
gtggagaaga tagtagatat ttaatgaagc tcagtggttg agacctaggg gttttcaact 1320
ttctgtatgt ttattattat ttttttaacg gcaagttaaa aaacaaaatg caagtgtttt 1380
ttctggtcag tgttttgcag aaaactcttg ttggcttcat ttgggattct tgttctatta 1440
gcttagagca cagcattgaa gcaagtgctt tagttaactg ctctggcact tcttaggaga 1500
catgcacttt tttcttccct gtgagaggtg taggcctgga gaaagtaatg attcctaaag 1560
caatctgaat tttttccaag gcagtagaaa gaccttctta aaaagggctg ggcgtggtgg 1620
ctcacaccta taatcccaac acttagggag gcggaggcag gtggatcacc tcaggtcagg 1680
aattcgagac tagcctggcc aacatggcaa aaccctgtct ctactaaaaa tataaaaatt 1740
agctgggcgt ggtggcaggg acctataatc ccaactactt gggaggctga ggcaggagaa 1800
tcgcttggag gcagaggttg cagtgagccg aggtcacgcc actgcactcc agcccgggtg 1860
acaatacaag actccatctc 1880

<210> SEQ ID NO 41
<211> LENGTH: 2685
<212> TYPE: DNA
<213> ORGANISM: Homo sapiens

<400> SEQUENCE: 41
ggacttggga ggcgcggtga ggagtcaggc ttaaaacttg ttggagggga gtaaccagcc 60
tgctcctctc gctctcctcc tcgtctgcgc cgcgtttcag agagaaaatt cctgttccaa 120
gagaaaataa ggcaacatca atgaaggaga gaagagccag ccagaaatta tccagcaaat 180
ctatcatgga tcctaatcag aacgtgaaat gcaagatagt tgtggtggga gacagtcagt 240
gtggaaaaac tgcgctgctc catgtcttcg ccaaggactg cttccccgag aattacgttc 300
ctacagtgtt tgagaattac acggccagtt ttgaaatcga cacacaaaga atagagttga 360
gcctgtggga cacttcgggt tctccttact atgacaatgt ccgcccccctc tcttaccctg 420
attcggatgc tgtgctgatt tgctttgaca tcagtagacc agagaccctg gacagtgtcc 480
tcaaaaagtg gaaaggtgaa atccaggaat tttgtccaaa taccaaaatg ctcttggtcg 540
gctgcaagtc tgatctgcgg acagatgtta gtacattagt agagctctcc aatcacaggc 600
agacgccagt gtcctatgac cagggggcaa atatggccaa acagattgga gcagctactt 660
atatcgaatg ctcagcttta cagtcggaaa atagcgtcag agacattttt cacgttgcca 720
ccttggcatg tgtaaataag acaaataaaa acgttaagcg gaacaaatca cagagagcca 780
caaagcggat ttcacacatg cctagcagac cagaactctc ggcagttgct acggacttac 840
gaaaggacaa agcgaagagc tgcactgtga tgtgaatctt tcattatctt taatgaagac 900
aaaggaatct agtgtaaaaa acaacagcaa acaaaaaggt gaagtctaaa tgaagtgcac 960
agccaaagtc atgtatacca gaggcttagg aggcgtttga gaggatactc atctttttgg 1020
aatcctgacc ttaggttcgg catgtagacc aagtgatgag aagtgaatac atggaagagt 1080
ttttaagtgt gacttgaaaa atatgccaaa aaatgagaga tacaaatgag ctagaggaag 1140
atgagggggg atgcgagtac ctccaagaag aaaaatcaca ctctgaatgg tgcttgcatt 1200
tttgggtttt ttttttttt gttataatct attcatggat ctccactttg atttaatttt 1260
taaatgtttt aatctccttt acaaaaagta tacgttaata taccgtcctc aagggggaac 1320
tggcactgtg accttagcat ttagttttct agaggatgtg atctaatttc tttctagctc 1380
atcattaaaa aggaaattgt atcaggaccc atgggatata tccagaggca aactttatga 1440
ggctttgaaa tcttgccttc ctgaagatag ctgagtagga tggttctaag gaaagccttt 1500
gcaatcttgc aagatttgta gaccagcact acaaagatcg catagatcaa ataggaaaaa 1560
aaatgtcgat ttttattcag tctgatggtt ctgttcttca ttgtgattgt cattaaaaag 1620
tggtaaattg ctcaatgtaa tatttttgtg cgctgtttag aagttgtgtg atttttttgcc 1680 atcgttgata aaaatgcaaa gtcaaataaa aggtgtcttg gtttgatgtc atagaatgat 1740
ccaaggagag aaaaaaggta gttactgttt tcaccagaaa aggtaatgag tgaaggaaag 1800
aatagtagca gaaagcacag tttgtgagta aagctgtctg gaattaagtt accaaaaata 1860
caaagcaaaa ggactattat tttgggttga agctccaaaa ctgacagcat ctgataatct 1920
gttggtttat ttcacttttc attaaatgaa cattgatgag agaagatgcc acttacccaa 1980
gctttagaga atccctagtg gaagattata tgataaactt tcagtcctga cataacacta 2040
gggcatttct agagtgtcat tgctaaaacc tcactgaaca gacgcagcca aggtctgtgt 2100
tcagcacttg gtctctgttg ttacgtaaaa taataagcat ttaaaatagt ttacagatat 2160
ttttgaccag ttccttttag agattctttc agagaagaaa ccagatctga cctgtttatt 2220
gttggcgctt gttgaaaacg agctttcttt cccatgatag tgcttcgttt ttgaagtgtt 2280
gaagctgtgc tccccttaaa tcgtggcagg agagattaag gtaattacaa cactcagttc 2340
tatgtcttac aagcactttg tcttgtctct gcaagaaaat tcgattccag tcatttccca 2400
taaaatacag acattttacc aacataatat gctttgattg atgcagcatt atgctttggg 2460
cagtattaca aaatagctgg cgagtgcttt ctgtatttaa atattgtaaa aagaaaataa 2520
gttataactg ttataaagca gaacttttgt tgcatttttt aaactgttga agtcactgtg 2580
tatgtttgtt tggtcaatgt ttccgcagta tttattaaaa catacttttt tttttcttca 2640
aataaaaaag taaccatgtc tttgtctaaa aaaaaaaaaa aaaaa 2685

<210> SEQ ID NO 42
<211> LENGTH: 4469
<212> TYPE: DNA
<213> ORGANISM: Homo sapiens

<400> SEQUENCE: 42
cctgcagcct ccggagtcag tgccgcgcgc ccgccgcccc gcgccttcct gctcgccgca 60
cctccgggag ccggggcgca cccagcccgc agcgccgcct ccccgcccgc gccgcctccg 120
accgcaggcc gagggccgcc actggccggg gggaccgggc agcagcttgc ggccgcggag 180
ccgggcaacg ctggggactg cgccttttgt ccccggaggt ccctggaagt ttgcggcagg 240

```
acgcgcgcgg ggaggcggcg gaggcagccc cgacgtcgcg gagaacaggg cgcagagccg    300
gcatgggcat cgggcgcagc gagggggggcc gccgcggggc cctgggcgtg ctgctggcgc    360
tgggcgcggc gcttctggcc gtgggctcgg ccagcgagta cgactacgtg agcttccagt    420
cggacatcgg cccgtaccag agcgggcgct tctacaccaa gccacctcag tgcgtggaca    480
tccccgcgga cctgcggctg tgccacaacg tgggctacaa gaagatggtg ctgcccaacc    540
tgctggagca cgagaccatg gcggaggtga agcagcaggc cagcagctgg gtgcccctgc    600
tcaacaagaa ctgccacgcc gggacccagg tcttcctctg ctcgctcttc gcgcccgtct    660
gcctggaccg gcccatctac ccgtgtcgct ggctctgcga ggccgtgcgc gactcgtgcg    720
agccggtcat gcagttcttc ggcttctact ggcccgagat gcttaagtgt gacaagttcc    780
cggaggggga cgtctgcatc gccatgacgc cgcccaatgc caccgaagcc tccaagcccc    840
aaggcacaac ggtgtgtcct ccctgtgaca acgagttgaa atctgaggcc atcattgaac    900
atctctgtgc cagcgagttt gcactgagga tgaaaataaa agaagtgaaa aaagaaaatg    960
gcgacaagaa gattgtcccc aagaagaaga agcccctgaa gttggggccc atcaagaaga   1020
aggacctgaa gaagcttgtg ctgtacctga agaatggggc tgactgtccc tgccaccagc   1080
tggacaacct cagccaccac ttcctcatca tgggccgcaa ggtgaagagc cagtacttgc   1140
tgacggccat ccacaagtgg gacaagaaaa acaaggagtt caaaaacttc atgaagaaaa   1200
tgaaaaacca tgagtgcccc acctttcagt ccgtgtttaa gtgattctcc cgggggcagg   1260
gtggggaggg agcctcgggt ggggtgggag cgggggggac agtgcccggg aacccgtggt   1320
cacacacacg cactgccctg tcagtagtgg acattgtaat ccagtcggct tgttcttgca   1380
gcattcccgc tccctttccc tccatagcca cgctccaaac cccagggtag ccatggccgg   1440
gtaaagcaag ggccatttag attaggaagg tttttaagat ccgcaatgtg gagcagcagc   1500
cactgcacag gaggaggtga caaaccattt ccaacagcaa cacagccact aaaacacaaa   1560
aagggggatt gggcggaaag tgagagccag cagcaaaaac tacattttgc aacttgttgg   1620
tgtggatcta ttggctgatc tatgcctttc aactagaaaa ttctaatgat tggcaagtca   1680
cgttgttttc aggtccagag tagtttcttt ctgtctgctt taaatggaaa cagactcata   1740
ccacacttac aattaaggtc aagcccagaa agtgataagt gcagggagga aaagtgcaag   1800
tccattatct aatagtgaca gcaaagggac caggggagag gcattgcctt ctctgcccac   1860
agtctttccg tgtgattgtc tttgaatctg aatcagccag tctcagatgc cccaaagttt   1920
cggttcctat gagcccgggg catgatctga tccccaagac atgtggaggg gcagcctgtg   1980
cctgcctttg tgtcagaaaa aggaaaccac agtgagcctg agagagacgg cgattttcgg   2040
gctgagaagg cagtagtttt caaaacacat agttaaaaaa gaaacaaatg aaaaaaattt   2100
tagaacagtc cagcaaattg ctagtcaggg tgaattgtga aattgggtga agagcttagg   2160
attctaatct catgtttttt ccttttcaca tttttaaaag aacaatgaca aacacccact   2220
tatttttcaa ggttttaaaa cagtctacat tgagcatttg aaaggtgtgc tagaacaagg   2280
tctcctgatc cgtccgaggc tgcttcccag aggagcagct ctccccaggc atttgccaag   2340
ggaggcggat ttccctggta gtgtagctgt gtggctttcc ttcctgaaga gtccgtggtt   2400
gccctagaac ctaacacccc ctagcaaaac tcacagagct ttccgttttt ttctttcctg   2460
taaagaaaca tttcctttga acttgattgc ctatggatca aagaaattca gaacagcctg   2520
cctgttcccc cgcacttttt acatatattt gtttcatttc tgcagatgga aagttgacat   2580
gggtggggtg tccccatcca gcgagagagt ttcaaaagca aaacatctct gcagtttttc   2640
```

-continued ccaagtaccc tgagatactt cccaaagccc ttatgtttaa tcagcgatgt atataagcca 2700
gttcacttag acaactttac ccttcttgtc caatgtacag gaagtagttc taaaaaaaat 2760
gcatattaat ttcttccccc aaagccggat tcttaattct ctgcaacact ttgaggacat 2820
ttatgattgt ccctctgggc caatgcttat acccagtgag gatgctgcag tgaggctgta 2880
aagtggcccc ctgcggccct agcctgaccc ggagaaagga tggtagattc tgttaactct 2940
tgaagactcc agtatgaaaa tcagcatgcc cgcctagtta cctaccggag agttatcctg 3000
ataaattaac ctctcacagt tagtgatcct gtcctttttaa cacctttttt gtggggttct 3060
ctctgacctt tcatcgtaaa gtgctgggga ccttaagtga tttgcctgta attttggatg 3120
attaaaaaat gtgtatatat attagctaat tagaaatatt ctacttctct gttgtcaaac 3180
tgaaattcag agcaagttcc tgagtgcgtg gatctgggtc ttagttctgg ttgattcact 3240
caagagttca gtgctcatac gtatctgctc attttgacaa agtgcctcat gcaaccgggc 3300
cctctctctg cggcagagtc cttagtggag ggtttacct ggaacataag tagttaccac 3360
agaatacgga agagcaggtg actgtgctgt gcagctctct aaatgggaat tctcaggtag 3420
gaagcaacag cttcagaaag agctcaaaat aaattggaaa tgtgaatcgc agctgtgggt 3480
tttaccaccg tctgtctcag agtcccagga ccttgagtgt cattagttac tttattgaag 3540
gttttagacc catagcagct ttgtctctgt cacatcagca atttcagaac caaaagggag 3600
gctctctgta ggcacagagc tgcactatca cgagcctttg tttttctcca caaagtatct 3660
aacaaaacca atgtgcagac tgattggcct ggtcattggt ctccgagaga ggaggtttgc 3720
ctgtgatttg cctgtgattt cctaattatc gctagggcca aggtgggatt tgtaaagctt 3780
tacaataatc attctggata gagtcctggg aggtccttgg cagaactcag ttaaatcttt 3840
gaagaatatt tgtagttatc ttagaagata gcatgggagg tgaggattcc aaaaacattt 3900
tatttttaaa atatcctgtg taacacttgg ctcttggtac ctgtgggtta gcatcaagtt 3960
ctccccaggg tagaattcaa tcagagctcc agtttgcatt tggatgtgta aattacagta 4020
atcccatttc ccaaacctaa aatctgtttt tctcatcaga ctctgagtaa ctggttgctg 4080
tgtcataact tcatagatgc aggaggctca ggtgatctgt ttgaggagag caccctaggc 4140
agcctgcagg gaataacata ctggccgttc tgacctgttg ccagcagata cacaggacat 4200
ggatgaaatt cccgtttcct ctagtttctt cctgtagtac tcctctttta gatcctaagt 4260
ctcttacaaa agctttgaat actgtgaaaa tgttttacat tccatttcat ttgtgttgtt 4320
tttttaactg cattttacca gatgttttga tgttatcgct tatgttaata gtaattcccg 4380
tacgtgttca ttttattttc atgctttttc agccatgtat caatattcac ttgactaaaa 4440
tcactcaatt aatcaatgaa aaaaaaaaa 4469

<210> SEQ ID NO 43
<211> LENGTH: 1607
<212> TYPE: DNA
<213> ORGANISM: Homo sapiens

<400> SEQUENCE: 43
gctctgtagc acccaggagc ggggaagcga agtgcgagag accccggacc ccagcgctgt 60
ctcttcccgc cgcccgaacc accatgaccc acttcaacaa gggcccttcc tatgggctct 120
cggccgaagt caagaacaag attgcttcca agtatgatca tcaggcagaa gaagatcttc 180
gcaattggat agaagaggtg acaggcatga gcattggccc caacttccag ctgggcttaa 240
aggatggcat catcctctgc gaacttataa acaagctaca gccaggctca gtgaagaagg 300

```
tcaacgagtc ctcactgaac tggcctcagt tggagaatat tggcaacttt attaaagcta    360
ttcaggctta tggtatgaag ccacatgaca tattcgaagc aaatgatctt tttgagaatg    420
gaaacatgac ccaggttcag actactctgg tggctctagc aggtctggct aaaacaaaag    480
gattccatac aaccattgac attggagtta agtatgcaga aaaacaaaca agacgttttg    540
atgaaggaaa attaaaagct ggccaaagtg taattggtct gcagatggga accaacaaat    600
gtgccagcca ggcaggtatg acagcttacg ggactaggag gcatctttat gatcccaaaa    660
tgcaaactga caaacctttt gaccagacca caattagtct gcagatgggc actaataaag    720
gagccagcca ggcagggatg ttagcaccag gtaccagaag agacatctat gatcagaagc    780
taacattaca gccggtggac aactcgacaa tttccctaca gatgggtacc aacaaagttg    840
cttcccagaa aggaatgagt gtgtatgggc ttgggcggca agtatatgat cccaaatact    900
gtgctgctcc tacagaacct gtcattcaca acggaagcca aggaacagga acaaatggtt    960
cggaaatcag tgatagtgat tatcaggcag aataccctga tgagtatcat ggcgagtacc   1020
aggatgacta ccccagagat taccaatata gcgaccaagg cattgattat tagatccaca   1080
cagaaggagc tcagtattta gtcctttgtt tttattcagt gagaaccaag ctagccttga   1140
gtaattttta tcttgtcttc ctaaaacact attaagctta ttgtactttt aagaaaaatt   1200
gccttacgta cattcctttt tcctttttct gcctcttccc tcaatagttg ccttttagtg   1260
ctgtaatagg ttaaatccta cagcataatc aataactcgc atatgaagta aaaaggaata   1320
ctgtgaaagg ggagtactct tgtacagcca gttcttttat gcaaaaatct atgcattttt   1380
acaatcttat attaaactgg tattttcaaa caataggaaa cttttttttt tttttttac   1440
agtttagtgt atctggtttc tacatggaag actaaactca tgcttattgc taaatgtggt   1500
ctttgccaac taaatttaag atgcagcatt ttagaaattt acatatcaat gtttctacag   1560
tattgtttgc taatttttaa ataaagtcat gatcagtgtg aaaaaaa                 1607
```

<210> SEQ ID NO 44
<211> LENGTH: 3144
<212> TYPE: DNA
<213> ORGANISM: Homo sapiens

<400> SEQUENCE: 44

```
ggcacgaggg tccgcccggg ggcgccgccc accgcgcctc gctcgggccg ttgccgtctg     60
cacccagacc ctgagccgcc gccgccggcc atggaggtgg cgccggagca gccgcgctgg    120
atggcgcacc cggccgtgct gaatgcgcag caccccgact cacaccaccc gggcctggcg    180
cacaactaca tggaacccgc gcagctgctg cctccagacg aggtggacgt cttcttcaat    240
cacctcgact cgcagggcaa cccctactat gccaaccccg ctcacgcgcg ggcgcgcgtc    300
tcctacagcc ccgcgcacgc ccgcctgacc ggaggccaga tgtgccgccc acacttgttg    360
cacagcccgg gtttgccctg gctggacggg ggcaaagcag ccctctctgc cgctgcggcc    420
caccaccaca acccctggac cgtgagcccc ttctccaaga cgccactgca cccctcagct    480
gctggaggcc ctggaggccc actctctgtg tacccagggg ctgggggtgg gagcggggga    540
ggcagcggga gctcagtggc ctccctcacc cctacagcag cccactctgg ctcccacctt    600
ttcggcttcc cacccacgcc acccaaagaa gtgtctcctg accctagcac cacgggggct    660
gcgtctccag cctcatcttc cgcgggggt agtgcagccc gaggagagga caaggacggc    720
gtcaagtacc aggtgtcact gacggagagc atgaagatgg aaagtggcag tcccctgcgc    780
ccaggcctag ctactatggg cacccagcct gctacacacc accccatccc cacctacccc    840
```

-continued

```
tcctatgtgc cggcggctgc ccacgactac agcagcggac tcttccaccc cggaggcttc    900
ctggggggac cggcctccag cttcacccct aagcagcgca gcaaggctcg ttcctgttca    960
gaaggccggg agtgtgtcaa ctgtggggcc acagccaccc ctctctggcg gcgggacggc   1020
accggccact acctgtgcaa tgcctgtggc ctctaccaca agatgaatgg gcagaaccga   1080
ccactcatca agcccaagcg aagactgtcg gccgccagaa gagccggcac ctgttgtgca   1140
aattgtcaga cgacaaccac caccttatgg cgccgaaacg ccaacgggga ccctgtctgc   1200
aacgcctgtg gcctctacta caagctgcac aatgttaaca ggccactgac catgaagaag   1260
gaagggatcc agactcggaa ccggaagatg tccaacaagt ccaagaagag caagaaaggg   1320
gcggagtgct tcgaggagct gtcaaagtgc atgcaggaga agtcatcccc cttcagtgca   1380
gctgccctgg ctggacacat ggcacctgtg ggccacctcc cgcccttcag ccactccgga   1440
cacatcctgc ccactccgac gcccatccac ccctcctcca gcctctcctt cggccacccc   1500
cacccgtcca gcatggtgac cgccatgggc tagggaacag atggacgtcg aggaccgggc   1560
actcccggga tgggtggacc aaacccttag cagcccagca tttcccgaag gccgacacca   1620
ctcctgccag cccggctcgg cccagcaccc cctctcctgg agggcgccca gcagcctgcc   1680
agcagttact gtgaatgttc cccaccgctg agaggctgcc tccgcacctg actgctgccc   1740
aggtggggtt tcctgcatgg acagttgttt ggagaacaac aaggacaact ttatgtagag   1800
aaaaggaggg gacgggacag acgaaggcaa ccatttttag aaggaaaaag gattaggcaa   1860
aaataattta ttttgctctt gtttctaaca aggacttgga gacttggtgg tctgagctgt   1920
cccaagtcct ccggttcttc ctcgggattg gcgggtccac ttgccagggc tctgggggca   1980
gatttgtggg gacctcagcc tgcaccctct tctcttctgg cttccctctc tgaaatagcc   2040
gaactccagg ctgggctgag ccaaagccag agtggccacg gcccagggag ggtgagctgg   2100
tgcctgcttt gacgggccag gccctggagg gcagagacaa tcacgggcgg tcctgcacag   2160
attcccaggc cagggctggg tcacaggaag gaaacaacat ttcttgaaa ggggaaacgt   2220
ctcccagatc gctcccttgg ctttgaggcc gaagctgctg tgactgtgtc cccttactga   2280
gcgcaagcca cagcctgtct tgtcaggtgg accctgtaaa tacatccttt ttctgctaac   2340
ccttcaaccc cctcgcctcc tactctgaga caaaagaaaa aatattaaaa aaatgcatag   2400
gcttaactcg ctgatgagtt aattgtttta tttttaaact ctttttgggt ccagttgatt   2460
gtacgtagcc acaggagccc tgctatgaaa ggaataaaac ctacacacaa ggttggagct   2520
ttgcaattct ttttggaaaa gagctgggat cccacagccc tagtatgaaa gctgggggtg   2580
gggaggggcc tttgctgccc ttggtttctg gggctggtt ggcatttgct ggcctggcag   2640
ggggtgaagg caggagttgg gggcaggtca ggaccaggac ccagggagag gctgtgtccc   2700
tgctggggtc tcaggtccag ctttactgtg gctgtctgga tccttcccaa ggtacagctg   2760
tatataaacg tgtcccgagc ttagattctg tatgcggtga cggcggggtg tggtggcctg   2820
tgaggggccc ctggcccagg aggaggattg tgctgatgta gtgaccaagt gcaatatggg   2880
cgggcagtcg ctgcagggag caccacggcc agaagtaact tattttgtac tagtgtccgc   2940
ataagaaaaa gaatcggcag tattttctgt ttttatgttt tatttggctt gttttatttt   3000
ggattagtga actaagttat tgttaattat gtacaacatt tatatattgt ctgtaaaaaa   3060
tgtatgctat cctcttattc ctttaaagtg agtactgtta agaataataa aatacttttt   3120
gtgaaaaaaa aaaaaaaaaa aaaa                                           3144
```

<210> SEQ ID NO 45
<211> LENGTH: 2038
<212> TYPE: DNA
<213> ORGANISM: Homo sapiens

<400> SEQUENCE: 45
cgaagggctc gaagatggcc ggttggcaga gctacgtgga taacctgatg tgcgatggct 60
gctgccagga ggccgccatt gtcggctact gcgacgccaa atacgtctgg gcagccacgg 120
ccgggggcgt ctttcagagc attacgccaa tagaaataga tatgattgta ggaaaagacc 180
gggaaggttt ctttaccaac ggtttgactc ttggcgcgaa gaaatgctca gtgatcagag 240
atagtctata cgtcgatggt gactgcacaa tggacatccg gacaaagagt caaggtgggg 300
agccaacata caatgtggct gtcggcagag ctggtagagt cttggtcttt gtaatgggaa 360
aagaaggggt ccatggaggc ggattgaata agaaggcata ctcaatggca aaatacttga 420
gagactctgg gttctagctg ctaggcagac tgttaagtat taggggaaaa ttgctcttaa 480
actttcctag ctataagctt aagtcttaat tctggaaatt ttattagcaa tgcagggtga 540
tggggtatga acctgtgtct cctttgtatc cctctgttgg tggggaaagg tgtctttctt 600
tctgccctcc ccccccaaaa taattctgtt cacttttgtt ttgtttcctt gtgtactcca 660
gcattggtta tagtcatggg aaaggaaggt gtccacggag gcacacttaa caagaaagca 720
tatgaactcg ctttatacct gaggaggtct gatgtgtaag cagcctctcc ccatctacct 780
agcaactgtc ttcatcaaca accctaatta tggtcacaat gctaccaaac tgtagatggt 840
agctaatttt tctttaccta ttttctaatg tcatgattcc tgtttgccca atggatcatt 900
tgtatgttaa ccactgtatg taaccaaccc ttatctggca acataattgc agcacaataa 960
tgatttgcat gataccttga aattgggggg agggggcatg ccaagttggg catcactttg 1020
tcttagcaat taatgggata ttgattacta aaataagtta atattaagca aggtgccggt 1080
tgtacaatct ctgatcagtg tcttttcagc actttgagca tttacttggc tcatttagtc 1140
ttccttttgt agcgcatggt tgggaggaaa aagtgcatgc atcattcctt cactcttctc 1200
tttttcccgc cccccccctcc cttcgcacat aggcatttgg tttgcttcca tctttttta 1260 tgcagtgcct gtttttttt aaccaattaa aatccctttt gttgatgagc tattgagagc 1320
tgcagtagtt tgcttttagt attgttgttg cacttgagca gagacaaacc tttattcata 1380
gtgtctacag gacatatgaa gagtgcaatg gcaaaacaag agcaaaaagc acttcctccc 1440
atgaccttac agtaaccata ctgattgaat ccccagggac attccatcat tgcaatagct 1500 cagattttc ttcctttttc tttgcacacc agctctactc tttagtaaaa ttgtaaaagg 1560
ctgccattat ggacattagg tatcccaaca taaccatctg gagtgtgtcc agtttgttct 1620
tcataggacc aatttttatt tgcagcttga gtttttatat gaagttgcat tattgtggac 1680
ttggctgtct tgtgatgaat ttttttcata tgtattctgt gccatactat tgttaaaatg 1740
aactgttgct attgtgagat ggattttaac tgacctatta agggtttctt tcgaatggca 1800
ctactttagg gacattctag tatttgcttc tattgtttgg gccttgtgga taatgtacag 1860
atttaaaaac aaatcttgtt gctgatttgt ccatttcttt ccctgcactt tgttacatct 1920
gggatacagt ctaactcatc tgatttaata tgcatttaaa aaaatgccat aactattaaa 1980
caccttgttt acagacagat gaaataaatt tattccaacc aaaaaaaaaa aaaaaaa 2038

<210> SEQ ID NO 46
<211> LENGTH: 5487
<212> TYPE: DNA
<213> ORGANISM: Homo sapiens

<400> SEQUENCE: 46
tctgtcgact tgccccagag ctgatccttg tctttgtcca cttctcagcg aggatggcac 60
ttcagggagc ccttccctta ctatcgcaga gagagcaggc cctccccagt catgtccaac 120
ccagaactct gttttgtttt cttcatagcc ctagcatcac agaaaatcac cctgtgcatt 180
catggatgtc cacgggggca agggctttgt gttgcttaac ccagcatcct gaaccgtgtt 240
tgttgaatga atacagaacc ccgtttgctc tgggagagca cagaaaacag tcttctatca 300
tatatcatag ccagctgcaa acagcagatg gcttcccata tcccagagag taagaaccag 360
agagagagag aaagagagag agtttgggtc tttctcctct gtgcctgctc tctccagaga 420
aactggaggg gtagcagtta gcattccccc gctggttcca ccaagcacag tcaaggtctc 480
taggacatgg ccacccctca cctgtggaag cggtcctgct ggggtgggtg ggtgttagtt 540
ggttctggtt tgggtcagag acacccagtg gcccaggtgg gcgtggggcc agggcgcaga 600
cgagaagggg cacgagggct ccgctccgag gacccagcgg caagcaccgg tcccgggcgc 660
gccccagccc acccactcgc gtgcccacgg cggcattatt ccctataagg atctgaacga 720
tccgggggcg gccccgcccc gttacccctt gcccccggcc ccgccccctt tttggagggc 780
cgatgaggta atgcggctct gccattggtc tgagggggcg ggccccaaca gcccgaggcg 840
gggtccccgg gggcccagcg ctatatcact cggccgccca ggcagcggcg cagagcgggc 900
agcaggcagg cggcgggcgc tcagacggct tctcctcctc ctcttgctcc tccagctcct 960
gctccttcgc cgggaggccg cccgccgagt cctgcgccag cgccgaggca gcctcgctgc 1020
gccccatccc gtcccgccgg gcactcggag ggcagcgcgc cggaggccaa ggttgccccg 1080
cacggcccgg cgggcgagcg agctcgggct gcagcagccc cgccggcggc gcgcacggca 1140
actttggaga ggcgagcagc agccccggca gcggcggcag cagcggcaat gaccccttgg 1200
ctcgggctca tcgtgctcct gggcagctgg agcctggggg actggggcgc cgaggcgtgc 1260
acatgctcgc ccagccaccc ccaggacgcc ttctgcaact ccgacatcgt gatccgggcc 1320
aaggtggtgg ggaagaagct ggtaaaggag gggcccttcg gcacgctggt ctacaccatc 1380
aagcagatga agatgtaccg aggcttcacc aagatgcccc atgtgcagta catccacacg 1440
gaagcttccg agagtctctg tggccttaag ctggaggtca acaagtacca gtacctgctg 1500
acaggtcgcg tctatgatgg caagatgtac acggggctgt gcaacttcgt ggagaggtgg 1560
gaccagctca ccctctccca gcgcaagggg ctgaactatc ggtatcacct gggttgtaac 1620
tgcaagatca agtcctgcta ctacctgcct tgctttgtga cttccaagaa cgagtgtctc 1680
tggaccgaca tgctctccaa tttcggttac cctggctacc agtccaaaca ctacgcctgc 1740
atccggcaga agggcggcta ctgcagctgg taccgaggat gggccccccc ggataaaagc 1800
atcatcaatg ccacagaccc ctgagcgcca gaccctgccc cacctcactt ccctcccttc 1860
ccgctgagct tcccttggac actaactctt cccagatgat gacaatgaaa ttagtgcctg 1920
ttttcttgca aatttagcac ttggaacatt taaagaaagg tctatgctgt catatggggt 1980
ttattgggaa ctatcctcct ggccccaccc tgccccttct tttggttttg gacatcattc 2040
atttccacct gggaatttct ggtgccatgc cagaaagaat gaggaacctg tattcctctt 2100
cttcgtgata atataatctc tattttttta ggaaaacaaa aatgaaaaac tactccattt 2160
gaggattgta attcccaccc ctcttgcttc ttccccacct caccatctcc cagaccctct 2220
tccctttgcc cttctcctcc aatacataaa ggacacagac aaggaacttg ctgaaaggcc 2280
aaccatttca ggatcagtca aaggcagcaa gcagatagac tcaaggtgtg tgaaagatgt 2340

-continued

```
tatacaccag gagctgccac tgcatgtccc aaccagactg tgtctgtctg tgtctgcatg   2400
taagagtgag ggagggaagg aaggaactac aagagagtcg gagatgatgc agcacacaca   2460
caattcccca gcccagtgat gcttgtgttg accagatgtt cctgagtctg gagcaagcac   2520
ccaggccaga ataacagagc tttcttagtt ggtgaagact taaacatctg cctgaggtca   2580
ggaggcaatt tgcctgcctt gtacaaaagc tcaggtgaaa gactgagatg aatgtctttc   2640
ctctccctgc ctcccaccag acttcctcct ggaaaacgct ttggtagatt tggccaggag   2700
ctttctttta tgtaaattgg ataaatacac acaccataca ctatccacag atatagccaa   2760
gtagatttgg gtagaggata ctatttccag aatagtgttt agctcaccta gggggatatg   2820
tttgtataca catttgcata tacccacatg ggacataag ctaatttttt tacaggacac   2880
agaattctgt tcaatgctgt taaatatgcc aatagtttaa tctcttctat tttgttgtcg   2940
ttgcttgttt gaagaaaatc atgacattcc aagttgacat ttttttttca ttttaattaa   3000
aatttgaaat tctgaacacc gtcagcaccc tctcttccct atcatgggtc atctgacccc   3060
tgtccgtctc cttgtccctg cttcatgttt gggggccttt ctttaactgc cttcctggct   3120
tagctcagat ggcagatgag agtgtagtca agggcctggg cacaggaggg agagctgcag   3180
agtgtcctgc ctgccttggc tggagggaca cctctcctgg gtgtggagac agcttggttc   3240
cctttcccta gctccctggt gggtgaatgc cacctcctga gatcctcacc tcttggaatt   3300
aaaattgttg gtcactgggg aaagcctgag tttgcaacca gttgtagggt ttctgttgtg   3360
ttttttttt ttttttgaa ataaaactat aatataaatt ctcctattaa ataaaattat   3420
tttaagtttt agtgtcaaaa gtgagatgct gagagtaggt gataatgtat attttacaga   3480
gtgggggttg gcaggatggt gacattgaac atgattgctc tctgtctctt ttttcagctt   3540
atgggtattt atcttctatt agtatttgta tcttcagttc attccacttt aggaaacaga   3600
gctgccaatt gaaacagaag aagaaaaaaa aaaaaagcag cagacaacac actgtagagt   3660
cttgcacaca cacaagtgcc caggcaaggt gcttggcaga accgcagagt gggaagagag   3720
taccggcatc gggtttcctt gggatcaatt tcattaccgt gtacctttcc cattgtggtc   3780
atgccatttg gcagggggag aatgggaggc ttggccttct ttgtgaggca gtgtgagcag   3840
aagctgatgc cagcatgtca ctggttttga agggatgagc ccagacttga tgttttggga   3900
ttgtccttat tttaacctca aggtctcgca tggtggggcc cctgaccaac ctacacaagt   3960
tccctcccac aagtggacat cagtgtcttc tctgtgaggc atctggccat tcgcactccc   4020
tggtgtggtc agcctctctc acacaaggag gaacttgggt gaaggctgag tgtgaggcac   4080
ctgaagtttc cctgcggagt cgataaatta gcagaaccac atccccatct gttaggcctt   4140
ggtgaggagg ccctgggcaa agaagggtct ttcgcaaagc gatgtcagag ggcggttttg   4200
agctttctat aagctatagc tttgtttatt tcacccgttc acttactgta taatttaaaa   4260
tcatttatgt agctgagaca cttctgtatt tcaatcatat catgaacatt ttattttgct   4320
aaatcttgtg tcatgtgtag gctgtaatat gtgtacattg tgtttaagag aaaaatgaaa   4380
cccacatgcc gccattttcc tgaatcaaat tctgcagtgg aatggagagg aaaatacttc   4440
taggcaagca gctagactgg tgaattgggg gaaatagaag gaactagtaa ctgagactcc   4500
tccagcctcc tccctattgg aatcccaatg gctcctggag taggaaaaaa gtttaaacta   4560
cattcatgtt cttgttctgt gtcactcggc cctgggtagt ctaccattta cttcacccca   4620
agtcctgctg cccatccagt tgggaagcca tgattttcct aagaatccag ggccatggga   4680
gatacaattc caagttctcg cttcctcctt tgggcatctc ttctgcctcc caatcaagga   4740
```

agctccatgc tcaggctctc agctctcggg ccagtgctct gctctgtcca gggtaggtaa 4800
tactgggaga ctcctgtctt ttaccctccc ctcgttccag acctgcctca tggtggcaac 4860
atggttcttg aacaattaaa gaaacaaatg actttttgga atagccctgt ctagggcaaa 4920
ctgtggcccc caggagacac tacccttcca tgccccagac ctctgtcttg catgtgacaa 4980
ttgacaatct ggactacccc aagatggcac ccaagtgttt ggcttctggc tacctaaggt 5040
taacatgtca ctagagtatt tttatgagag acaaacatta taaaaatctg atggcaaaag 5100
caaaacaaaa tggaaagtag gggaggtgga tgtgacaaca acttccaaat tggctctttg 5160
gaggcgagag gaaggggaga acttggagaa tagtttttgc tttgggggta gaggcttctt 5220
agattctccc agcatccgcc tttcccttta gccagtctgc tgtcctgaaa cccagaagtg 5280
atggagagaa accaacaaga gatctcgaac cctgtctaga aggaatgtat ttgttgctaa 5340
atttcgtagc actgtttaca gttttcctcc atgttattta tgaattttat attccgtgaa 5400
tgtatattgt cttgtaatgt tgcataatgt tcacttttta tagtgtgtcc tttattctaa 5460
acagtaaagt ggttttattt ctatcac 5487

<210> SEQ ID NO 47
<211> LENGTH: 2407
<212> TYPE: DNA
<213> ORGANISM: Homo sapiens

<400> SEQUENCE: 47
ggcacgaggc ggagggggct cagtccgcag ccgccgccgc caccgccgcg cctcggcctc 60
ggtgcaggca gcggccgccg ccgccgagac agctgcgcgg gcgagcatcc ccacgcagca 120
ccttggaagt tgttttcaac catatccagc ctttgccgaa tacatcctat ctgccacaca 180
tccagcgtga ggtccctcca gctacaaggt gggcaccatg gcggagaagt ttgactgcca 240
ctactgcagg gatcccttgc aggggaagaa gtatgtgcaa aaggatggcc accactgctg 300
cctgaaatgc tttgacaagt tctgtgccaa cacctgtgtg gaatgccgca agcccatcgg 360
tgcggactcc aaggaggtgc actataagaa ccgcttctgg catgacacct gcttccgctg 420
tgccaagtgc cttcacccct tggccaatga gacctttgtg gccaaggaca acaagatcct 480
gtgcaacaag tgcaccactc gggaggactc ccccaagtgc aaggggtgct tcaaggccat 540
tgtggcagga gatcaaaacg tggagtacaa ggggaccgtc tggcacaaag actgcttcac 600
ctgtagtaac tgcaagcaag tcatcgggac tggaagcttc ttccctaaag gggaggactt 660
ctactgcgtg acttgccatg agaccaagtt tgccaagcat tgcgtgaagt gcaacaaggc 720
catcacatct ggaggaatca cttaccagga tcagccctgg catgccgatt gctttgtgtg 780
tgttacctgc tctaagaagc tggctgggca gcgtttcacc gctgtggagg accagtatta 840
ctgcgtggat tgctacaaga actttgtggc caagaagtgt gctggatgca agaaccccat 900
cactgggttt ggtaaaggct ccagtgtggt ggcctatgaa ggacaatcct ggcacgacta 960
ctgcttccac tgcaaaaaat gctccgtgaa tctggccaac aagcgctttg ttttccacca 1020
ggagcaagtg tattgtcccg actgtgccaa aaagctgtaa actgacaggg gctcctgtcc 1080
tgtaaaatgg catttgaatc tcgttctttg tgtccttact ttctgcccta taccatcaat 1140
aggggaagag tggtccttcc cttctttaaa gttctccttc cgtcttttct cccattttac 1200
agtattactc aaataagggc acacagtgat catattagca tttagcaaaa agcaaccctg 1260
cagcaaagtg aatttctgtc cggctgcaat ttaaaaatga aaacttaggt agattgactc 1320
ttctgcatgt ttctcataga gcagaaaagt gctaatcatt tagccactta gtgatgtaag 1380
caagaagcat aggagataaa acccccactg agatgcctct catgcctcag ctgggaccca 1440
ccgtgtagac acacgacatg caagagttgc agcggctgct ccaactcact gctcaccctc 1500
ttctgtgagc aggaaaagaa ccctactgac atgcatggtt taacttcctc atcagaactc 1560
tgcccttcct tctgttcttt tgtgctttca aataactaac acgaacttcc agaaaattaa 1620
catttgaact tagctgtaat tctaaactga cctttccccg tactaacgtt tggtttcccc 1680
gtgtggcatg ttttctgagc gttcctactt taaagcatgg aacatgcagg tgatttggga 1740
agtgtagaaa gacctgagaa aacgagcctg tttcagagga acatcgtcac aacgaatact 1800
tctggaagct taacaaaact aaccctgctg tcctttttat tgtttttaat taatattttt 1860
gttttaattg atagcaaaat agtttatggg tttggaaact tgcatgaaaa tattttagcc 1920
ccctcagatg ttcctgcagt gctgaaattc atcctacgga agtaaccgca aaactctaga 1980
gggggagttg agcaggcgcc agggctgtca tcaacatgga tatgacattt cacaacagtg 2040
actagttgaa tcccttgtaa cgtagtagtt gtctgctctt tgtccatgtg ttaatgagga 2100
ctgcaaagtc ccttctgttg tgattcctag gacttttcct caagaggaaa tctggatttc 2160
cacctaccgc ttacctgaaa tgcaggatca cctacttact gtattctaca ttattatatg 2220
acatagtata atgagacaat atcaaaagta aacatgtaat gacaatacat actaacattc 2280
ttgtaggagt ggttagagaa gctgatgcct catttctaca ttctgtcatt agctattatc 2340
atctaacgtt tcagtgtatc cttacagaaa taaagcagca tatgaaaaaa aaaaaaaaaa 2400
aaaaaaa 2407

<210> SEQ ID NO 48
<211> LENGTH: 2649
<212> TYPE: DNA
<213> ORGANISM: Homo sapiens

<400> SEQUENCE: 48
tccgaattaa ttggatttca ttcactgggg aggaacaaaa actatctggg cagcttcatt 60
gagagagatt cattgacact aagagccagc ggctgcagct gggtgcagag agaacctccg 120
gctttacttc tgtctcgtct gccccaaccg ctagcctcgg cttgggtaag gcgaggcgga 180
attaaacccc gctccgagag cggcagcttc gcgcgcggtg cgctcggcct atgcctgccc 240
cgaggggcgt ctggtaggca ccccgccctc tcccgcagct cgacccccat gatagatacg 300
ctcagacccg tgcccttcgc gtcggaaatg gcgatcagca agacggtggc gtggctcaac 360
gagcagctgg agctgggcaa cgagcggctg ctgctgatgg actgccggcc gcaggagcta 420
tacgagtcgt cgcacatcga gtcggccatc aacgtggcca tcccgggcat catgctgcgg 480
cgcctgcaga agggtaacct gccggtgcgc gcgctcttca cgcgcggcga ggaccgggac 540
cgcttcaccc ggcgctgtgg caccgacaca gtggtgctct acgacgagag cagcagcgac 600
tggaacgaga atacgggcgg cgagtcgttg ctcgggctgc tgctcaagaa gctcaaggac 660
gagggctgcc gggcgttcta cctggaaggt ggcttcagta agttccaagc cgagttctcc 720
ctgcattgcg agaccaatct agacggctcg tgtagcagca gctcgccgcc gttgccagtg 780
ctggggctcg gggcctgcgg gatcagctct gactcttcct cggacatcga gtctgacctt 840
gaccgagacc ccaatagtgc aacagactcg gatggtagtc cgctgtccaa cagccagcct 900
tccttcccag tggagatctt gcccttcctc tacttgggct gtgccaaaga ctccaccaac 960
ttggacgtgt tggaggaatt cggcatcaag tacatcttga acgtcacccc caatttgccg 1020
aatctctttg agaacgcagg agagtttaaa tacaagcaaa tccccatctc ggatcactgg 1080

-continued

```
agccaaaacc tgtcccagtt tttccctgag gccatttctt tcatagatga agcccggggc   1140
aagaactgtg gtgtcttggt acattgcttg gctggcatta gccgctcagt cactgtgact   1200
gtggcttacc ttatgcagaa gctcaatctg tcgatgaacg atgcctatga cattgtcaaa   1260
atgaaaaaat ccaacatatc ccctaacttc aacttcatgg gtcagctgct ggacttcgag   1320
aggacgctgg gactcagcag cccatgtgac aacagggttc cagcacagca gctgtatttt   1380
accacccctt ccaaccagaa tgtataccag gtggactctc tgcaatctac gtgaaagacc   1440
ccacatccct ccttgctgga atgtgtctgg cccttcagca gtttctcttg gcagcatcag   1500
ctgggctgct ttctttgtgt gtggccccag gtgtcaaaat gacaccagct gtctgtacta   1560
gacaaggtta ccaagtgcgg aattggttaa tactaacaga gagatttgct ccattctctt   1620
tggaataaca ggacatgctg tatagataca ggcagtaggt ttgctctgta cccatgtgta   1680
cagcctaccc atgcagggac tgggattcga ggacttccag gcgcataggg tagaaccaaa   1740
tgatagggta ggagcatgtg ttctttaggg ccttgtaagg ctgtttcctt ttgcatctgg   1800
aactgactat ataattgtct tcaatgaaga ctaattcaat tttgcatata gaggagccaa   1860
agagagattt cagctctgta tttgtggtat cagtttggaa aaaaaaatct gatactccat   1920
ttgattattg taaatatttg atcttgaatc acttgacagt gtttgtttga attgtgtttg   1980
ttttttcctt tgatgggctt aaaagaaatt atccaaaggg agaaagagca gtatgccact   2040
tcttaaaaca gaacaaaaca aaaaaagaaa attgtgctct tttctaatcc aaagggtata   2100
tttgcagcat gcttgacttt accaattctg atgacatctt tacggacact attatcacta   2160
agaccttgtt atggcgaagt ctttagtctt tttcatgtat tttcctcatg atttttttctc  2220
tttatgtagt ttgactatgc cttacctttg taaatatttt tgcttgtgtt gtcgcaaagg   2280
ggataatctg ggaaagacac caaatcatgg gctcacttta aaaaaagaaa gaataaaaaa   2340
accttcagct gtgctaaaca gtatattacc tctgtataaa attcttcagg gagtgtcacc   2400
tcaaatgcaa tactttgggt tggtttcttt cctttaaaaa aatttgtata aaactggaag   2460
tgtgtgtgtg tgagcatggg tacccatttg ataagagaaa tgcatttgat tgtgaagaag   2520
ggagagttaa attctccatt atgttcgtgg tgtaaagttt agagctggaa tttattataa   2580
gaatgtaaaa ccttaaatta ttaataaata actattttgg ctattgaaaa aaaaaaaaaa   2640
aaaaaaaaa                                                            2649
```

```
<210> SEQ ID NO 49
<211> LENGTH: 670
<212> TYPE: DNA
<213> ORGANISM: Homo sapiens

<400> SEQUENCE: 49

cggccacgag gcggaatccc ttctgctctc ccagcgcagc gccgccgccc ggcccctcca     60
gcttcccgga ccatggccaa cctggagcgc accttcatcg ccatcaagcc ggacggcgtg    120
cagcgcggcc tggtgggcga gatcatcaag cgcttcgagc agaagggatt ccgcctcgtg    180
gccatgaagt tcctccgggc ctctgaagaa cacctgaagc agcactacat tgacctgaaa    240
gaccgaccat tcttccctgg gctggtgaag tacatgaact cagggccggt tgtggccatg    300
gtctgggagg ggctgaacgt ggtgaagaca ggccgagtga tgcttgggga gaccaatcca    360
gcagattcaa agccaggcac cattcgtggg gacttctgca ttcaggttgg caggaacatc    420
attcatggca gtgattcagt aaaaagtgct gaaaaagaaa tcagcctatg gtttaagcct    480
gaagaactgg ttgactacaa gtcttgtgct catgactggg tctatgaata agaggtggac    540
```

```
acaacagcag tctccttcag cacggcgtgg tgtgtccctg gacacagctc ttcattccat    600

tgacttagag gcaacaggat tgatcattct tttatagagc atatttgcca ataaagcttt    660

tggaagccgg                                                           670


<210> SEQ ID NO 50
<211> LENGTH: 1675
<212> TYPE: DNA
<213> ORGANISM: Homo sapiens

<400> SEQUENCE: 50

ccagccgtcc attccggtgg aggcagaggc agtcctgggg ctctggggct cgggctttgt     60

caccgggacc cgcaggagcc agaaccactc ggcgccgcct ggtgcatggg aggggagccg    120

ggccaggagt aagtaactca tacgggcgcc ggggacccgg gtcgggctgg gggcttccaa    180

ctcagaggga gtgtgatttg cctgatcctc ttcggcgttg tcctgctctg ccgcatccag    240

ccctgtaccg ccatcccact tcccgccgtt cccatctgtg ttccgggtgg gatcggtctg    300

gaggcggccg aggacttccc aggcaggagc tcggggcgga ggccgggtcc gcggcagacc    360

agggcagcga ggcgctggcc ggcagggggc gctgcggtgc cagcctgagg ctgggctgct    420

ccgcgaggat acagcggccc ctgccctgtc ctgtcctgcc ctgccctgtc ctgtcctgcc    480

ctgccctgcc ctgtcctgtc ctgccctgcc ctgccctgtg tcctcagaca atatgttagc    540

cgtgcacttt gacaagccgg gaggaccgga aaacctctac gtgaaggagg tggccaagcc    600

gagcccgggg gagggtgaag tcctcctgaa ggtggcggcc agcgccctga accgggcgga    660

cttaatgcag agacaaggcc agtatgaccc acctccagga gccagcaaca ttttgggact    720

tgaggcatct ggacatgtgg cagagctggg gcctggctgc cagggacact ggaagatcgg    780

ggacacagcc atggctctgc tccccggtgg gggccaggct cagtacgtca ctgtccccga    840

agggctcctc atgcctatcc cagagggatt gaccctgacc caggctgcag ccatcccaga    900

ggcctggctc accgccttcc agctgttaca tcttgtggga aatgttcagg ctggagacta    960

tgtgctaatc catgcaggac tgagtggtgt gggcacagct gctatccaac tcacccggat   1020

ggctggagct attcctctgg tcacagctgg ctcccagaag aagcttcaaa tggcagaaaa   1080

gcttggagca gctgctggat tcaattacaa aaaagaggat ttctctgaag caacgctgaa   1140

attcaccaaa ggtgctggag ttaatcttat tctagactgc ataggcggat cctactggga   1200

gaagaacgtc aactgcctgg ctcttgatgg tcgatgggtt ctctatggtc tgatgggagg   1260

aggtgacatc aatgggcccc tgttttcaaa gctacttttt aagcgaggaa gtctgatcac   1320

cagtttgctg aggtctaggg acaataagta caagcaaatg ctggtgaatg ctttcacgga   1380

gcaaattctg cctcacttct ccacggaggg cccccaacgt ctgctgccgg ttctggacag   1440

aatctaccca gtgaccgaaa tccaggaggc ccataagtac atggaggcca acaagaacat   1500

aggcaagatc gtcctggaac tgccccagtg aaggaggatg ggcaggacag gacgcggcc    1560

accccaggcc tttccagagc aaacctggag aagattcaca atagacaggc caagaaaccc   1620

ggtgcttcct ccagagccgt ttaaagctga tatgaggaaa taaagagtga actgg        1675


<210> SEQ ID NO 51
<211> LENGTH: 4099
<212> TYPE: DNA
<213> ORGANISM: Homo sapiens

<400> SEQUENCE: 51

cagctgccag ccgaggaggc gcggcggaga ggggactgcg gtcagctgcg tccacttggg     60
```

-continued

```
gctgtgcggc ggtcccgcgc ccggcgatgt tcccgggcac tccctgagta gcggcagctt    120
atcccccgcc cgctagcccg ccctggtccc cggctcgctc gctggctggc gcggccccgg    180
ccccgctctg cgtcggcccc gccgcggtgg aggcgcgcga gggggacgcg gccggggatg    240
agcggattgc gggtgaactc gccgcccggg ggccccgcga agccgtgagc cgctgctttt    300
ctccgagtcg ccgccctgcc cttggatttg agatcatgtc catccacatc gtggcgctgg    360
ggaacgaggg ggacacattc caccaggaca accggccgtc ggggcttatc cgcacttacc    420
tggggagaag ccctctggtc tccggggacg agagcagctt gttgctgaac gcggccagca    480
cggtcgcgcg tccggtgttc accgagtatc aggccagtgc gtttgggaat gtcaagctgg    540
tggtccacga ctgtcccgtc tgggacatat ttgacagtga ttggtacact tctcgaaatc    600
taattggggg cgctgacatc attgtgatca aatacaacgt taatgacaag ttttcattcc    660
atgaagtaaa ggataattat attccagtga taaaaagagc attaaattca gttccagtaa    720
ttattgctgc tgttggtacc agacaaaatg aagagttacc ttgtacatgc ccactatgta    780
cctcagacag agggagctgt gttagtacaa ctgaagggat ccaacttgca aaagaactag    840
gagcaaccta tcttgaactc cacagccttg atgacttcta cataggaaag tattttggag    900
gagtgttgga gtattttatg attcaagcct taaatcagaa gacaagtgaa aaaatgaaga    960
aaagaaaaat gagcaactcc tttcatggaa ttagaccacc tcaacttgaa caaccagaaa   1020
aaatgcctgt cttaaaggct gaagcgtcac attataactc tgacttaaat aacttgctgt   1080
tctgctgcca gtgtgtggac gtggtatttt ataaccccga tttaaagaaa gttgtagagg   1140
cccacaagat cgttctctgc gctgtaagcc atgttttcat gctgcttttc aatgtgaaga   1200
gtcccactga cattcaggat tccagtatca tccgaactac ccaggatctt tttgctataa   1260
acagagatac tgcatttcca ggtgctagcc atgaatcttc aggcaaccca ccattacgag   1320
tcattgttaa agacgccctc ttctgttctt gtttatcaga catccttcgc ttcatttatt   1380
caggtgcttt tcagtgggaa gaattggaag aagatatcag gaagaagttg aaagattctg   1440
ggatgtttc aaatgtaatc gagaaagtta aatgcatttt aaaaacacca ggaaagatta   1500
attgcctaag gaattgcaaa acctatcaag ccagaaaacc tttgtggttt tataacactt   1560
ccctcaagtt tttccttaat aagccgatgc ttgccgatgt tgtcttcgaa attcaaggta   1620
cgacagtgcc agcccacagg gccatcctgg tggcccgttg tgaagtgatg gcagccatgt   1680
ttaatggtaa ttacatggaa gcaaagagtg tcctgattcc cgtttatggt gtttccaaag   1740
agactttctt gtcattttta gaatacctgt acacagactc ctgctgccca gctggcatat   1800
tccaggccat gtgtctcctg atctgtgccg agatgtacca agtgtccaga ctgcagcaca   1860
tctgtgagct gttcatcatt acccagctgc agagcatgcc aagcagggaa ctggcatcca   1920
tgaaccttga tatagttgac ctgcttaaaa aggccaagtt tcaccactct gattgccttt   1980
caacctggct acttcatttc attgctacta actacctcat cttcagtcaa aagcctgaat   2040
ttcaggatct ttcagtggaa gaacgcagtt ttgttgaaaa gcacagatgg ccgtcgaata   2100
tgtacttgaa gcagcttgcg gaatacagga agtatattca ctcccggaaa tgtcgttgct   2160
tagtaatgta acctggagct tttatacact acatttcttt tttattatta tgaagaatgg   2220
gatacctcca ggttccagta aaattcttct gaccgaaacc aatgtgggtg ttagaaaaat   2280
taccatatag cttaatatgt ttattagttc tctttggaaa aaaactacca ctgtggtctt   2340
aaaagggaac aaaatatacc ataggctaaa actaaggctt tcactctaga atgcaaagct   2400
gttttgcagc tgttttccct taaagatgtc ctgttgcttt agtgatattt agacccctct   2460
```

cagttaagaa atgcttagat taaaaaaaaa aaattacgta ggattaatac agaaatttaa 2520
tcatgtctga ttaattgctc tattaaaata aggggcattt aaagacccag cataaccatt 2580
tgtataatga gaaatctagg ggaaaaccaa tcagtccaac atgagatttt aggaatagaa 2640
atttgccggc catttggaaa gtgaaatgcc acttagttct caattgatga cagtgtttga 2700
atcatcataa aaaaaatacc tgcttttcat ctggacaacc caattgagcc actttatctc 2760
cttttggcaa tctgagtagg cggggaacct aggcagggct ggctttctta gcgtgtaact 2820
tgtgtagcag cacagggccc acacttagaa ggaccccaca cttggttcaa ggctctgcta 2880
tagcggaaat tcttaataat gtttgaagaa gggccccatg atttcatttt gtgctgagcc 2940
ctcaaaatta tgtctgtttc gtggtgggaa atatcctatg ttttcttgct caaacacctt 3000
tctctctgaa agcagaaaaa ggcactgata taaagggaag agaaggaggc tcaccggagg 3060
gaagagaaca tagtgaagat tcccgccttt ggggaggtct ggaccaccca gggcctccac 3120
tgccaccttg gctggcaagg gagaaatgtg ttgtgttgtc ttagctttaa aacagtcaca 3180
gttcttgctc tatcatagat gaacaaatac tttcttgatc attctgtaag accaggaggt 3240
tggtaagagt gactaaccag cctaacttta atacacatgt ataaagatgt tcacagagaa 3300
agatgctctg tagagaattt gctaccgaag ttggctcaag aatttgtttt tagtgttatt 3360
taccaagatt aggacgtcag tggcttaaat tctttgaatt cttttcaagg actgcaagat 3420
tatttgataa agagtagcat gaatcttgtg ctctaatatt acacagtaag ttcaaagaaa 3480
ggatgtaagt caaagacttg ttacatagag ggaaaatgga ctgggataga ggacagactg 3540
atagtttctt tctttcatat cacatgtata gagaaataat tatatcagaa actcacaaac 3600
ctagacatgg aaaaacagat tactgtctat tgtcagcatc attttcatct gtaagtcact 3660
actggaatat atttttcttt taatttccag tgactttaga atacacacag tttttccgac 3720
ttttcaaaaa tttgattaaa tggttttata gtataatatt gggaccccat accgttagcc 3780
cttgtatgta taccaacact gccaaagtaa aacattaggt caggcatggt ggctcaggcc 3840
tgtaatccca gcattttggg aggctgaggc aagtggataa cttgaggtca tgagttcgaa 3900
accagcctgg ccaaaacagt gaaaccccgt ctctactaaa aatacaaaat tagccagatg 3960
tggtggcgca cacctgtaat cccagctact caggaagctg aggcaggaaa atcgcttgaa 4020
cctgggaggt ggaagttgca gtgagccgag atcgcaccac tgcactccag cctgggtgac 4080
aagagcgaaa ctccatctc 4099

<210> SEQ ID NO 52
<211> LENGTH: 2508
<212> TYPE: DNA
<213> ORGANISM: Homo sapiens

<400> SEQUENCE: 52
cgcgcccctc cctcctcgcg gacctggcgg tgccggcgcc cggagtggcc ctttaaaagg 60
cagcttattg tccggagggg gcgggcgggg ggcgccgacc gcggcctgag gcccggcccc 120
tcccctctcc ctccctctgt ccccgcgtcg ctcgctggct agctcgctgg ctcgctcgcc 180
cgtccggcgc acgctccgcc tccgtcagtt ggctccgctg tcgggtgcgc ggcgtggagc 240
ggcagccggt ctggacgcgc ggccggggct gggggctggg agcgcggcgc gcaagatctc 300
cccgcgcgag agcggcccct gccaccgggc gaggcctgcg ccgcgatggc agagatgggc 360
agtaaagggg tgacggcggg aaagatcgcc agcaacgtgc agaagaagct cacccgcgcg 420
caggagaagg ttctccagaa gctggggaag gcagatgaga ccaaggatga gcagtttgag 480

```
cagtgcgtcc agaatttcaa caagcagctg acggagggca cccggctgca gaaggatctc    540
cggacctacc tggcctccgt caaagccatg cacgaggctt ccaagaagct gaatgagtgt    600
ctgcaggagg tgtatgagcc cgattggccc ggcagggatg aggcaaacaa gatcgcagag    660
aacaacgacc tgctgtggat ggattaccac cagaagctgg tggaccaggc gctgctgacc    720
atggacacgt acctgggcca gttccccgac atcaagtcac gcattgccaa gcgggggcgc    780
aagctggtgg actacgacag tgcccggcac cactacgagt cccttcaaac tgccaaaaag    840
aaggatgaag ccaaaattgc caagcctgtc tcgctgcttg agaaagccgc cccccagtgg    900
tgccaaggca aactgcaggc tcatctcgta gctcaaacta acctgctccg aaatcaggcc    960
gaggaggagc tcatcaaagc ccagaaggtg tttgaggaga tgaatgtgga tctgcaggag   1020
gagctgccgt ccctgtggaa cagccgcgta ggtttctacg tcaacacgtt ccagagcatc   1080
gcgggcctgg aggaaaactt ccacaaggag atgagcaagc tcaaccagaa cctcaatgat   1140
gtgctggtcg gcctggagaa gcaacacggg agcaacacct tcacggtcaa ggcccagccc   1200
agtgacaacg cgcctgcaaa agggaacaag agcccttcgc ctccagatgg ctcccctgcc   1260
gccacccccg agatcagagt caaccacgag ccagagccgg ccggcggggc cacgcccggg   1320
gccaccctcc ccaagtcccc atctcagttt gaggccccgg ggcctttctc ggagcaggcc   1380
agtctgctgg acctggactt tgaccccctc ccgcccgtga cgagccctgt gaaggcaccc   1440
acgccctctg gtcagtcaat tccatgggac ctctgggagc ccacagagag tccagccggc   1500
agcctgcctt ccggggagcc cagcgctgcc gagggcacct ttgctgtgtc ctggcccagc   1560
cagacggccg agccggggcc tgcccaacca gcagaggcct cggaggtggc gggtgggacc   1620
caacctgcgg ctggagccca ggagccaggg gagacggcgg caagtgaagc agcctccagc   1680
tctcttcctg ctgtcgtggt ggagaccttc ccagcaactg tgaatggcac cgtggagggc   1740
ggcagtgggg ccgggcgctt ggacctgccc ccaggtttca tgttcaaggt acaggcccag   1800
cacgactaca cggccactga cacagacgag ctgcagctca aggctggtga tgtggtgctg   1860
gtgatcccct tccagaaccc tgaagagcag gatgaaggct ggctcatggg cgtgaaggag   1920
agcgactgga accagcacaa ggagctggag aagtgccgtg gcgtcttccc cgagaacttc   1980
actgagaggg tcccatgacg gcggggccca ggcagcctcc gggcgtgtga agaacacctc   2040
ctcccgaaaa atgtgtggtt cttttttttg ttttgttttc gtttttcatc ttttgaagag   2100
caaagggaaa tcaagaggag acccccaggc agaggggcgt tctcccaaag attaggtcgt   2160
tttccaaaga gccgcgtccc ggcaagtccg gcggaattca ccagtgttcc tgaagctgct   2220
gtgtcctcta gttgagtttc tggcgcccct gcctgtgccc gcatgtgtgc ctggccgcag   2280
ggcggggctg gggctgccg agccaccatg cttgcctgaa gcttcggccg cgccacccgg   2340
gcaagggtcc tcttttcctg gcagctgctg tgggtggggc ccagacacca gcctagcctg   2400
gctctgcccc gcagacggtc tgtgtgctgt ttgaaaataa atcttagtgt tcaaaacaaa   2460
atgaaacaaa aaaaaaatga taaaaactct caaaaaaaaa aaaaaaaa                2508
```

<210> SEQ ID NO 53
<211> LENGTH: 2278
<212> TYPE: DNA
<213> ORGANISM: Homo sapiens

<400> SEQUENCE: 53

```
ggggagtgct ccattttccc cgacagcgaa tttcccctga gaaacgatac tagaccctgg     60
gtttgcccac cttgtaactc ttccttatct cctccttttc atccctaatt catcctccct    120
```

```
ctggcatgga attgacgccc gtgcagtaca tttgccaagt ggcaccttct ttcaatttat    180
gttttatttt gctatggtgg tgattcttta tttgctggtt gtcttttctc acacatcttt    240
ctctctgtct ctctctttcc tgctctttgt ttttctgccc agaaaaacct gacttcgata    300
ccaaaaaaga tgaaactaca gaaactcaaa tttaaaaaaa actttaaaag aaacaaaaaa    360
atactcaacg attctttcag ctttattaac attttccatt gtttcttgcg acttgtgtct    420
cgttctttgt agtattgatg atgaacattt gataatgaat gttcttgtat attcagataa    480
agaaaaaaaa aaccaaaaaa gcggtctgaa tttaatagtg tttataataa aaattttaaa    540
aatgaccctc atagcacgca aaacaggatg gggaatttcc cctcttcttt ctgtgacaat    600
gcgcatcatt cctgcattag tttttaacac cagactacct acattcatca tttccctcat    660
ttttctttta ttttcttgca tttgtgaatt agttcaagaa tgctagaaaa gtgtcgagtt    720
gtgcacatcc atttcttgtt tcacaatgtt taaaagtgac agtaattcat tttgtaaact    780
aaaaaaaaaa aaaaaaaggt tggaatagtg agcataatag gtacaaccta acacattatt    840
atgtttatta actttgagac ccagaaataa attcttttct tttcttgatt cttgctctta    900
aaaatacaaa aaaaaaaatg ttttgttttg tgttattttt ggtttgttta ttggggggct    960
ttttttaatt gtcaggatta tgatcttgct gtttttcttc aatatgtata caaggtgatg   1020
tgaaaagatg acttgggcag aggagtaaga acaagtaggc ttgttcttct actttgcttc   1080
agaattcagt taatgccaaa agcgaagatc aagcccatgt tgatgtctcg ttgctcacct   1140
gcatttccag agagtgtgac actcatgcag tccctgagaa aaataaaatc agggacatac   1200
ttctcctttt agcctttttaa aaattcaaaa acgtttagtc caagggaact ttttatgcta   1260
tcaggaaagg tttttgctgt ttttgattct gattatcaca gccaagtact ttgttttatt   1320
tctccctaat taataactac attccatgag gcctcttcca accaaagagg cctttttcttc   1380
caggagagtc ccgcaggaga tgctggtatg atgggcacca ttggttaagt aaactacatg   1440
caggaagaag tccttggggc cagtctgcca gctgagtcct ggttttggat gaagagttaa   1500
tgagatattg ggccaggctc aatgctgtag ttttaatgct aagaggttac gtttacttca   1560
cagagtacac ctcttagtaa cctctgactt aggcagctgc ttaaagcaaa ttgcaaaact   1620
ggcttgattt ggaatgtttt tattagagga aaaaagaaag ccatattatc tggaaaaaaa   1680
ttcattttaa ataccatcat tcaacaaatt atgttcagaa agtggtcaga acttaagcaa   1740
gaaaagtaaa gaaagaatgc agaattgtgg agcaatgctt taggaaatat ttctacctga   1800
acacttgtac tcttgaagtc acaacaaaat aatgatgagc ttttcacatc acctttatgg   1860
tttcaatccc tagctcaaag cttcctggaa tcttttattt tttgtaaact ttttttttctt   1920
ttgttaaaat aaataaaaca ttcaatgttt ttctcctttt ctctcttatt acttctttcc   1980
tttggcattt tcaatttgaa atgctttcct ttggttgttg gttttattct ccccctaccc   2040
ctccccttttt cttattattc agaatataaa cctgcaaagc tctgctctgt tttggttttg   2100
aaagtttaag cttttctgct tctgtgagag cacaggcttc tgtccctttt gattccaact   2160
gaacttttgt gttctctaat gatactaaca cggtgtaggt tttacagtct cctaatttgt   2220
actggtaatg catattccaa ataaatagtt tcttttgttg caaaaaaaaa aaaaaaaa     2278
```

<210> SEQ ID NO 54
<211> LENGTH: 4322
<212> TYPE: DNA
<213> ORGANISM: Homo sapiens

<400> SEQUENCE: 54

-continued

```
cccccagagg cgccggagcc cggaatcccg ctcggagcca gccagccgtc ccgagctacc     60
agcaggtttc attgaaaaca gatcctgcaa aagttccagg tgcccacact ggaaacttgg    120
agatcctgct tcccagacca cagctgtggg gaacttgggg tggagcagag aagtttctgt    180
attcagctgc ccaggcagag gagaatgggg tctccacagc ctgaagaatg aagacacgac    240
agaataaaga ctcgatgtca atgaggagtg gacggaagaa agaggcccct gggccccggg    300
aagaactgag atcgaggggc cgggcctccc ctggaggggt cagcacgtcc agcagtgatg    360
gcaaagctga gaagtccagg cagacagcca agaaggcccg agtagaggaa gcctccaccc    420
caaaggtcaa caagcagggt cggagtgagg agatctcaga gagtgaaagt gaggagacca    480
atgcaccaaa aaagaccaaa actgaggaac tccctcggcc acagtctccc tccgatctgg    540
atagcttgga cgggcggagc cttaatgatg atggcagcag cgaccctagg gatatcgacc    600
aggacaaccg aagcacgtcc cccagtatct acagccctgg aagtgtggag aatgactctg    660
actcatcttc tggcctgtcc cagggcccag cccgccccta ccacccacct ccactctttc    720
ctccttcccc tcaaccgcca gacagcaccc ctcgacagcc agaggctagc tttgaacccc    780
atccttctgt gacacccact ggatatcatg ctcccatgga gccccccaca tctcgaatgt    840
tccaggctcc tcctggggcc cctccccctc acccacagct ctatcccggg ggcactggtg    900
gagttttgtc tggaccccca atgggtccca agggggggagg ggctgcctca tcagtggggg    960
gccctaatgg gggtaagcag caccccccac ccactactcc catttcagta tcaagctctg   1020
gggctagtgg tgctccccca acaaagccgc ctaccactcc agtgggtggt gggaacctac   1080
cttctgctcc accaccagcc aacttccccc atgtgacacc gaacctgcct cccccacctg   1140
ccctgagacc cctcaacaat gcatcagcct ctcccccctgg cctgggggcc caaccactac   1200
ctggtcatct gccctctccc cacgccatgg gacagggtat cggtggactt cctcctggcc   1260
cagagaaggg cccaactctg gctccttcac cccactctct gcctcctgct tcctcttctg   1320
ctccagcgcc ccccatgagg tttccttatt catcctctag tagtagctct gcagcagcct   1380
cctcttccag ttcttcctcc tcttcctctg cctccccctt cccagcttcc caggcattgc   1440
ccagctaccc ccactctttc cctcccccaa caagcctctc tgtctccaat cagcccccca   1500
agtatactca gccttctctc ccatcccagg ctgtgtggag ccagggtccc ccaccacctc   1560
ctccctatgg ccgcctctta gccaacagca atgcccatcc aggccccttc cctccctcta   1620
ctggggccca gtccaccgcc cacccaccag tctcaacaca tcaccatcac caccagcaac   1680
agcaacagca gcagcagcag cagcagcagc agcagcatca cggaaactct gggccccctc   1740
ctcctggagc atttccccac ccactggagg gcggtagctc ccaccacgca caccccttacg   1800
ccatgtctcc ctccctgggg tctctgaggc cctacccacc agggccagca cacctgcccc   1860
cacctcacag ccaggtgtcc tacagccaag caggccccaa tggccctcca gtctcttcct   1920
cttccaactc ttcctcttcc acttctcaag ggtcctaccc atgttcacac ccctcccctt   1980
cccagggccc tcaaggggcg ccctaccctt tcccaccggt gcctacggtc accacctctt   2040
cggctaccct ttccacggtc attgccaccg tggcttcctc gccagcagc tacaaaaacgg   2100
cctccccacc tgggccccca ccgtacggaa agagagcccc gtccccgggg gcctacaaga   2160
cagccacccc acccggatac aaacccgggt cgcctccctc cttccgaacg gggaccccac   2220
cgggctatcg aggaacctcg ccacctgcag gcccagggac cttcaagccg ggctcgccca   2280
ccgtgggacc tgggcccctg ccacctgcgg ggccctcagg cctgccatcg ctgccaccac   2340
cacctgcggc ccctgcctca gggccgcccc tgagcgccac gcagatcaaa caggagccgg   2400
```

ctgaggagta tgagaccccc gagagcccgg tgcccccagc ccgcagcccc tcgccccctc 2460
ccaaggtggt agatgtaccc agccatgcca gtcagtctgc caggttcaac aaacacctgg 2520
atcgcggctt caactcgtgc gcgcgcagcg acctgtactt cgtgccactg gagggctcca 2580
agctggccaa gaagcgggcc gacctggtgg agaaggtgcg gcgcgaggcc gagcagcgcg 2640
cgcgcgaaga aaaggagcgc gagcgcgagc gggaacgcga gaaagagcgc gagcgcgaga 2700
aggagcgcga gcttgaacgc agcgtgaagt tggctcagga gggccgtgct ccggtggaat 2760
gcccatctct gggcccagtg ccccatcgcc ctccatttga accgggcagt gcggtggcta 2820
cagtgccccc ctacctgggt cctgacactc cagccttgcg cactctcagt gaatatgccc 2880
ggcctcatgt catgtctcct ggcaatcgca accatccatt ctacgtgccc ctgggggcag 2940
tggacccggg gctcctgggt tacaatgtcc cggccctgta cagcagtgat ccagctgccc 3000
gggagaggga acgggaagcc cgtgaacgag acctccgtga ccgcctcaag cctggctttg 3060
aggtgaagcc tagtgagctg gaacccctac atggggtccc tgggccgggc ttggatccct 3120
ttccccgaca tgggggcctg gctctgcagc ctggcccacc tggcctgcac cctttcccct 3180
ttcatccgag cctggggccc ctggagcgag aacgtctagc gctggcagct gggccagccc 3240
tgcggcctga catgtcctat gctgagcggc tggcagctga gaggcagcac gcagaaaggg 3300
tggcggccct gggcaatgac ccactggccc ggctgcagat gctcaatgtg actccccatc 3360
accaccagca ctcccacatc cactcgcacc tgcacctgca ccagcaagat gctatccatg 3420
cagcctctgc ctcggtgcac cctctcattg accccctggc ctcagggtct caccttaccc 3480
ggatccccta cccagctgga actctcccta acccctgct tcctcaccct ctgcacgaga 3540
acgaagttct tcgtcaccag ctctttgctg ccccttaccg ggacctgccg gcctcccttt 3600
ctgccccgat gtcagcagct catcagctgc aggccatgca cgcacagtca gctgagctgc 3660
agcgcttggc gctggaacag cagcagtggc tgcatgccca tcacccgctg cacagtgtgc 3720
cgctgcctgc ccaggaggac tactacagtc acctgaagaa ggaaagcgac aagccactgt 3780
agaacctgcg atcaagagag caccatggct cctacattgg accttggagc acccccaccc 3840
tccccccacc gtgcccttgg cctgccaccc agagccaaga gggtgctgct cagttgcagg 3900
gcctccgcag ctggacagag agtgggggag ggagggacag acagaaggcc aaggcccgat 3960
gtggtgtgca gaggtgggga ggtggcgagg atggggacag aaagcgcaca gaatcttgga 4020
ccaggtctct cttccttgtc ccccctgctt ttctcctccc ccatgcccaa cccctgtggc 4080
cgccgcccct cccctgcccc gttggtgtga ttatttcatc tgttagatgt ggctgttttg 4140
cgtagcatcg tgtgccaccc ctgcccctcc ccgatccctg tgtgcgcgcc ccctctgcaa 4200
tgtatgcccc ttgccccttc cccacactaa taatttatat atataaatat ctatatgacg 4260
ctcttaaaaa aacatcccaa ccaaaaccaa ccaaacaaaa acatcctcac aactccccag 4320
ga 4322

<210> SEQ ID NO 55
<211> LENGTH: 808
<212> TYPE: DNA
<213> ORGANISM: Homo sapiens

<400> SEQUENCE: 55
tgctcccttg ggctctagag aggaggcccc tcttagccct cagcccctcc ttcctctcta 60
tcttaaagta atttgatcct caggaatttg ttccgccctc atctggcccg gccaaatccc 120
gatttgacaa atgccaggaa aaggaaactg ttgagaaacc gaaactactg gggaaaggga 180
gggctcactg agtaaccatc ccagtaaccc gaccgccgct ggtcttcgct ggacaccatg 240
agtcacactg tccaaacctt cttctctcct gtcaacagtg gccagccccc caactatgag 300
atgctcaagg aggagcacga ggtggctgtg ctgggggggc cccacaaccc tgctcccccg 360
acgtccaccg tgatccacat ccgcagcgag acctccgtgc ccgaccatgt cgtctggtcc 420
ctgttcaaca ccctcttcat gaacccctgc tgcctgggct tcatagcatt cgcctactcc 480
gtgaagtcta gggacaggaa gatggttggc gacgtgaccg gggcccaggc ctatgcctcc 540
accgccaagt gcctgaacat ctgggccctg attctgggca tcctcatgac cattctgctc 600
atcgtcatcc cagtgctgat cttccaggcc tatggataga tcaggaggca tcactgaggc 660
caggagctct gcccatgacc tgtatcccac gtactccaac ttccattcct cgccctgccc 720
ccggagccga gtcctgtatc agccctttat cctcacacgc ttttctacaa tggcattcaa 780
taaagtgcac gtgtttctgg tgctgctg 808

<210> SEQ ID NO 56
<211> LENGTH: 3454
<212> TYPE: DNA
<213> ORGANISM: Homo sapiens

<400> SEQUENCE: 56
ggaaatgact gctgtccatg caggcaacat aaacttcaag tgggatccta aaagtctaga 60
gatcaggact ctggcagttg agagactgtt ggagcctctt gttacacagg ttacaaccct 120
tgtaaacacc aatagtaaag ggccctctaa taagaagaga ggtcgttcta agaaggccca 180
tgttttggct gcatctgttg aacaagcaac tgagaatttc ttggagaagg gggataaaat 240
tgcaaaagag agccagtttc tcaaggagga gcttgtggtt gctgtagaag atgttcgaaa 300
acaaggtgat ttgatgaagg ctgctgctgg agagttcgca gatgatccct gctcttctgt 360
gaagcgaggc aacatggttc gggcagctcg agctttgctc tctgctgtta cccggttgct 420
cattttggct gacatggcag atgtctacaa attacttgtt cagctgaaag ttgtggaaga 480
tggtatattg aaactgagga atgctggcaa tgaacaagac ttagggaatc agtataaagc 540
cctaaaacct gaagtggata agctgaacat tatggcagca aaaagacaac aggaattgaa 600
agatgttggg catcgtgatc agatggctgc ggctagagga atcctgcaga gcaacgttcc 660
gatcctctat actgcatccc aggcatgcct acagcacccct gatgtcgcag cctataaggc 720
caacagggac ctgatataca agcagctgca gcaggcggtc acagggattt ccaatgcagc 780
ccaggccact gcctcagacg atgcctcaca gcaccagggt ggaggaggag gagaactggc 840
atatgcactc aataactttg acaaacaaat cattgtggac cccttgagct tcagcgagga 900
gcgctttagg ccttccctgg aggagcgtct ggaaagcatc attagtgggg ctgccttgat 960
ggccgactcg tcctgcacgc gtgatgaccg tcgtgagcga attgtggcag agtgtaatgc 1020
tgtccgccag gcctgcagga cctgcgtttc ggagtacatg ggcaatgctg gacgtaaaga 1080
aagaagtgat gcactcaatt ctgcaataga taaaatgacc aagaagacca gggacttgcg 1140
tagacagctt cgcaaagctg tcatggacca cgtttcagat tctttcctgg aaaccaatgt 1200
tccacttttg gtattgattg aagctgcaaa gaatggaaat gagaaagaag ttaaggaata 1260
tgcccaagtt ttccgtgaac atgccaacaa attgattgag gttgccaact tggcctgttc 1320
catctcaaat aatgaagaag gtgtaaagct tgttcgaatg tctgcaagcc agttagaagc 1380
cggttgtcct caggttatta atgctgcaac ctgggcttta gcaccaaaac cacagagtaa 1440
actggcccaa gagaacatgg atctttttaa agaacaatgg gaaaaacaag tccgtgttct 1500

```
cacagatgct gtcgatgaca ttacttccat tgatgacttc ttggctgtct cagagaatca   1560
cattttggaa gatgtgaaca aatgtgtcat tgctctccaa gagaaggatg tggatggcct   1620
ggaccgcaca gctggtgcaa ttcgaggccg ggcagcccgg gtcattcacg tagtcacctc   1680
agagatggac aactatgagc caggagtcta cacagagaag gttctggaag ccactaagct   1740
gctctccaac acagtcatgc cacgttttac tgagcaagta gaagcagccg tggaagccct   1800
cagctcggac cctgcccagc ccatggatga gaatgagttt atcgatgctt cccgcctggt   1860
atatgatggc atccgggaca tcaggaaagc agtgctgatg ataaggaccc ctgaggagtt   1920
ggatgactct gactttgaga cagaggattt tgatgtcaga agcgagacga gcgtccagac   1980
agaagacgat cagctgatag ctggccagag tgcccgggcg atcatggctc agcttcccca   2040
ggagcaaaaa gcgaagattc gggaacaggt ggccagcttc caggaagaaa agagcaagct   2100
ggatgctgaa gtgtccaaat gggacgacag tggcaatgac atcattgtgc tggccaagca   2160
gatgtgcatg attatgatgg agatgacaga ctttacccga ggtaaaggac cactcaaaaa   2220
tacatcggat gtcatcagtg ctgccaagaa aattgctgag gcaggatcca ggatggacaa   2280
gcttggccgg accattcgag accattgccc cgactcggct tgcaagcagg acctgctggc   2340
ctacctgcaa cgcatcgccc tctactgcca ccagctgaac atctgcagca aggtcaaggc   2400
cgaggtgcag aatctcggcg gggagcttgt tgtctctggg gtggacagcg ccatgtccct   2460
gatccaggca gccaagaact tgatgaatgc tgtggtgcag acagtgaagg catcctacgt   2520
cgcctctacc aaataccaaa agtcacaggg tatggcttcc ctcaaccttc ctgctgtgtc   2580
aatgaagatg aaggcaccag agaaaaagcc attggtgaag agagagaaac aggatgagac   2640
acagaccaag attaaacggg catctcagaa gaagcacgtg aacccagtgc aggccctcag   2700
cgagttcaaa gctatggaca gcatctaagt ctgcccaggc cggccgcccc cacccctctg   2760
gctcctgaat atcagtcact gttcgtcact caaatgaatt tgctaaatac aacactgata   2820
ctagattcca cagggaaatg ggcagactga accagtccag gtggtgaatt ttccaagaac   2880
atagtttaag ttgattaaaa atgcttttag aatgcaggag cctacttcta gctgtatttt   2940
ttgtatgctt aaataaaata aaattcataa ccaagagatc cacattagct tgttagtaat   3000
gctctgacca agccgagatg ccattctctt agtgatggcg gcgttaggtt tgagagaagg   3060
aattggctca acttcagttg agagggtgca gtccagacag cttgactgct tttaaatgac   3120
caaagatgac ctgtggtaag caacctggca tcttaggaag cagtccttga gaaggcatgt   3180
tccagaaagg tctctgagga caaactcact cagtaaaaca taatgtatca tgaagaaaac   3240
tgattctcta tgacatgaaa tgaaaatttt aatgcattgt tataattact aatgtacgct   3300
gctgcaggac attaataaag ttgctttttt aggctacagt gtctcgatgc cataatcaga   3360
acacactttt tttcctcttt ctcccagctt caaatgcaca attcatcatt gggctcactt   3420
ctaataactg cagtgtttcc gccttgcgtt gcag                                3454
```

```
<210> SEQ ID NO 57
<211> LENGTH: 5128
<212> TYPE: DNA
<213> ORGANISM: Homo sapiens

<400> SEQUENCE: 57

ccgagtgcct cgcagcccct cccgaggcgc agccgccaga ccagtggagc cggggcgcag     60
ggcgggggcg gaggcgccgg ggcgggggat gcggggccgc ggcgcagccc cccggccctg    120
agagcgagga cagcgccgcc cggcccgcag ccgtcgccgc ttctccacct cggcccgtgg    180
```

```
agccggggcg tccgggcgta gccctcgctc gcctgggtca gggggtgcgc gtcgggggag    240
gcagaagcca tggatcccgg gcagcagccg ccgcctcaac cggcccccca gggccaaggg    300
cagccgcctt cgcagccccc gcaggggcag ggcccgccgt ccggacccgg gcaaccggca    360
cccgcggcga cccaggcggc gccgcaggca ccccccgccg ggcatcagat cgtgcacgtc    420
cgcggggact cggagaccga cctggaggcg ctcttcaacg ccgtcatgaa ccccaagacg    480
gccaacgtgc cccagaccgt gcccatgagg ctccggaagc tgcccgactc cttcttcaag    540
ccgccggagc ccaaatccca ctcccgacag gccagtactg atgcaggcac tgcaggagcc    600
ctgactccac agcatgttcg agctcattcc tctccagctt ctctgcagtt gggagctgtt    660
tctcctggga cactgacccc cactggagta gtctctggcc cagcagctac acccacagct    720
cagcatcttc gacagtcttc ttttgagata cctgatgatg tacctctgcc agcaggttgg    780
gagatggcaa agacatcttc tggtcagaga tacttcttaa atcacatcga tcagacaaca    840
acatggcagg accccaggaa ggccatgctg tcccagatga acgtcacagc ccccaccagt    900
ccaccagtgc agcagaatat gatgaactcg gcttcagcca tgaaccagag aatcagtcag    960
agtgctccag tgaaacagcc accacccctg gctccccaga gcccacaggg aggcgtcatg   1020
ggtggcagca actccaacca gcagcaacag atgcgactgc agcaactgca gatggagaag   1080
gagaggctgc ggctgaaaca gcaagaactg cttcggcagg tgaggccaca ggagttagcc   1140
ctgcgtagcc agttaccaac actggagcag gatggtggga ctcaaaatcc agtgtcttct   1200
cccgggatgt ctcaggaatt gagaacaatg acgaccaata gctcagatcc tttccttaac   1260
agtggcacct atcactctcg agatgagagt acagacagtg gactaagcat gagcagctac   1320
agtgtccctc gaaccccaga tgacttcctg aacagtgtgg atgagatgga tacaggtgat   1380
actatcaacc aaagcaccct gccctcacag cagaaccgtt tcccagacta ccttgaagcc   1440
attcctggga caaatgtgga ccttggaaca ctggaaggag atggaatgaa catagaagga   1500
gaggagctga tgccaagtct gcaggaagct ttgagttctg acatccttaa tgacatggag   1560
tctgttttgg ctgccaccaa gctagataaa gaaagctttc ttacatggtt atagagccct   1620
caggcagact gaattctaaa tctgtgaagg atctaaggag acacatgcac cggaaatttc   1680
cataagccag ttgcagtttt caggctaata cagaaaaaga tgaacaaacg tccagcaaga   1740
tactttaatc ctctattttg ctcttccttg tccattgctg ctgttaatgt attgctgacc   1800
tctttcacag ttggctctaa agaatcaaaa gaaaaaaact ttttatttct tttgctatta   1860
aaactactgt tcattttggg ggctggggga agtgagcctg tttggatgat ggatgccatt   1920
ccttttgccc agttaaatgt tcaccaatca ttttaactaa atactcagac ttagaagtca   1980
gatgcttcat gtcacagcat ttagtttgtt caacagttgt ttcttcagct tcctttgtcc   2040
agtggaaaaa catgatttac tggtctgaca agccaaaaat gttatatctg atattaaata   2100
cttaatgctg atttgaagag atagctgaaa ccaaggctga agactgtttt actttcagta   2160
ttttcttttc ctcctagtgc tatcattagt cacataatga ccttgatttt attttaggag   2220
cttataaggc atgagacaat ttccatataa atatattaat tattgccaca tactctaata   2280
tagattttgg tggataattt tgtgggtgtg cattttgttc tgttttgttg ggtttttttgt   2340
ttttttgtt tttggcaggg tcggtggggg ggttggttgg ttggttggtt ttgtcggaac   2400
ctaggcaaat gaccatatta gtgaatctgt taatagttgt agcttgggat ggttattgta   2460
gttgttttgg taaaatcttc atttcctggt tttttttacc accttattta aatctcgatt   2520
atctgctctc tcttttatat acatacacac acccaaacat aacatttata atagtgtggt   2580
```

-continued

```
agtggaatgt atccttttt aggtttccct gctttccagt taatttttaa aatggtagcg   2640
ctttgtatgc atttagaata catgactagt agtttatatt tcactggtag tttaaatctg   2700
gttggggcag tctgcagatg tttgaagtag tttagtgttc tagaaagagc tattactgtg   2760
gatagtgcct aggggagtgc tccacgccct ctgggcatac ggtagatatt atctgatgaa   2820
ttggaaagga gcaaaccaga aatggcttta ttttctccct tggactaatt tttaagtctc   2880
gattggaatt cagtgagtag gttcataatg tgcatgacag aaataagctt tatagtggtt   2940
taccttcatt tagctttgga agttttcttt gccttagttt tggaagtaaa ttctagtttg   3000
tagttctcat ttgtaatgaa cacattaacg actagattaa aatattgcct tcaagattgt   3060
tcttacttac aagacttgct cctacttcta tgctgaaaat tgaccctgga tagaatacta   3120
taaggttttg agttagctgg aaaagtgatc agattaataa atgtatattg gtagttgaat   3180
ttagcaaaga aatagagata atcatgatta tacctttatt tttacaggaa gagatgatgt   3240
aactagagta tgtgtctaca ggagtaataa tggtttccaa agagtatttt ttaaaggaac   3300
aaaacgagca tgaattaact cttcaatata agctatgaag taatagttgg ttgtgaatta   3360
aagtggcacc agctagcacc tctgtgtttt aagggtcttt caatgtttct agaataagcc   3420
cttattttca agggttcata acaggcataa aatctcttct cctggcaaaa gctgctatga   3480
aaagcctcag cttgggaaga tagatttttt tccccccaat tacaaaatct aagtattttg   3540
gcccttcaat ttggaggagg gcaaaagttg gaagtaagaa gttttatttt aagtactttc   3600
agtgctcaaa aaaatgcaat cactgtgttg tatataatag ttcataggtt gatcactcat   3660
aataattgac tctaaggctt ttattaagaa aacagcagaa agattaaatc ttgaattaag   3720
tctgggggga aatggccact gcagatggag ttttagagta gtaatgaaat tctacctaga   3780
atgcaaaatt gggtatatga attacatagc atgttgttgg gattttttt aatgtgcaga   3840
agatcaaagc tacttggaag gagtgcctat aatttgccag tagccacaga ttaagattat   3900
atcttatata tcagcagatt agctttagct tagggggagg gtgggaaagt ttgggggggg   3960
ggttgtgaag atttaggggg accttgatag agaactttat aaacttcttt ctctttaata   4020
aagacttgtc ttacaccgtg ctgccattaa aggcagctgt tctagagttt cagtcaccta   4080
agtacaccca caaaacaata tgaatatgga gatcttcctt taccccctcaa ctttaatttg   4140
cccagttata cctcagtgtt gtagcagtac tgtgatacct ggcacagtgc tttgatctta   4200
cgatgccctc tgtactgacc tgaaggagac ctaagagtcc tttccctttt tgagtttgaa   4260
tcatagcctt gatgtggtct cttgttttat gtccttgttc ctaatgtaaa agtgcttaac   4320
tgcttcttgg ttgtattggg tagcattggg ataagatttt aactgggtat tcttgaattg   4380
cttttacaat aaaccaattt tataatcttt aaatttatca actttttaca tttgtgttat   4440
tttcagtcag ggcttcttag atctacttat ggttgatgga gcacattgat ttggagtttc   4500
agatcttcca aagcactatt tgttgtaata actttctaa atgtagtgcc tttaaaggaa   4560
aaatgaacac agggaagtga ctttgctaca aataatgttg ctgtgttaag tattcatatt   4620
aaatacatgc cttctatatg gaacatggca gaaagactga aaaataacag taattaattg   4680
tgtaattcag aattcatacc aatcagtgtt gaaactcaaa cattgcaaaa gtgggtggca   4740
atattcagtg cttaacactt ttctagcgtt ggtacatctg agaaatgagt gctcaggtgg   4800
attttatcct cgcaagcatg ttgttataag aattgtgggt gtgcctatca taacaattgt   4860
tttctgtatc ttgaaaaagt attctccaca ttttaaatgt tttatattag agaattcttt   4920
aatgcacact tgtcaaatat atatatatag taccaatgtt accttttat tttttgtttt   4980
```

agatgtaaga gcatgctcat atgttaggta cttacataaa ttgttacatt attttttctt 5040
atgtaatacc tttttgtttg tttatgtggt tcaaatatat tctttcctta aaaaaaaaaa 5100
aaaaaaaaaa aaaaaaaaaa aaaaaaaa 5128

<210> SEQ ID NO 58
<211> LENGTH: 1454
<212> TYPE: DNA
<213> ORGANISM: Homo sapiens

<400> SEQUENCE: 58
aattgcttcc ggggagttgc gagggagcga gggggaataa aggacccgcg aggaagggcc 60
cgcggatggc gcgtccctga gggtcgtggc gagttcgcgg agcgtgggaa ggagcggacc 120
ctgctctccc cgggctgcgg gccatggcca cggcggagcg gagagccctc ggcatcggct 180
tccagtggct ctctttggcc actctggtgc tcatctgcgc cgggcaaggg ggacgcaggg 240
aggatggggg tccagcctgc tacggcggat ttgacctgta cttcattttg gacaaatcag 300
gaagtgtgct gcaccactgg aatgaaatct attactttgt ggaacagttg gctcacaaat 360
tcatcagccc acagttgaga atgtccttta ttgttttctc cacccgagga acaaccttaa 420
tgaaactgac agaagacaga gaacaaatcc gtcaaggcct agaagaactc cagaaagttc 480
tgccaggagg agacacttac atgcatgaag gatttgaaag ggccagtgag cagatttatt 540
atgaaaacag acaagggtac aggacagcca gcgtcatcat tgctttgact gatggagaac 600
tccatgaaga tctctttttc tattcagaga gggaggctaa taggtctcga gatcttggtg 660
caattgttta ctgtgttggt gtgaaagatt tcaatgagac acagctggcc cggattgcgg 720
acagtaagga tcatgtgttt cccgtgaatg acggctttca ggctctgcaa ggcatcatcc 780
actcaatttt gaagaagtcc tgcatcgaaa ttctagcagc tgaaccatcc accatatgtg 840
caggagagtc atttcaagtt gtcgtgagag gaaacggctt ccgacatgcc cgcaacgtgg 900
acagggtcct ctgcagcttc aagatcaatg actcggtcac actcaatgag aagcccttt 960 ctgtggaaga cacttattta ctgtgtccag cgcctatctt aaaagaagtt ggcatgaaag 1020
ctgcactcca ggtcagcatg aacgatggcc tctcttttat ctccagttct gtcatcatca 1080
ccaccacaca ctgttctgac ggttccatcc tggccatcgc cctgctgatc ctgttcctgc 1140
tcctagccct ggctctcctc tggtggttct ggcccctctg ctgcactgtg attatcaagg 1200
aggtccctcc accccctgcc gaggagagtg aggaaaataa aataaaataa caagaagaag 1260
aaagaaagaa atcccacaga aacagataac ctaacacagc ccgtgcaacg tattttatac 1320
aatgctctga aaatcatagt ctcaatctag acagtctttt cctctagttc cctgtattca 1380
aatcccagtg tctaacattc aataaatagc tatatgaaat caaaaaaaaa aaaaaaaaaa 1440
aaaaaaaaaa aaaa 1454

<210> SEQ ID NO 59
<211> LENGTH: 2828
<212> TYPE: DNA
<213> ORGANISM: Homo sapiens

<400> SEQUENCE: 59
agcagccggc acggggacag ccggccgcac aacggatctg caggcgcgga gcaaaatgca 60
cccgccgcgc cgcgcggtcc tgcagccccg ccacggcccc gcggcccgca cccccccggg 120
gcgacagtga gcctctcccg ccaccaccgg gggccgagcg gagggctctc gggtgggaga 180
gcgggaccag atctcgacag ctgttcattt ccaggaagcc accgcagcca gagcgaaagg 240

-continued

```
ggaccttctg ccaccagcgg ggcatcagcc agcggcgcgc atggatttat gaagacactc    300
atgcaagaag tgggcaggac ttggacaaac ttttccaccg gctccgcgtc cgccgctccc    360
cgcgcctcgt ctcctttccc ctcctctccc ggcggccgcc gctgcccgcg atggtggccg    420
cgctgctggg cggcggcggc gaggcccgcg gggggacagt gccgggcgcc tggctgtgcc    480
tgatggcgct gctgcagctg ctgggctcgg cgccgcgggg atcggggctg gcgcacggcc    540
gccgcctcat ctgctggcag gcgctgctgc agtgccaggg ggagccggag tgcagctacg    600
cctacaacca gtacgccgag gcgtgcgcgc cggtgctggc gcagcacggc gggggcgacg    660
cgcccggggc cgccgccgcc gctttcccgg cctcggccgc ctctttctcg tcgcgctggc    720
gctgcccgag tcactgcatc tcggccctca ttcagctcaa ccacacgcgc cgcgggcccg    780
ccctggagga ctgtgactgc gcgcaggacg agaactgcaa gtccaccaag cgcgccattg    840
agccgtgcct gccccggacg agcggcggcg gcgcgggcgg ccccggcgcg ggcggggtca    900
tgggctgcac cgaggcccgg cggcgctgcg accgcgacag ccgctgcaac ctggcgctga    960
gccgctacct gacctactgc ggcaaagtct tcaacgggct gcgctgcacg gacgaatgcc   1020
gcaccgtcat tgaggacatg ctggctatgc ccaaggtggc gctgctcaac gactgcgtgt   1080
gcgacggcct cgagcggccc atctgcgagt cggtcaagga gaacatggcc cgcctgtgct   1140
tcggcgccga gctgggcaac ggccccggca gcagcggctc ggacgggggc ctggacgact   1200
actacgatga ggactacgat gacgagcagc gcaccggggg cgcgggtggt gagcagccgc   1260
tggacgacga cgacggcgtc ccgcacccac cgcgcccggg cagcggcgct gctgcatcgg   1320
gcggccgcgg ggacctgccc tatgggcctg ggcgcaggag cagcggcggc ggcggccgct   1380
tggcgccccg gggcgcctgg accccactcg cctccatctt gctgctgctg cttgggccgc   1440
tcttttagcc ctcgcgcccc ccgccgttgg ctgcgggaga gcccgcgtcc cactcccgtg   1500
ctcgcctcga ccccgcgccg ggcacctgtg gcttgggaca gatagaaggg atggttgggg   1560
atacttccca aaactttttc caagtcaact tggtgtagcc ggttccccgg ccacgactct   1620
gggcacttcc cctgaagctc ctctccggag cttgacttct tggacctcct cccccgcccc   1680
aattccaagc tccagaaact cccaactcgt ctgccgtcca gaaagctagc tgcagtgttc   1740
aggacgtccg ggaggaagca agcatgtggg ggacagaaca gtagtcctgg actcgaaagg   1800
gaaggtgctg accagtgggg ccttagcaat ttgaagggtt gggaaggagg aattatattt   1860
gcaaagggc tgtctattag catatttcct ttgagggggc aaaaaaaagt gccagtatcg   1920
acttttacag attgtggcca gtgaggatat tataatccta tgtaaacaga aaagtcccac   1980
ttaccgattc attctttcac tgtttgtatc tgcgcccaga attctcagtg acgtgggggt   2040
gagggtgggt ggcgattgcc ttagagggaa cccctaaatt ggttttggat aagtttgagc   2100
ccttgacctt aatttcattg ctaccactct gatctcttag cacatttctt aggattaagg   2160
gtccaaaaat gctgatctaa ggggttgcca tggtgttgaa caatgcaact ttttatttaa   2220
aaaagctctg cactgccatg tatgaaagtc tctttatgat gtttgttttt ttgtcatttt   2280
tgttctttac atcaagaaat tttatgttta aatatgcgga gaatgtatat tgcctctgct   2340
cctatcaggg ttgctaaacc ctggtacatc gtatataaaa tgtattaaaa ctggggtttg   2400
ttaccagttg ctgtactttg tatatagaat ttttataaat tgtatgcttc agaaataatt   2460
tatttttaaa aagaaattaa aagttttaaa ctcacatcca tattacacct ttcccccctg   2520
aaatgtatag aatccatttg tcatcaggaa tcaaaaccca cagtccattg tgaagtgtgc   2580
tatatttaga acagtcttaa aatgtacagt gtattttata gaattgaagt taacattctt   2640
```

attttcaaga gaatttatgg acgttgtaga aatgtacaaa tgcatttcca aactgcctta 2700
aacgttgtat ttttatagac atgttttttt aaaaatccta agtttttaaa taactatgga 2760
tttgtgtatt ttttttggtt atttgtttta ttaaaacatg tacatcagta aagagtttta 2820
aacaatga 2828

<210> SEQ ID NO 60
<211> LENGTH: 7568
<212> TYPE: DNA
<213> ORGANISM: Homo sapiens

<400> SEQUENCE: 60
gcgcggaggc agggaaccgg agccttggag cgacccaacc cctcgtctcg ctgccctccc 60
gcgcctgcaa cggtgcgcgg agactccggc gaactcagac acccaacggc ggagaacaga 120
agcggcaggc ggcggacgtg gcccggaagc tgcgcgccga acgcagcgca cccgctgccg 180
agcagaggag ccgcgccttt ccccgaccct cggctccagc cccggcgcc tgccgcctcg 240 cagcccctct gcgtcctcgg ctcgggggcc ggcaccggcg atgccgagcg gacgctccag 300
tcctccgacc cgctgaagaa gcagcagccg ctcgcccgga gcctacgggg attgtgcgag 360
cggatcgtgc tcggtggagg ctcgggctgc ggggcgcggg gactccgggg ggcgggggga 420
gggaccgctc tgtcggtgcc cggcgccagc cgcggctttg aagggtctcc ctcccctgcc 480
cttagcagct ctgccacgga ctccgggagg ctgcgggcgg cgtcctgagg gctccccagc 540
agacccaatc ggacttgaga aggtgatcgc tctgctctcc caaccccctt ccctccccat 600
tccccccact taacttttg tctccgttca tccgcggctt cgtcccctcc ccggcagacc 660
cacccgcggc tgtgacaacc gcccggggca tgggcccccc aacacggctc ctagaggccc 720
cgcggcctcg caagatgtga gaggccctcc ccgggcagaa tcggagcttc aggagaggag 780
ctaatacccc gcccccgtc cctcacatca ggcggggtgg aggtgcgcgc tgagccccg 840 cggtgctgag cgtcccggag cgcccaatcc tgggctggaa cgagtagctg gccggaggcg 900
cgccgcggag agccggctgt catgccctat tgatccccct ctgcccccg ccaagtatgt 960 ttgggctgga ccaattcgag ccccaggtca acagcaggaa cgctggccag ggcgagagga 1020
actttaacga gaccggactg agcatgaaca cccactttaa ggccccggct ttccacactg 1080
gggggccccc tggccctgtg gatcctgcta tgagcgcgct ggggcaaccc ccgatcttgg 1140
gcatgaacat ggagccctac ggcttccacg cgcgcggcca ctcggagttg cacgcagggg 1200
ggctgcaagc gcagcctgtg cacggcttct ttggcggcca gcagcctcac cacggccacc 1260
cgggaagtca tcatccccac cagcatcacc cccactttgg gggcaacttc ggtggcccgg 1320
accccggggc ctcgtgcctg cacgggggtc gcctgctcgg ctacggcggc gcagccggag 1380
gcctgggcag ccagccgccc ttcgccgagg gctatgagca catggcggag agccaggggc 1440
ctgagagctt cggcccgcag cgaccgggga acctcccgga cttccacagt tcaggtgcct 1500
ccagccaccg cgtgccggcc ccatgcctgc cgctggacca gagccctaac cgagccgcct 1560
ccttccacgg cctgccgtcc tccagcggct ccgattccca cagtctggag ccacggaggg 1620
tgacgaacca aggagccgtc gactcgctgg aatacaatta ccgggcgagg cgccctcggg 1680
acattttgac atgttttcgc cctctgactc cgaagggcag ctgcctcatt atgcagcggg 1740
tcgccaggtt cctgggggc ggctttcccg gggcgccctc ggccatgccc agagctgcgg 1800
gcatggtggg cttgtccaaa atgcacgccc agccaccgca gcagcagccc cagcagcagc 1860
agcagcccca gcagcagcag cagcatggtg tgttctttga gaggttcagt ggggccagaa 1920

-continued

```
agatgcctgt gggtctggag ccctcagtgg gctccaggca cccgttaatg cagcctcccc   1980
agcaggcccc gccacccct cagcagcagc ccccgcagca gccgccacag cagcagccgc   2040
cgccgccacc cgggcttcta gtccgacaaa attcgttgcc cgcctgcgct ccctcggccc   2100
cagcagggcg aggcgggcac gcccagcggc ggcctgcagg acggaggccc catgctgccc   2160
agccagcacg cgcaattcga gtatcccatc caccggctgg agaaccggag catgcaccct   2220
tattccgagc ctgttttcag catgcagcat cctcctccgc agcaggcgcc caaccagcgg   2280
ctgcagcatt tcgacgcgcc cccctacatg aacgtggcca agaggcgcgc ttcgactttc   2340
cgggcagcgc gggagtggac cgctgcgctt cgtggaacgg cagcatgcac aacggcgctc   2400
tggataatca cctctcccct tccgcctacc caggcctacc cggcgagttc acaccgcctg   2460
tgcccgacag cttcccttcg gggccgcccc tgcagcatcc ggccccggac caccagtccc   2520
tgcaacagca gcagcagcag cagcagcagc agcaacagca gcagcagcag cagcaacagc   2580
aacagcaaca gcagcagcag cagcagcgcc aaaacgcggc cctcatgatt aagcagatgg   2640
cgtcgcggaa tcagcagcag cggctgcgcc agcccaacct ggctcagcta ggccaccccg   2700
gggacgtggg ccagggcggc ctggtgcatg gcggcccggt gggcggcttg gcccagccga   2760
actttgagcg cgaaggcggc agcacgggcg ccgggcgtct gggcaccttc gagcagcagg   2820
cgccgcactt ggcgcaagag agcgcgtggt tctcaggtcc gcatccgccg cccggagacc   2880
tgctgccccg taggatgggc ggctcgggtc tgcccgctga ctgtggcccg cacgacccca   2940
gcctggcgcc ccctcctccg cctggtggct cgggggtgct gttccggggc cctctgcagg   3000
agccgatgag gatgcccgga gaggccacgt gccgcgctgc cttcaccggc ctgcagttcg   3060
ggggcagtct gggaggcctg ggtcagctgc agtcgcccgg ggcgggcgtg gggctcccca   3120
gcgctgcttc ggagcgccgg cccccgccgc cggactttgc tacgtctgcg ctcgggggcc   3180
agccgggctt tccgtttggt gcagccggcc ggcagtccac gccgcacagc ggtccaggcg   3240
tgaactcgcc ccccagcgcg ggagggggcg gtggcagctc tggtggcggc ggtggcgggg   3300
gtgcctaccc gccgcagcct gatttccagc ccagccagcg cacctcggcc agtaaattgg   3360
gcgcgctctc gctgggctcc ttcaacaagc ccagctccaa ggacaacctg ttcggccaga   3420
gctgcctggc tgcgctctcc accgcttgcc agaacatgat cgccagcctc ggggccccca   3480
acctcaacgt gaccttcaac aagaagaacc cgccagaggg caagaggaaa ctgagccaga   3540
acgagaccga cggcgcggca gtggccggca acccgggctc ggattacttc ccaggaggga   3600
ctgctcctgg gggccccagg acccggaggc cgtccgggac cagtagcagc ggctccaaag   3660
cctcggggcc gcccaaccct ccagcccagg gggacggcac cagcctctcc cccaactaca   3720
ccctggaatc cacgtcgggg aatgacggca agccggtctc cgggggcggc ggccggggac   3780
ggggtcgcag aaaaagggac agtggtcacg tgagccctgg caccttcttt gacaagtact   3840
cggcggctcc ggacagcggg ggcgcacctg ggtgagccc agggcagcag caagcgtcag   3900
gcgcagccgt cgggggaagc tccgcaggcg agacgcgcgg ggcaccgacg ccccacgaaa   3960
aggcgctcac gtcgccatcc tgggggaagg gggctgagtt gctcctgggg gatcagccgg   4020
acctcattgg gtccctggac ggcggggcca agtcggacag tagttcgcca aacgtgggtg   4080
agttcgcctc ggacgaggtg agcacgagct acgccaatga ggacgaggtg tcgtccagct   4140
ctgacaaccc ccaggcacta gttaaagcga gcaggagtcc cctggtgacc ggctcgccca   4200
aactccctcc ccgtggggta ggcgccgggg aacacggacc gaaggcgccc ccgcccgccc   4260
tcggcctggg catcatgtct aactctacct cgaccccctga cagctacggc ggcggtgggg   4320
```

-continued

```
gcccgggcca tccgggcact ccgggcctgg agcaggtccg caccccgacg agcagcagcg   4380
gcgccccgcc acccgacgag atccaccccc tggagatcct tcaggcgcag atccagctac   4440
agaggcagca gttcagcatc tccgaggacc agcctctggg gctgaagggt ggcaagaagg   4500
gtgagtgcgc cgtcggggcc tcaggggcgc agaatggcga cagcgagctg ggcagctgct   4560
gctccgaggc ggtcaagagc gccatgagca ccattgacct ggactcgctg atggcagagc   4620
acagcgctgc ctggtacatg cccgctgaca aggccctggt ggacagcgcg gacgacgaca   4680
agacgttggc gccctgggag aaggccaaac cccagaaccc caacagcaaa gaagcccacg   4740
acctccctgc aaacaaggcc tcagcatccc agcctggcag ccacttgcag tgcctgtctg   4800
tccactgcac agacgacgtg ggtgacgcca aggctcgagc ctccgtgccc acctggcggt   4860
ccctgcattc tgacatctcc aacagatttg ggacattcgt ggctgcccta acttgaatga   4920
caagaaagat cccctcctct accaggccct tcctctcccc ctgtctgttt ccttcccccct   4980
caaccttacc ccacccctct gttaatttga aagggccact attgctgagt ggatgagttt   5040
ttttttttc ctctaggttg gtacctgctt agtggcatat ggaccggaaa gggttaattt   5100
aaagggggg aacctcaaaa gttttttaa aaaagaaact tgtctgccac agtatgttac   5160
cagtgttaac ccttctgcag ttagcaaact tttgcttaag ccttttcct ctagatactc   5220
cccatgtttc ggtaatcttg gcatacattt tttagatgac ctctttcctt gttttgtttt   5280
catgctgctg tatgtccaag tattgttatt tcataataag acaagagttg ctttcttttt   5340
tattcttttt ccttttctta ccccctcccc ttttatttc tttttgcttt gttcactgct   5400
tattaaaatg gaaatcctgg agaatagtag ttctggaata ttgccgggtg aaagtccaat   5460
tgtcatcaca atgttatata ttgacacccc agtgtcatca gtcaggcagg agccaaacaa   5520
tgaatgcccc tcttaggtat tccgcctggg attttgtttt gtctgttccc taagaaaata   5580
tattttcatt cctgcaaaca cagtgctcag ccttcagttc ccttccactt gagttctctc   5640
ttctcctgct ggaagccgcc cctctctgcg atggacgtga ggacgtgtcc agctctgctc   5700
tgtgggaagg agttggaatg ttcgacagca gtgttttctc tccttttctg ggcctcctcg   5760
caaatgccca ggccctgcat tttcacgctg tgctaagcag cctttggtct gcatggggga   5820
tggtgtgctc ccagcctgca gtctttggag caaggctgct gcccgtgcct tgggtgctgg   5880
agttggagga ggctgttctc agccctttcc cttttctgaa agctgttcct ggccgggcat   5940
cccagggaag aaggagggga ctgcgtgtat ctcctccacc tctcccattc catccccagt   6000
ccagcctggg caaccccacc cctgggaggg atgaggcacc ctcttgctca gcctgctcag   6060
ccttctctga gcctttgcag ggatctgcag actcctgagg gctagaggac agagaaagag   6120
aatagaatga aatgactttg attcctgcgc cttttagttt tgaactctgg aattcctctg   6180
ccccctcccc aacatttttt tggaatctca ccctgttgca aaactagagc catgtcccaa   6240
gcatctcaca aaggaataac tgctctgagc agagatgagt ggtggttggc aggggcaggc   6300
aactttgggt gctgctgatg cctgcaaaag ccatttatgg cttgtggtgg ggggcacata   6360
gattccccgg tgggttagac aggaagtaac tgatatcact tcacccaaat atataaccgt   6420
gatggttatc tatttaattt cagtttttgt taacgagcgt gtcttactaa aacgctccac   6480
tttgagctcc cccacccccct ccaggtcctc agagtttgca gatctgggct ttctaaagca   6540
agtgacctga aggctctggg ctcaccatac aacacccacg ttgtttattt caaagaactt   6600
ttcagcgaag ggagaggagc tttcagaaaa acctcactct ttcccctccc ttctcccctc   6660
tttccttctg ccggtccttt tggctggggt ctgagtctgc ggttctcgcc tgggcagtct   6720
```

```
tgacgaggag caaaccccgc cttcagaggg cagacaaagc aggtggcatg aattgatcag   6780

cgagaaaggt gtgagccgag gcagttcctg cgttctgcta caaaaggaat ggaaagggaa   6840

gggaatttcc ccccaccatg ggctgtggga gagttgaccg tattctgggc aagactccat   6900

gacccctctg attctgcagt gtacagctgt ttgagagcct catcatttta cttttgaaac   6960

aggaatgatt tctccttaat tgcttaaggc cggggagcaa agtgtcttaa cttctgtctt   7020

tgactttccc agcgttgagt catcaacact ttgccaatta gctcatggtc ctggcaacct   7080

cagaaacccc tgaagtttta aaaactttct cgctccccac gaccccagaa tgaaacagct   7140

ttaaaaatag ccttaagcaa aaggatgtta tttcattaaa tttggtttaa tggaaagaat   7200

aaaagtaaat gaaaaacaca ccctacacac tagactccga acactggtaa tcagtactgc   7260

atagcaaact ctttgggaaa gaaaacgaaa atgttattgc acatgtaaaa tatgaaaact   7320

taactctgct gtgtgttagg caatcctgta atctttttttg actcttaaaa gaaattcatt   7380

tctgaaatgc ttggttggaa gactgtgaca atagctcatg aaattgagtg ttattttttt   7440

ctttcttttt taaaaaaata tgtaaagtgc agtcttctgt attcctgcat attgtatata   7500

cctgtatatg ttttcctgag cagttaaata acaataaata tgacgttaat ggtgaaaaaa   7560

aaaaaaaa                                                            7568
```

<210> SEQ ID NO 61
<211> LENGTH: 691
<212> TYPE: DNA
<213> ORGANISM: Homo sapiens

<400> SEQUENCE: 61

```
gacccctcac actcacctag ccaccatgga catcgccatc caccacccct ggatccgccg     60

ccccttcttt cctttccact cccccagccg cctctttgac cagttcttcg gagagcacct    120

gttggagtct gatcttttcc cgacgtctac ttccctgagt cccttctacc ttcggccacc    180

ctccttcctg cgggcaccca gctggtttga cactggactc tcagagatgc gcctggagaa    240

ggacaggttc tctgtcaacc tggatgtgaa gcacttctcc ccagaggaac tcaaagttaa    300

ggtgttggga gatgtgattg aggtgcatgg aaaacatgaa gagcgccagg atgaacatgg    360

tttcatctcc agggagttcc acaggaaata ccggatccca gctgatgtag accctctcac    420

cattacttca tccctgtcat ctgatggggt cctcactgtg aatggaccaa ggaaacaggt    480

ctctggccct gagcgcacca ttcccatcac ccgtgaagag aagcctgctg tcaccgcagc    540

cccaagaaa tagatgccct ttcttgaatt gcattttttta aaacaagaaa gtttccccac    600

cagtgaatga aagtcttgtg actagtgctg aagcttatta atgctaaggg caggcccaaa    660

ttatcaagct aataaaatat cattcagcaa c                                   691
```

<210> SEQ ID NO 62
<211> LENGTH: 874
<212> TYPE: DNA
<213> ORGANISM: Homo sapiens

<400> SEQUENCE: 62

```
gcggccgcgt cgaccgctgc gcctgttggg gctgcacctc ggaccagggc ttctgctgca     60

tctgcagcca tgtcgggccg ctcagtgcca catgcccacc cggccaccgc cgagtacgaa    120

tttgccaacc cgagccgcct gggtgagcag cgcttcggag aaggcctcct gccagaagag    180

atcctgaccc ccacactcta ccatggctac tatgtccggc ctcgggccgc cccagctggg    240

gagggcagca gggcaggggc ctccgagctt aggctcagtg agggcaagtt ccaggcattt    300
```

ctggatgtga gccactttac cccagacgag gtgactgtga ggactgtgga taacctgctg 360
gaggtgtctg cccggcaccc ccagcgcctg gaccgccacg gcttcgtgtc ccgagagttc 420
tgccgcacct atgtcctgcc tgctgatgtc gacccctggc gagtccgagc tgctctctcc 480
catgatggca tcttaaacct ggaagcacct cggggtggcc gacatttgga cacagaggtc 540
aatgaggtct acatctccct gctccctgcg cctcctgatc cagaggaaga ggaggaggca 600
gccatagttg agccctgatt gccacagacc cagcacccag caaatccctc tctacctccc 660
aaggtgatat gggcagctgc ccaccactcc agaggtagca gcatccttgg gggaagggaa 720
aggtgcatgg tccacaatgt atggtttggt cccatgggac atgtcatagc cttggtttag 780
ttttgggtgg agctgaataa acccaaattt cagggcaaaa aaaaaaaaaa aaaagaaaaa 840
aaaaaaaaaa aaaaaaaaaa gtcgacgcgg ccgc 874

<210> SEQ ID NO 63
<211> LENGTH: 2569
<212> TYPE: DNA
<213> ORGANISM: Homo sapiens

<400> SEQUENCE: 63
tccctcgtct ctctcgggca acatggcggg cgtggaggag gtagcggcct ccgggagcca 60
cctgaatggc gacctggatc cagacgacag ggaagaagga gctgcctcta cggctgagga 120
agcagccaag aaaaaaagac gaaagaagaa gaagagcaaa gggccttctg cagcagggga 180
acaggaacct gataaagaat caggagcctc agtggatgaa gtagcaagac agttggaaag 240
atcagcattg gaagataaag aaagagatga agatgatgaa gatggagatg gcgatggaga 300
tggagcaact ggaaagaaga agaaaaagaa gaagaagaag agaggaccaa aagttcaaac 360
agaccctccc tcagttccaa tatgtgacct gtatcctaat ggtgtatttc ccaaaggaca 420
agaatgcgaa tacccaccca cacaagatgg gcgaacagct gcttggagaa ctacaagtga 480
agaaaagaaa gcattagatc aggcaagtga agagatttgg aatgattttc gagaagctgc 540
agaagcacat cgacaagtta gaaaatacgt aatgagctgg atcaagcctg ggatgacaat 600
gatagaaatc tgtgaaaagt tggaagactg ttcacgcaag ttaataaaag agaatggatt 660
aaatgcaggc ctggcatttc ctactggatg ttctctcaat aattgtgctg cccattatac 720
tcccaatgcc ggtgacacaa cagtattaca gtatgatgac atctgtaaaa tagactttgg 780
aacacatata agtggtagga ttattgactg tgcttttact gtcactttta atcccaaata 840
tgatacgtta ttaaaagctg taaaagatgc tactaacact ggaataaagt gtgctggaat 900
tgatgttcgt ctgtgtgatg ttggtgaggc catccaagaa gttatggagt cctatgaagt 960
tgaaatagat gggaagacat atcaagtgaa accaatccgt aatctaaatg gacattcaat 1020
tgggcaatat agaatacatg ctggaaaaac agtgccgatt gtgaaaggag gggaggcaac 1080
aagaatggag gaaggagaag tatatgcaat tgaaaccttt ggtagtacag gaaaaggtgt 1140
tgttcatgat gatatggaat gttcacatta catgaaaaat tttgatgttg gacatgtgcc 1200
aataaggctt ccaagaacaa aacacttgtt aaatgtcatc aatgaaaact ttggaaccct 1260
tgccttctgc cgcagatggc tggatcgctt gggagaaagt aaatacttga tggctctgaa 1320
gaatctgtgt gacttgggca ttgtagatcc atatccacca ttatgtgaca ttaaaggatc 1380
atatacagcg caatttgaac ataccatcct gttgcgtcca acatgtaaag aagttgtcag 1440
cagaggagat gactattaaa cttagtccaa agccacctca acacctttat tttctgagct 1500
ttgttggaaa acatgatacc agaattaatt tgccacatgt tgtctgtttt aacagtggac 1560
ccatgtaata cttttatcca tgtttaaaaa agaaggaatt tggacaaagg caaaccgtct 1620
aatgtaatta accaacgaaa aagctttccg gacttttaaa tgctaactgt ttttcccctt 1680
cctgtctagg aaaatgctat aaagctcaaa ttagttagga atgacttata cgttttgttt 1740
tgaataccta agagatactt tttggatatt tatattgcca tattcttact tgaatgcttt 1800
gaatgactac atccagttct gcacctatac cctctggtgt tgctttttaa ccttcctgga 1860
atccattttc taaaaaataa agacacattc ttctcagcac cacacaacac ctattccaaa 1920
atcgaccaca tatttggaag taaagctctc ctcagcaaat gtaaaagaac agaaattata 1980
acaaactgtc tctcagacca cagtataacc aaactagaac tcaggattaa gaaactcact 2040
caaaaccaca caactacatg gaaactgaac aacctgctcc tgaatgacta ctggatacat 2100
aacaaaatga aggcagaaat aaagatgttc tttaaaacca atgagaacaa agacacaaca 2160
taccagaatc tctgggacac attcaaagca gtgtgtagag ggaaatttat agcactaaat 2220
gcccacaaga gaaagcagga aatatctaaa attgacaccc taacatcaca attaaaagaa 2280
ctagagaagc aagagcaaac acattgaaaa gctaagagaa ggcaagaaat aactaagatc 2340
agagcagaac tgaaggaaat agagacacaa aaaactcttc aaaaaatcaa tgaatccagg 2400
agctggtttt ttgaaacgat caacaaaatt gatagacact agcaagacta ataaagaaga 2460
aaggagagaa gaatcaaata gaagcaataa aaaatgataa aggggatatc accaccaatc 2520
ccacagaaat aaaccaccat cagagaatac tacaaacacc tctacgcaa 2569

<210> SEQ ID NO 64
<211> LENGTH: 3672
<212> TYPE: DNA
<213> ORGANISM: Homo sapiens

<400> SEQUENCE: 64
acatgtgcat atttcattcc ccaggcagac attttttaga aatcaataca tgccccaata 60
ttggaaagac ttgttcttcc acggtgacta cagtacatgc tgaagcgtgc cgtttcagcc 120
ctcatttaat tcaatttgta agtagcgcac gagcctctgt gggggaggat aggctgaaaa 180
aaaaaagtgg gctcgtattt atctacagga ctccatatag tcatatatag gcatataaat 240
ctatgctttt tctttgtttt tttctttctt cctttctttc aaaggtttgc attaactttt 300
caaagtagtt cctataggggg cattgaggag cttcctcatt ctgggaaaac tgagaaaacc 360
catattctcc taatacaacc cgtaatagca tttttgcctg cctcgaggca gagtttcccg 420
tgagcaataa actcagcttt tttgtggggc acagtactgg atttgacagt gattccccac 480
gtgtgttcat ctgcacccac cgagccaggc agaggccagc cctccgtggt gcacacagca 540
cgcgcctcag tccatcccat tttagtcttt aaaccctcag gaagtcacag tctccggaca 600
ccacaccaca ttgagcccaa caggtccacg atggatccac ctagtcccac cccagccttt 660
ttctttcatc tgaacagaat gtgcattttt ggaagcctcc ctcactctcc atgctggcag 720
agcaggaggg agactgaagt aagagatggc agagggagat ggtggcaaaa aggtttagat 780
gcaggagaac agtaagatgg atggttccgg ccagagtcga tgtggggagg aacagagggc 840
tgaagggaga gggggctgac tgttccattc tagctttggc acaaagcagc agaaaggggg 900
aaaagccaat agaaatttcc ttagcttccc caccatatgt attttcatgg atttgagagg 960
aaagagagga aaatggggga atgggttgca aaatagaaat gagcttaatc caggccgcag 1020
agccagggaa ggtgagtaac cttaggaggg tgctagactt tagaagccag ataggaagaa 1080
tcagtctaaa ctggccatgc tttggaaggg acaagactat gtgctccgct gcccaccttc 1140

-continued agcctgcaat gagggactga ggcccacgag tctttccagc tcttcctcca ttctggccag 1200
tccctgcatc ctccctgggg tggaggatgg aaggaaagct gggacaagca gggaacgcat 1260
gattcaggga tgctgtcact cggcagccag attccgaaac tcccattctc caatgacttc 1320
ctcaaccaat gggtggcctt gtgactgttc tttaaggctg aagatatcca ggaaaggggg 1380
cttggacact ggccaaggag accccttcgt gctgtggaca cagctctctt cactctttgc 1440
tcatggcatg acacagcgga gaccgcctcc aacaacgaat ttggggctac gaagaggaat 1500
agcgaaaaag caaatctgtt tcaactgatg ggaaccctat agctatagaa cttgggggct 1560
atctcctatg cccctggaca ggacagttgg ctggggacag gagaagtgct caatcttcat 1620
gagacaaagg ggcccgatca aggcagccac aaggccttga cctgccgagt cagcatgccc 1680
catctctctc gacagctgtc ccctaaaccc aactcacgtt tctgtatgtc ttaggccagt 1740
atcccaaacc tcttccacgt cactgttctt tccacccatt ctccctttgc atcttgagca 1800
gttatccaac taggatctgc caagtggata ctggggtgcc actcccctga gaaaagactg 1860
agccaggaac tacaagctcc ccccacattc ctcccagcct ggacctaatt cttgagaggg 1920
gctctctctt cacggactgt gtctggactt tgagcaggct tctgcccctt gcgttggctc 1980
tttgctgcca gccatcaggt gggggattag agcctggtgt aagtgcgcca gactcttccg 2040
gtttccaaag ttcgtgcctg cgaacccaaa cctgtgagtc tcttctgcat gcaggagttt 2100
ctcctgggca gctggtcact ccccagagaa gctgggcctt catggacaca tggaactaag 2160
cctcccaaat gggagttctg gctgagccca gggtggggag atcctgggaa gggaggcact 2220
ggaggaagac ggcacctctt cccccatggc agggtgtgag ggaggcaggt ttggaatggt 2280
gcgagtatgg caatctaagc aggggtctgg tctctttgac tccaggctcg ctttggccga 2340
ctgtctgctc acccagagac cttggactcc ggactatcca tggctccgaa tctaagtgct 2400
gcccactccc atgctcacac ccacagaagg tcttcccatc ccctttagat tcgtgcctca 2460
ctccaccagt gaggaagatg cctctgtctt tcccacgact gccaggagat agggaagccc 2520
agccaggact gaccctcctt cctccagcct gccctgaccc acctggcaaa gcagggcaca 2580
tggggaggaa gagactggaa cctttctttg acagccaggc ctagacagac aggcctgggg 2640
acactggccc atgaggggag gaaggcaggc gcacgaggtc cagggaggcc cttttctgat 2700
catgcccctt ctctcccacc ccatctcccc accaccacct ctgtggcctc catggtaccc 2760
ccacagggct ggcctcccct agagggtggg cctcaaccac ctcgtcccgc cacgcaccgg 2820
ttagtgagac agggctgcca cgcaaccgcc aagcccccct caaggtggga cagtaccccg 2880
gacccatcca ctcactcctg agaggctccg gcccagaatg ggaacctcag agaagagctc 2940
taaggagaag aaaccccata gcgtcagaga ggatatgtct ggcttccaag agaaaggagg 3000
ctccgttttg caaagtggag gagggacgag ggacaggggt ttcaccagcc agcaacctgg 3060
gccttgtact gtctgtgttt ttaaaaccac taaagtgcaa gaattacatt gcactgtttc 3120
tccacttttt attttctctt aggcttttgt ttctatttca aacatacttt cttggttttc 3180
taatggagta tatagtttag tcatttcaca gactctggcc tcctctcctg aaatcctttt 3240
ggatggggaa agggaaggtg gggagggtcc gaggggaagg ggaccccagc ttccctgtgc 3300
ccgctcaccc cactccacca gtccccggtc gccagccgga gtctcctctc taccgccact 3360
gtcacaccgt agcccacatg gatagcacag ttgtcagaca agattccttc agattccgag 3420
ttgctaccgg ttgttttcgt tgttgttgtt gttgttttc tttttctttt tttttttgaa 3480
gacagcaata accacagtac atattactgt agttctctat agttttacat acattcatac 3540

-continued cataactctg ttctctcctc ttttttgttt tcaactttaa aaacaaaaat aaacgatgat 3600
aatctttact ggtgaaaagg atggaaaaat aaatcaacaa atgcaaccag tttgtgagaa 3660
aaaaaaaaaa aa 3672

<210> SEQ ID NO 65
<211> LENGTH: 1826
<212> TYPE: DNA
<213> ORGANISM: Homo sapiens

<400> SEQUENCE: 65
agtctgcact ggagctgcct ggtgaccaga agtttggagt ccgctgacgt cgccgcccag 60
atggcctcca ggctgaccct gctgaccctc ctgctgctgc tgctggctgg ggatagagcc 120
tcctcaaatc caaatgctac cagctccagc tcccaggatc cagagagttt gcaagacaga 180
ggcgaaggga aggtcgcaac aacagttatc tccaagatgc tattcgttga acccatcctg 240
gaggtttcca gcttgccgac aaccaactca acaaccaatt cagccaccaa aataacagct 300
aataccactg atgaacccac cacacaaccc accacagagc ccaccaccca acccaccatc 360
caacccaccc aaccaactac ccagctccca acagattctc ctacccagcc cactactggg 420
tccttctgcc caggacctgt tactctctgc tctgacttgg agagtcattc aacagaggcc 480
gtgttggggg atgctttggt agatttctcc ctgaagctct accacgcctt ctcagcaatg 540
aagaaggtgg agaccaacat ggccttttcc ccattcagca tcgccagcct ccttacccag 600
gtcctgctcg gggctgggca gaacaccaaa acaaacctgg agagcatcct ctcttacccc 660
aaggacttca cctgtgtcca ccaggccctg aagggcttca cgaccaaagg tgtcacctca 720
gtctctcaga tcttccacag cccagacctg gccataaggg acacctttgt gaatgcctct 780
cggaccctgt acagcagcag ccccagagtc ctaagcaaca acagtgacgc caacttggag 840
ctcatcaaca cctgggtggc caagaacacc aacaacaaga tcagccggct gctagacagt 900
ctgccctccg atacccgcct tgtcctcctc aatgctatct acctgagtgc caagtggaag 960
acaacatttg atcccaagaa aaccagaatg gaaccctttc acttcaaaaa ctcagttata 1020
aaagtgccca tgatgaatag caagaagtac cctgtggccc atttcattga ccaaactttg 1080
aaagccaagg tggggcagct gcagctctcc cacaatctga gtttggtgat cctggtaccc 1140
cagaacctga aacatcgtct tgaagacatg gaacaggctc tcagcccttc tgttttcaag 1200
gccatcatgg agaaactgga gatgtccaag ttccagccca ctctcctaac actaccccgc 1260
atcaaagtga cgaccagcca ggatatgctc tcaatcatgg agaaattgga attcttcgat 1320
ttttcttatg accttaacct gtgtgggctg acagaggacc cagatcttca ggtttctgcg 1380
atgcagcacc agacagtgct ggaactgaca gagactgggg tggaggcggc tgcagcctcc 1440
gccatctctg tggcccgcac cctgctggtc tttgaagtgc agcagccctt cctcttcgtg 1500
ctctgggacc agcagcacaa gttccctgtc ttcatggggc gagtatatga ccccagggcc 1560
tgagacctgc aggatcaggt tagggcgagc gctacctctc cagcctcagc tctcagttgc 1620
agccctgctg ctgcctgcct ggacttgccc ctgccacctc ctgcctcagg tgtccgctat 1680
ccaccaaaag ggctcctgag ggtctgggca agggacctgc ttctattagc ccttctccat 1740
ggccctgcca tgctctccaa accacttttt gcagctttct ctagttcaag ttcaccagac 1800
tctataaata aaacctgaca gaccat 1826

<210> SEQ ID NO 66
<211> LENGTH: 5489

<212> TYPE: DNA
<213> ORGANISM: Homo sapiens

<400> SEQUENCE: 66

```
ggctgagttt tatgacgggc ccggtgctga agggcaggga acaacttgat ggtgctactt     60
tgaactgctt ttcttttctc ctttttgcac aaagagtctc atgtctgata tttagacatg    120
atgagctttg tgcaaaaggg gagctggcta cttctcgctc tgcttcatcc cactattatt    180
ttggcacaac aggaagctgt tgaaggagga tgttcccatc ttggtcagtc ctatgcggat    240
agagatgtct ggaagccaga accatgccaa atatgtgtct gtgactcagg atccgttctc    300
tgcgatgaca taatatgtga cgatcaagaa ttagactgcc ccaacccaga aattccattt    360
ggagaatgtt gtgcagtttg cccacagcct ccaactgctc ctactcgccc tcctaatggt    420
caaggacctc aaggccccaa gggagatcca ggccctcctg gtattcctgg gagaaatggt    480
gaccctggta ttccaggaca accagggtcc cctggttctc ctggcccccc tggaatctgt    540
gaatcatgcc ctactggtcc tcagaactat tctccccagt atgattcata tgatgtcaag    600
tctggagtag cagtaggagg actcgcaggc tatcctggac cagctggccc cccaggccct    660
cccggtcccc ctggtacatc tggtcatcct ggttcccctg gatctccagg ataccaagga    720
ccccctggtg aacctgggca agctggtcct tcaggccctc caggacctcc tggtgctata    780
ggtccatctg gtcctgctgg aaaagatgga gaatcaggta gacccggacg acctggagag    840
cgaggattgc ctggacctcc aggtatcaaa ggtccagctg ggatacctgg attccctggt    900
atgaaaggac acagaggctt cgatggacga aatggagaaa agggtgaaac aggtgctcct    960
ggattaaagg gtgaaaatgg tcttccaggc gaaaatggag ctcctggacc catgggtcca   1020
agaggggctc ctggtgagcg aggacggcca ggacttcctg gggctgcagg tgctcggggt   1080
aatgacggtg ctcgaggcag tgatggtcaa ccaggccctc ctggtcctcc tggaactgcc   1140
ggattccctg gatcccctgg tgctaagggt gaagttggac ctgcagggtc tcctggttca   1200
aatggtgccc ctggacaaag aggagaacct ggacctcagg gacacgctgg tgctcaaggt   1260
cctcctggcc ctcctgggat taatggtagt cctggtggta aaggcgaaat gggtcccgct   1320
ggcattcctg gagctcctgg actgatggga gcccggggtc ctccaggacc agccggtgct   1380
aatggtgctc ctggactgcg aggtggtgca ggtgagcctg gtaagaatgg tgccaaagga   1440
gagcccggac cacgtggtga acgcggtgag gctggtattc caggtgttcc aggagctaaa   1500
ggcgaagatg gcaaggatgg atcacctgga gaacctggtg caaatgggct tccaggagct   1560
gcaggagaaa ggggtgcccc tgggttccga ggacctgctg gaccaaatgg catcccagga   1620
gaaaagggtc ctgctggaga gcgtggtgct ccaggccctg cagggcccag aggagctgct   1680
ggagaacctg gcagagatgg cgtccctgga ggtccaggaa tgaggggcat gcccggaagt   1740
ccaggaggac caggaagtga tgggaaacca gggcctcccg gaagtcaagg agaaagtggt   1800
cgaccaggtc ctcctgggcc atctggtccc cgaggtcagc ctggtgtcat gggcttcccc   1860
ggtcctaaag gaaatgatgg tgctcctggt aagaatggag aacgaggtgg ccctggagga   1920
cctggccctc agggtcctcc tggaaagaat ggtgaaactg gacctcaagg acccccaggg   1980
cctactgggc ctggtggtga caaaggagac acaggacccc ctggtccaca aggattacaa   2040
ggcttgcctg gtacaggtgg tcctccagga gaaaatggaa aacctgggga accaggtcca   2100
aagggtgatg ccggtgcacc tggagctcca ggaggcaagg gtgatgctgg tgcccctggt   2160
gaacgtggac ctcctggatt ggcaggggcc ccaggactta gaggtggagc tggtccccct   2220
ggtcccgaag gaggaaaggg tgctgctggt cctcctgggc cacctggtgc tgctggtact   2280
```

-continued

```
cctggtctgc aaggaatgcc tggagaaaga ggaggtcttg gaagtcctgg tccaaagggt   2340
gacaagggtg aaccaggcgg cccaggtgct gatggtgtcc cagggaaaga tggcccaagg   2400
ggtcctactg gtcctattgg tcctcctggc ccagctggcc agcctggaga taagggtgaa   2460
ggtggtgccc ccggacttcc aggtatagct ggacctcgtg gtagccctgg tgagagaggt   2520
gaaactggcc ctccaggacc tgctggtttc cctggtgctc ctggacagaa tggtgaacct   2580
ggtggtaaag gagaaagagg ggctccgggt gagaaaggtg aaggaggccc tcctggagtt   2640
gcaggacccc ctggaggttc tggacctgct ggtcctcctg gtccccaagg tgtcaaaggt   2700
gaacgtggca gtcctggtgg acctggtgct gctggcttcc ctggtgctcg tggtcttcct   2760
ggtcctcctg gtagtaatgg taacccagga cccccaggtc ccagcggttc tccaggcaag   2820
gatgggcccc caggtcctgc gggtaacact ggtgctcctg gcagccctgg agtgtctgga   2880
ccaaaaggtg atgctggcca accaggagag aagggatcgc ctggtgccca gggcccacca   2940
ggagctccag gcccacttgg gattgctggg atcactggag cacggggtct tgcaggacca   3000
ccaggcatgc caggtcctag gggaagccct ggccctcagg gtgtcaaggg tgaaagtggg   3060
aaaccaggag ctaacggtct cagtggagaa cgtggtcccc ctggacccca gggtcttcct   3120
ggtctggctg gtacagctgg tgaacctgga agagatggaa accctggatc agatggtctt   3180
ccaggccgag atggatctcc tggtggcaag ggtgatcgtg gtgaaaatgg ctctcctggt   3240
gcccctggcg ctcctggtca tccaggccca cctggtcctg tcggtccagc tggaaagagt   3300
ggtgacagag gagaaagtgg ccctgctggc cctgctggtg ctcccggtcc tgctggttcc   3360
cgaggtgctc ctggtcctca aggcccacgt ggtgacaaag gtgaaacagg tgaacgtgga   3420
gctgctggca tcaaaggaca tcgaggattc cctggtaatc caggtgcccc aggttctcca   3480
ggccctgctg gtcagcaggg tgcaatcggc agtccaggac ctgcaggccc cagaggacct   3540
gttggaccca gtggacctcc tggcaaagat ggaaccagtg gacatccagg tcccattgga   3600
ccaccagggc ctcgaggtaa cagaggtgaa agaggatctg agggctcccc aggccaccca   3660
gggcaaccag gccctcctgg acctcctggt gcccctggtc cttgctgtgg tggtgttgga   3720
gccgctgcca ttgctgggat tggaggtgaa aaagctggcg gttttgcccc gtattatgga   3780
gatgaaccaa tggatttcaa aatcaacacc gatgagatta tgacttcact caagtctgtt   3840
aatggacaaa tagaaagcct cattagtcct gatggttctc gtaaaaaccc cgctagaaac   3900
tgcagagacc tgaaattctg ccatcctgaa ctcaagagtg gagaatactg ggttgaccct   3960
aaccaaggat gcaaattgga tgctatcaag gtattctgta atatggaaac tggggaaaca   4020
tgcataagtg ccaatccttt gaatgttcca cggaaacact ggtggacaga ttctagtgct   4080
gagaagaaac acgtttggtt tggagagtcc atggatggtg gttttcagtt tagctacggc   4140
aatcctgaac ttcctgaaga tgtccttgat gtgcagctgg cattccttcg acttctctcc   4200
agccgagctt cccagaacat cacatatcac tgcaaaaata gcattgcata catggatcag   4260
gccagtggaa atgtaaagaa ggccctgaag ctgatggggt caaatgaagg tgaattcaag   4320
gctgaaggaa atagcaaatt cacctacaca gttctggagg atggttgcac gaaacacact   4380
ggggaatgga gcaaaacagt ctttgaatat cgaacacgca aggctgtgag actacctatt   4440
gtagatattg caccctatga cattggtggt cctgatcaag aatttggtgt ggacgttggc   4500
cctgtttgct tttataaac caaactctat ctgaaatccc aacaaaaaaa atttaactcc   4560
atatgtgttc ctcttgttct aatcttgtca accagtgcaa gtgaccgaca aaattccagt   4620
tatttatttc caaaatgttt ggaaacagta taatttgaca aagaaaaatg atacttctct   4680
```

tttttgctg ttccaccaaa tacaattcaa atgctttttg ttttattttt ttaccaattc 4740
caatttcaaa atgtctcaat ggtgctataa taaataaact tcaacactct ttatgataac 4800
aacactgtgt tatattcttt gaatcctagc ccatctgcag agcaatgact gtgctcacca 4860
gtaaaagata acctttcttt ctgaaatagt caaatacgaa attagaaaag ccctccctat 4920
tttaactacc tcaactggtc agaaacacag attgtattct atgagtccca gaagatgaaa 4980
aaaattttat acgttgataa aacttataaa tttcattgat taatctcctg gaagattggt 5040
ttaaaaagaa aagtgtaatg caagaattta aagaaatatt tttaaagcca caattatttt 5100
aatattggat atcaactgct tgtaaaggtg ctcctctttt ttcttgtcat tgctggtcaa 5160
gattactaat atttgggaag gctttaaaga cgcatgttat ggtgctaatg tactttcact 5220
tttaaactct agatcagaat tgttgacttg cattcagaac ataaatgcac aaaatctgta 5280
catgtctccc atcagaaaga ttcattggca tgccacaggg attctcctcc ttcatcctgt 5340
aaaggtcaac aataaaaacc aaattatggg gctgcttttg tcacactagc atagagaatg 5400
tgttgaaatt taactttgta agcttgtatg tggttgttga tcttttttttt ccttacagac 5460 acccataata aaatatcata ttaaaattc 5489

<210> SEQ ID NO 67
<211> LENGTH: 5222
<212> TYPE: DNA
<213> ORGANISM: Homo sapiens

<400> SEQUENCE: 67
ttctgcccgc cgccgccgct gccgagcgcc gcctttgttc cctgcaggaa gggcgagcgc 60
gcgggccagc gctcagccag cgcctcacga cccttcgtcc tccgctaagc tccaacgctc 120
tgctcgacta gccgcgcgcc ttccggggct ccgcagaccc gcgagatggc accaaggagg 180
aacaacgggc agtgctggtg tctgctgatg ctgctctcgg tctccacgcc cctccctgct 240
gtcacccaga cccgcggtgc gacagagact gcttcccagg gtcacctgga cctcacgcag 300
ctcatcggtg tcccgctgcc ctcgtccgta tcctttgtca caggctatgg tggcttcccg 360
gcctacagtt tcgggcctgg tgccaatgtt ggccgcccag ccaggactct catcccatcc 420
accttcttca gggacttcgc catcagggtc gtggtgaagc ccagcagcac ccgtggtggc 480
gtgctcttcg ccatcactga cgccttccag aaggtcatct acctgggcct gcggctctca 540
ggtgtggagg acggccacca gcggatcatc ctctactaca cggagccagg ctcccatgtg 600
tcccaagaag ctgctgcctt ctcggtgcct gtgatgaccc acaggtggaa ccgcttcgcc 660
atgattgtcc agggtgagga agtgaccctc ctcgtgaact gtgaggagca cagccgcatc 720
cccttccagc ggtcctccca ggctttggct tttgagtcca gcgctggaat cttcatgggc 780
aatgcaggag ctacagggct cgagagattc actggctccc tccagcagct caccgtgcac 840
cccgacccca ggactcccga ggagctgtgt gaccctgaag agtcctcggc atctggagag 900
accagtgggc tgcaggaggc agacggagta gctgagatct tagaagccgt cacctacact 960
caagcctcgc ccaaagaagc aaaagttgaa cccataaaca cacctccaac tccatcctcc 1020
ccctttgaag acatggaact ttctggtgaa cctgtacccg aggggaccct ggaaaccacc 1080
aacatgagca tcatccagca cagcagcccc aaacaagggt ctggtgagat cctgaatgac 1140
acactggagg gggttcattc tgtggatggt gaccccatta ctgacagcgg ctcaggggct 1200
ggggccttcc ttgacattgc tgaagaaaag aatttagcag caacagcagc ggggctggcc 1260
gaggtgccca tcagcactgc tggagaagca gaggccagca gtgtgcccac cgggggacca 1320

-continued

```
accctctcta tgtccacgga gaacccagag gaaggggtca ctccaggtcc agataatgaa   1380
gagcgtttac gagcaacagc agcaggggag gccgaggcac tcgccagcat gcctggggaa   1440
gtggaggcca gtggtgtggc ccccggggag ctggacctct ccatgtccgc ccagagcctc   1500
ggggaagagg ccactgtggg tccaagcagt gaagacagtt taacaacagc tgcagctgca   1560
accgaagtgt ccctcagtac ttttgaggat gaggaagcca gtggggtccc cacagatggc   1620
ctggctcccc tcacagccac catggcccct gagcgggcag tcacttctgg tcctggtgat   1680
gaagaagact tggcagcagc cacaacagag gagcccctca tcacagctgg ggtgaagag   1740
tccggcagcc ctccccctga tgggccaccg ctgcccctgc ccacagtggc tcctgaaaga   1800
tggatcactc cagctcaaag agaacatgtg ggaatgaaag gacaggctgg gcccaaagga   1860
gaaaagggtg atgctgggga ggagcttcct ggccctcctg aaccttctgg gcctgttgga   1920
cccacggcag gagcagaagc agagggctct ggcctaggct ggggctcgga cgtcggctct   1980
ggctctggtg acctggtggg cagtgagcag ctgctgagag gtcctccagg accccccaggg   2040
ccacctggct tacctgggat tccaggaaaa ccaggaactg atgttttcat gggaccccct   2100
ggatctcctg gagaggatgg acctgctggt gaacctgggc cccgggcccc tgagggacag   2160
cctggagttg atggagccac cggccttccc gggatgaaag gggagaaggg agcaagaggg   2220
cctaatggct cagttggtga aaagggtgac cctggcaaca gaggcttacc tggacccccg   2280
gggaaaaagg gacaagctgg ccctcctggg gtcatgggac cccagggcc tcctggaccc   2340
cctgggcccc caggccctgg atgcacaatg ggacttggat tcgaggatac cgaaggctct   2400
ggaagcaccc agctattgaa tgaacccaaa ctctccagac caacggctgc aattggtctc   2460
aaaggagaga aaggagaccg gggacccaag ggagaaaggg ggatggatgg agccagtatt   2520
gtgggacccc ctgggccgag agggccacct gggcacatca aggtcttgtc taattccttg   2580
atcaatatca cccatggatt catgaatttc tcggacattc ctgagctggt ggggcctccg   2640
gggccggacg ggttgcctgg gctgccagga tttccaggtc ctagaggacc aaaaggtgac   2700
actggtttac ctggctttcc aggactaaaa ggagaacagg gcgagaaggg agagccgggt   2760
gccatcctga cagaggacat tcctctggaa aggctgatgg ggaaaaaggg tgaacctgga   2820
atgcatggag ccccaggacc aatggggccc aaaggaccac caggacataa aggagaattt   2880
ggccttcccg ggcgacctgg tcgcccagga ctgaatggcc tcaagggtac caaaggagat   2940
ccaggggtca ttatgcaggg cccacctggc ttacctggcc ctccaggccc ccctgggcca   3000
cctggagctg tgattaacat caaaggagcc attttcccaa tacccgtccg accacactgc   3060
aaaatgccag ttgatactgc tcatcctggg agtccagagc tcatcacttt tcacggtgtt   3120
aaaggagaga aaggatcctg gggtcttcct ggctcaaagg gagaaaaagg cgaccaggga   3180
gcccagggac caccaggtcc tccacttgat ctagcttacc tgagacactt tctgaacaac   3240
ttgaaggggg agaatggaga caaggggttc aaaggtgaaa aaggagaaaa aggagacatt   3300
aatggcagct tccttatgtc tgggcctcca ggcctgcccg gaaatccagg cccggctggc   3360
caaaaagggg agacagtcgt tgggccccaa ggacccccag gtgctcctgg tctgcctggg   3420
ccacctggct ttggaagacc tggtgatcct gggccaccgg ggcccccggg gccaccagga   3480
cctccagcta tcctgggagc agctgtggcc cttccaggtc cccctggccc tccaggacag   3540
ccagggcttc ccggatccag aaacctggtc acagcattca gcaacatgga tgacatgctg   3600
cagaaagcgc atttggttat agaaggaaca ttcatctacc tgagggacag cactgagttt   3660
ttcattcgtg ttagagatgg ctggaaaaaa ttacagctgg gagaactgat ccccattcct   3720
```

```
gccgacagcc ctccaccccc tgcgctttcc agcaacccac atcagcttct gcctccacca   3780
aaccctattt caagtgccaa ttatgagaag cctgctctgc atttggctgc tctgaacatg   3840
ccattttctg ggacattcg agctgatttt cagtgcttca agcaggccag agctgcagga   3900
ctgttgtcca cctaccgagc attcttatct tcccatttgc aagatctgtc caccattgtg   3960
aggaaagcag agagatacag ccttcccata gtgaacctca agggccaagt actttttaat   4020
aattgggact caatttttc tggccacgga ggtcagttca atatgcatat tccaatatac   4080
tcctttgatg gtcgagacat aatgacagat ccttcttggc cccagaaagt catttggcat   4140
ggctccagcc cccatggcgt ccgccttgtg gataactact gtgaagcatg gcgaaccgcg   4200
gacacagcgg tcacgggact tgcctccccg ctgagcacgg ggaagattct ggaccagaaa   4260
gcatacagct gtgctaatcg gctaattgtc ctatgtatcg aaaacagttt catgacagac   4320
gctaggaagt aatggccttc tgatgattct taaagagttt tcaatttttt cttatgtgaa   4380
gagttgacac tgaaatctaa aatgtttaat tgttgtaaat attacagttt tttttttttt   4440
actacatatt ctttacaaca gcaaccaaag aaaacatacc tcaatacact caaaactgaa   4500
gacatagagg actcagatca aagacaaaat ctgatccata tattggtgct agattctgca   4560
ggaaacccca gcagtgtgaa cgcatcccaa cataggttaa gagcaagttg aaaacaaagg   4620
ccagattctg ccactgcatc cttcagacag ttatatcctc cttttaaacc attgttgttg   4680
agtgtaagat gtccttcatg ttttcttata aagtcagtgt ttagaaatgt taccctttct   4740
aagttatata cagatcaaat gctttttttct ttcacgtaca tccatcattt gcaactgctg   4800
ttcgtacaca gaaacaggac tgctcaaatg atcctatttg tattttctga tgctatcaga   4860
ctctaatgtt tttttcccta aaatattatt gccatcatgc tttaggaatt tttatatttt   4920
tacacaatca tattttagta tggtgtctgt ttatgtaact ctgacttgct ggaaaagttg   4980
aaactccaaa taatctgaaa ctagaaaaga aatagcacat aattactacc ttccccttgg   5040
cggctctcct cccccaaccc ccaccccaca attttatgac ttccatttgg caattgttga   5100
attataactg cgactgaaac aaacaggttc atagagatga attttctgag aaacatatat   5160
ctacatgttg tataattgga ttttttttcc atgtaagtga acataaaaac atcttttccg   5220
gg                                                                  5222
```

<210> SEQ ID NO 68
<211> LENGTH: 4079
<212> TYPE: DNA
<213> ORGANISM: Homo sapiens

<400> SEQUENCE: 68

```
ggagcggcgg gcgggcggga gggctggcgg ggcgaacgtc tgggagacgt ctgaaagacc     60
aacgagactt tggagaccag agacgcgcct ggggggacct ggggcttggg gcgtgcgaga    120
tttcccttgc attcgctggg agctcgcgca gggatcgtcc catggccggg gctcggagcc    180
gcgacccttg gggggcctcc gggatttgct acctttttgg ctccctgctc gtcgaactgc    240
tcttctcacg ggctgtcgcc ttcaatctgg acgtgatggg tgccttgcgc aaggagggcg    300
agccaggcag cctcttcggc ttctctgtgg ccctgcaccg gcagttgcag ccccgacccc    360
agagctggct gctggtgggt gctccccagg ccctggctct tcctgggcag caggcgaatc    420
gcactggagg cctcttcgct tgcccgttga gcctggagga gactgactgc tacagagtgg    480
acatcgacca gggagctgat atgcaaaagg aaagcaagga gaaccagtgg ttgggagtca    540
gtgttcggag ccaggggcct gggggcaaga ttgttacctg tgcacaccga tatgaggcaa    600
```

ggcagcgagt ggaccagatc ctggagacgc gggatatgat tggtcgctgc tttgtgctca 660
gccaggacct ggccatccgg gatgagttgg atggtgggga atggaagttc tgtgagggac 720
gcccccaagg ccatgaacaa tttgggttct gccagcaggg cacagctgcc gccttctccc 780
ctgatagcca ctacctcctc tttggggccc caggaaccta taattggaag ggttgcttt 840
ttgtgaccaa cattgatagc tcagaccccg accagctggt gtataaaact ttggaccctg 900
ctgaccggct cccaggacca gccggagact tggccctcaa tagctactta ggcttctcta 960
ttgactcggg gaaaggtctg gtgcgtgcag aagagctgag ctttgtggct ggagcccccc 1020
gcgccaacca caagggtgct gtggttatcc tgcgcaagga cagcgccagt cgcctggtgc 1080
ccgaggttat gctgtctggg gagcgcctga cctccggctt tggctactca ctggctgtgg 1140
ctgacctcaa cagtgatggc tggccagacc tgatagtggg tgccccctac ttctttgagc 1200
gccaagaaga gctggggggt gctgtgtatg tgtacttgaa ccaggggggt cactgggctg 1260
ggatctcccc tctccggctc tgcggctccc ctgactccat gttcgggatc agcctggctg 1320
tcctggggga cctcaaccaa gatggctttc cagatattgc agtgggtgcc ccctttgatg 1380
gtgatgggaa agtcttcatc taccatggga gcagcctggg ggttgtcgcc aaaccttcac 1440
aggtgctgga gggcgaggct gtgggcatca agagcttcgg ctactccctg tcaggcagct 1500
tggatatgga tgggaaccaa taccctgacc tgctggtggg ctccctggct gacaccgcag 1560
tgctcttcag ggccagaccc atcctccatg tctcccatga ggtctctatt gctccacgaa 1620
gcatcgacct ggagcagccc aactgtgctg gcggccactc ggtctgtgtg gacctaaggg 1680
tctgtttcag ctacattgca gtccccagca gctatagccc tactgtggcc ctggactatg 1740
tgttagatgc ggacacagac cggaggctcc ggggccaggt tccccgtgtg acgttcctga 1800
gccgtaacct ggaagaaccc aagcaccagg cctcgggcac cgtgtggctg aagcaccagc 1860
atgaccgagt ctgtggagac gccatgttcc agctccagga aaatgtcaaa gacaagcttc 1920
gggccattgt agtgaccttg tcctacagtc tccagacccc tcggctccgg cgacaggctc 1980
ctggccaggg gctgcctcca gtggccccca tcctcaatgc ccaccagccc agcacccagc 2040
gggcagagat ccacttcctg aagcaaggct gtggtgaaga caagatctgc cagagcaatc 2100
tgcagctggt ccacgcccgc ttctgtaccc gggtcagcga cacggaattc caacctctgc 2160
ccatggatgt ggatggaaca acagccctgt ttgcactgag tgggcagcca gtcattggcc 2220
tggagctgat ggtcaccaac ctgccatcgg acccagccca gccccaggct gatggggatg 2280
atgcccatga agcccagctc ctggtcatgc ttcctgactc actgcactac tcaggggtcc 2340
gggccctgga ccctgcggag aagccactct gcctgtccaa tgagaatgcc tcccatgttg 2400
agtgtgagct ggggaacccc atgaagagag gtgcccaggt caccttctac ctcatcctta 2460
gcacctccgg gatcagcatt gagaccacgg aactggaggt agagctgctg ttggccacga 2520
tcagtgagca ggagctgcat ccagtctctg cacgagcccg tgtcttcatt gagctgccac 2580
tgtccattgc aggaatggcc attccccagc aactcttctt ctctggtgtg gtgaggggcg 2640
agagagccat gcagtctgag cgggatgtgg gcagcaaggt caagtatgag gtcacggttt 2700
ccaaccaagg ccagtcgctc agaaccctgg gctctgcctt cctcaacatc atgtggcctc 2760
atgagattgc caatgggaag tggttgctgt acccaatgca ggttgagctg gagggcgggc 2820
aggggcctgg gcagaaaggg ctttgctctc ccaggcccaa catcctccac ctggatgtgg 2880
acagtaggga taggaggcgg cgggagctgg agccacctga gcagcaggag cctggtgagc 2940
ggcaggagcc cagcatgtcc tggtggccag tgtcctctgc tgagaagaag aaaaacatca 3000
ccctggactg cgcccggggc acggccaact gtgtggtgtt cagctgccca ctctacagct 3060
ttgaccgcgc ggctgtgctg catgtctggg gccgtctctg gaacagcacc tttctggagg 3120
agtactcagc tgtgaagtcc ctggaagtga ttgtccgggc caacatcaca gtgaagtcct 3180
ccataaagaa cttgatgctc cgagatgcct ccacagtgat cccagtgatg gtatacttgg 3240
accccatggc tgtggtggca gaaggagtgc cctggtgggt catcctcctg gctgtactgg 3300
ctgggctgct ggtgctagca ctgctggtgc tgctcctgtg gaagatggga ttcttcaaac 3360
gggcgaagca ccccgaggcc accgtgcccc agtaccatgc ggtgaagatt cctcgggaag 3420
accgacagca gttcaaggag gagaagacgg gcaccatcct gaggaacaac tggggcagcc 3480
cccggcggga gggcccggat gcacacccca tcctggctgc tgacgggcat cccgagctgg 3540
gccccgatgg gcatccaggg ccaggcaccg cctaggttcc catgtcccag cctggcctgt 3600
ggctgccctc catcccttcc ccagagatgg ctccttggga tgaagagggt agagtgggct 3660
gctggtgtcg catcaagatt tggcaggatc ggcttcctca ggggcacaga cctctcccac 3720
ccacaagaac tcctcccacc caacttcccc ttagagtgct gtgagatgag agtgggtaaa 3780
tcagggacag ggccatgggg tagggtgaga agggcagggg tgtcctgatg caaaggtggg 3840
gagaagggat cctaatccct tcctctccca ttcaccctgt gtaacaggac cccaaggacc 3900
tgcctccccg gaagtgcctt aacctagagg gtcggggagg aggttgtgtc actgactcag 3960
gctgctcctt ctctagtttc ccctctcatc tgaccttagt ttgctgccat cagtctagtg 4020
gtttcgtggt ttcgtctatt tattaaaaaa tatttgagaa caaaaaaaaa aaaaaaaaa 4079

<210> SEQ ID NO 69
<211> LENGTH: 6276
<212> TYPE: DNA
<213> ORGANISM: Homo sapiens

<400> SEQUENCE: 69
gagtgtggct gcagtgcgcc gggacaccag ggctccgcgc tccgcactca agaggctccc 60
gcgtcccaac ccctcgcgcc cgcgcgttcg cggatccagg ccgaggaccg aaaggggccg 120
cccgagcccc cggggccggc gcccagagag cccagcaagg ccggccgccc tgccggtgtg 180
ccgccggcgg gtgcttctgg aagggccaat gcgttcgggc agcagccctg aagccgagcc 240
cgaggctaag tgggactgac cggggcccag agtggacgaa ccgccagcat ggggagagac 300
cagcgcgcgg tggccggccc tgccctacgg cggtggctgc tgctggggac agtgaccgtg 360
gggttcctcg cccagagcgt cttggcgggt gtgaagaagt ttgatgtgcc gtgtggagga 420
agagattgca gtgggggctg ccagtgctac cctgagaaag gtggacgtgg tcagcctggg 480
ccagtgggcc cccaggggta caatgggcca ccaggattac aaggattccc cgggctgcag 540
ggacgtaaag gagacaaggg tgaaagggga gcccccggag taacaggacc caagggcgac 600
gtgggagcaa gaggcgtttc tggattccct ggtgccgatg gaattcctgg acacccgggg 660
caaggtgggc ccaggggaag gccgggctac gatggctgca acggaaccca gggagactca 720
ggtccacagg ggcccccggg ctctgagggg ttcaccgggc ctcccgggcc ccaaggacca 780
aaagggcaga aaggtgagcc ttatgcactg cctaaagagg agcgcgacag atatcggggt 840
gaacctggag agcctggatt ggtcggtttc cagggacctc ccggccgccc tgggcatgtg 900
ggacagatgg gtccagttgg agctccaggg agaccaggac cacctggacc ccctggacca 960
aaaggacagc aaggcaacag aggacttggt ttctacggag ttaagggtga aaagggtgac 1020
gtagggcagc cgggacccaa cgggattcca tcagacaccc tccaccccat catcgcgccc 1080

-continued

```
acaggagtca ccttccaccc agatcagtac aagggtgaaa aaggcagtga gggggaacca   1140
ggaataagag gcatttcctt gaagggagaa gaaggaatca tgggctttcc tggacttagg   1200
ggttaccctg gcttgagtgg tgaaaaagga tcaccaggac agaagggaag ccgaggcctg   1260
gatggctatc aagggcctga tggaccccgg ggacctaagg gagaagccgg agacccaggg   1320
ccccctggac tacctgccta ctcccctcac ccttccctag caaaaggtgc cagaggtgac   1380
ccaggattcc caggggccca aggggagcca ggaagccagg gtgagccagg agacccgggc   1440
ctcccaggtc cccctggcct ctccattgga gatggagatc agaggagagg cctgccgggt   1500
gagatgggac ccaagggctt catcggagac cccggcatcc ctgcgctcta cgggggccca   1560
cctggacctg atggaaagcg agggcctcca ggacccccg ggctccctgg accacctgga   1620
cctgatggct tcctgtttgg gctgaaagga gcaaaaggaa gagcaggctt ccctgggctt   1680
cccggctccc ctggagcccc cggaccaaag ggtggaaag gtgacgctgg ggaatgcaga   1740
tgtacagaag gcgacgaagc tatcaaaggt cttccaggac tgccaggacc caagggcttc   1800
gcaggcatca acggggagcc ggggaggaaa ggggacaaag gagaccccgg ccaacacggc   1860
ctccctgggt tcccagggct caagggagtg cctggcaaca ttggtgctcc cggacccaaa   1920
ggagcaaaag gagattccag aacaatcaca accaaaggtg agcggggaca gcccggcgtc   1980
ccaggtgtgc ccgggatgaa aggtgacgat ggcagcccag gccgcgatgg gctcgatgga   2040
ttccccggcc tcccaggccc tcccggtgat ggcatcaagg gccctccagg ggacccaggt   2100
tatccaggaa tacctggaac gaagggtact ccaggagaaa tgggcccccc aggactgggc   2160
cttcccggcc tcaaaggcca acgtggtttc cctggagacg ccggcttacc tggaccacca   2220
ggcttcctgg gccctcctgg ccccgcaggg accccaggac aaatagattg tgacacagat   2280
gtgaaaaggg ccgttggagg tgacagacag gaggccatcc agccaggttg cataggaggg   2340
cccaagggat tgccaggcct gccaggaccc ccaggcccca caggtgccaa aggcctccga   2400
ggaatcccag gcttcgcagg agctgatgga ggaccagggc ccaggggctt gccaggagac   2460
gcaggtcgtg aagggttccc aggaccccca gggttcatag gaccccgagg atccaaaggt   2520
gcagtgggcc tccctggccc agatggatcc ccaggtccca tcggcctgcc agggccagat   2580
gggcccccctg gggaaagggg cctccctgga gaagtcctgg gagctcagcc cgggccacgg   2640
ggagatgctg gtgtgcctgg acagcctggg cttaaaggcc ttcccggaga cagaggcccc   2700
cctggattca gaggaagcca agggatgcct gggatgccag ggctgaaggg ccagccaggc   2760
ctcccaggac cttccggcca gccaggcctg tatgggcctc caggactgca tggattccca   2820
ggagctcctg gccaagaggg gcccttgggg ctgccaggaa tcccaggccg tgaaggtctg   2880
cctggtgata gaggggaccc tggggacaca ggcgctcctg gccctgtggg catgaaaggt   2940
ctctctggtg acagaggaga tgctggcttc acaggggagc aaggccatcc aggaagccct   3000
ggatttaaag gaattgatgg aatgcctggg acccccgggc taaaaggaga tagaggctca   3060
cctgggatgg atggtttcca aggcatgcct ggactcaaag ggagacccgg gtttccaggg   3120
agcaaaggcg aggctggatt tttcggaata cccggtctga agggtctggc tggtgagcca   3180
ggttttaaag gcagccgagg ggaccctggg cccccaggac cacctcctgt catcctgcca   3240
ggaatgaaag acattaaagg agagaaagga gatgaagggc ctatggggct gaaaggatac   3300
ctgggcgcaa aaggtatcca aggaatgcca ggcatcccag ggctgtcagg aatccctggg   3360
ctgcctggga ggcccggcca catcaaagga gtcaagggag acatcggagt ccccggcatc   3420
cccggtttgc caggattccc tggggtggct ggcccccctg gaattacggg attcccagga   3480
```

```
ttcataggaa gccggggtga caaaggtgcc ccagggagag caggcctgta tggcgagatt   3540
ggcgcgactg gtgatttcgg tgacatcggg gacactataa atttaccagg aagaccaggc   3600
ctgaaggggg agcggggcac cactggaata ccaggtctga agggattctt tggagagaag   3660
ggaacagaag gtgacatcgg cttccctggg ataacaggcg tgactggagt ccaaggccct   3720
cctggactta aaggacaaac aggctttcca gggctgactg ggcctccagg gtcgcaggga   3780
gagctggggc ggattggact gcctggtggc aaaggagatg atggctggcc gggagctccg   3840
ggcttaccag gttttccggg actccgtggg atccgcggct tacacggctt gccaggcacc   3900
aagggctttc caggatcccc aggttctgac atccacggag acccaggctt cccaggccct   3960
cctggggaaa gaggtgaccc aggagaggcc aacacccttc caggccctgt gggagtccca   4020
ggacagaaag gagaccaagg agctccaggg gaacgaggcc cacctgggag cccaggactt   4080
caggggttcc caggcatcac accccccttcc aacatctctg gggcacctgg tgacaaaggg   4140
gcgccaggga tatttggcct gaaaggttat cggggcccac cagggccacc aggttctgct   4200
gctcttcctg gaagcaaagg tgacacaggg aacccaggag ctccaggaac cccagggacc   4260
aaaggatggg ccggggactc cgggccccag ggcaggcctg gtgtgtttgg tctcccagga   4320
gaaaaagggc ccaggggtga acaaggcttc atggggaaca ctggacccac cggggcggtg   4380
ggcgacagag gccccaaggg acccaaggga gacccaggat tccctggtgc cccccgggact   4440
gtgggagccc ccgggattgc aggaatcccc cagaagattg ccgtccaacc agggacagtg   4500
ggtccccagg ggaggcgagg ccccccctggg gcaccggggg agatggggcc ccagggcccc   4560
cccggagaac caggttttcg tggggctcca gggaaagctg ggccccaagg aagaggtggt   4620
gtgtctgctg ttcccggctt ccggggagat gaaggaccca taggccacca ggggccgatt   4680
ggccaagaag gtgcaccagg ccgtccaggg agcccgggcc tgccgggtat gccaggccgc   4740
agcgtcagca tcggctacct cctggtgaag cacagccaga cggaccagga gcccatgtgc   4800
ccggtgggca tgaacaaact ctggagtgga tacagcctgc tgtacttcga gggccaggag   4860
aaggcgcaca accaggacct ggggctggcg ggctcctgcc tggcgcggtt cagcaccatg   4920
cccttcctgt actgcaaccc tggtgatgtc tgctactatg ccagccggaa cgacaagtcc   4980
tactggctct ctaccactgc gccgctgccc atgatgcccg tggccgagga cgagatcaag   5040
ccctacatca gccgctgttc tgtgtgtgag gccccggcca tcgccatcgc ggtccacagt   5100
caggatgtct ccatcccaca ctgcccagct gggtggcgga gtttgtggat cggatattcc   5160
ttcctcatgc acacggcggc gggagacgaa ggcggtggcc aatcactggt gtcaccgggc   5220
agctgtctag aggacttccg cgccacacca ttcatcgaat gcaatggagg ccgcggcacc   5280
tgccactact acgccaacaa gtacagcttc tggctgacca ccattcccga gcagagcttc   5340
cagggctcgc cctccgccga cacgctcaag gccggcctca tccgcacaca catcagccgc   5400
tgccaggtgt gcatgaagaa cctgtgagcc ggcgcgtgcc aggaagggcc attttggtgc   5460
ttattcttaa cttattacct caggtgccaa cccaaaaatt ggctttattt ttttcttaaa   5520
aaaaaaaaag tctaccaaag gaatttgcat ccagcagcag cacttagacc tgccagccac   5580
tgtcaccgag cgggtgcaag cactcggggt ccctggaggg caagccctgc ccacagaaag   5640
ccaggagcag ccctggcccc catcagccct gctagacgca ccgcctgaag gcacagctaa   5700
ccacttcgca cacacccatg taaccactgc actttccaat gccacagaca actcacattg   5760
ttcaactccc ttctcggggt gggacagacg agacaacagc acacaggcag ccagccgtgg   5820
ccagaggctc gaggggctca ggggctcagg cacccgtccc cacacgaggg ccccgtgggt   5880
```

```
gggcctggcc ctgctttcta cgccaatgtt atgccagctc catgttctcc caaataccgt   5940

tgatgtgaat tattttaaag gcaaaaccgt gctctttatt ttagaaaaca ctgataatca   6000

cactgcggta ggtcattctt ttgccacatc cctatagacc actgggtttg gcaaaactca   6060

ggcagaagtg gagacccttc tagacatcac tgtcagcctt gctacttgaa ggtacacccc   6120

atagggtcgg aggtgctgtc cccactgccc cacgttgtcc ctgagattta acccctccac   6180

tgctgggggt gagctgtact cttctgactg ccccctcctg tgtaacgact acaaaataaa   6240

acttggttct gaatattttt aaaaaaaaaa aaaaaa                             6276
```

<210> SEQ ID NO 70
<211> LENGTH: 1018
<212> TYPE: DNA
<213> ORGANISM: Homo sapiens

<400> SEQUENCE: 70

```
ggcacgaggc tcaagattca cagcatctca gacgcagcct aggttcccat ggacttgtca     60

taagacaaaa gaggacagct gtgctgaggg ggcagggtct gcagcctcct ggctgtgcca    120

ggaccacacc taccaaggcc gcaccaggat gtcggacacc gaggagcagg aatatgagga    180

ggagcagccg gaagaggagg ctgcggagga ggaggaggaa gaagaggaac gccccaaacc    240

aagccgcccc gtggtgcctc ctttgatccc gccaaagatc ccagaagggg agcgcgttga    300

cttcgatgac atccaccgca agcgcatgga gaaagacctg ctggagctgc agacactcat    360

cgatgtacat ttcgagcagc ggaagaagga ggaagaggag ctggttgcct tgaaggagcg    420

cattgagcgg cgccggtcag agagagccga gcaacagcgc ttcagaactg agaaggaacg    480

cgaacgtcag gctaagctgg cggaggagaa gatgaggaag gaagaggaag aggccaagaa    540

gcgggcagag gatgatgcca agaaaaagaa ggtgctgtcc aacatggggg cccattttgg    600

cggctacctg gtcaaggcag aacagaagcg tggtaagcgg cagacggggc gggagatgaa    660

ggtgcgcatc ctctccgagc gtaagaagcc tctggacatt gactacatgg gggaggaaca    720

gctccgggag aaagcccagg agctgtcgga ctggatccac cagctggagt ctgagaagtt    780

cgacctgatg gcgaagctga aacagcagaa atatgagatc aacgtgctgt acaaccgcat    840

cagccacgcc cagaagttcc ggaagggggc agggaagggc cgcgttggag gccgctggaa    900

gtgaggatgc cgccccggac agtggcacct gggaagcctg ggagtgtttg tcccatcggt    960

agcttgaaat aaacgctccc ctcagacact caaaaaaaaa aaaaaaaaaa aaaaaaaa     1018
```

<210> SEQ ID NO 71
<211> LENGTH: 2895
<212> TYPE: DNA
<213> ORGANISM: Homo sapiens

<400> SEQUENCE: 71

```
ccgaggagcg ctcgggctgt ctgcggaccc tgccgcgtgc aggggtcgcg gccggctgga     60

gctgggagtg aggcggcgga ggagccaggt gaggaggagc caggaaggca gttggtggga    120

agtccagctt gggtccctga gagctgtgag aaggagatgc ggctgctgct ggccctgttg    180

ggggtcctgc tgagtgtgcc tgggcctcca gtcttgtccc tggaggcctc tgaggaagtg    240

gagcttgagc cctgcctggc tcccagcctg gagcagcaag agcaggagct gacagtagcc    300

cttgggcagc ctgtgcggct gtgctgtggg cgggctgagc gtggtggcca ctggtacaag    360

gagggcagtc gcctggcacc tgctggccgt gtacggggct ggaggggccg cctagagatt    420

gccagcttcc tacctgagga tgctggccgc tacctctgcc tggcacgagg ctccatgatc    480
```

-continued

```
gtcctgcaga atctcacctt gattacaggt gactccttga cctccagcaa cgatgatgag    540
gaccccaagt cccataggga cctctcgaat aggcacagtt acccccagca agcaccctac    600
tggacacacc cccagcgcat ggagaagaaa ctgcatgcag tacctgcggg gaacaccgtc    660
aagttccgct gtccagctgc aggcaacccc acgcccacca tccgctggct taaggatgga    720
caggcctttc atggggagaa ccgcattgga ggcattcggc tgcgccatca gcactggagt    780
ctcgtgatgg agagcgtggt gccctcggac cgcggcacat acacctgcct ggtagagaac    840
gctgtgggca gcatccgcta taactacctg ctagatgtgc tggagcggtc cccgcaccgg    900
cccatcctgc aggccgggct cccggccaac accacagccg tggtgggcag cgacgtggag    960
ctgctgtgca aggtgtacag cgatgcccag ccccacatcc agtggctgaa gcacatcgtc   1020
atcaacggca gcagcttcgg agccgacggt ttcccctatg tgcaagtcct aaagactgca   1080
gacatcaata gctcagaggt ggaggtcctg tacctgcgga acgtgtcagc cgaggacgca   1140
ggcgagtaca cctgcctcgc aggcaattcc atcggcctct cctaccagtc tgcctggctc   1200
acggtgctgc caggtactgg gcgcatcccc cacctcacat gtgacagcct gactccagca   1260
ggcagaacca agtctcccac tttgcagttc tccctggagt caggctcttc cggcaagtca   1320
agctcatccc tggtacgagg cgtgcgtctc tcctccagcg gccccgcctt gctcgccggc   1380
ctcgtgagtc tagatctacc tctcgaccca ctatgggagt tcccccggga caggctggtg   1440
cttgggaagc ccctaggcga gggctgcttt ggccaggtag tacgtgcaga ggcctttggc   1500
atggaccctg cccggcctga ccaagccagc actgtggccg tcaagatgct caaagacaac   1560
gcctctgaca aggacctggc cgacctggtc tcggagatgg aggtgatgaa gctgatcggc   1620
cgacacaaga acatcatcaa cctgcttggt gtctgcaccc aggaagggcc cctgtacgtg   1680
atcgtggagt gcgccgccaa gggaaacctg cgggagttcc tgcgggcccg gcgcccccca   1740
ggccccgacc tcagccccga cggtcctcgg agcagtgagg ggccgctctc cttcccagtc   1800
ctggtctcct gcgcctacca ggtggcccga ggcatgcagt atctggagtc ccggaagtgt   1860
atccaccggg acctggctgc ccgcaatgtg ctggtgactg aggacaatgt gatgaagatt   1920
gctgactttg ggctggcccg cggcgtccac cacattgact actataagaa aaccagcaac   1980
ggccgcctgc ctgtgaagtg gatggcgccc gaggccttgt ttgaccgggt gtacacacac   2040
cagagtgacg tgtggtcttt tgggatcctg ctatgggaga tcttcaccct cgggggctcc   2100
ccgtatcctg gcatcccggt ggaggagctg ttctcgctgc tgcgggaggg acatcggatg   2160
gaccgacccc cacactgccc cccagagctg tacgggctga tgcgtgagtg ctggcacgca   2220
gcgccctccc agaggcctac cttcaagcag ctggtggagg cgctggacaa ggtcctgctg   2280
gccgtctctg aggagtacct cgacctccgc ctgaccttcg gaccctattc cccctctggt   2340
ggggacgcca gcagcacctg ctcctccagc gattctgtct tcagccacga cccccctgcca  2400
ttgggatcca gctccttccc cttcgggtct ggggtgcaga catgagcaag gctcaaggct   2460
gtgcaggcac ataggctggt ggccttgggc cttggggctc agccacagcc tgacacagtg   2520
ctcgaccttg atagcatggg gcccctggcc cagagttgct gtgccgtgtc caagggccgt   2580
gcccttgccc ttggagctgc cgtgcctgtg tcctgatggc ccaaatgtca gggttctgct   2640
cggcttcttg gaccatggcg cttagtcccc atcccgggtt tggctgagcc tggctggaga   2700
gctgctatgc taaacctcct gcctcccaat accagcagga ggttctgggc ctctgaaccc   2760
cctttcccca cacctccccc tgctgctgct gccccagcgt cttgacggga gcattggccc   2820
ctgagcccag agaagctgga agcctgccga aaacaggagc aaatggcgtt ttataaatta   2880
```

tttttttgaa ataaa 2895

<210> SEQ ID NO 72
<211> LENGTH: 1356
<212> TYPE: DNA
<213> ORGANISM: Homo sapiens

<400> SEQUENCE: 72
ttctcccgca accttccctt cgctccctcc cgtccccccc agctcctagc ctccgactcc 60 ctcccccccct cacgcccgcc ctctcgcctt cgccgaacca aagtggatta attacacgct 120
ttctgtttct ctccgtgctg ttctctcccg ctgtgcgcct gcccgcctct cgctgtcctc 180 tctcccccctc gccctctctt cggccccccc ctttcacgtt cactctgtct ctcccactat 240
ctctgccccc ctctatcctt gatacaacag ctgacctcat ttcccgatac cttttccccc 300
ccgaaaagta caacatctgg cccgccccag cccgaagaca gcccgtcctc cctggacaat 360
cagacgaatt ctcccccccc ccccaaaaaa aaaagccatc cccccgctct gccccgtcgc 420
acattcggcc cccgcgactc ggccagagcg gcgctggcag aggagtgtcc ggcaggaggg 480
ccaacgcccg ctgttcggtt tgcgacacgc agcagggagg tgggcggcag cgtcgccggc 540
ttccagacac caatgggaat cccaatgggg aagtcgatgc tggtgcttct caccttcttg 600
gccttcgcct cgtgctgcat tgctgcttac cgcccccagtg agaccctgtg cggcggggag 660
ctggtggaca ccctccagtt cgtctgtggg gaccgcggct tctacttcag caggcccgca 720
agccgtgtga gccgtcgcag ccgtggcatc gttgaggagt gctgtttccg cagctgtgac 780
ctggccctcc tggagacgta ctgtgctacc cccgccaagt ccgagaggga cgtgtcgacc 840
cctccgaccg tgcttccgga caacttcccc agataccccg tgggcaagtt cttccaatat 900
gacacctgga agcagtccac ccagcgcctg cgcaggggcc tgcctgccct cctgcgtgcc 960
cgccggggtc acgtgctcgc caaggagctc gaggcgttca gggaggccaa acgtcaccgt 1020
cccctgattg ctctacccac ccaagacccc gcccacgggg gcgccccccc agagatggcc 1080
agcaatcgga agtgagcaaa actgccgcaa gtctgcagcc cggcgccacc atcctgcagc 1140
ctcctcctga ccacggacgt ttccatcagg ttccatcccg aaaatctctc ggttccacgt 1200
ccccctgggg cttctcctga cccagtcccc gtgccccgcc tccccgaaac aggctactct 1260
cctcggcccc ctccatcggg ctgaggaagc acagcagcat cttcaaacat gtacaaaatc 1320
gattggcttt aaacaccctt cacataccct cccccc 1356

<210> SEQ ID NO 73
<211> LENGTH: 2281
<212> TYPE: DNA
<213> ORGANISM: Homo sapiens

<400> SEQUENCE: 73
aaacaataag catatctaag caactacgat atctgtatgg atcaggccaa agtcccgcta 60
agattctcca atgttttcat ggtctgagcc cccctcctgt tcccatctcc actgcccctc 120
ggccctgtct gtgccctgcc tctcagagga gggggctcag atggtgcggc ctgagtgtgc 180
ggccggcggc atttgggata cacccgtagg gtgggcgggg tgtgtcccag gcctaattcc 240
atctttccac catgacagag atgcccttgt gaggctggcc tccttggcgc ctgtccccac 300
ggcccccgca gcgtgagcca cgatgctccc cataccccac ccattcccga tacaccttac 360
ttactgtgtg ttggcccagc cagagtgagg aaggagtttg gccacattgg agatggcggt 420
agctgagcag acatgccccc acgagtagcc tgactccctg gtgtgctcct ggaaggaaga 480

```
tcttggggac ccccccaccg gagcacacct agggatcatc tttgcccgtc tcctggggac    540

cccccaagaa atgtggagtc ctcgggggcc gtgcactgat gcggggagtg tgggaagtct    600

ggcggttgga ggggtgggtg gggggcagtg ggggctgggc ggggggagtc ctggggtagg    660

aagtggtccc gggagatttt ggatggaaaa gtcaggagga ttgacagcag acttgcagaa    720

ttacatagag aaattaggaa cccccaaatt tcatgtcaat tgatctattc cccctctttg    780

tttcttgggg catttttcct tttttttttt tttgtttttt ttttacccct ccttagcttt    840

atgcgctcag aaaccaaatt aaaccccccc cccatgtaac aggggggcag tgacaaaagc    900

aagaacgcac gaagccagcc tggagaccac cacgtcctgc cccccgccat ttatcgccct    960

gattggattt tgtttttcat ctgtccctgt tgcttgggtt gagttgaggg tggagcctcc   1020

tggggggcac tggccactga gccccccttgg agaagtcaga ggggagtgga gaaggccact   1080

gtccggcctg gcttctgggg acagtggctg gtccccagaa gtcctgaggg cggagggggg   1140

ggttgggcag ggtctcctca ggtgtcagga gggtgctcgg aggccacagg agggggctcc   1200

tggctggcct gaggctggcc ggagggggaag gggctagcag gtgtgtaaac agagggttcc   1260

atcaggctgg ggcagggtgg ccgccttccg cacacttgag gaaccctccc ctctccctcg   1320

gtgacatctt gcccgcccct cagcaccctg ccttgtctcc aggaggtccg aagctctgtg   1380

ggacctcttg gggggcaaggt ggggtgaggc cggggagtag ggaggtcagg cgggtctgag   1440

cccacagagc aggagagctg ccaggtctgc ccatcgacca ggttgcttgg gccccggagc   1500

ccacgggtct ggtgatgcca tagcagccac caccgcggcg cctagggctg cggcagggac   1560

tcggcctctg ggaggtttac ctcgccccca cttgtgcccc cagctcagcc cccctgcacg   1620

cagcccgact agcagtctag aggcctgagg cttctgggtc ctggtgacgg ggctggcatg   1680

accccggggg tcgtccatgc cagtccgcct cagtcgcaga gggtccctcg gcaagcgccc   1740

tgtgagtggg ccattcggaa cattggacag aagcccaaag agccaaattg tcacaattgt   1800

ggaacccaca ttggcctgag atccaaaacg cttcgaggca ccccaaatta cctgcccatt   1860

cgtcaggaca cccacccacc cagtgttata ttctgcctcg ccggagtggg tgttcccggg   1920

ggcacttgcc gaccagcccc ttgcgtcccc aggtttgcag ctctcccctg ggccactaac   1980

catcctggcc cgggctgcct gtctgacctc cgtgcctagt cgtggctctc catcttgtct   2040

cctccccgtg tccccaatgt cttcagtggg gggcccccctc ttgggtcccc tcctctgcca   2100

tcacctgaag acccccacgc caaacactga atgtcacctg tgcctgccgc ctcggtccac   2160

cttgcggccc gtgtttgact caactcagct cctttaacgc taatatttcc ggcaaaatcc   2220

catgcttggg ttttgtcttt aaccttgtaa cgcttgcaat cccaataaag cattaaaagt   2280

c                                                                   2281
```

<210> SEQ ID NO 74
<211> LENGTH: 1124
<212> TYPE: DNA
<213> ORGANISM: Homo sapiens

<400> SEQUENCE: 74

```
cgggaaacct gcactgactt ttttctcctt ttggagggag agcagagacc atgtctgaca     60

tagaagaggt ggtggaagag tacgaggagg aggagcagga agaagcagct gttgaagagc    120

aggaggaggc agcggaagag gatgctgaag cagaggctga gaccgaggag accagggcag    180

aagaagatga agaagaagag gaagcaaagg aggctgaaga tggcccaatg gaggagtcca    240

aaccaaagcc caggtcgttc atgcccaact tggtgcctcc caagatcccc gatggagaga    300
```

gagtggactt tgatgacatc caccggaagc gcatggagaa ggacctgaat gagttgcagg 360
cgctgattga ggctcacttt gagaacagga agaaagagga ggaggagctc gtttctctca 420
aagacaggat cgagagacgt cgggcagagc gggccgagca gcagcgcatc cggaatgagc 480
gggagaagga gcggcagaac cgcctggctg aagagagggc tcgacgagag gaggaggaga 540
acaggaggaa ggctgaggat gaggcccgga agaagaaggc tttgtccaac atgatgcatt 600
ttgggggtta catccagaag caggcccaga cagagcggaa aagtgggaag aggcagactg 660
agcgggaaaa gaagaagaag attctggctg agaggaggaa ggtgctggcc attgaccacc 720
tgaatgaaga tcagctgagg gagaaggcca aggagctgtg gcagagcatc tataacttgg 780
aggcagagaa gttcgacctg caggagaagt tcaagcagca gaaatatgag atcaatgttc 840
tccgaaacag gatcaacgat aaccagaaag tctccaagac ccgcgggaag gctaaagtca 900
ccgggcgctg gaaatagagc ctggcctcct tcaccaaaga tctgctcctc gctcgcacct 960
gcctccggcc tgcactcccc cagttcccgg gccctcctgg gcaccccagg cagctcctgt 1020
ttggaaatgg ggagctggcc taggtgggag ccaccactcc tgcctgcccc cacacccact 1080
ccacaccagt aataaaaagc caccacacac tgaaaaaaaa aaaa 1124

<210> SEQ ID NO 75
<211> LENGTH: 855
<212> TYPE: DNA
<213> ORGANISM: Homo sapiens

<400> SEQUENCE: 75
atctcatctc ccagacgcca cgtctctcgg tttcttctta gatcactcct ctgccaaaga 60
tcccaacaag acaacatggc tcccaagaag cctgagccta agaaggaggc agccaagcca 120
gctccagctc cagctccagc ccctgcacca gcccctgccc cagctcctga ggctcccaag 180
gaacctgcct ttgaccccaa gagtgtaaag atagacttca ctgccgacca gattgaagag 240
ttcaaagagg ccttttcatt gtttgaccgg accccgactg gagagatgaa gatcacctac 300
ggccagtgcg gggatgtact gcgggccctg ggccagaacc ctaccaatgc cgaggtgctg 360
cgtgtgctgg gcaagcccaa gcctgaagag atgaatgtca agatgctgga ctttgagacg 420
ttcttgccca tcctgcagca catttcccgc aacaaggagc agggcaccta tgaggacttc 480
gtggagggcc tgcgtgtctt tgacaaggag agcaatggca cggtcatggg tgctgagctt 540
cggcacgtcc ttgccaccct gggagagaag atgactgagg ctgaagtgga gcagctgtta 600
gctgggcaag aggatgccaa tggctgcatc aattatgaag cctttgtcaa gcacatcatg 660
tcagggtgaa gcagagtctt ccaggtgcct ggcccttggc tttagccata ccagggtgag 720
ttaaagagag gccccggctg ggtgagctga gatggagtcc tcgacttatc accacaccac 780
tgccccaagg accttacagg ccctccctgt taataaacag ctctaacacg gccaggctgg 840
gctctgggat tctga 855

<210> SEQ ID NO 76
<211> LENGTH: 1404
<212> TYPE: DNA
<213> ORGANISM: Homo sapiens

<400> SEQUENCE: 76
gccgggcagc catggctgag acactcttct ggactcctct cctcgtggtt ctcctggcag 60
ggctggggga caccgaggcc cagcagacca cgctacaccc acttgtgggc cgtgtctttg 120
tgcacacctt ggaccatgag acgtttctga gccttcctga gcatgtcgct gtcccacccg 180

```
ctgtccacat cacctaccac gcccacctcc agggacaccc agacctgccc cggtggctcc    240

gctacaccca gcgcagcccc caccaccctg gcttcctcta cggctctgcc accccagaag    300

atcgtgggct ccaggtcatt gaggtcacag cctacaatcg ggacagcttt gataccactc    360

ggcagaggct ggtgctggag attggggacc cagaaggccc cctgctgcca taccaagccg    420

agttcctggt gcgcagccac gatgcggagg aggtgctgcc ctcaacacct gccagccgct    480

tcctctcagc cttgggggga ctctgggagc ccggagagct tcagctgctc aacgtcacct    540

ctgccttgga ccgtgggggc cgtgtccccc ttcccattga gggccgaaaa gaaggggtat    600

acattaaggt gggttctgcc tcaccttttt ctacttgcct gaagatggtg gcatccccccg    660

atagccacgc ccgctgtgcc cagggccagc ctccacttct gtcttgctac gacaccttgg    720

caccccactt ccgcgttgac tggtgcaatg tgaccctggt ggataagtca gtgccggagc    780

ctgcagatga ggtgcccacc ccaggtgatg ggatcctgga gcatgacccg ttcttctgcc    840

cacccactga ggccccagac cgtgacttct tggtggatgc tctggtcacc ctcctggtgc    900

ccctgctggt ggccctgctt ctcaccttgc tgctggccta tgtcatgtgc tgccggcggg    960

agggaaggct gaagagagac ctggctacct ccgacatcca gatggtccac cactgcacca   1020

tccacgggaa cacagaggag ctgcggcaga tggcggccag ccgcgaggtg ccccggccac   1080

tctccaccct gcccatgttc aatgtgcaca caggtgagcg gctgcctccc cgcgtggaca   1140

gcgcccaggt gcccctcatt ctggaccagc actgacagcc cagccagtgg ttccaggtcc   1200

agccctgact tcatcctccc ttctctgtcc acaccacgag tggcacatcc cacctgctga   1260

ttccagctcc tggccctcct ggaacccagg ctctaaacaa gcagggagag gggtggggt   1320

ggggtgagag tgtgtggagt aaggacattc agaataaata tctgctgctc tgctcaccaa   1380

ttgctgctgg cagcctctcc cgtc                                          1404
```

<210> SEQ ID NO 77
<211> LENGTH: 1610
<212> TYPE: DNA
<213> ORGANISM: Homo sapiens

<400> SEQUENCE: 77

```
gcatcagaaa ccagcacacc agagcaccag ggcgggggc ttctccgcag caagtttcca      60

aacaagccct cagtgaacat cattgaagcg tgactgcctg tctgcaggga gaaggattcc    120

atttttcttc tcagctggtc cccaggccca cgggcacagg gagagggaca actgcagcag    180

tggggaggag gcacagctag ctgcacagtt ctctcttctc cttgtcctag tcagatgaag    240

gaggctgcac tacaaaccca aattctgcaa aaaaaataaa aataagccac aaaactaaaa    300

ggcctggccc cattctggaa aaggcaaagc tgcatgagac acagccttct gcctcctcgc    360

ctctcctgga ctggcttcct ctttgagaaa atgcacaaag ccctgggaga tgacaagcac    420

aaggactgac tcaagctgtg tctttcagac caaggaacat cagagaagct gtggggctgc    480

ctgccaggca ggatcatggc tgccatcaag ccttttctgg atccagccat caaggacatg    540

tttgtggtgt gatgcacact tttgcaagcg tgtaagatgt tacctggttt gtctcttttg    600

gaaaacaaaa atcagaaggc tgcattctag agggcagaga aattcccccg aagactgagc    660

tggttgcctg catcctctat cttctttgac ccttatgact gaaagatcat cagtttggaa    720

ggtactggtc caatttattt aggaagtatc tcttggagtt tcagaaatgc tagcttggac    780

aactgaaaag tcacatcaca gctggcattc tgggggctac caaaacaccc cttctggagt    840

agaagctgct ggaaggcagg cctgagccat tcaccacgga caggaagagc agctctggct    900
```

atcaccactg gcctctgggg tcttcatatc ttgccatctc atccagggtt ccatgaaagt 960
tacccagggt cctcatgtcc ttccttagag cctgagtggt gtgaggtgac aggtctctct 1020
ctccactgcc cctttctggt ttaaaaaaat ggtgcttgat gagggaaggt agactcttcc 1080
ctaggactga cgagttacgg ctgccagatg cctgcatggg aagaggtgga catctgcatc 1140
ttccattggt ggtcaaggat gggtgtggga gaaccacacc tagtgcaagc ctggtactca 1200
gtaaatattt gttgaaatga atgataagag cattggtccc caagccagag agccagaagc 1260
catcacccaa tgaccgcccc ttccttccgg tctacaagag ctctcaaggc tgggtctgcc 1320
accactctgc tttgcccaag tgtgacagca ctggggagga gagacaggat aaagggcaga 1380
tgtcagcaat actaagggct tcctcatggg agggcatgag gctccactca ttgtcttgtg 1440
acttccatcc ctgctgaatg gggctgcaag gccaaggctc cttaggggag aggtccttac 1500
ctctgatcca cttagagcaa taaccacttt ttaaatgtaa aataaaaaga caaatgaaaa 1560
ggcaaaaaaa aaaaaaaaaa aaaaaaaaaa aaaaaaaaaa aaaaaaaaaa 1610

<210> SEQ ID NO 78
<211> LENGTH: 1356
<212> TYPE: DNA
<213> ORGANISM: Homo sapiens

<400> SEQUENCE: 78
ttctcccgca accttccctt cgctccctcc cgtccccccc agctcctagc ctccgactcc 60
ctccccccct cacgcccgcc ctctcgcctt cgccgaacca aagtggatta attacacgct 120
ttctgtttct ctccgtgctg ttctctcccg ctgtgcgcct gcccgcctct cgctgtcctc 180
tctccccctc gccctctctt cggccccccc ctttcacgtt cactctgtct ctcccactat 240
ctctgccccc ctctatcctt gatacaacag ctgacctcat ttcccgatac cttttccccc 300
ccgaaaagta caacatctgg cccgccccag cccgaagaca gcccgtcctc cctggacaat 360
cagacgaatt ctcccccccc ccccaaaaaa aaaagccatc cccccgctct gccccgtcgc 420
acattcggcc cccgcgactc ggccagagcg gcgctggcag aggagtgtcc ggcaggaggg 480
ccaacgcccg ctgttcggtt tgcgacacgc agcagggagg tgggcggcag cgtcgccggc 540
ttccagacac caatgggaat cccaatgggg aagtcgatgc tggtgcttct caccttcttg 600
gccttcgcct cgtgctgcat tgctgcttac cgcccccagtg agaccctgtg cggcggggag 660
ctggtggaca ccctccagtt cgtctgtggg gaccgcggct tctacttcag caggcccgca 720
agccgtgtga gccgtcgcag ccgtggcatc gttgaggagt gctgtttccg cagctgtgac 780
ctggccctcc tggagacgta ctgtgctacc cccgccaagt ccgagaggga cgtgtcgacc 840
cctccgaccg tgcttccgga caacttcccc agataccccg tgggcaagtt cttccaatat 900
gacacctgga agcagtccac ccagcgcctg cgcaggggcc tgcctgccct cctgcgtgcc 960
cgccggggtc acgtgctcgc caaggagctc gaggcgttca gggaggccaa acgtcaccgt 1020
cccctgattg ctctacccac ccaagacccc gcccacgggg gcgccccccc agagatggcc 1080
agcaatcgga agtgagcaaa actgccgcaa gtctgcagcc cggcgccacc atcctgcagc 1140
ctcctcctga ccacggacgt ttccatcagg ttccatcccg aaaatctctc ggttccacgt 1200
ccccctgggg cttctcctga cccagtcccc gtgccccgcc tccccgaaac aggctactct 1260
cctcggcccc ctccatcggg ctgaggaagc acagcagcat cttcaaacat gtacaaaatc 1320
gattggcttt aaacaccctt cacataccct cccccc 1356

<210> SEQ ID NO 79
<211> LENGTH: 2330
<212> TYPE: DNA
<213> ORGANISM: Homo sapiens

<400> SEQUENCE: 79
gaattcggca cgagcgacgc ggcccagagg ccaggaacat tccgcgcgtg gaccagccgg 60
gccagggcga tgctgcgggt gcggtgtctg cgcggcggga gccgcggcgc cgaggcggtg 120
cactacatcg gatctcggct tggacgaacc ttgacaggat gggtgcagcg aactttccag 180
agcacccagg cagctacggc ttcctcccgg aactcctgtg cagctgacga caaagccact 240
gagcctctgc ccaaggactg ccctgtctct tcttacaacg aatgggaccc cttagaggaa 300
gtgatagtgg gcagagcaga aaacgcctgt gttccaccgt tcaccatcga ggtgaaggcc 360
aacacatatg aaaagtactg gccattttac cagaagcaag gagggcatta ttttcccaaa 420
gatcatttga aaaaggctgt tgctgaaatt gaagaaatgt gcaatatttt aaaaacggaa 480
ggagtgacag taaggaggcc tgaccccatt gactggtcat tgaagtataa aactcctgat 540
tttgagtcta cgggtttata cagtgcaatg cctcgagaca tcctgatagt tgtgggcaat 600
gagattatcg aggctcccat ggcatggcgt tcacgcttct ttgagtaccg agcgtacagg 660
tcaattatca aagactactt ccaccgtggc gccaagtgga caacagctcc taagcccaca 720
atggctgatg agctttataa ccaggattat cccatccact ctgtagaaga cagacacaaa 780
ttggctgctc agggaaaatt tgtgacaact gagtttgagc catgctttga tgctgctgac 840
ttcattcgag ctggaagaga tatttttgca cagagaagcc aggttacaaa ctacctaggc 900
attgaatgga tgcgtaggca tcttgctcca gactacagag tgcatatcat ctcctttaaa 960
gatcccaatc ccatgcatat tgatgctacc ttcaacatca ttggacctgg tattgtgctt 1020
tccaaccctg accgaccatg tcaccagatt gatcttttca agaaagcagg atggactatc 1080
attactcctc caacaccaat catcccagac gatcatccac tctggatgtc atccaaatgg 1140
ctttccatga atgtcttaat gctagatgaa aaacgtgtta tggtggatgc caatgaagtt 1200
ccaattcaaa agatgtttga aaagctgggt atcactacca ttaaagttaa cattcgtaat 1260
gccaattccc tgggaggagg cttccattgc tggacctgcg atgtccggcg ccgaggcacc 1320
ctacagtcct acttggactg aacaggcctg atggagcttg tggctggcct cagatacacc 1380
taagaagctt aggggcaagg ttcattctcc tgctttaaaa agtgcatgaa ctgtagtgct 1440
ttaaacaatc atctccttaa caggggtcgt aagcctggtt tgcttctatt acttttcttt 1500
gacataaaga aaataacttc tgctaggtat tactctctac tcctaaagtt atttactatt 1560
tggcttcaag tataaaattt tggtgaatgt gtaccaagaa aaaattagtc acctgagtaa 1620
cttggccact aataattaac catctacctc tgtttttaat tttctttcca aaaggcagct 1680
tgaaatgttg gtcctaatct taattttttt tcctcttcta tagacttgag aatgtttttc 1740
tctaaatgag agaaagactt agaatgtaca cagatccaaa atagaatcag attatctctt 1800
tttttctaaa ggagagaaag acttagaaca tacacagatc ctaagtagaa ccaggtaatt 1860
gtctcttttt ctaataagga atttgggtaa tttttaattt tttgtttttt aaaaaataac 1920
ctagactatg caaaacatca aagtgaattt tccatgaatg tttttaatat tctcatctca 1980
acattgtgat atatgctact aaaaaccttt tcatatacat cttacctcat ttcaagtgaa 2040
ttattttaat ctttttctct ctttccaaaa atttacagga atgtttagtg taattggatt 2100
tcgctatcag ttcccatcct taagttttga tattcaatat ctgatagata cactgcatct 2160
ttggtcatct aagatttgtt tacaaatgtg caaattattt agagcataga ctttataagc 2220
attaaaaaaa actaatggag gtaaaaccta aatgcgatgt gaaataattt tagtgttgat 2280
actgtatgtg tatttttatt ctaataaact tttgtgttcc agattgaaaa 2330

<210> SEQ ID NO 80
<211> LENGTH: 2436
<212> TYPE: DNA
<213> ORGANISM: Homo sapiens

<400> SEQUENCE: 80
ggctcccaca gtgggtggcg gaaaacaact ttcagagctt tgtaaatgcc agttgtgccc 60
atcctcagct gctaaaagga agaagcattt ttgctgttag cccagatggc tttgtgtgtg 120
atgattttcc caaaccccag atcacggttc agccagaaac acagtcggca ataaaaggtt 180
ccaatttgag tttcatctgc tcagctgcca gcagcagtga ttccccaatg acttttgctt 240
ggaaaaaaga caatgaacta ctgcatgatg ctgaaatgga aaattatgca cacctccggg 300
cccaaggtgg cgaggtgatg gagtatacca ccatccttcg gctgcgcgag gtggaatttg 360
ccagtgaggg gaaatatcag tgtgtcatct ccaatcactt tggttcatcc tactctgtca 420
aagccaagct tacagtaaat atgcttccct cattcaccaa gacccccatg gatctcacca 480
tccgagctgg ggccatggca cgcttggagt gtgctgctgt ggggcaccca gccccccaga 540
tagcctggca gaaggatggg ggcacagact tcccagctgc acgggagaga cgcatgcatg 600
tgatgcccga ggatgacgtg ttctttatcg tggatgtgaa gatagaggac attggggtat 660
acagctgcac agctcagaac agtgcaggaa gtatttcagc aaatgcaact ctgactgtcc 720
tagaaacacc atcattttg cggccactgt tggaccgaac tgtaaccaag ggagaaacag 780
ccgtcctaca gtgcattgct ggaggaagcc ctcccccctaa actgaactgg accaaagatg 840
atagcccatt ggtggtaacc gagaggcact tttttgcagc aggcaatcag cttctgatta 900
ttgtggactc agatgtcagt gatgctggga aatacacatg tgagatgtct aacacccttg 960
gcactgagag aggaaacgtg cgcctcagtg tgatccccac tccaacctgc gactcccctc 1020
agatgacagc cccatcgtta gacgatgacg gatgggccac tgtgggtgtc gtgatcatag 1080
ccgtggtttg ctgtgtggtg ggcacgtcac tcgtgtgggt ggtcatcata taccacacaa 1140
ggcggaggaa tgaagattgc agcattacca acacagatga gaccaacttg ccagcagata 1200
ttcctagtta tttgtcatct cagggaacgt tagctgacag gcaggatggg tacgtgtctt 1260
cagaaagtgg aagccaccac cagtttgtca catcttcagg tgctggattt ttcttaccac 1320
aacatgacag tagtgggacc tgccatattg acaatagcag tgaagctgat gtggaagctg 1380
ccacagatct gttcctttgt ccgtttttgg gatccacagg ccctatgtat ttgaagggaa 1440
atgtgtatgg ctcagatcct tttgaaacat atcatacagg ttgcagtcct gacccaagaa 1500
cagttttaat ggaccactat gagcccagtt acataaagaa aaaggagtgc tacccatgtt 1560
ctcatccttc agaagaatcc tgcgaacgga gcttcagtaa tatatcgtgg ccttcacatg 1620
tgaggaagct acttaacact agttactctc acaatgaagg acctggaatg aaaaatctgt 1680
gtctaaacaa gtcctcttta gattttagtg caaatccaga gccagcgtcg gttgcctcga 1740
gtaattcttt catgggtacc tttggaaaag ctctcaggag acctcaccta gatgcctatt 1800
caagctttgg acagccatca gattgtcagc caagagcctt ttatttgaaa gctcattctt 1860
ccccagactt ggactctggg tcagaggaag atgggaaaga aaggacagat tttcaggaag 1920
aaaatcacat ttgtaccttt aaacagactt tagaaaacta caggactcca aattttcagt 1980
cttatgactt ggacacatag actgaatgag accaaaggaa aagcttaaca tactacctca 2040

```
agtgaacttt tatttaaaag agagagaatc ttatgttttt taaatggagt tatgaatttt   2100

aaaaggataa aaatgcttta tttatacaga tgaaccaaaa ttacaaaaag ttatgaaaat   2160

ttttatactg ggaatgatgc tcatataaga atacettttt aaactatttt ttaactttgt   2220

tttatgcaaa aaagtatctt acgtaaatta atgatataaa tcatgattat tttatgtatt   2280

tttataatgc cagatttctt tttatggaaa atgagttact aaagcatttt aaataatacc   2340

tgccttgtac cattttttaa atagaagtta cttcattata ttttgcacat tatatttaat   2400

aaaatgtgtc aatttgaaaa aaaaaaaaaa aaaaaa                             2436


<210> SEQ ID NO 81
<211> LENGTH: 2121
<212> TYPE: DNA
<213> ORGANISM: Homo sapiens

<400> SEQUENCE: 81

ctgctcgcgg ccgccaccgc cgggccccgg ccgtccctgg ctcccctcct gcctcgagaa     60

gggcagggct tctcagaggc ttggcgggaa aaaagaacgg agggagggat cgcgctgagt    120

ataaaagccg gttttcgggg ctttatctaa ctcgctgtag taattccagc gagaggcaga    180

gggagcgagc gggcggccgg ctagggtgga agagccgggc gagcagagct gcgctgcggg    240

cgtcctggga agggagatcc ggagcgaata gggggcttcg cctctggccc agccctcccg    300

cttgatcccc caggccagcg gtccgcaacc cttgccgcat ccacgaaact ttgcccatag    360

cagcgggcgg gcactttgca ctggaactta caacacccga gcaaggacgc gactctcccg    420

acgcggggag gctattctgc ccatttgggg acacttcccc gccgctgcca ggacccgctt    480

ctctgaaagg ctctccttgc agctgcttag acgctggatt tttttcgggt agtggaaaac    540

cagcagcctc ccgcgacgat gcccctcaac gttagcttca ccaacaggaa ctatgacctc    600

gactacgact cggtgcagcc gtatttctac tgcgacgagg aggagaactt ctaccagcag    660

cagcagcaga gcgagctgca gcccccggcg cccagcgagg atatctggaa gaaattcgag    720

ctgctgccca ccccgcccct gtcccctagc cgccgctccg ggctctgctc gccctcctac    780

gttgcggtca caccettctc ccttcgggga gacaacgacg gcggtggcgg gagcttctcc    840

acggccgacc agctggagat ggtgaccgag ctgctgggag gagacatggt gaaccagagt    900

ttcatctgcg acccggacga cgagaccttc atcaaaaaca tcatcatcca ggactgtatg    960

tggagcggct tctcggccgc cgccaagctc gtctcagaga agctggcctc ctaccaggct   1020

gcgcgcaaag acagcggcag cccgaacccc gcccgcggcc acagcgtctg ctccacctcc   1080

agcttgtacc tgcaggatct gagcgccgcc gcctcagagt gcatcgaccc ctcggtggtc   1140

ttcccctacc ctctcaacga cagcagctcg cccaagtcct gcgcctcgca agactccagc   1200

gccttctctc cgtcctcgga ttctctgctc tcctcgacgg agtcctcccc gcagggcagc   1260

cccgagcccc tggtgctcca tgaggagaca ccgcccacca ccagcagcga ctctgaggag   1320

gaacaagaag atgaggaaga aatcgatgtt gtttctgtgg aaaagaggca ggctcctggc   1380

aaaaggtcag agtctggatc accttctgct ggaggccaca gcaaacctcc tcacagccca   1440

ctggtcctca agaggtgcca cgtctccaca catcagcaca actacgcagc gcctccctcc   1500

actcggaagg actatcctgc tgccaagagg gtcaagttgg acagtgtcag agtcctgaga   1560

cagatcagca acaaccgaaa atgcaccagc cccaggtcct cggacaccga ggagaatgtc   1620

aagaggcgaa cacacaacgt cttggagcgc cagaggagga acgagctaaa acggagcttt   1680

tttgccctgc gtgaccagat cccggagttg gaaaacaatg aaaaggcccc caaggtagtt   1740
```

-continued

```
atccttaaaa aagccacagc atacatcctg tccgtccaag cagaggagca aaagctcatt   1800

tctgaagagg acttgttgcg gaaacgacga gaacagttga aacacaaact tgaacagcta   1860

cggaactctt gtgcgtaagg aaaagtaagg aaaacgattc cttctaacag aaatgtcctg   1920

agcaatcacc tatgaacttg tttcaaatgc atgatcaaat gcaacctcac aaccttggct   1980

gagtcttgag actgaaagat ttagccataa tgtaaactgc ctcaaattgg actttgggca   2040

taaaagaact tttttatgct taccatcttt tttttttctt taacagattt gtatttaaga   2100

attgttttta aaaaatttta a                                             2121
```

```
<210> SEQ ID NO 82
<211> LENGTH: 2121
<212> TYPE: DNA
<213> ORGANISM: Homo sapiens

<400> SEQUENCE: 82

ctgctcgcgg ccgccaccgc cgggccccgg ccgtccctgg ctcccctcct gcctcgagaa     60

gggcagggct tctcagaggc ttggcgggaa aaaagaacgg agggagggat cgcgctgagt    120

ataaaagccg gttttcgggg ctttatctaa ctcgctgtag taattccagc gagaggcaga    180

gggagcgagc gggcggccgg ctagggtgga agagccgggc gagcagagct gcgctgcggg    240

cgtcctggga agggagatcc ggagcgaata gggggcttcg cctctggccc agccctcccg    300

cttgatcccc caggccagcg gtccgcaacc cttgccgcat ccacgaaact ttgcccatag    360

cagcgggcgg gcactttgca ctggaactta caacacccga gcaaggacgc gactctcccg    420

acgcggggag gctattctgc ccatttgggg acacttcccc gccgctgcca ggacccgctt    480

ctctgaaagg ctctccttgc agctgcttag acgctggatt tttttcgggt agtggaaaac    540

cagcagcctc ccgcgacgat gcccctcaac gttagcttca ccaacaggaa ctatgacctc    600

gactacgact cggtgcagcc gtatttctac tgcgacgagg aggagaactt ctaccagcag    660

cagcagcaga gcgagctgca gcccccggcg cccagcgagg atatctggaa gaaattcgag    720

ctgctgccca ccccgcccct gtcccctagc cgccgctccg ggctctgctc gccctcctac    780

gttgcggtca cacccttctc ccttcgggga gacaacgacg gcggtggcgg gagcttctcc    840

acggccgacc agctggagat ggtgaccgag ctgctgggag gagacatggt gaaccagagt    900

ttcatctgcg acccggacga cgagaccttc atcaaaaaca tcatcatcca ggactgtatg    960

tggagcggct tctcggccgc cgccaagctc gtctcagaga agctggcctc ctaccaggct   1020

gcgcgcaaag acagcggcag cccgaacccc gcccgcggcc acagcgtctg ctccacctcc   1080

agcttgtacc tgcaggatct gagcgccgcc gcctcagagt gcatcgaccc ctcggtggtc   1140

ttcccctacc ctctcaacga cagcagctcg cccaagtcct gcgcctcgca agactccagc   1200

gccttctctc cgtcctcgga ttctctgctc tcctcgacgg agtcctcccc gcagggcagc   1260

cccgagcccc tggtgctcca tgaggagaca ccgcccacca ccagcagcga ctctgaggag   1320

gaacaagaag atgaggaaga aatcgatgtt gtttctgtgg aaaagaggca ggctcctggc   1380

aaaaggtcag agtctggatc accttctgct ggaggccaca gcaaacctcc tcacagccca   1440

ctggtcctca agaggtgcca cgtctccaca catcagcaca actacgcagc gcctccctcc   1500

actcggaagg actatcctgc tgccaagagg gtcaagttgg acagtgtcag agtcctgaga   1560

cagatcagca acaaccgaaa atgcaccagc cccaggtcct cggacaccga ggagaatgtc   1620

aagaggcgaa cacacaacgt cttggagcgc cagaggagga acgagctaaa acggagcttt   1680

tttgccctgc gtgaccagat cccggagttg gaaaacaatg aaaaggcccc caaggtagtt   1740
```

atccttaaaa aagccacagc atacatcctg tccgtccaag cagaggagca aaagctcatt 1800
tctgaagagg acttgttgcg gaaacgacga gaacagttga aacacaaact tgaacagcta 1860
cggaactctt gtgcgtaagg aaaagtaagg aaaacgattc cttctaacag aaatgtcctg 1920
agcaatcacc tatgaacttg tttcaaatgc atgatcaaat gcaacctcac aaccttggct 1980
gagtcttgag actgaaagat ttagccataa tgtaaactgc ctcaaattgg actttgggca 2040
taaaagaact tttttatgct taccatcttt tttttttctt taacagattt gtatttaaga 2100
attgttttta aaaaatttta a 2121

<210> SEQ ID NO 83
<211> LENGTH: 3597
<212> TYPE: DNA
<213> ORGANISM: Homo sapiens

<400> SEQUENCE: 83
ggcgaatgga gcaggggcgc gcagataatt aaagatttac acacagctgg aagaaatcat 60
agagaagccg ggcgtggtgg ctcatgccta taatcccagc acttttggag gctgaggcgg 120
gcagatcact tgagatcagg agttcgagac cagcctggtg ccttggcatc tcccaatggg 180
gtggctttgc tctgggctcc tgttccctgt gagctgcctg gtcctgctgc aggtggcaag 240
ctctgggaac atgaaggtct tgcaggagcc cacctgcgtc tccgactaca tgagcatctc 300
tacttgcgag tggaagatga atggtcccac caattgcagc accgagctcc gcctgttgta 360
ccagctggtt tttctgctct ccgaagccca cacgtgtatc cctgagaaca acggaggcgc 420
ggggtgcgtg tgccacctgc tcatggatga cgtggtcagt gcggataact atacactgga 480
cctgtgggct gggcagcagc tgctgtggaa gggctccttc aagcccagcg agcatgtgaa 540
acccagggcc ccaggaaacc tgacagttca caccaatgtc tccgacactc tgctgctgac 600
ctggagcaac ccgtatcccc ctgacaatta cctgtataat catctcacct atgcagtcaa 660
catttggagt gaaaacgacc cggcagattt cagaatctat aacgtgacct acctagaacc 720
ctccctccgc atcgcagcca gcaccctgaa gtctgggatt tcctacaggg cacgggtgag 780
ggcctgggct cagtgctata acaccacctg gagtgagtgg agccccagca ccaagtggca 840
caactcctac agggagccct tcgagcagca cctcctgctg ggcgtcagcg tttcctgcat 900
tgtcatcctg gccgtctgcc tgttgtgcta tgtcagcatc accaagatta agaaagaatg 960
gtgggatcag attcccaacc cagcccgcag ccgcctcgtg gctataataa tccaggatgc 1020
tcaggggtca cagtgggaga agcggtcccg aggccaggaa ccagccaagt gcccacactg 1080
gaagaattgt cttaccaagc tcttgccctg ttttctggag cacaacatga aaagggatga 1140
agatcctcac aaggctgcca aagagatgcc tttccagggc tctggaaaat cagcatggtg 1200
cccagtggag atcagcaaga cagtcctctg gccagagagc atcagcgtgg tgcgatgtgt 1260
ggagttgttt gaggccccgg tggagtgtga ggaggaggag gaggtagagg aagaaaaagg 1320
gagcttctgt gcatcgcctg agagcagcag ggatgacttc caggagggaa gggagggcat 1380
tgtggcccgg ctaacagaga gcctgttcct ggacctgctc ggagaggaga atgggggctt 1440
ttgccagcag gacatggggg agtcatgcct tcttccacct tcgggaagta cgagtgctca 1500
catgccctgg gatgagttcc caagtgcagg gcccaaggag gcacctccct ggggcaagga 1560
gcagcctctc cacctggagc caagtcctcc tgccagcccg acccagagtc cagacaacct 1620
gacttgcaca gagacgcccc tcgtcatcgc aggcaaccct gcttaccgca gcttcagcaa 1680
ctccctgagc cagtcaccgt gtcccagaga gctgggtcca gacccactgc tggccagaca 1740

```
cctggaggaa gtagaacccg agatgccctg tgtcccccag ctctctgagc caaccactgt   1800

gccccaacct gagccagaaa cctgggagca gatcctccgc cgaaatgtcc tccagcatgg   1860

ggcagctgca gcccccgtct cggcccccac cagtggctat caggagtttg tacatgcggt   1920

ggagcagggt ggcacccagg ccagtgcggt ggtgggcttg ggtcccccag gagaggctgg   1980

ttacaaggcc ttctcaagcc tgcttgccag cagtgctgtg tccccagaga aatgtgggtt   2040

tggggctagc agtggggaag aggggtataa gcctttccaa gacctcattc ctggctgccc   2100

tggggaccct gccccagtcc ctgtcccctt gttcaccttt ggactggaca gggagccacc   2160

tcgcagtccg cagagctcac atctcccaag cagctcccca gagcacctgg gtctggagcc   2220

gggggaaaag gtagaggaca tgccaaagcc cccacttccc caggagcagg ccacagaccc   2280

ccttgtggac agcctgggca gtggcattgt ctactcagcc cttacctgcc acctgtgcgg   2340

ccacctgaaa cagtgtcatg gccaggagga tggtggccag acccctgtca tggccagtcc   2400

ttgctgtggc tgctgctgtg gagacaggtc ctcgcccccct acaacccccc tgagggcccc   2460

agacccctct ccaggtgggg ttccactgga ggccagtctg tgtccggcct ccctggcacc   2520

ctcgggcatc tcagagaaga gtaaatcctc atcatccttc catcctgccc ctggcaatgc   2580

tcagagctca agccagaccc ccaaaatcgt gaactttgtc tccgtgggac ccacatacat   2640

gagggtctct taggtgcatg tcctcttgtt gctgagtctg cagatgagga ctagggctta   2700

tccatgcctg ggaaatgcca cctcctggaa ggcagccagg ctggcagatt tccaaaagac   2760

ttgaagaacc atggtatgaa ggtgattggc cccactgacg ttggcctaac actgggctgc   2820

agagactgga ccccgcccag cattgggctg ggctcgccac atcccatgag agtagagggc   2880

actgggtcgc cgtgccccac ggcaggcccc tgcaggaaaa ctgaggccct tgggcacctc   2940

gacttgtgaa cgagttgttg gctgctccct ccacagcttc tgcagcagac tgtccctgtt   3000

gtaactgccc aaggcatgtt ttgcccacca gatcatggcc cacgtggagg cccacctgcc   3060

tctgtctcac tgaactagaa gccgagccta gaaactaaca cagccatcaa gggaatgact   3120

tgggcggcct tgggaaatcg atgagaaatt gaacttcagg gagggtggtc attgcctaga   3180

ggtgctcatt catttaacag agcttcctta ggttgatgct ggaggcagaa tcccggctgt   3240

caaggggtgt tcagttaagg ggagcaacag aggacatgaa aaattgctat gactaaagca   3300

gggacaattt gctgccaaac acccatgccc agctgtatgg ctgggggctc ctcgtatgca   3360

tggaaccccc agaataaata tgctcagcca ccctgtgggc cgggcaatcc agacagcagg   3420

cataaggcac cagttaccct gcatgttggc ccagacctca ggtgctaggg aaggcgggaa   3480

ccttgggttg agtaatgctc gtctgtgtgt tttagtttca tcacctgtta tctgtgtttg   3540

ctgaggagag tggaacagaa ggggtggagt tttgtataaa taaagtttct ttgtctc      3597
```

<210> SEQ ID NO 84
<211> LENGTH: 2709
<212> TYPE: DNA
<213> ORGANISM: Homo sapiens

<400> SEQUENCE: 84

```
gggaatagca gaataggagc aagccagcac tagtcagcta actaagtgac tcaaccaagg     60

cctttttcc ttgttatctt tgcagatact tcattttctt agcgtttctg gagattacaa    120

catcctgcgg ttccgtttct gggaacttta ctgatttatc tccccccctca cacaaataag    180

cattgattcc tgcatttctg aagatctcaa gatctggact actgttgaaa aaatttccag    240

tgaggctcac ttatgtctgt aaagatggga aaaaaataca agaacattgt tctactaaaa    300
```

-continued

```
ggattagagg tcatcaatga ttatcatttt agaatggtta agtccttact gagcaacgat    360
ttaaaactta atttaaaaat gagagaagag tatgacaaaa ttcagattgc tgacttgatg    420
gaagaaaagt tccgaggtga tgctggtttg ggcaaactaa taaaaatttt cgaagatata    480
ccaacgcttg aagacctggc tgaaactctt aaaaaagaaa agttaaaagt aaaaggacca    540
gccctatcaa gaaagaggaa gaaggaagtg catgctactt cacctgcacc ctccacaagc    600
agcactgtca aaactgaagg agcagaggca actcctggag ctcagaaaag aaaaaaatca    660
accaaagaaa aggctggacc caaagggagt aaggtgtccg aggaacagac tcagcctccc    720
tctcctgcag gagccggcat gtccacagcc atgggccgtt ccccatctcc caagacctca    780
ttgtcagctc cacccaacag ttcttcaact gagaacccga aaacagtggc caaatgtcag    840
gtaactccca gaagaaatgt tctccaaaaa cgcccagtga tagtgaaggt actgagtaca    900
acaaagccat ttgaatatga gaccccagaa atggagaaaa aaataatgtt tcatgctaca    960
gtggctacac agacacagtt cttccatgtg aaggttttaa acaccagctt gaaggagaaa   1020
ttcaatggaa agaaaatcat catcatatca gattatttgg aatatgatag tctcctagag   1080
gtcaatgaag aatctactgt atctgaagct ggtcctaacc aaacgtttga ggttccaaat   1140
aaaatcatca acagagcaaa ggaaactctg aagattgata ttcttcacaa acaagcttca   1200
ggaaatattg tatatggggt atttatgcta cataagaaaa cagtaaatca gaagaccaca   1260
atctacgaaa ttcaggatga tagaggaaaa atggatgtag tggggacagg acaatgtcac   1320
aatatcccct gtgaagaagg agataagctc cagcttttct gctttcgact tagaaaaaag   1380
aaccagatgt caaaactgat ttcagaaatg catagtttta tccagataaa gaaaaaaaca   1440
aacccgagaa acaatgaccc caagagcatg aagctacccc aggaacagcg tcagcttcca   1500
tatccttcag aggccagcac aaccttccct gagagccatc ttcggactcc tcagatgcca   1560
ccaacaactc catccagcag tttcttcacc aagaaaagtg aagacacaat ctccaaaatg   1620
aatgacttca tgaggatgca gatactgaag gaagggagtc attttccagg accgttcatg   1680
accagcatag gcccagctga gagccatccc cacactcctc agatgcctcc atcaacacca   1740
agcagcagtt tcttaaccac gttgaaacca agactgaaga ctgaacctga agaagtttcc   1800
atagaagaca gtgcccagag tgacctcaaa gaagtgatgg tgctgaacgc aacagaatca   1860
tttgtatatg agcccaaaga gcagaagaaa atgtttcatg ccacagtggc aactgagaat   1920
gaagtcttcc gagtgaaggt ttttaatatt gacctaaagg agaagttcac cccaaagaag   1980
atcattgcca tagcaaatta tgtttgccgc aatgggttcc tggaggtata tcctttcaca   2040
cttgtggctg atgtgaatgc tgaccgaaac atggagatcc caaaaggatt gattagaagt   2100
gccagcgtaa ctcctaaaat caatcagctt tgctcacaaa ctaaaggaag ttttgtgaat   2160
ggggtgtttg aggtacataa gaaaaatgta aggggtgaat tcacttatta tgaaatacaa   2220
gataatacag ggaagatgga agtggtggtg catggacgac tgaacacaat caactgtgag   2280
gaaggagata aactgaaact caccagcttt gaattggcac cgaaaagtgg gaataccggg   2340
gagttgagat ctgtaattca tagtcacatc aaggtcatca agaccaggaa aaacaagaaa   2400
gacatactca atcctgattc aagtatggaa acttcaccag actttttctt ctaaaatctg   2460
gatgtcattg acgataatgt ttatggagat aaggtctaag tccctaaaaa aatgtacata   2520
tacctggttg aaatacaaca ctatacatac acaccaccat atatactagc tgttaatcct   2580
atggaatggg ggtattggga gtgctttttt aatttttcat agtttttttt taataaaatg   2640
gcatattttg catctacaac ttctataata agaaaaaata aataaacatt atcttttttg   2700
```

tgaaaaaaa 2709

<210> SEQ ID NO 85
<211> LENGTH: 777
<212> TYPE: DNA
<213> ORGANISM: Homo sapiens

<400> SEQUENCE: 85
ttcttcaaac cctcctcttc cctgtgttct cctacagaga ttgctgattt ctccttaagc 60
aagagattca ctgccgctaa gcatggctca gaccaactcg ttcttcatgc tgatctcctc 120
cctgatgttc ctgtctctga gccaaggcca agaggcccag acagagttgc cccaggcccg 180
gatcagctgc ccagaaggca ccaatgccta tcgctcctac tgctactact ttaatgaaga 240
ccgtgagacc tgggttgatg cagatctcta ttgccagaac atgaattcgg gcaacctggt 300
gtctgtgctc acccaggccg agggtgcctt tgtggcctca ctgattaagg agagtggcac 360
tgatgacttc aatgtctgga ttggcctcca tgaccccaaa aagaaccgcc gctggcactg 420
gagcagtggg tccctggtct cctacaagtc ctggggcatt ggagccccaa gcagtgttaa 480
tcctggctac tgtgtgagcc tgacctcaag cacaggattc cagaaatgga aggatgtgcc 540
ttgtgaagac aagttctcct ttgtatgcaa gttcaaaaac tagaggcagc tggaaaatac 600
atgtctagaa ctgatccagc aattacaacg gagtcaaaaa ttaaaccgga ccatctctcc 660
aactcaactc aacctggaca ctctcttctc tgctgagttt gccttgttaa tcttcaatag 720
ttttacctac cccagtcttt ggaaccctaa ataataaaaa taaacatgtt ttccact 777

<210> SEQ ID NO 86
<211> LENGTH: 2043
<212> TYPE: DNA
<213> ORGANISM: Homo sapiens

<400> SEQUENCE: 86
gtgcttaggc actgcagttg agtggctcac aaggagctaa aatttcacta atgcgtattc 60
agtgggtggt tctggtttgc ctgatttttg cctctgggca tggctgtttc agcctgagag 120
gctgttccaa gaatgttgct ttactaggag ctcatgccgc ctggtggtaa atatgaagta 180
cagcagtgca acagaccagt tttactccaa ggaaaccctg tagagatgac agcaatggtt 240
ggtgatttct gcctcaatta tgaaagtgat ctggtgttac agggccagag aagactaggg 300
gagttcgggt tttctagacc aaacagacac tcagtcctgg gcctggaggt ctctgcagtg 360
aggtgctgcc acagacagag ccaccttaac tcctcaggac aaccagtggc ttccgacaca 420
cactatgcac tggagggcaa gcagctctca gcttgggagc aactgaggat ggtgaacagc 480
ctgggcaagg agtgctctga ggctaagacc ctgaacagca ggaaccgaag tgcagctccc 540
cacttcaggt aatgtgattc taccctttgc ctgagaaaca tatccatcct aattgccatg 600
tgctcagctg gaccactaga gggagccatc ctgtaacggg tgaggtcaac ctaacaaatg 660
gtatcagtcg agtattgatc ggaggccaac gcaagaagtt accagtagcc tatttcagat 720
ttattaaaaa acacataggt aacgagtcag agctttggct aggaatgatt tggaaaagaa 780
ctgaaggcat aattccacag gacattcaca gttgtgtgct agagacagag aggagcagga 840
aagtgtttta gaagcatttg cggtggacaa tggaaggccc ggcttcatcg tattcctgtt 900
tgctgatcca catctgctgg aaggtggaca gagaggccag gatggagcca ccgatccaga 960
cagagtattt gcgctccgga ggggcaatga tctgtcagtc aagatgaaaa agaatggtca 1020
ttaatgtcat cattagtgca gtcgttagtg cggtaggaca gagcctggat gttctaccat 1080
ggcctagttt cttgttcagc agggacacag gcttgtctgt tagatgccaa ttgtgtccta 1140
attgtgtcat gttcttggca ggaccgccag agggagccat ggatttagaa attcttcagt 1200
ggtttcatgg atgccagcag actccatccc tggaaaagag acacaggcca tggtccttaa 1260
gtggagagta aaacccaggc tagacatgga agaccagact tgaacatctg gatgatcttg 1320
cagtggactg aggctgggaa gacataataa tctaggaacc acctgtctga gagacaaaag 1380
ggtcttgtta tgctctatgt cttcctgcct gccttctaat gaggaaggcc tgctgcagca 1440
tcctgaggtg tgggctacaa cagaaatgct tttggtcttg gggcaaccgt cacttgtctc 1500
catgttctgg aggctggctt gatatggaag aagacaatga ctccccttcc caggaaaagg 1560
gcgtttgttg cctaccgatg aaggatggct ggaacagggt ctctgggcag cggaaacgtt 1620
catttccgat ggtgatcact tgcccatcag gcaactcgta actcttctca agggaggatg 1680
aggatgcggc agtggccatc tcattttcaa agtccagagc tacataacac agtttctcct 1740
tgatgtcccg gacaatctca cgctcagctg tcaaccagat acaaacattg tggcaaacat 1800
tagggtctgc acaggtggca aagattcacc tgccctactg cagtctctcc ctcaagacat 1860
gtgccatcaa aaaatgtgtc agttcaatat tctgcaatcc aaaatccaca atgataatga 1920
cgtagtaggg ccaccaggga accacctctg ttcctaggac agtgtctcat gcatagtagg 1980
ccctcagcat gcattgtctg ggaaatgcat aacaagaata aaatgagcta gctagagaaa 2040
ggc 2043

<210> SEQ ID NO 87
<211> LENGTH: 1501
<212> TYPE: DNA
<213> ORGANISM: Homo sapiens

<400> SEQUENCE: 87
agcgagtcct tcttttcctg actgcagctc ttttcatttt gccatccttc tccagctcca 60
tgatggttct gcaggtttct gcggcccccc ggacagtggc tctgacggcg ttactgatgg 120
tgctgctcac atctgtggtc cagggcaggg ccactccaga gaattacgtg taccagggac 180
ggcaggaatg ctacgcgttt aatgggacac agcgcttcct ggagagatac atctacaacc 240
gggaggagta cgcgcgcttc gacagcgacg tgggggagtt ccgggcggtg acggagctgg 300
ggcggcctgc tgcggagtac tggaacagcc agaaggacat cctggaggag aagcgggcag 360
tgccggacag ggtatgcaga cacaactacg agctggacga ggccgtgacc ctgcagcgcc 420
gagtccagcc taaggtgaac gtttccccct ccaagaaggg gcccctgcag caccacaacc 480
tgcttgtctg ccacgtgaca gatttctacc caggcagcat tcaagtccga tggttcctga 540
atggacagga ggaaacagct ggggtcgtgt ccaccaacct gatccgtaat ggagactgga 600
ccttccagat cctggtgatg ctggaaatga ccccccagca gggagacgtc tacatctgcc 660
aagtggagca caccagcctg gacagtcctg tcaccgtgga gtggaaggca cagtctgatt 720
ctgcccagag taagacattg acgggagctg ggggcttcgt gctggggctc atcatctgtg 780
gagtgggcat cttcatgcac aggaggagca agaaagttca acgaggatct gcataaacag 840
ggttcctgac ctcaccgaaa agactaatgt gccttagaac aagcatttgc tgtgttttgt 900
taacacctgg ttccaggaca gaccctcagc ttcccaagag gatactgctg ccaagaagtt 960
gctctgaagt cagtttctat cgttctgctc tttgattcaa agcactgttt ctctcactgg 1020
gcctccaacc atgttccctt cttcttagca ccacaaataa tcaaaaccca acataagtgt 1080
ttgctttcct ttaaaaatat gcatcaaatc gtctctcatt acttttctct gagggtttta 1140
gtaaacagta ggagttaata aagaagttca ttttggttta cacgtaggaa agaagagaag 1200
catcaaagtg gagatatgtt aactattgta taatgtggcc tgttatacat gacactcttc 1260
tgaattgact gtatttcagt gagctgcccc caaatcaagt ttagtgccct catccattta 1320
tgtctcagac cgctattctt aactattcaa tggtgagcag actgcaaatc tgcctgatag 1380
gacccatatt cccacagcac taattcaaca tatatcttac tgagagcatg ttttatcatt 1440
accattaaga agttaaatga acatcagaat ttaaaatcat aaatataatc taatacactt 1500
t 1501

<210> SEQ ID NO 88
<211> LENGTH: 1096
<212> TYPE: DNA
<213> ORGANISM: Homo sapiens

<400> SEQUENCE: 88
atgatcctaa acaaagctct gctgctgggg gccctcgctc tgaccaccgt gatgagcccc 60
tgtggaggtg aagacattgt ggctgaccac gttgcctctt gtggtgtaaa cttgtaccag 120
ttttacggtc cctctggcca gtacacccat gaatttgatg gagatgagca gttctacgtg 180
gacctggaga ggaaggagac tgcctggcgg tggcctgagt tcagcaaatt tggaggtttt 240
gacccgcagg gtgcactgag aaacatggct gtggcaaaac acaacttgaa catcatgatt 300
aaacgctaca actctaccgc tgctaccaat gaggttcctg aggtcacagt gttttccaag 360
tctcccgtga cactgggtca gcccaacacc ctcatttgtc ttgtggacaa catctttcct 420
cctgtggtca acatcacatg gctgagcaat gggcagtcag tcacagaagg tgtttctgag 480
accagcttcc tctccaagag tgatcattcc ttcttcaaga tcagttacct caccttcctc 540
ccttctgctg atgagattta tgactgcaag gtggagcact ggggcctgga ccagcctctt 600
ctgaaacact gggagcctga gattccagcc cctatgtcag agctcacaga gactgtggtc 660
tgtgccctgg ggttgtctgt gggcctcatg ggcattgtgg tgggcactgt cttcatcatc 720
caaggcctgc gttcagttgg tgcttccaga caccaagggc cattgtgaat cccatcctgg 780
aagggaaggt gcatcgccat ctacaggagc agaagaatgg acttgctaaa tgacctagca 840
ctattctctg gcccgattta tcatatccct tttctcctcc aaatatttct cctctcacct 900
tttctctggg acttaagctg ctatatcccc tcagagctca caaatgcctt tacattcttt 960
ccctgacctc ctgatttttt ttttcttttc tcaaatgtta cctacaatac atgcctgggg 1020
taagccaccc ggctacctaa ttcctcagta acctccatct aaaatctcca aggaagcaat 1080
aaattccttt tatgag 1096

<210> SEQ ID NO 89
<211> LENGTH: 1100
<212> TYPE: DNA
<213> ORGANISM: Homo sapiens

<400> SEQUENCE: 89
ctaaagctgg gttggtagct cctacctact gtgtggcaag aaggtatggg tcatgaacag 60
aaccaaggag ctgcgctgct acagatgtta ccacttctgt ggctgctacc ccactcctgg 120
gccgtccctg aagctcctac tccaatgtgg ccagatgacc tgcaaaacca cacattcctg 180
cacacagtgt actgccagga tgggagtccc agtgtgggac tctctgaggc ctacgacgag 240
gaccagcttt tcttcttcga cttttcccag aacactcggg tgcctcgcct gcccgaattt 300
gctgactggg ctcaggaaca gggagatgct cctgccattt tatttgacaa agagttctgc 360

```
gagtggatga tccagcaaat agggccaaaa cttgatggga aaatcccggt gtccagaggg    420
tttcctatcg ctgaagtgtt cacgctgaag cccctggagt ttggcaagcc caacactttg    480
gtctgttttg tcagtaatct cttcccaccc atgctgacag tgaactggca gcatcattcc    540
gtccctgtgg aaggatttgg gcctactttt gtctcagctg tcgatggact cagcttccag    600
gccttttctt acttaaactt cacaccagaa ccttctgaca ttttctcctg cattgtgact    660
cacgaaattg accgctacac agcaattgcc tattgggtac cccggaacgc actgccctca    720
gatctgctgg agaatgtgct gtgtggcgtg gcctttggcc tgggtgtgct gggcatcatc    780
gtgggcattg ttctcatcat ctacttccgg aagccttgct caggtgactg attcttccag    840
accagagttt gatgccagca gcttcggcca tccaaacaga ggatgctcag atttctcaca    900
tcctgcccag gatctcctct tagggtagaa gaagtctctg ggacatccct ggggtgtgtg    960
tgtagatttc ccacctgggg actctgctgt ccctgggctt gcatcccagg gatcccagag   1020
tggcctgcct atcacaacca catcccttcc ccccacaagg caataaatct catttcttta   1080
aaaaaaaaaa aaaaaaaaaa                                               1100
```

```
<210> SEQ ID NO 90
<211> LENGTH: 3526
<212> TYPE: DNA
<213> ORGANISM: Homo sapiens

<400> SEQUENCE: 90

ccacgcgtcc ggacaggctt aagcatggcc aagaagcttg agagaagaaa aatttcagaa     60
aaattgtctc aatttgacta gaatatcaat gaaccaggaa aactgaagca ccttccctaa    120
agaaaacttg ggtatacaat tactccacag acagagctga gggtttttta cccaaatcag    180
tcactggatt ttgctgcctg atacgtgaat cttcttggaa tttttctcat gtggatctaa    240
ggggaatgct ttattatggc tgctgttgtc caacagaacg acctagtatt tgaatttgct    300
agtaacgtca tggaggatga acgacagctt ggtgatccag ctatttttcc tgccgtaatt    360
gtggaacatg ttcctggtgc tgatattctc aatagttatg ccggtctagc ctgtgtggaa    420
gagcccaatg acatgattac tgagagttca ctggatgttg ctgaagaaga aatcatagac    480
gatgatgatg atgacatcac ccttacagtt gaagcttctt gtcatgacgg ggatgaaaca    540
attgaaacta ttgaggctgc tgaggcactc ctcaatatgg attcccctgg ccctatgctg    600
gatgaaaaac gaataaataa taatatattt agttcacctg aagatgacat ggttgttgcc    660
ccagtcaccc atgtgtccgt cacattagat gggattcctg aagtgatgga aacacagcag    720
gtgcaagaaa aatatgcaga ctcaccggga gcctcatcac cagaacagcc taagaggaaa    780
aaaggaagaa aaactaaacc accacgacca gattccccag ccactacgcc aaatatatct    840
gtgaagaaga aaaacaaaga tggaaaggga aacacaattt atctttggga gtttttactg    900
gcactgctcc aggacaaggc tacttgtcct aaatacatca agtggaccca gcgagagaaa    960
ggcattttta aattggtgga ttctaaagca gtgtccaggt tgtgggggaa gcacaaaaac   1020
aaacctgata tgaattatga gaccatggga agagcactca ggtactatta ccaaaggggt   1080
attctggcaa aagtggaagg tcagcgcttg gtgtatcagt ttaaagaaat gccaaaagat   1140
cttatatata taaatgatga ggatccaagt tccagcatag agtcttcaga tccatcacta   1200
tcttcatcag ccacttcaaa taggaatcaa accagccggt cgagagtatc ttcaagtcca   1260
ggggtaaaag gaggagccac tacagttcta aaaccaggga attctaaagc tgcaaaaccc   1320
aaagatcctg tggaagttgc acaaccatca gaagttttga ggacagtgca gcccacgcag   1380
```

```
tctccatatc ctacccagct cttccggact gttcatgtag tacagccagt acaggctgtc   1440
ccagagggag aagcagctag aaccagtacc atgcaggatg aaacattaaa ttcttccgtt   1500
cagagtatta ggactataca ggctccaacc caagttccag tggttgtgtc tcctaggaat   1560
cagcagttgc atacagtaac actccaaaca gtgccactca caacagttat agccagcaca   1620
gatccatcag caggtactgg atctcagaag tttattttac aagccattcc atcatcacag   1680
cccatgacag tactgaaaga aaatgtcatg ctgcagtcac aaaaggcggg ctctcctcct   1740
tcaattgtct tgggccctgc ccaggttcag caggtcctta ctagcaatgt tcagaccatt   1800
tgcaatggaa ccgtcagtgt ggcttcctct ccatccttca gtgctactgc acctgtggtg   1860
accttttctc ctcgcagttc acagctggtt gctcacccac ctggcactgt aatcacttca   1920
gttatcaaaa ctcaagaaac aaaaactctt acacaggaag tagagaaaaa ggaatctgaa   1980
gatcatttga aagagaacac tgagaaaacg gagcagcagc cacagcctta tgtgatggta   2040
gtgtccagtt ccaatggatt tacttctcag gtagctatga aacaaaacga actgctggaa   2100
cccaactctt tttagttaat ataccaaagc ttatgaataa ttgtttgtta attgaacatt   2160
ttcaattata tgcagactga ctgattctaa gataaattct aaggaggttt ctaattttgt   2220
aattgttaaa aatagagtta attttgactt tgttagatga gggaggaaaa ctcaactgtt   2280
tctctttgtt atctaaatgt ttcagaattc aatcgtgaag gaacaggcat tttacactat   2340
gaagacattc ttttgagatt tttatttcag ttgctatatc ataagcattt ttaaagtttc   2400
ttttctaatt ttacattgta ttagattttc tgattctttt gtaaatacag aacttaaata   2460
gaaggcaaca ggaaatttat ataggaacta ttttcattcc acttgtgtaa gttaagtctt   2520
gactctttca aatgcaaaaa acctatttta tgctttgtta aaattatggt gtcacttaga   2580
ttgactttag ttgactgcac tatataatat agaactatga atatgtagaa taacatgaaa   2640
aattggaggt gctggtggta tggctgaccc tgtttcagaa gcaggatagt ataaaagcat   2700
cagcctaaga atggcactcc cactaactag ctatgtaatc ttgacctctt tgggctttag   2760
ttcctctcat aaaaggaaga gatgtattgg attagactag attatcacca ctttctcttc   2820
tagttctaat ttttttaatt ctaataccta tattttcaag ttatgtcaat taaatcatta   2880
tcaggttatt tcctaatgta agaatagcta aaatgttgca gagaaataag tgacccaaca   2940
aaatttattc atctgttatg ggtaagatct gccataaatt cttcctaaat aatttgttta   3000
ctaactcttt aggccactgt gctttgcggt ccattagtaa acttgtgttg ctaagtgcta   3060
aacagaatac tgctattttg agagagtcaa gactctttct taagggccaa gaaagcaact   3120
tgagccttgg gctaatctgg ctgagtagtc agttataaaa gcataattgc tttatatttt   3180
ggatcatttt ttactggggg cggacttggg gggggttgca tacaaagata acatatatat   3240
ccaactttct gaaatgaaat gtttttagat tactttttca actgtaaata atgtacattt   3300
aatgtcacaa gaaaaaaatg tcttctgcaa attttctagt ataacagaaa tttttgtaga   3360
tgaaaaaaat cattatgttt agaggtctaa tgctatgttt tcatattaca gagtgaattt   3420
gtatttaaac aaaaatttaa attttggaat cctctaaaca tttttgtatc tttaattggt   3480
ttattattaa ataaatcata taaaaattct caaaaaaaaa aaaaaa                  3526
```

<210> SEQ ID NO 91
<211> LENGTH: 1968
<212> TYPE: DNA
<213> ORGANISM: Homo sapiens

<400> SEQUENCE: 91
aattccgccg ggcgcttaga acagaggctt gcacaggtgg agatgtggaa gtctgtagtg 60
ggccatgatg tgtctgtttc cgtggagacc cagggtgatg attgggacac agatcctgac 120
tttgtgaatg acatctctga aaaggagcaa cgatggggag ccaagaccat cgaggggtct 180
ggacgcacag aacacatcaa catccaccag ctgaggaaca aagtatcaga ggagcatgat 240
gttctcagga agaaagagat ggagtcaggg cccaaagcat cccatggcta tggaggtcgg 300
tttggagtag aaagagaccg aatggacaag agtgcagtgg gccatgagta tgttgccgag 360
gtggagaagc actcttctca gacggatgct gccaaaggct ttgggggcaa gtacggagtt 420
gagagggaca gggcagacaa gtcagcagtc ggctttgatt ataaaggaga agtggagaag 480
catacatctc agaaagatta ctctcgtggc tttggtggcc ggtacggggt ggagaaggat 540
aaatgggaca aagcagctct gggatatgac tacaagggag agacggagaa acacgagtcc 600
cagagagatt atgccaaggg ctttggtggc cagtatggaa tccagaagga ccgagtggat 660
aagagcgctg tcggcttcaa tgaaatggag gccccgacca cagcttataa gaagacgacg 720
cccatagaag ccgcttctag tggtgcccgt gggctgaagg cgaaatttga gtccatggct 780
gaggagaaga ggaagcgaga ggaagaggag aaggcacagc aggtggccag gaggcaacag 840
gagcgaaagg ctgtgacaaa gaggagccct gaggctccac agccagtgat agctatggaa 900
gagccagcag taccggcccc actgcccaag aaaatctcct cagaggcctg gcctccagtt 960
gggactcctc catcatcaga gtctgagcct gtgagaacca gcagggaaca cccagtgccc 1020
ttgctgccca ttaggcagac tctcccggag gacaatgagg agcccccagc tctgcccccct 1080 aggactctgg aaggcctcca ggtggaggaa gagccagtgt acgaagcaga gcctgagcct 1140
gagcccgagc ctgagcccga gcctgagaat gactatgagg acgttgagga gatggacagg 1200
catgagcagg aggatgaacc agaggggggac tatgaggagg tgctcgagcc tgaagattct 1260
tctttttctt ctgctctggc tggatcatca ggctgcccgg ctggggctgg ggctggggct 1320
gtggctctgg ggatctcagc tgtggctcta tatgattacc aaggagaggg aagtgatgag 1380
ctttcctttg atccggacga cgtaatcact gacattgaga tggtggacga gggctggtgg 1440
cggggacgtt gccatggcca ctttggactc ttccctgcaa attatgtcaa gcttctggag 1500
tgactagagc tcactgtcta ctgcaactgt gatttcccat gtccaaagtg gctctgctcc 1560 acccccctccc tattcctgat gcaaatgtct aaccagatga gtttctggac agacttccct 1620
ctcctgcttc attaagggct tggggcagag acagcatggg gaaggaggtc cccttcccca 1680
agagtcctct ctatcctgga tgagctcatg aacatttctc ttgtgttcct gactccttcc 1740
caatgaacac ctctctgcca ccccaagctc tgctctcctc ctctgtgagc tctgggcttc 1800
ccagtttgtt tacccggaa agtacgtcta gattgtgtgg tttgcctcat tgtgctattt 1860
gcccactttc cttccctgaa gaaatatctg tgaaccttct ttctgttcag tcctaaaatt 1920
cgaaataaag tgagactatg gttcacctgt aaaaaaaaaa aaggaatt 1968

<210> SEQ ID NO 92
<211> LENGTH: 2088
<212> TYPE: DNA
<213> ORGANISM: Homo sapiens

<400> SEQUENCE: 92
gaattcggca cgagcgcgcg gcgaatctca acgctgcgcc gtctgcgggc gcttccgggc 60
caccagtttc tctgctttcc accctggcgc cccccagccc tggctcccca gctgcgctgc 120
cccgggcgtc cacgccctgc gggcttagcg ggttcagtgg gctcaatctg cgcagcgcca 180
cctccatgtt gaccaagcct ctacaggggc ctcccgcgcc ccccgggacc cccacgccgc 240
cgccaggagg caaggatcgg gaagcgttcg aggccgagta tcgactcggc cccctcctgg 300
gtaagggggg ctttggcacc gtcttcgcag gacaccgcct cacagatcga ctccaggtgg 360
ccatcaaagt gattccccgg aatcgtgtgc tgggctggtc cccccttgtca gactcagtca 420 catgcccact cgaagtcgca ctgctatgga aagtgggtgc aggtggtggg caccctggcg 480
tgatccgcct gcttgactgg tttgagacac aggaaggctt catgctggtc ctcgagcggc 540
ctttgcccgc ccaggatctc tttgactata tcacagagaa gggcccactg ggtgaaggcc 600
caagccgctg cttctttggc caagtagtgg cagccatcca gcactgccat tcccgtggag 660
ttgtccatcg tgacatcaag gatgagaaca tcctgataga cctacgccgt ggctgtgcca 720
aactcattga ttttggttct ggtgccctgc ttcatgatga accctacact gactttgatg 780
ggacaagggt gtacagcccc ccagagtgga tctctcgaca ccagtaccat gcactcccgg 840
ccactgtctg gtcactgggc atcctcctct atgacatggt gtgtggggac attccctttg 900
agagggacca ggagattctg gaagctgagc tccacttccc agcccatgtc tccccagact 960
gctgtgccct aatccgccgg tgcctggccc ccaaaccttc ttcccgaccc tcactggaag 1020
agatcctgct ggacccctgg atgcaaacac cagccgagga tgttacccct caacccctcc 1080
aaaggaggcc ctgccccttt ggcctggtcc ttgctaccct aagcctggcc tggcctggcc 1140
tggcccccaa tggtcagaag agccatccca tggccatgtc acagggatag atggacattt 1200
gttgacttgg ttttacaggt cattaccagt cattaaagtc cagtattact aaggtaaggg 1260
attgaggatc aggggttaga agacataaac caagtttgcc cagttccctt cccaatccta 1320
caaaggagcc ttcctcccag aacctgtggt ccctgatttt ggagggggaa cttcttgctt 1380
ctcattttgc taaggaagtt tattttggtg aagttgttcc cattttgagc cccgggactc 1440
ttattttgat gatgtgtcac cccacattgg cacctcctac taccaccaca caaacttagt 1500
tcatatgctt ttacttgggc aagggtgctt tccttccaat accccagtag cttttatttt 1560
agtaaaggga ccctttcccc tagcctaggg tcccatattg ggtcaagctg cttacctgcc 1620
tcagcccagg atttttttatt ttgggggagg taatgccctg ttgttacccc aaggcttctt 1680 ttttttttt ttttttttg ggtgagggga ccctactttg ttatcccaag tgctcttatt 1740
ctggtgagaa gaaccttaat tccataattt gggaaggaat ggaagatgga caccaccgga 1800
caccaccaga caataggatg ggatggatgg ttttttgggg gatgggctag gggaaataag 1860
gcttgctgtt tgttttcctg ggcgctcccc tccaattttg cagatttttg caacctcctc 1920
ctgagccggg attgtccaat tactaaaatg taaataatca cgtattgtgg ggaggggagt 1980
tccaagtgtg ccctcctttt ttttcctgcc tggattattt aaaaagccat gtgtggaaac 2040
ccactattta ataaaagtaa tagaatcaga aaaaaaaaaa aaaaaaaa 2088

<210> SEQ ID NO 93
<211> LENGTH: 415
<212> TYPE: DNA
<213> ORGANISM: Homo sapiens

<400> SEQUENCE: 93
ccgctgcgtg ttttcctctt gatcgggaac tcctgcttct ccttgcctcg aaatggaccc 60
caactgctcc tgctcgcctg ttggctcctg tgcctgtgcc ggctcctgca aatgcaaaga 120
gtgcaaatgc acctcctgca agaagagctg ctgctcctgc tgccctgtgg gctgtgcmaa 180
gtgtgcccag ggctgcatct gcaaagggac gtcagacaag tgcagctgct gtgcctgatg 240
ccaggacagc tgtgctctca gatgtaaata gagcaaccta tataaacctg gattttttt 300 tttttttttt tgtacaaccc tgacccgttt gctacatctt tttttctatg aaatatgtga 360
atggcaataa attcatctag actaaaaaaa aaaaaaaaaa aaaaaaaaaa aaaaa 415

<210> SEQ ID NO 94
<211> LENGTH: 5725
<212> TYPE: DNA
<213> ORGANISM: Homo sapiens

<400> SEQUENCE: 94
cctggaggag ggctctggaa gtcacgtcag gttggctctt caggttcatt tccatagttc 60
cctgcggcct ctgccttggg gagttatgtt ttgttaccga gatccgcgct accagattgc 120
accggggctg atttgggggc tgggaatttg ccattctgct gtacagacac tgattttttt 180
ttcttctttt taaaaagcaa ggtttgtttt cattttggat tttaggtgat gggcaagtca 240
gaaagtcaga tggatataac tgatatcaac actccaaagc caaagaagaa acagcgatgg 300
actcgactgg agatcagcct ctcggtcctt gtcctgctcc tcaccatcat agctgtgaga 360
atgatcgcac tctatgcaac ctacgatgat ggtatttgca agtcatcaga ctgcataaaa 420
tcagctgctc gactgatcca aaacatggat gccaccactg agccttgtag agactttttc 480
aaatatgctt gcggaggctg gttgaaacgt aatgtcattc ccgagaccag ctcccgttac 540
ggcaactttg acattttaag agatgaacta gaagtcgttt tgaaagatgt ccttcaagaa 600
cccaaaactg aagatatagt agcagtgcag aaagcaaaag cattgtacag gtcttgtata 660
aatgaatctg ctattgatag cagaggtgga gaacctctac tcaaactgtt accagacata 720
tatgggtggc cagtagcaac agaaaactgg gagcaaaaat atggtgcttc ttggacagct 780
gaaaaagcta ttgcacaact gaattctaaa tatgggaaaa aagtccttat taatttgttt 840
gttggcactg atgataagaa ttctgtgaat catgtaattc atattgacca acctcgactt 900
ggcctccctt ctagagatta ctatgaatgc actggaatct ataaagaggc ttgtacagca 960
tatgtggatt ttatgatttc tgtggccaga ttgattcgtc aggaagaaag attgcccatc 1020
gatgaaaacc agcttgcttt ggaaatgaat aaagttatgg aattggaaaa agaaattgcc 1080
aatgctacgg ctaaacctga agatcgaaat gatccaatgc ttctgtataa caagatgaga 1140
ttggcccaga tccaaaataa cttttcacta gagatcaatg ggaagccatt cagctggttg 1200
aatttcacaa atgaaatcat gtcaactgtg aatattagta ttacaaatga ggaagatgtg 1260
gttgtttatg ctccagaata tttaaccaaa cttaagccca ttcttaccaa atattctgcc 1320
agagatcttc aaaatttaat gtcctggaga ttcataatgg atcttgtaag cagcctcagc 1380
cgaacctaca aggagtccag aaatgctttc cgcaaggccc tttatggtac aacctcagaa 1440
acagcaactt ggagacgttg tgcaaactat gtcaatggga atatggaaaa tgctgtgggg 1500
aggctttatg tggaagcagc atttgctgga gagagtaaac atgtggtcga ggatttgatt 1560
gcacagatcc gagaagtttt tattcagact ttagatgacc tcacttggat ggatgccgag 1620
acaaaaaaga gagctgaaga aaaggcctta gcaattaaag aaaggatcgg ctatcctgat 1680
gacattgttt caaatgataa caaactgaat aatgagtacc tcgagttgaa ctacaaagaa 1740
gatgaatact tcgagaacat aattcaaaat ttgaaattca gccaaagtaa acaactgaag 1800
aagctccgag aaaaggtgga caaagatgag tggataagtg gagcagctgt agtcaatgca 1860
ttttactctt caggaagaaa tcagatagtc ttcccagccg gcattctgca gccccccttc 1920
tttagtgccc agcagtccaa ctcattgaac tatgggggca tcggcatggt cataggacac 1980

```
gaaatcaccc atggcttcga tgacaatggc agaaacttta acaaagatgg agacctcgtt   2040
gactggtgga ctcaacagtc tgcaagtaac tttaaggagc aatcccagtg catggtgtat   2100
cagtatggaa acttttcctg ggacctggca ggtggacagc accttaatgg aattaataca   2160
ctgggagaaa acattgctga taatggaggt cttggtcaag catacagagc ctatcagaat   2220
tatattaaaa agaatggcga agaaaaatta cttcctggac ttgacctaaa tcacaaacaa   2280
ctatttttct tgaactttgc acaggtgtgg tgtggaacct ataggccaga gtatgcggtt   2340
aactccatta aaacagatgt gcacagtcca ggcaatttca ggattattgg gactttgcag   2400
aactctgcag agttttcaga agcctttcac tgccgcaaga attcatacat gaatccagaa   2460
aagaagtgcc gggtttggtg atcttcaaaa gaagcattgc agcccttggc tagacttgcc   2520
aacaccacag aaatggggaa ttctctaatc gaaagaaaat gggccctagg ggtcactgta   2580
ctgacttgag ggtgattaac agagagggca ccatcacaat acagataaca ttaggttgtc   2640
ctagaaaggg tgtggaggga ggaagggggt ctaaggtcta tcaagtcaat catttctcac   2700
tgtgtacata atgcttaatt tctaaagata atattactgt ttatttctgt ttctcatatg   2760
gtctaccagt ttgctgatgt ccctagaaaa caatgcaaaa cctttgaggt agaccaggat   2820
ttctaatcaa aagggaaaag aagatgttga agaatagagt taggcaccag aagaagagta   2880
ggtgacacta tagtttaaaa cacattgcct aactactagt ttttactttt atttgcaaca   2940
tttacagtcc ttcaaaatcc ttccaaagaa ttcttataca cattggggcc ttggagctta   3000
catagtttta aactcatttt tgccatacat cagttattca ttctgtgatc atttatttta   3060
agcactctta aagcaaaaaa tgaatgtcta aaattgtttt ttgttgtacc tgctttgact   3120
gatgctgaga ttcttcaggc ttcctgcaat tttctaagca atttcttgct ctatctctca   3180
aaacttggta tttttcagag atttatataa atgtaaaaat aataattttt atatttaatt   3240
attaactaca tttatgagta actattatta taggtaatca atgaatattg aagtttcagc   3300
ttaaaataaa cagttgtgaa ccaagatcta taaagcgata tacagatgaa aatttgagac   3360
tatttaaact tataaatcat attgatgaaa agatttaagc acaaacttta gggtaaaaat   3420
tgcgattgga cagttgtcta gagatatata tacttgtggt tttcaaattg gactttcaaa   3480
attaaatctg tccctgagag tgtctctgat aaaagggcaa atctgcacct atgtagctct   3540
gcatctcctg tcttttcagg tttgtcatca gatggaaata ttttgataat aaattgaaat   3600
tgtgaactca ttgctcccta agactgtgac aactgtctaa ctttagaagt gcatttctga   3660
atagaaatgg gaggcctctg atggaccttc tagaattata agtcacaaag agttctggaa   3720
aagaactgtt tactgcttga taggaattca tcttttgagg cttctgttcc tctcttttcc   3780
tgttgtattg actattttcg ttcattactt gattaagatt ttacaaaaga ggagcacttc   3840
caaaattctt atttttccta acaaaagatg aaagcaggga atttctatct aaatgatgag   3900
tattagttcc ctgtctcttg aaaaatgccc atttgccttt aaaaaaaaaa gttacagaaa   3960
tactataaca tatgtacata aattgcataa agcataagta tacagttcaa taaacttaac   4020
tttaactgaa caatggccct gtagccagca cctgtaagaa acagagcagt accagcgctc   4080
taaaagcacc tccttgtcac tttattactc ccagaacaac aactatcctg acttctaata   4140
tcattcacta gctttgcctg gttttgtctt ttatgcagat agaatcaatc agtatgtatt   4200
cttttgtgcc tggcttcttt ctctcagcct tacatttgtg agattcctct gtattgtgct   4260
gattgtggat cttttcattc tcattgcaga ataatgttct attgtgggac ttattacaat   4320
ttgttcatcc tattgttgat gggcacttga gaactttcca ttttggcgct attacaaata   4380
```

gtgcaactat gaatgtactg catgttacca tcttacttga gcctttaatg gacttatttc 4440
ttcaaatcct tccaaaaatt attataagca ttgaaattat agtttcaagc caactgtgga 4500
tacccttacc ctttcctcct ttatcacaac caccgttaca agtatactta tatttcccta 4560
aaatacattt aaaacttacc taagtgacat ttgtagttgg agtaatagga gcttccagct 4620
ctaataaaac agctgtctct aacttatttt atttccatca tgtcagagca ggtgaagagc 4680
cagaagtgaa gagtgactag tacaaattat aaaaagccac tagactcttc actgttagct 4740
ttttaaaaca ttaggctccc atccctatgg aggaacaact ctccagtgcc tggatcccct 4800
ctgtctacaa atataagatt ttctgggcct aaaggataga tcaaagtcaa aaatagcaat 4860
gcctccctat ccctcacaca tccagacatc atgaatttta catggtactc ttgttgagtt 4920
ctatagagcc ttctgatgtc tctaaagcac taccgattct ttggagttgt cacatcagat 4980
aagacatatc tctaattcca tccataaatc cagttctact atggctgagt tctggtcaaa 5040
gaaagaaagt ttagaagctg agacacaaag ggttgggagc tgatgaaact cacaaatgat 5100
ggtaggaaga agctctcgac aatacccgtt ggcaaggagt ctgcctccat gctgcagtgt 5160
tcgagtggat tgtaggtgca agatggaaag gattgtaggt gcaagctgtc cagagaaaag 5220
agtccttgtt ccagccctat tctgccactc ctgacagggt gaccttgggt atttgcaata 5280
ttcctttggg cctctgcttc tctcacctaa aaaaagagaa ttagattata ttggtggttc 5340
tcagcaagag aaggagtatg tgtccaatgc tgccttccca tgaatctgtc tcccagttat 5400
gaatcagtgg gcaggataaa ctgaaaactc ccatttaagt gtctgaatcg agtgagacaa 5460
aattttagtc caaataacaa gtaccaaagt tttatcaagt ttgggtctgt gctgctgtta 5520
ctgttaacca tttaagtggg gcaaaacctt gctaattttc tcaaaagcat ttatcattct 5580
tgttgccaca gctggagctc tcaaactaaa agacatttgt tattttggaa agaagaaaga 5640
ctctattctc aaagtttcct aatcagaaat ttttatcagt ttccagtctc aaaaatacaa 5700
aataaaaaca aacgttttta atact 5725

<210> SEQ ID NO 95
<211> LENGTH: 3259
<212> TYPE: DNA
<213> ORGANISM: Homo sapiens

<400> SEQUENCE: 95
gacgcgcgcc gggagccggc ggccgggcca gccggcgccg gggcccagtg cgccgcgctc 60
gcagccggta gcgcgccagc cgtaggcgtc gctcggcagc cgcggggccc taggcgtgcc 120
ggggaggggg cgagggcggc caggcgcctg ccgccccgga ggcaggatga gcatcgagat 180
cccggcggga ctgacggagc tgctgcaggg cttcacggtg gaggtgctga ggcaccagcc 240
cgcggacctg ctggagttcg cgctgcagca cttcacccgc ctgcagcagg agaacgagcg 300
caaaggcacc gcgcgcttcg gccatgaggg caggacctgg ggggacctgg gcgccgctgc 360
cgggggcggc acccccagca agggggtcaa cttcgccgag gagcccatgc agtccgactc 420
cgaggacggg gaggaggagg aggcggcgcc cgcggacgca ggggcgttca atgctccagt 480
aataaaccga ttcacaaggc gtgcctcagt atgtgcagaa gcttataatc ctgatgaaga 540
agaagatgat gcagagtcca ggattataca tccaaaaact gatgatcaaa gaaataggtt 600
gcaagaggct tgcaaagaca tcctgctgtt taagaatctg gatccggagc agatgtctca 660
agtattagat gccatgtttg aaaaattggt caaagatggg gagcatgtaa ttgatcaagg 720
tgacgatggt gacaactttt atgtaattga tagaggcaca tttgatattt atgtgaaatg 780

```
tgatggtgtt ggaagatgtg ttggtaacta tgataatcgt gggagtttcg gcgaactggc    840
cttaatgtac aatacaccca gagcagctac aatcactgct acctctcctg gtgctctgtg    900
gggtttggac agggtaacct tcaggagaat aattgtgaaa aacaatgcca aaaagagaaa    960
aatgtatgaa agctttattg agtcactgcc attccttaaa tctttggagt tttctgaacg   1020
cctgaaagta gtagatgtga taggcaccaa agtatacaac gatggagaac aaatcattgc   1080
tcagggagat tcggctgatt cttttttcat tgtagaatct ggagaagtga aaattactat   1140
gaaaagaaag ggtaaatcag aagtggaaga gaatggtgca gtagaaatgc ctcgatgctc   1200
gcggggacag tactttggag agcttgccct ggtaactaac aaacctcgag cagcttctgc   1260
ccacgccatt gggactgtca aatgtttagc aatggatgtg caagcatttg aaaggcttct   1320
gggaccttgc atggaaatta tgaaaaggaa catcgctacc tatgaagaac agttagttgc   1380
cctgtttgga acgaacatgg atattgttga acccactgca tgaagcaaaa gtatggagca   1440
agacctgtag tgacaaaatt acacagtagt ggttagtcca ctgagaatgt gtttgtgtag   1500
atgccaagca ttttctgtga tttcaggttt tttccttttt ttacatttac aacgtatcaa   1560
taaacagtag tgatttaata gtcaataggc tttaacatca ctttctaaag agtagttcat   1620
aaaaaaatca acatactgat aaaatgactt tgtactccac aaaattatga ctgaaaggtt   1680
tattaaaatg attgtaatat atagaaagta tctgtgttta agaagataat taaaggatgt   1740
tatcataggc tatatgtgtt ttacttattc agactgataa tcatattagt gactatcccc   1800
atgtaagagg gcacttggca attaaacatg ctacacagca tggcatcact tttttttata   1860
actcattaaa cacagtaaaa ttttaatcat ttttgtttta aagttttcta gcttgataag   1920
ttatgtgctg ccttggccta ttggtgaaat ggtataaaat atcatatgca gttttaaaac   1980
tttttatatt tttgcaataa agtacatttt gactttgttg gcataatgtc agtaacatac   2040
atattccagt ggttttatgg acaggcaatt tagtcattat gataataagg aaaacagtgt   2100
tttagatgag agatcattaa tgcatttttc cctcatcaag catatatctg ctttttttta   2160
ttttgcaatt ctctgtattc tatgtcttta aaaatttgat cttgacattt aatgtcacaa   2220
agttttgttt ttttaaaaag tgatttaaac ttaagatccg acatttttttg tattctttaa   2280
gattttacac ctaaaaaatc tctcctatcc caaaaataat gtgggatcct tatcagcatg   2340
cccacagttt atttctttgt tcttcactag gcctgcataa tacagtccta tgtagacatc   2400
tgttcccttg ggtttccgtt ctttcttagg atggttgcca acccacaatc tcattgatca   2460
gcagccaata tgggtttgtt tggttttttt aattcttaaa aacatcctct agaggaatag   2520
aaacaaattt ttatgagcat aaccctatat aaagacaaaa tgaatttctg accttaccat   2580
atataccatt aggccttgcc attgctttaa tgtagactca tagttgaaat tagtgcagaa   2640
agaactcaga tgtactagat tttcattgtt cattgatatg ctcagtatgc tgccacataa   2700
gatgaattta attatattca accaaagcaa tatactctta catgatttct aggccccatg   2760
acccagtgtc tagagacatt aattctaacc agttgtttgc ttttaaatga gtgatttcat   2820
tttgggaaac aggtttcaaa tgaatatata tacatgggta aaattactct gtgctagtgt   2880
agtcttacta gagaatgttt atggtcccac ttgtatatga aaatgtggtt agaatgttaa   2940
ttggataatg tatatataag aagttaaagt atgtaaagta taacttcagc cacattttta   3000
gaacactgtt taacattttt gcaaaacctt cttgtaggaa aagagagctc tctacatgaa   3060
gatgacttgt tttatatttc agattttatt ttaaaagcca tgtctgttaa acaagaaaaa   3120
acacaaaaga actccagatt cctggttcat cattctgtat tcttactcac tttttcaagt   3180
```

tatctatttt gttgcataaa ctaattgtta actattcatg gaacagcaaa cgcctgttta 3240
ataaagaact ttgaccaag 3259

<210> SEQ ID NO 96
<211> LENGTH: 2376
<212> TYPE: DNA
<213> ORGANISM: Homo sapiens

<400> SEQUENCE: 96
cgagggcagc gccggtcggg agcgcagcgc ggcgcagctc ggcgcgcacg gcgggagcgg 60
cgcgcgagtg gtcgggcctg gcggctggac gggcgcccct cgctgccccg cgcgctcccc 120
gccgcccccc atgagcgcag ccccgcgcgg cccgggtccg taggcggcgg ggcgcccccc 180
atgctgctgc agcccgcgcc gtgcgccccg agcgcgggct tcccgcggcc cctggccgcc 240
cccggcgcca tgcacggctc gcagaaggac accacgttca ccaagatctt cgtgggcggc 300
ctgccgtacc acactaccga cgcctcgctc aggaagtact tcgagggctt cggcgacatc 360
gaggaggccg tggtcatcac cgaccgccag acgggcaagt cccgcggcta cggcttcgtg 420
accatggccg accgggcggc agctgagagg gcttgcaaag acccgaaccc catcatcgac 480
ggccgcaagg ccaacgtgaa cctggcatat ctgggcgcca agccgcggag cctccagacg 540
ggctttgcca ttggggtgca gcagctgcac cccaccttga tccagcggac ttacgggctg 600
accccgcact acatctaccc accagccatc gtgcagccca gcgtggtgat cccagccgcc 660
cctgtcccgt cgctgtcctc gccctacatt gagtacacgc cggccagccc ggcctacgcc 720
cagtacccac cggccaccta tgaccagtac ccatacgccg cctcgcctgc cacggctgcc 780
agcttcgtgg gctacagcta ccctgccgcc gtgccccagg ccctctcagc cgcagcaccc 840
gcgggcacca ctttcgtgca gtaccaggcg ccgcagctgc agcctgacag gatgcagtga 900
ggggcgttcc tgccccgagg actgtggcat tgtcaccttc acagcagaca gagctgccag 960
gccatgatgg gctggcgaca gcccggctga gctttagtga ggtgccacca gcacccgtgc 1020
ctccgaagac cgctcgggca ttccgcctgc gccctgggac agcggagaga tggcttctct 1080
ttaatctagg tcccattgtg tcttgaggga ggactttaag aatgactgag aactatttaa 1140
agacgcaatc ccaggttcct tgcacaccat ggcagcctct tcttgcacct tctcctgcct 1200
ctccacactc caggttccct caggcttgtg tccccactgc tgcatcgtgg cggggtgtca 1260
cagaccctct gcagcccctg gctgccctgg actgtgcaga gatgcctgac tccagggaaa 1320
cctgaaagca agaagttaat ggactgttta ttgtaacttg atcctcccga gctgtgagcg 1380
cagtctgagg tgtgaggaca cggcctcctg ttggagtccc attttctcca tcagggcacg 1440
tgggcggctt cctcaagccc ggaggagctc ccaggcgcac aggggccgcc ggtaacaggg 1500
gccgccggcc aaaggcccct ttccagtcat agcactgaag ttgcaacttt tttcttgtaa 1560
ttgttttgct actaagataa tttcagaagt tcagtctatt ttttcagcgg atactgccgc 1620
caccaagaat ccaaaaccta tttttgactt ggagagactt gcttttgttg gttccgcccg 1680
tggagacgac gacagtgttt ctgtataata aagtgtctgc cggctcgcgg gccaggatcc 1740
tctcggtggg atgggcacca cagacaggag gcccctcagg cccgtgcggg ccactgtctg 1800
ctgccgcctg ccggggtggc agagtgagtt gtctcaggac cccgtcactg cgacgttgac 1860
actctctcct tccttccttc cccaactccc caaacactgt ggaagggaag aaggaagtga 1920
tccacagcat tcaggccact tggggtctag accatggtgg tgccagcctg gggggggcag 1980
tggccctcag ctctgcccgc tggagcggtt gagtgcagaa gggtgcgcct cttccctcta 2040

-continued

```
cccccgcacc acctgctgtg tgccagcctg agacggttcc tgcctgtctt gggggttggt   2100

ggagggtgga ggcagttctg ccagccgtgg cagggctgct atggggcatc cagggctgtg   2160

ggggtctgga ggaggggaca tgaggtgaga ggtatcctgg ccgagggcgg ggggcagcgg   2220

ggggtctccc tccggaccta cctcagggag ctgagcgtgc aggcgctcca gggcaggcct   2280

gggacagagt caaggctcag agaataaagg tagctaatct catcataata tttttattag   2340

aatgttctga tgataaaaat aaaacttgtt ttcttt                             2376


<210> SEQ ID NO 97
<211> LENGTH: 21
<212> TYPE: DNA
<213> ORGANISM: Artificial Sequence
<220> FEATURE:
<223> OTHER INFORMATION: Primer

<400> SEQUENCE: 97

gttgtaaaac gacggccagt g                                               21


<210> SEQ ID NO 98
<211> LENGTH: 19
<212> TYPE: DNA
<213> ORGANISM: Artificial Sequence
<220> FEATURE:
<223> OTHER INFORMATION: Primer

<400> SEQUENCE: 98

cacacaggaa acagctatg                                                  19


<210> SEQ ID NO 99
<211> LENGTH: 21
<212> TYPE: DNA
<213> ORGANISM: Artificial Sequence
<220> FEATURE:
<223> OTHER INFORMATION: Primer

<400> SEQUENCE: 99

tttttttttt tttttttttt v                                               21
```